US012797495B2

(12) United States Patent
Wang et al.

(10) Patent No.: US 12,797,495 B2

(45) Date of Patent: Nov. 17, 2026

(54) PEPTIDE UREA DERIVATIVE, PHARMACEUTICAL COMPOSITION CONTAINING PEPTIDE UREA DERIVATIVE, AND APPLICATION OF PEPTIDE UREA DERIVATIVE

(71) Applicant: BIVISION PHARMACEUTICALS, INC, Jiangsu (CN)

(72) Inventors: Eric Yanjun Wang, Jiangsu (CN); Haihua Yu, Jiangsu (CN); Kevin Yu Wang, Jiangsu (CN); Jinqiu He, Jiangsu (CN)

(73) Assignee: BIVISION PHARMACEUTICALS, INC, Jiangsu (CN)

( * ) Notice: Subject to any disclaimer, the term of this patent is extended or adjusted under 35 U.S.C. 154(b) by 197 days.

(21) Appl. No.: 18/729,913

(22) PCT Filed: Jan. 30, 2023

(86) PCT No.: PCT/CN2023/073860

§ 371 (c)(1),
(2) Date: Jul. 18, 2024

(87) PCT Pub. No.: WO2023/143612

PCT Pub. Date: Aug. 3, 2023

(65) Prior Publication Data

US 2025/0108139 A1 Apr. 3, 2025

(30) Foreign Application Priority Data

Jan. 30, 2022 (CN) ......................... 202210116230.9

(51) Int. Cl.

*A61K 51/08* (2006.01)
*A61K 49/00* (2006.01)
*A61K 51/04* (2006.01)

(52) U.S. Cl.

CPC ........ *A61K 51/088* (2013.01); *A61K 49/0002* (2013.01); *A61K 51/0482* (2013.01); *A61K 2121/00* (2013.01); *A61K 2123/00* (2013.01)

(58) Field of Classification Search

CPC .............. A61K 51/088; A61K 49/0002; A61K 51/0482
USPC ......................................................... 424/1.69
See application file for complete search history.

(56) References Cited

U.S. PATENT DOCUMENTS

| | | | |
|---|---|---|---|
| 10,011,632 B2 | 7/2018 | Wang et al. | |
| 10,975,089 B2 | 4/2021 | Zia et al. | |
| 2016/0228587 A1 | 8/2016 | Eder et al. | |
| 2017/0081298 A1 | 3/2017 | Ray et al. | |
| 2017/0189568 A1 | 7/2017 | Kung et al. | |
| 2021/0032286 A1 | 2/2021 | Wang et al. | |
| 2021/0393809 A1 | 12/2021 | Haberkorn et al. | |
| 2022/0105194 A1* | 4/2022 | Akaiwa | C07K 16/3007 |
| 2022/0354974 A1* | 11/2022 | Wilbur | C07B 59/004 |
| 2024/0366813 A1* | 11/2024 | Yu | A61K 51/0402 |

FOREIGN PATENT DOCUMENTS

| | | |
|---|---|---|
| CN | 105636924 A | 6/2016 |
| CN | 108541302 A | 9/2018 |
| CN | 111285918 A | 6/2020 |
| CN | 112770785 A | 5/2021 |
| CN | 115745903 A | 3/2023 |

(Continued)

OTHER PUBLICATIONS

Meder et al., Bioconjugate Chem 2012, 23:688-697.

(Continued)

*Primary Examiner* — Michael G. Hartley
*Assistant Examiner* — Sean R Donohue
(74) *Attorney, Agent, or Firm* — Houston Beshining Law Office PLLC; Liangang Ye

(57) ABSTRACT

Disclosed are a peptide urea derivative, a pharmaceutical composition containing the peptide urea derivative, and an application of the peptide urea derivative. The derivative is as represented by formula I, wherein R is a group containing radioactive metal ions or a group capable of optical imaging. The derivative can be used for preoperative imaging diagnosis and grading of PSMA positive prostate cancer, can also be used for treatment of various types and stages of prostate cancer, achieves the integration of diagnosis and treatment, and has a wide application prospect.

I

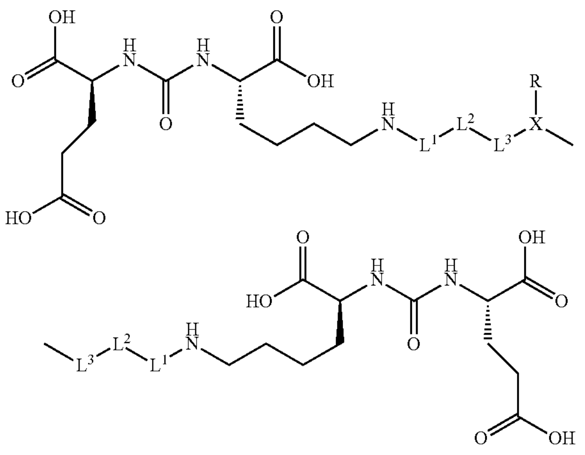

3 Claims, 7 Drawing Sheets

(56) References Cited

FOREIGN PATENT DOCUMENTS

| | | | | | |
|---|---|---|---|---|---|
| WO | WO-2013082338 | A1 * | 6/2013 | ............. | A61K 38/06 |
| WO | WO-2021013978 | A1 * | 1/2021 | ............. | A61K 45/06 |
| WO | 2021245263 | A1 | 12/2021 | | |

OTHER PUBLICATIONS

Zhou Xu et al., Current Status and Progress of Diagnostic Radiopharmaceuticals Targeting Prostate-Specific Membrane Antigen 2022 , 421-433.
May 19, 2023 International Search Report issued in International Patent Application No. PCT/CN2023/073860.
May 19, 2023 Written Opinion of the International Searching Authority issued in International Patent Application No. PCT/CN2023/073860.
May 10, 2024 Chinese Office Action issued in Chinese Patent Application No. 202310067352.8.
May 9, 2024 First Search Report issued in Chinese Patent Application No. 202310067352.8.

* cited by examiner

PEPTIDE UREA DERIVATIVE, PHARMACEUTICAL COMPOSITION CONTAINING PEPTIDE UREA DERIVATIVE, AND APPLICATION OF PEPTIDE UREA DERIVATIVE

The present application is a National Stage of International Application No. PCT/CN2023/073860, filed on Jan. 30, 2023, which claims the priority of Chinese patent application 202210116230.9, filed on Jan. 30, 2022. The content of the above application is incorporated herein by reference in its entirety.

TECHNICAL FIELD

The present disclosure relates to a peptide urea derivative, a pharmaceutical composition containing the same, and a use thereof.

BACKGROUND

According to the "Global Cancer Statistics 2018" report published online in the official journal of American Cancer Society, CA: A Cancer Journal for Clinicians, the evaluation results of the incidence and mortality rates of 36 types of cancer in 185 countries indicate that prostate cancer is the second most common cancer in men, following lung cancer. The "Cancer Statistics 2018" report in the United States predicts that the incidence rate of prostate cancer among American men accounts for approximately 19% of all tumor incidences, ranking first. Data from the National Cancer Center of China show that the incidence rate of prostate cancer among Chinese men was 3.25% in 2014, ranking sixth, but it has shown a rising trend in recent years. Therefore, prostate cancer is a highly prevalent type of cancer both globally and within China.

Early imaging diagnosis and treatment of prostate cancer have become urgent issues that need to be addressed in China and around the whole world. Prostate cancer begins in the tissues surrounding the prostate and gradually metastasizes to other vital organs, such as the lungs and bones, as it grows. In the early stages, there are no obvious symptoms, but as the prostate cancer progresses, it can cause issues such as urethral compression and urinary obstruction, and further spread to the spine or pelvis. For the diagnosis of prostate cancer, imaging diagnosis methods such as SPECT (Single Photon Emission Computed Tomography) and PET (Positron Emission Tomography) are currently being used. These methods involve the use of PSMA-targeted polypeptide substance labeled by radioisotopes that emit gamma rays or positrons, which specifically target and distribute within prostate cancer cells. This allows the presence and distribution of tumor cells to be visualized in tomographic and three-dimensional images. These imaging diagnostic methods have recently seen significant advancements and widespread adoption due to the development of SPECT-CT/MRI and PET-CT/MRI combined with CT or MRI Currently, the radiopharmaceuticals used for specific imaging of prostate cancer are targeted at PSMA ligands. These ligands can bind to the protein PSMA (prostate-specific membrane antigen) that is specifically expressed in prostate cancer. PSMA is a type II transmembrane glycoprotein, also known as glutamate carboxypeptidase, and serves as a specific molecular marker for prostate cancer. It is minimally expressed in the kidney, small intestine, and brain tissues, with expression levels in tumor tissues being significantly higher than in normal tissues. Representative PSMA ligands are peptide derivatives such as Glu-urea-Lys (GUL) or Glu-urea-Cys (GUC). Therefore, by labeling these peptide ligands with radioisotopes, the prepared radiopharmaceuticals can be used for PET or SPECT imaging of prostate cancer, or for the treatment of prostate cancer (MEder et al., Bioconjugate Chem 2012, 23:688-697). The radioisotopes used for labeling peptides are primarily α-ray-emitting radionuclides, β-ray-emitting radionuclides, γ-ray-emitting radionuclides, and positron-emitting radionuclides. Among these, α-ray-emitting radionuclides and β-ray-emitting radionuclides are used for treatment, while γ-ray-emitting radionuclides and positron-emitting radionuclides are used for nuclear imaging diagnosis. There are generally two methods for labeling ligands with radioisotopes: the method of directly combining the ligand with the radioisotope, or the method of chelating the radioisotope with the ligand using bifunctional chelating agent (BFCA) such as DTPA, DOTA, TETA, HYNIC, N2S2, and MAG3. The direct binding method is mainly used for labeling with various non-metallic radionuclides such as 1251 and 1311. In contrast, the method of using bifunctional chelating agent (BFCA) is primarily for labeling with various metallic radionuclides, and the type of BFCA can be chosen based on the properties of the ligand and the radioisotope.

Currently, the mainstream treatment options for prostate cancer are castration surgery, anti-androgen castration methods, and androgen receptor inhibitors. Although these treatment options are very effective in the initial stage, a significant number of patients may develop castration-resistant prostate cancer (CRPC) or even metastatic castration-resistant prostate cancer (mCRPC). mCRPC is a disease with limited treatment options and significant unmet medical needs, making PSMA-targeted radiopharmaceuticals a research focus in recent years.

A series of clinical studies have been conducted on using PSMA-targeted radiopharmaceuticals to treat mCRPC patients. Although initial clinical results of radiopharmaceuticals like $^{177}$Lu-PSMA-617 and $^{177}$Lu-PSMA I&T are encouraging, some issues remain, for example, about 30% of patients do not respond to this treatment. One possible explanation is that suboptimal pharmacokinetics leading to insufficient delivery of the radiopharmaceutical to the tumor sites. Another concern is the prolonged accumulation of radiopharmaceuticals like 177Lu-PSMA-617 in organs such as the kidneys and salivary glands. Therefore, developing a PSMA-targeted radiopharmaceutical with high activity, high selectivity, and improved pharmacokinetics remains a continuing focus in the treatment and diagnosis of mCRPC.

Content of the Present Invention

The technical problem to be solved by the present disclosure is limited structural variety of existing peptide urea derivatives, and radiopharmaceuticals are taken up and retained for long periods of time in non-target organs such as the kidneys, while the uptake and retention time in the desired target tumor are insufficient. To this end, the present disclosure provides a peptide urea derivative, a pharmaceutical composition containing the same, and a use thereof. The derivative can be used for preoperative imaging diagnosis and grading of PSMA positive prostate cancer, and can also be used for treatment of various types and stages of prostate cancer, achieving the integration of diagnosis and treatment, with a wide application prospect. Compared with the reference compound PSMA-617, the compounds disclosed in the present disclosure exhibit better selectivity and pharmacokinetics, significantly enhancing the uptake and retention time of the radiopharmaceuticals within the target tumor.

The present disclosure provides a peptide urea derivative of formula I, a pharmaceutically acceptable salt thereof, a solvate thereof, or a solvate of the pharmaceutically acceptable salt thereof;

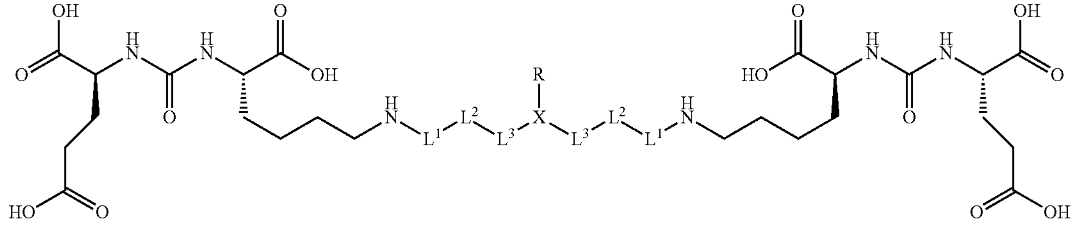
I
wherein X is
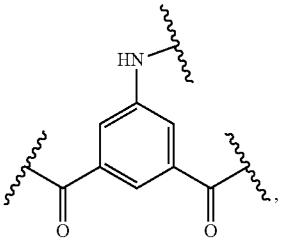
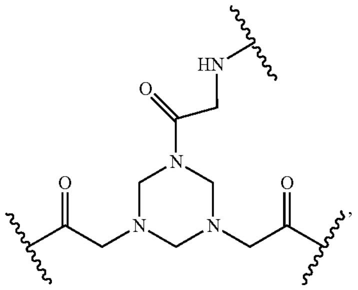
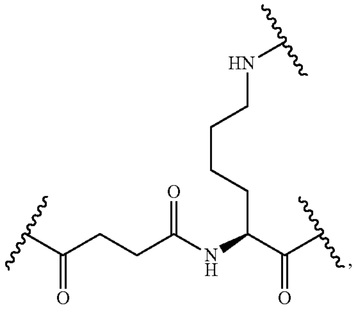
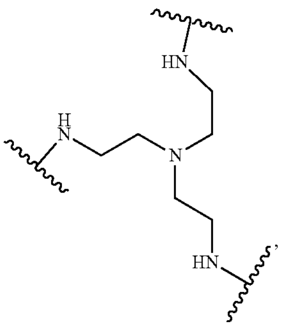
-continued
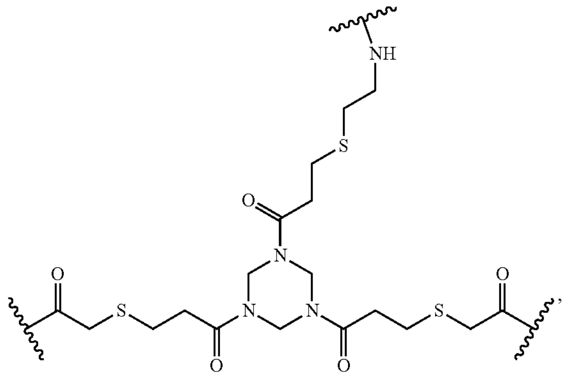
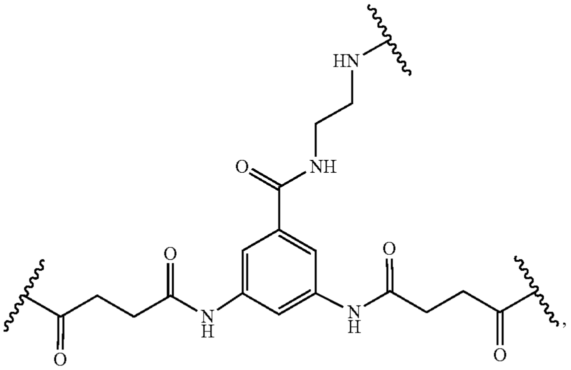
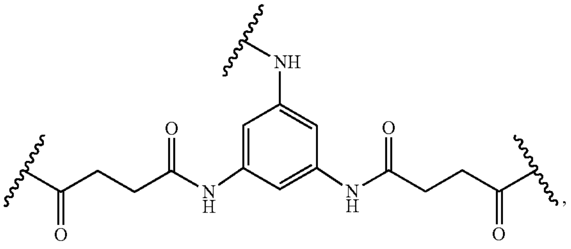
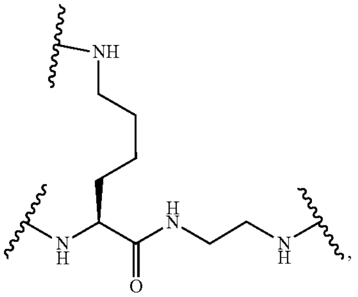

-continued
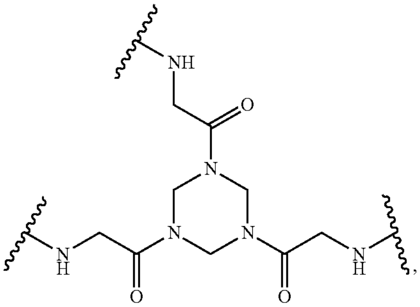
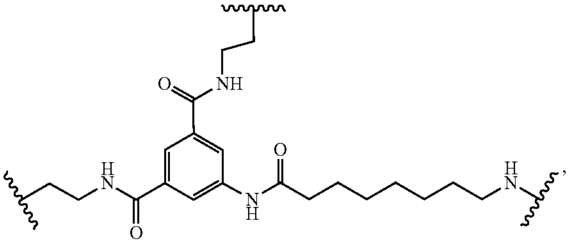
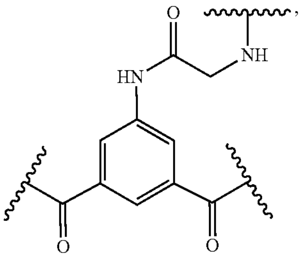
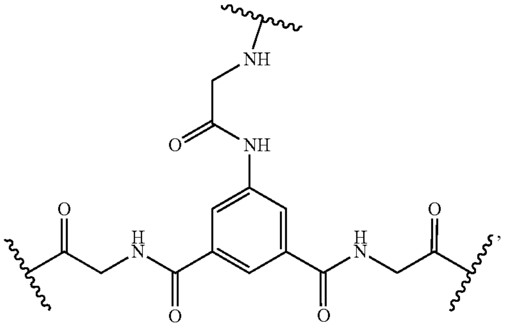
or
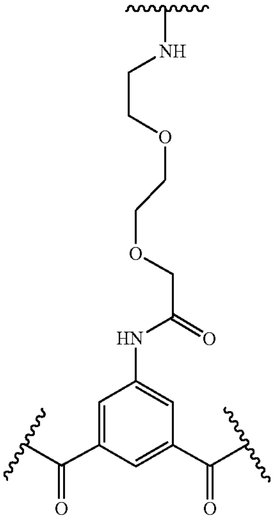
;
R is a group containing a radioactive metal ion or a group capable of optical imaging;
$L^1$ is a chemical bond,
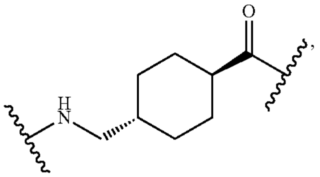
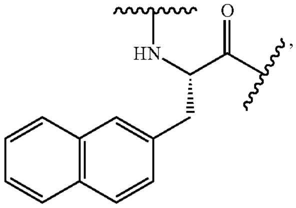
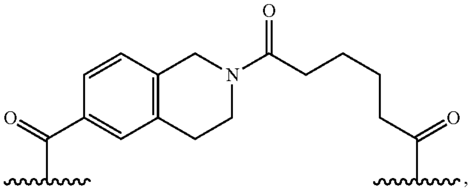
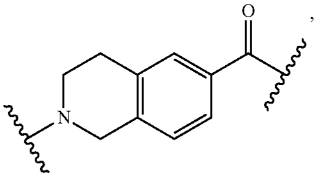
, or
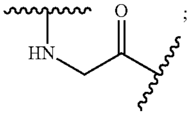
;
$L^2$ is
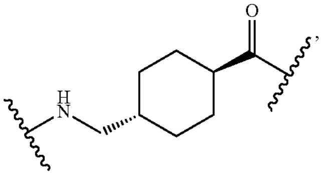
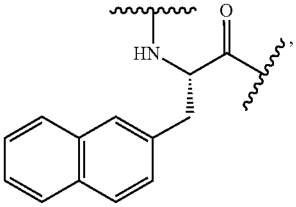
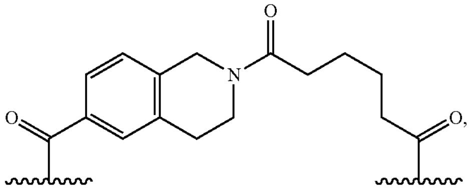
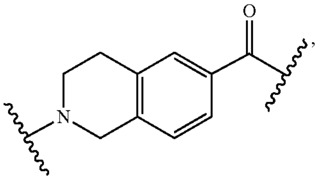

-continued

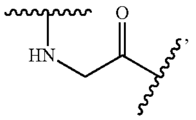

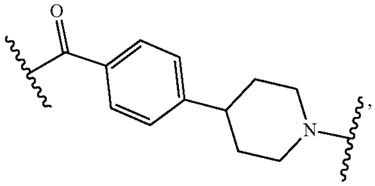

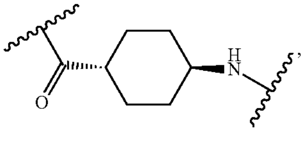

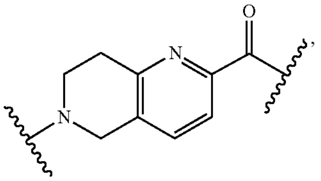

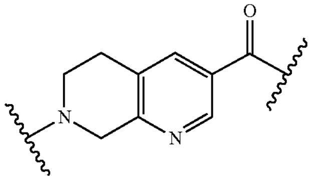
, or

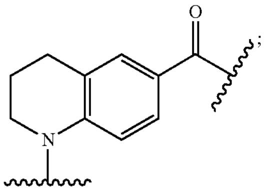

$L^3$ is

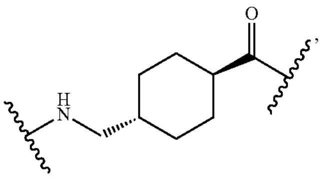

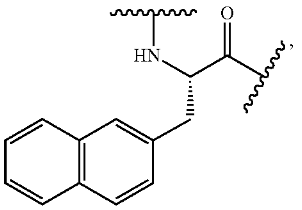

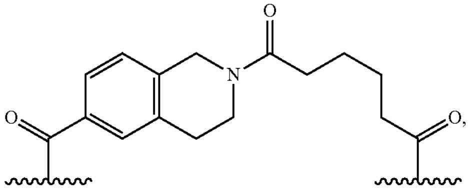

-continued

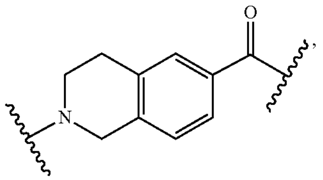

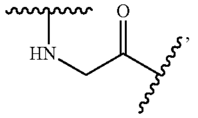

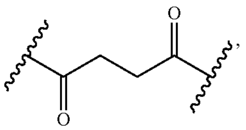

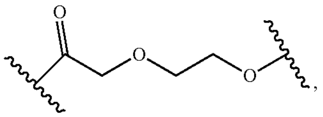

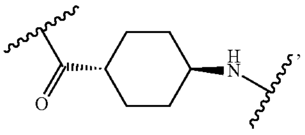

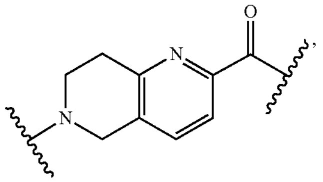

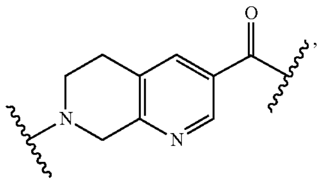
, or

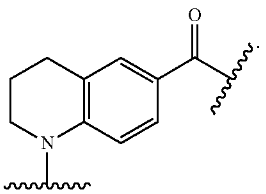

In one embodiment, in the peptide urea derivative of formula I, the pharmaceutically acceptable salt thereof, the solvate thereof, or the solvate of the pharmaceutically acceptable salt thereof, some groups are as defined below, while the definitions of the remaining groups are as described in any other embodiment (hereinafter referred to as "in one embodiment").

X is
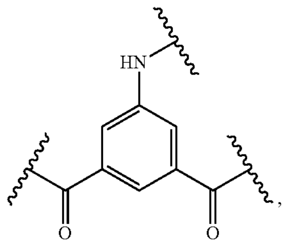
,
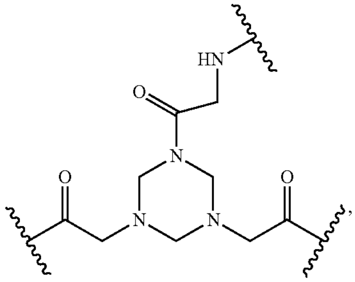
,
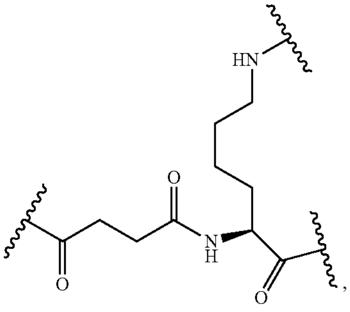
,
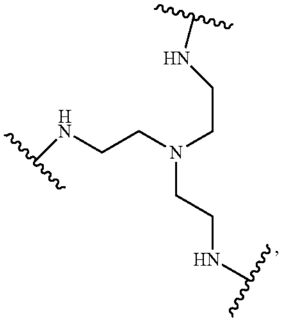
,
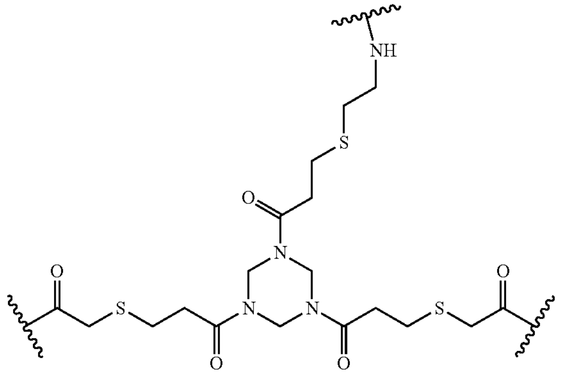
,
-continued
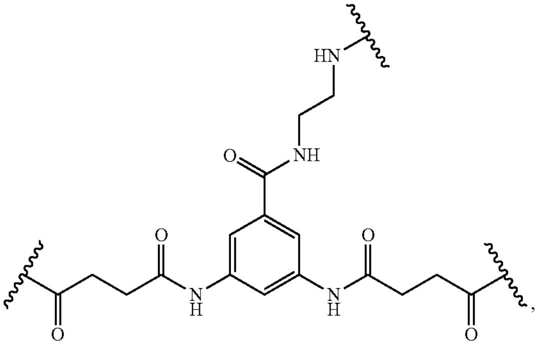
, or
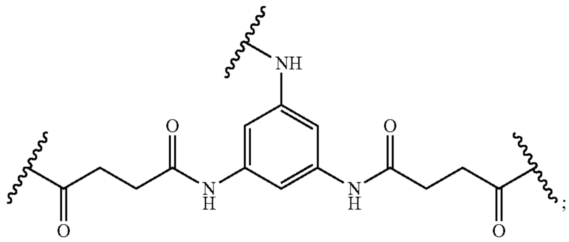
;
R is a group containing a radioactive metal ion or a group capable of optical imaging;
$L^1$ is a chemical bond,
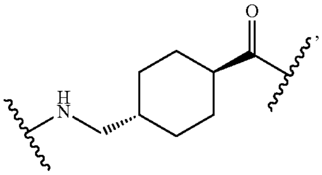
,
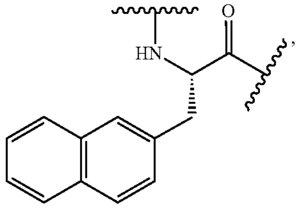
,
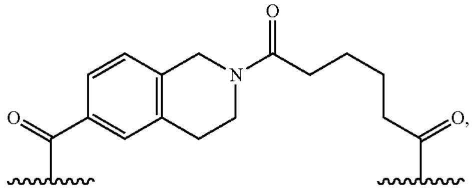
O,
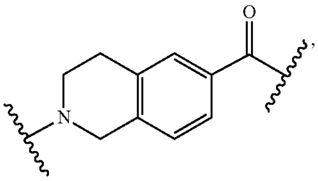
, or
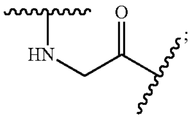
; $L^2$ is -continued
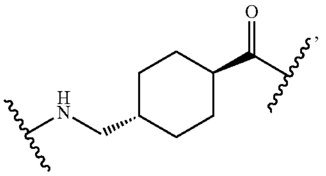
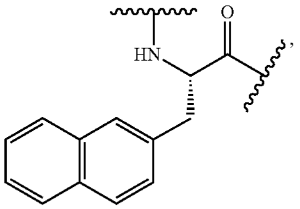
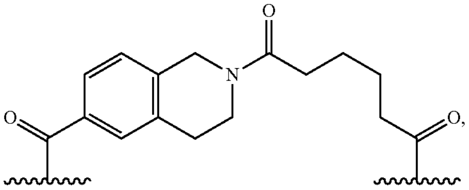
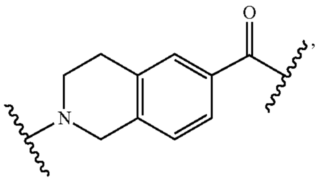
, or
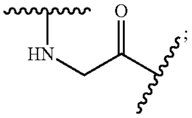
; $L^3$ is
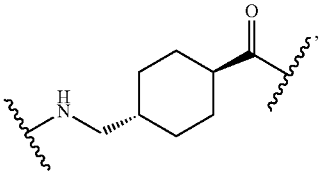
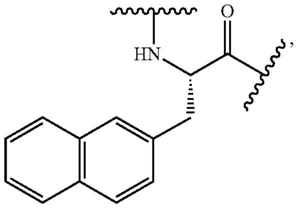
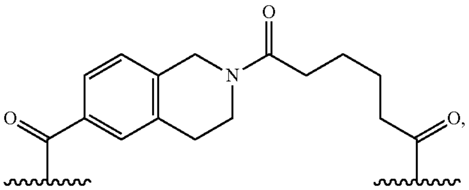
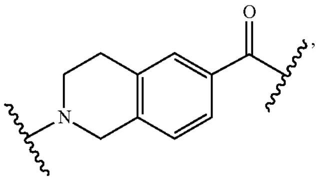
, or
-continued
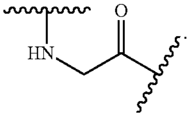
In one embodiment, the carbonyl terminal of $L^1$ is connected with
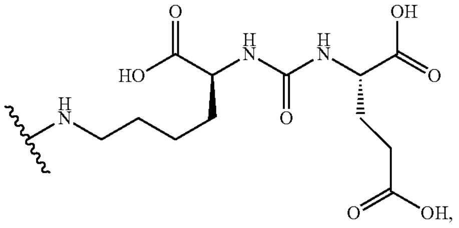 [SMILES: *NCCCC[C@H](NC(=O)N[C@@H](CCC(=O)O)C(=O)O)C(=O)O]
the carbonyl terminal of $L^1$ is connected with $L^1$, and the carbonyl terminal of $L^3$ is connected with $L^2$.
In one embodiment, $L^1$ is a chemical bond,
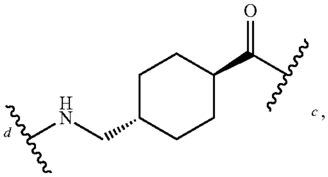
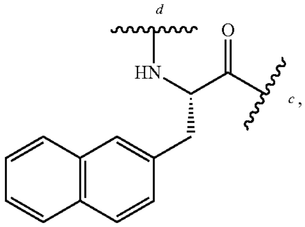
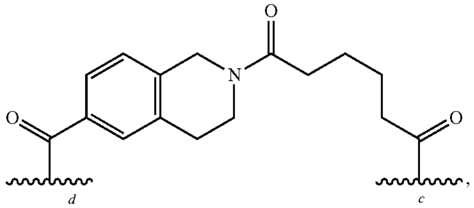
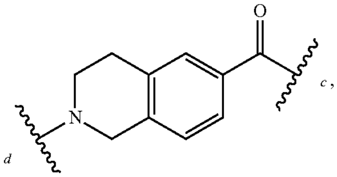
or
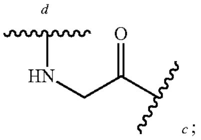

L² is
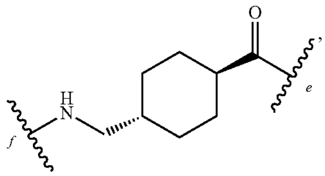
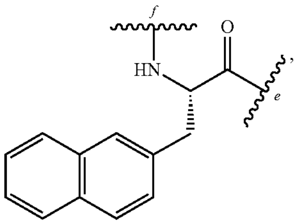
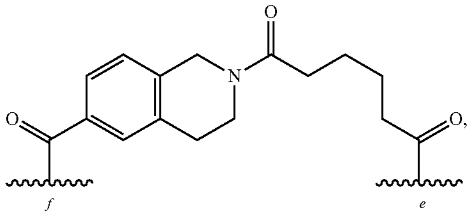
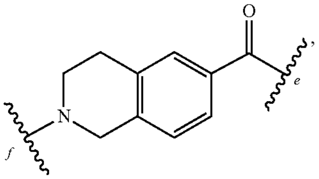
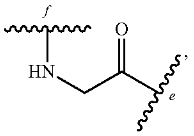
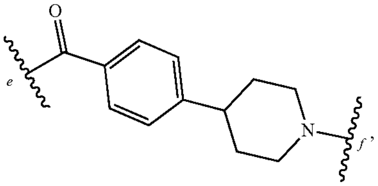
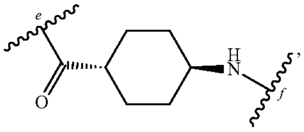
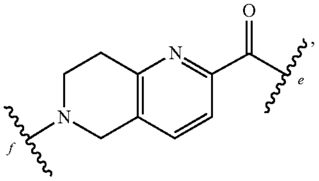
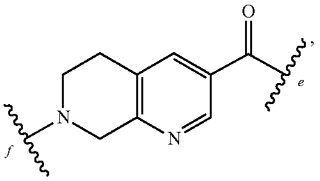
or
-continued
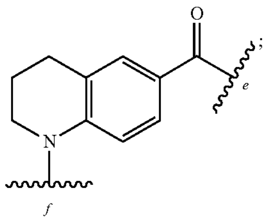
L³ is
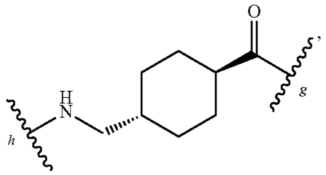
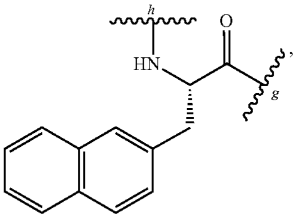
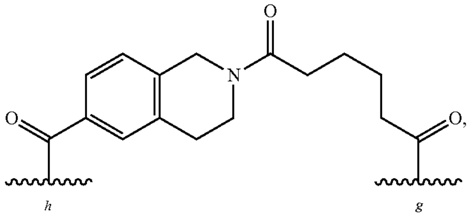
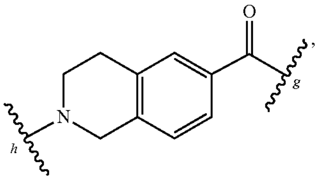
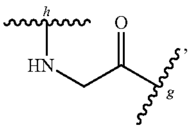
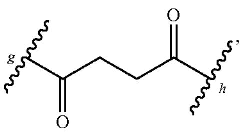
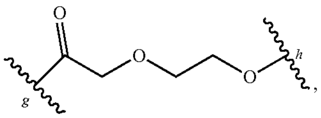
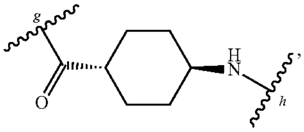

-continued
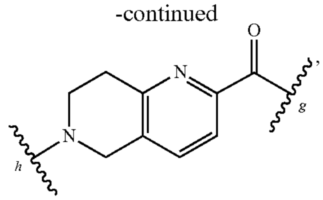
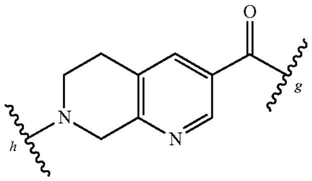
, or
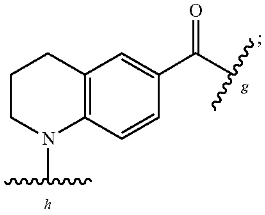
;
the c-terminal of $L^1$ is connected with
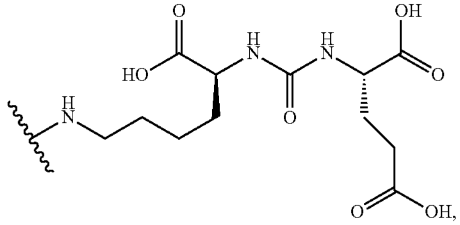 [SMILES: *NCCCC[C@H](NC(=O)N[C@@H](CCC(=O)O)C(=O)O)C(=O)O]
,
the e-terminal of $L^2$ is connected with $L^1$, and the g-terminal of $L^3$ is connected with $L^2$.
In one embodiment, $L^1$ is a chemical bond,
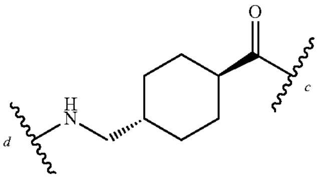
,
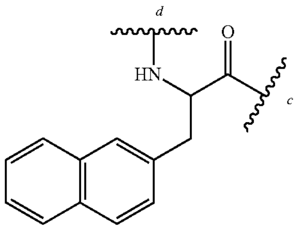
,
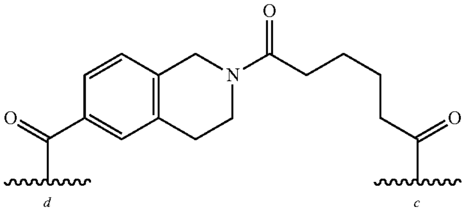
,
-continued
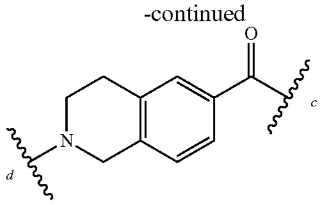
, or
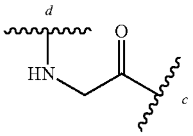
;
$L^2$ is
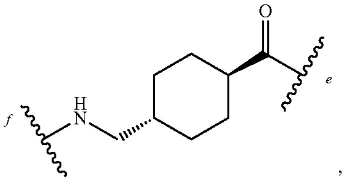
,
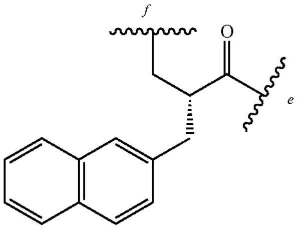
,
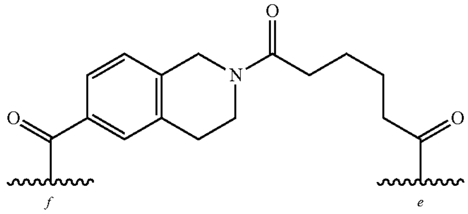
,
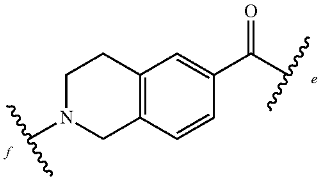
, or
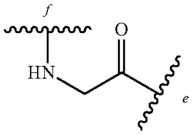
;
$L^3$ is
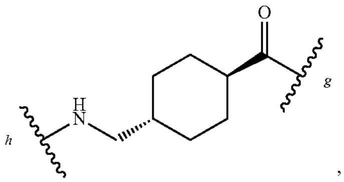
,
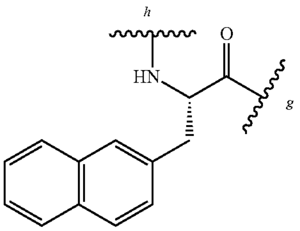
, -continued
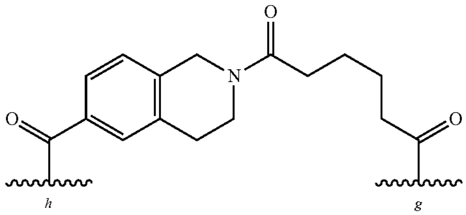
,
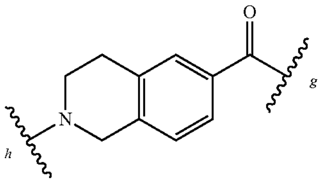
, or
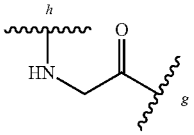
;
the c-terminal of $L^1$ is connected with
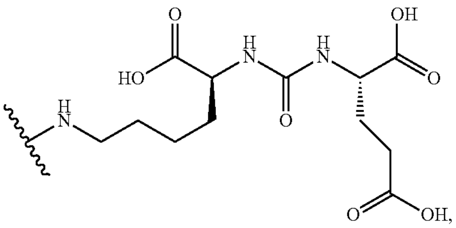 [SMILES: *NCCCC[C@H](NC(=O)N[C@@H](CCC(=O)O)C(=O)O)C(=O)O]
the e-terminal of $L^2$ is connected with $L^1$, and the g-terminal of $L^3$ is connected with $L^2$.
In one embodiment, X is
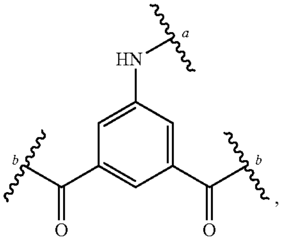
,
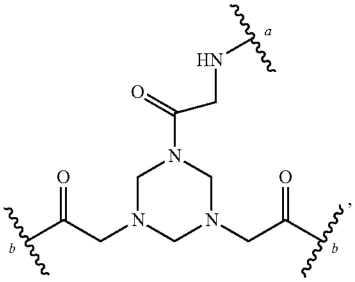
,
-continued
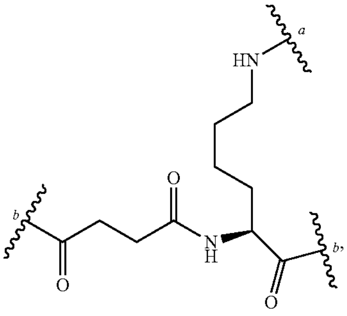
,
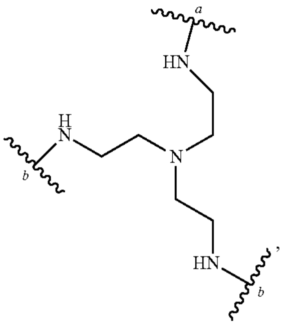
,
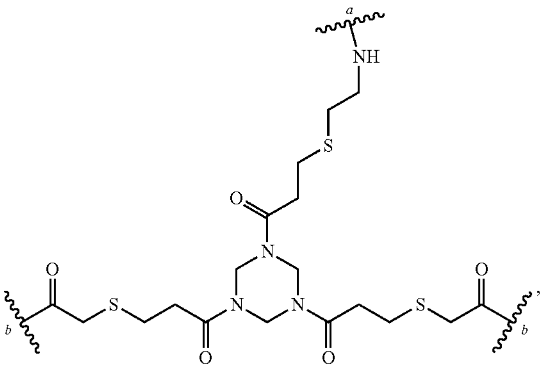
,
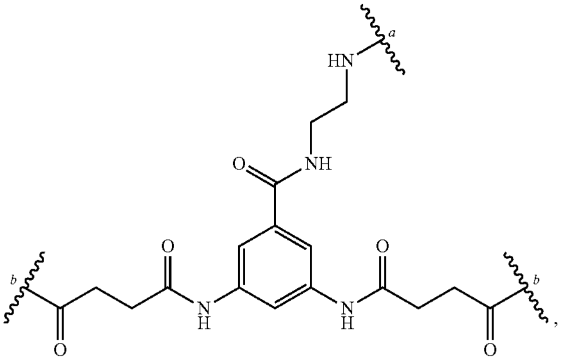
,
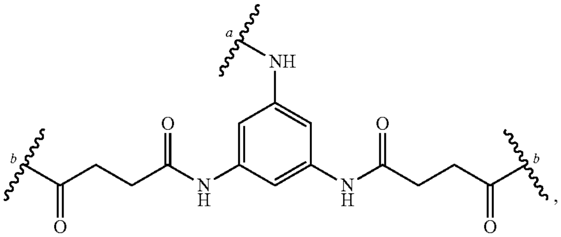
, -continued
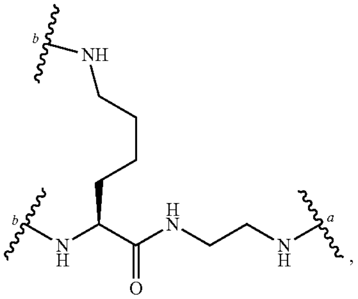
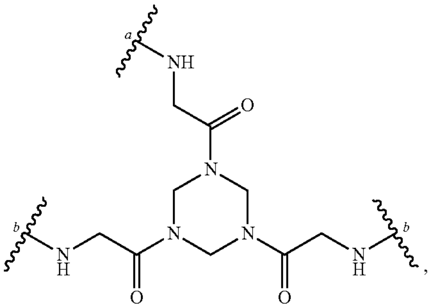
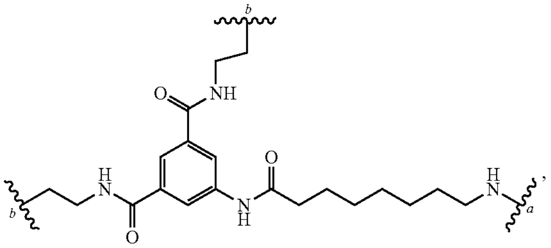
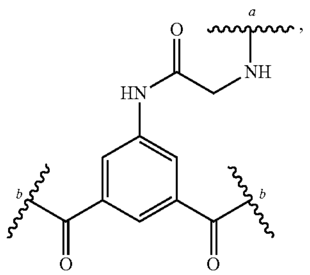
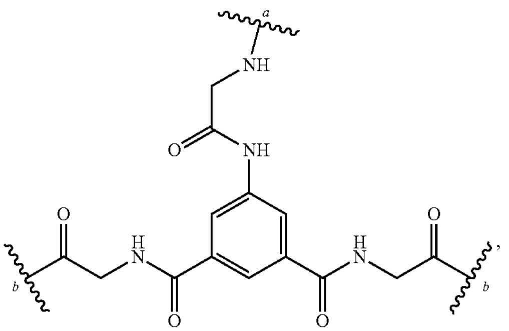
or
-continued
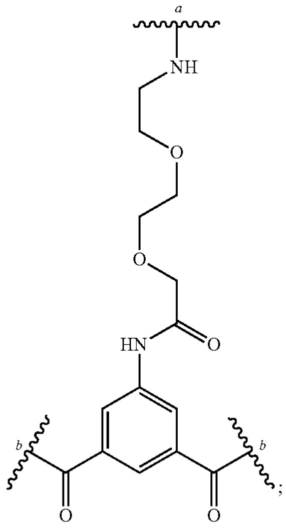
the a-terminal of X is connected with R, and the two b-terminals of X are each connected to two $L^3$ groups.
In one embodiment, X is
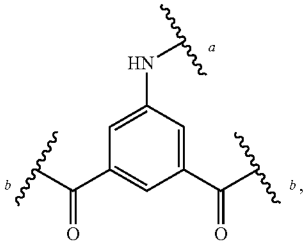
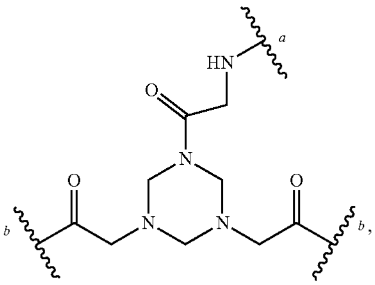
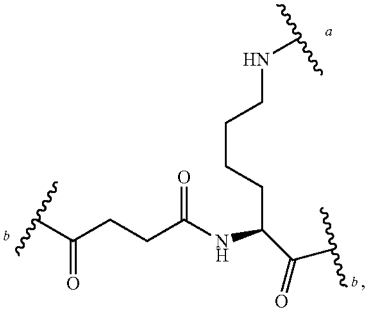

-continued

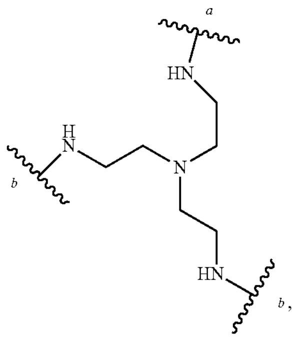

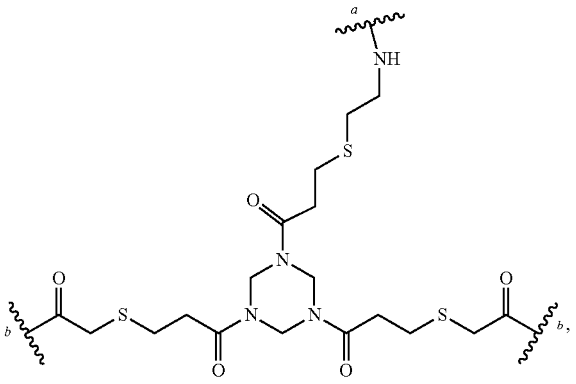

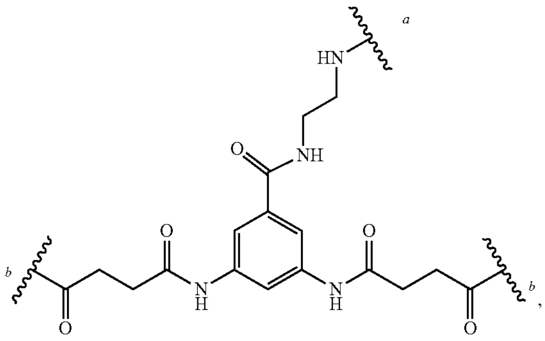

or

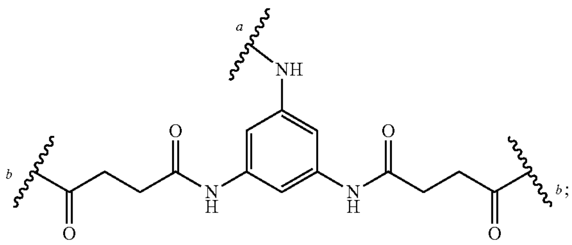

the a-terminal of X is connected with R, and the two b-terminals of X are each connected to two $L^3$ groups.

In one embodiment, the group containing a radioactive metal ion consists of a radioactive metal ion and a group with metal ion chelating functionality, wherein the radioactive metal ion is chelated with the group with metal ion chelating functionality.

In one embodiment, the group with metal ion chelating functionality is

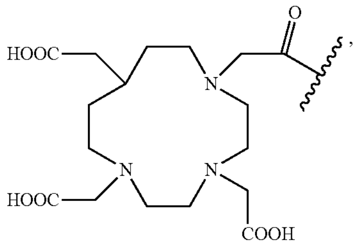

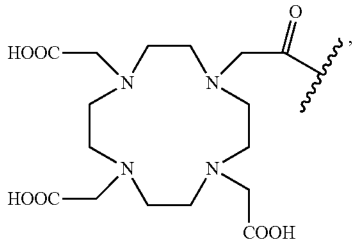

DOTA

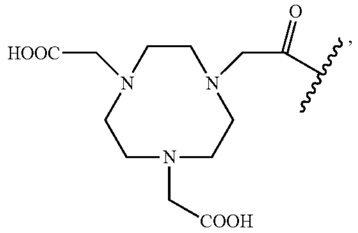

NOTA

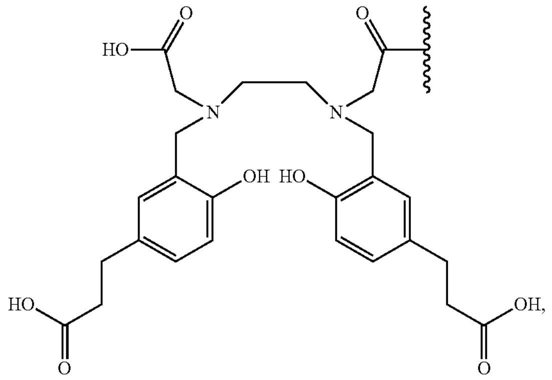

HBED-CC

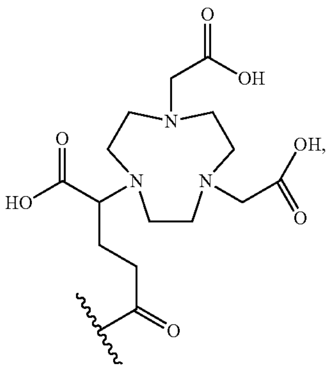

NODAGA

-continued
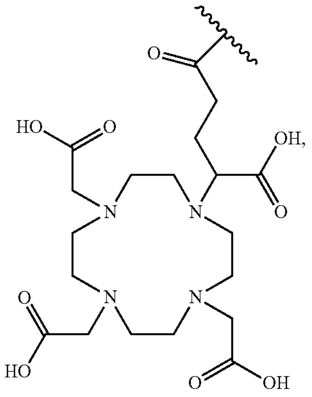
DOTAGA
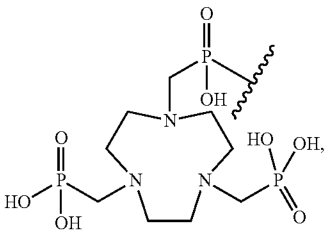
TRAP
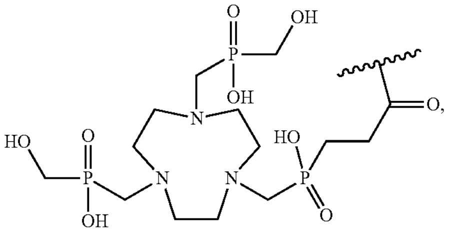
NOPO
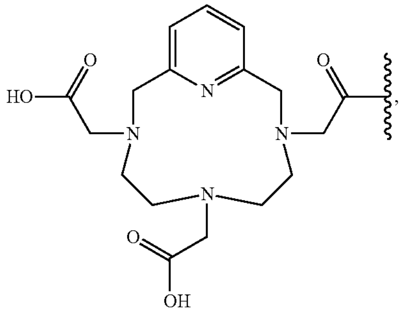
PCTA
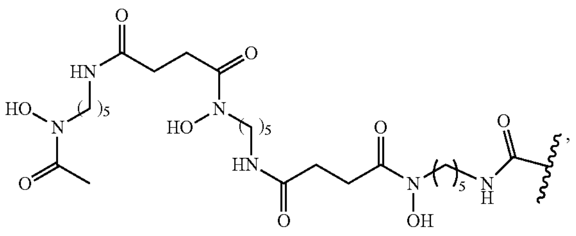
DFO
-continued
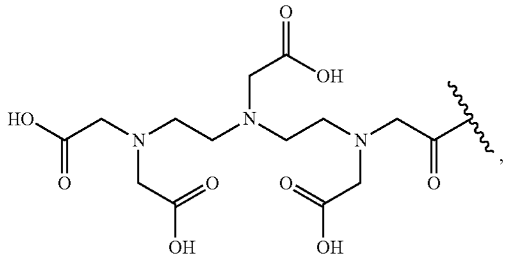
DTPA
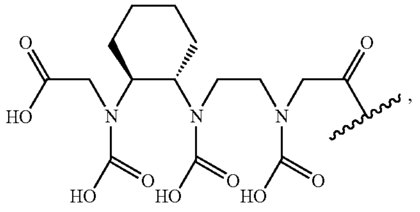
CHX-DTPA
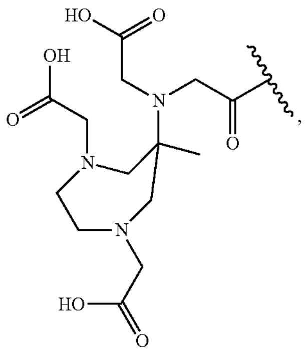
AAZTA
or
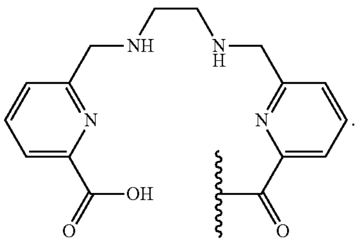
DEDPA
In one embodiment, the group with metal ion chelating functionality is
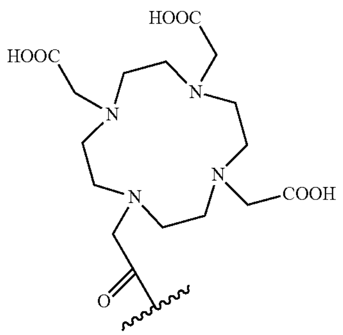 [SMILES: *C(=O)CN1CCN(CC(=O)O)CCN(CC(=O)O)CCN(CC(=O)O)CC1]
or -continued

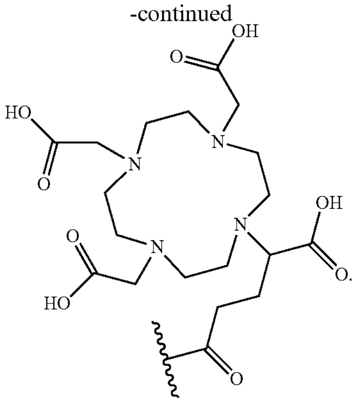

In one embodiment, the group with metal ion chelating functionality is

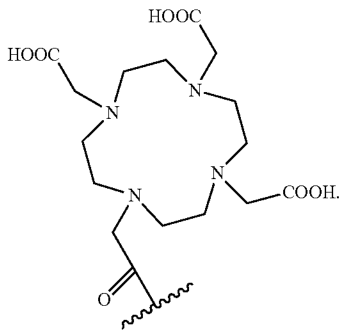

In one embodiment, the radioactive metal ion serves one or more of the following functions:

(1) PET imaging;

(2) SPECT imaging;

(3) radiotherapy.

In one embodiment, the radioactive metal ion serves one or more of the following functions:

(1) tracing;

(2) delivery;

(3) imaging;

(4) therapy.

In one embodiment, the radioactive metal ion is a radioactive metal ion that emits α, β, or γ ray.

In one embodiment, the radioactive metal ion is $^{68}Ga$, $^{89}Zr$, $^{64}Cu$, $^{86}Y$, $^{99m}Tc$, $^{111}In$, $^{90}Y$, $^{67}Ga$, $^{177}Lu$, $^{211}At$, $^{153}Sm$, $^{186}Re$, $^{188}Re$, $^{67}Cu$, $^{212}Pb$, $^{225}Ac$, $^{213}Bi$, $^{212}Bi$, or $^{212}Pb$.

In one embodiment, the radioactive metal ion is $^{68}Ga^{3+}$, $^{89}Z^{4+}$, $^{64}Cu^{2+}$, $^{86}Y^{3+}$, $^{99m}Tc^{4+}$, $^{111}In^{3+}$, $^{90}Y$, $^{67}Ga^{3+}$, $^{177}Lu^{3+}$, $^{211}At^{3+}$, $^{153}Sm^{3+}$, $^{186}Re^{3+}$, $^{188}Re^{3+}$, $^{67}Cu^{2+}$, $^{212}Pb^{2+}$, $^{225}Ac^{3+}$, $^{213}Bi^{3+}$, $^{212}Bi$, or $^{212}Pb^{2+}$.

In one embodiment, the radioactive metal ion is $^{68}Ga$ or $^{177}Lu$.

In one embodiment, the radioactive metal ion is $^{68}Ga^{3+}$ or $^{177}Lu^{3+}$.

In one embodiment, the group containing a radioactive metal ion is any one of the following groups:

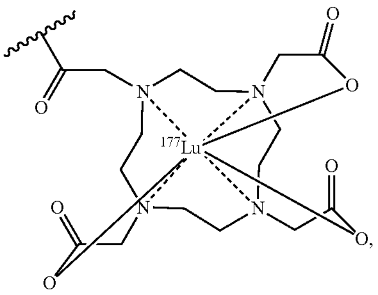

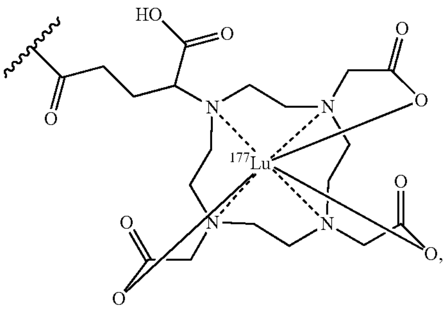

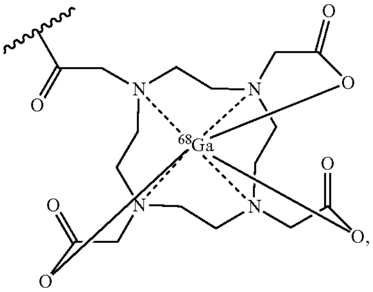

and

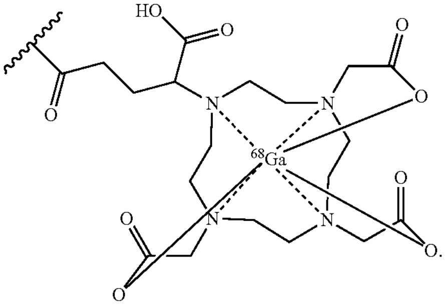

In one embodiment, the peptide urea derivative of formula I is of the following structure:

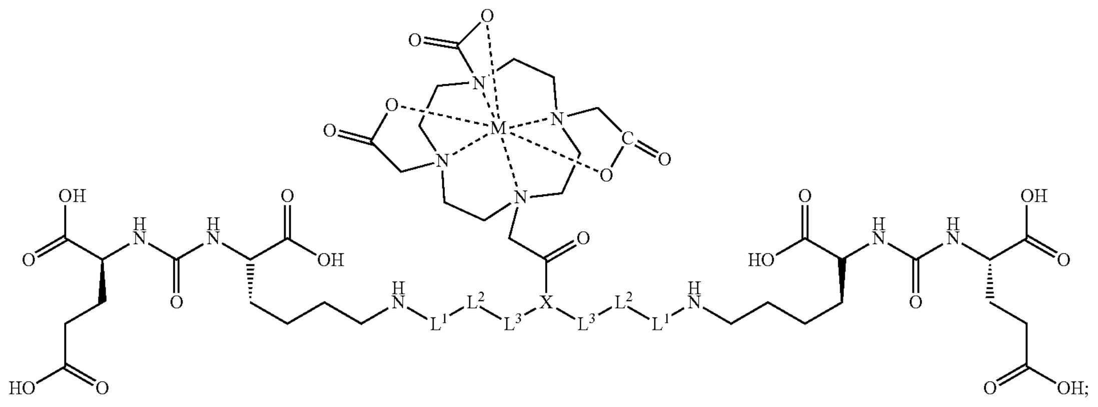

wherein M is a radioactive metal ion; the radioactive metal ion is a trivalent radioactive metal ion, such as $^{68}Ga^{3+}$, $^{86}Y^{3+}$, $^{111}In^{3+}$, $^{67}Ga^{3+}$, $^{17}Lu^{3+}$, $^{211}At^{3+}$, $^{153}Sm^{3+}$, $^{186}Re^{3+}$, $^{188}Re^{3+}$, $^{225}Ac^{3+}$, or $^{213}Bi^{3+}$, preferably $^{68}Ga^{3+}$ or $^{177}Lu^{3+}$.

In one embodiment, the group capable of optical imaging can be a fluorescent group, such as cy3, cy5, or cy7.

In one embodiment, the peptide urea derivative of formula I is a compound formed by chelation of compound A with a radioactive metal ion (e.g., $^{68}Ga^{3+}$ or $^{177}Lu^{3+}$), wherein the structure of compound A is any one of the following:

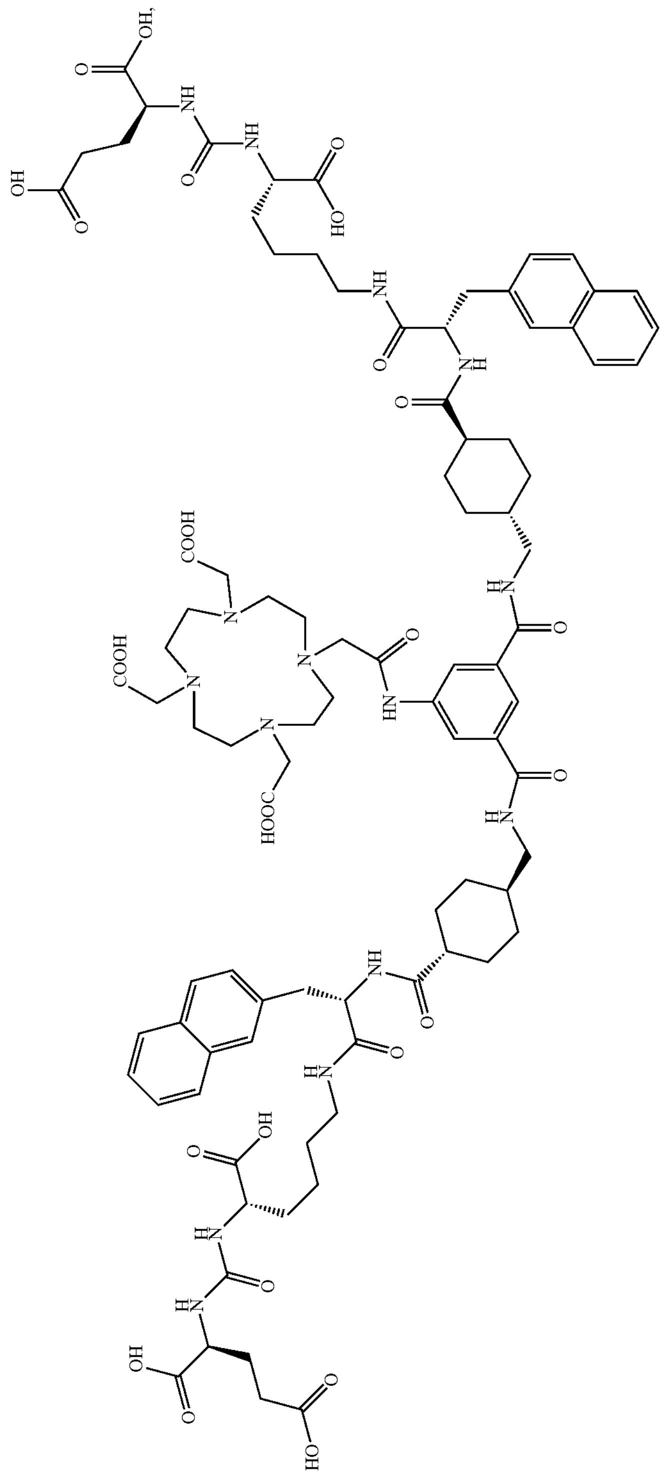

-continued
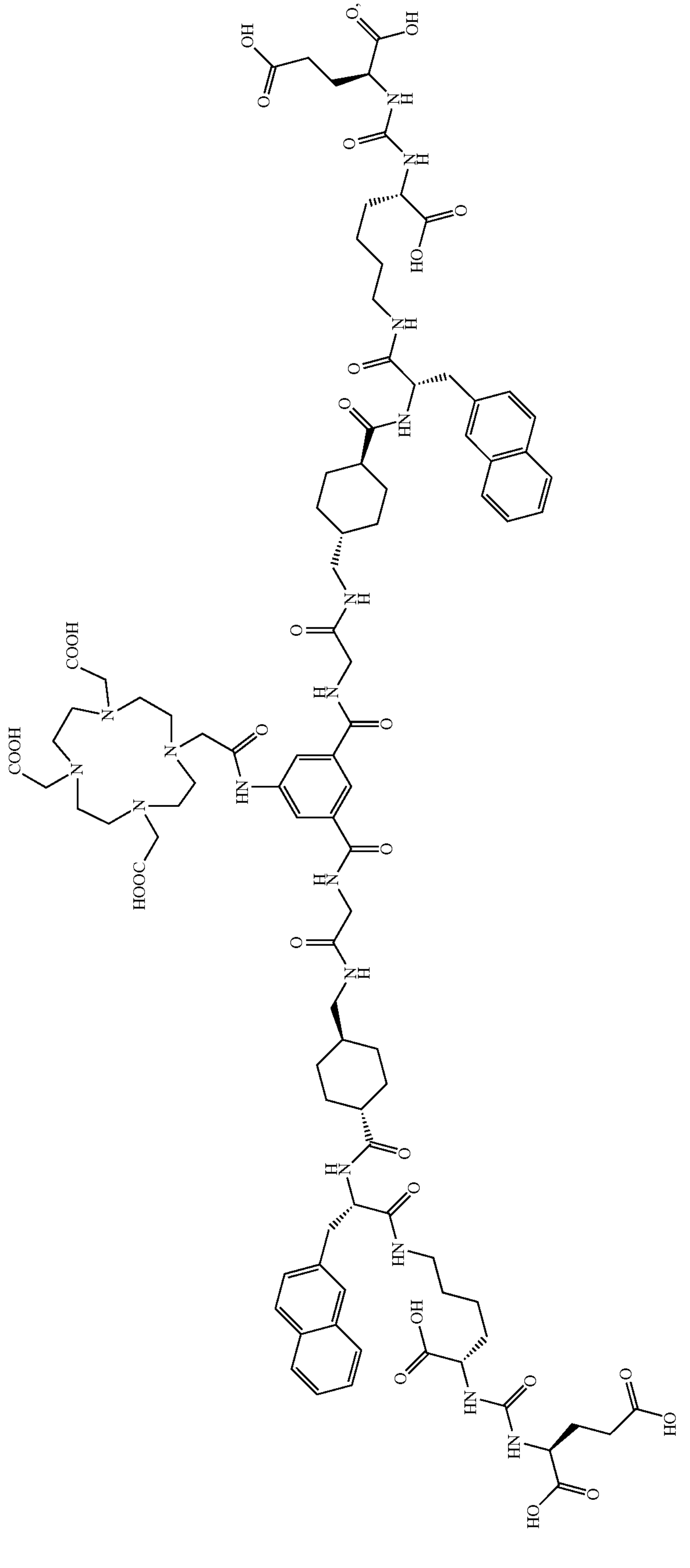

-continued
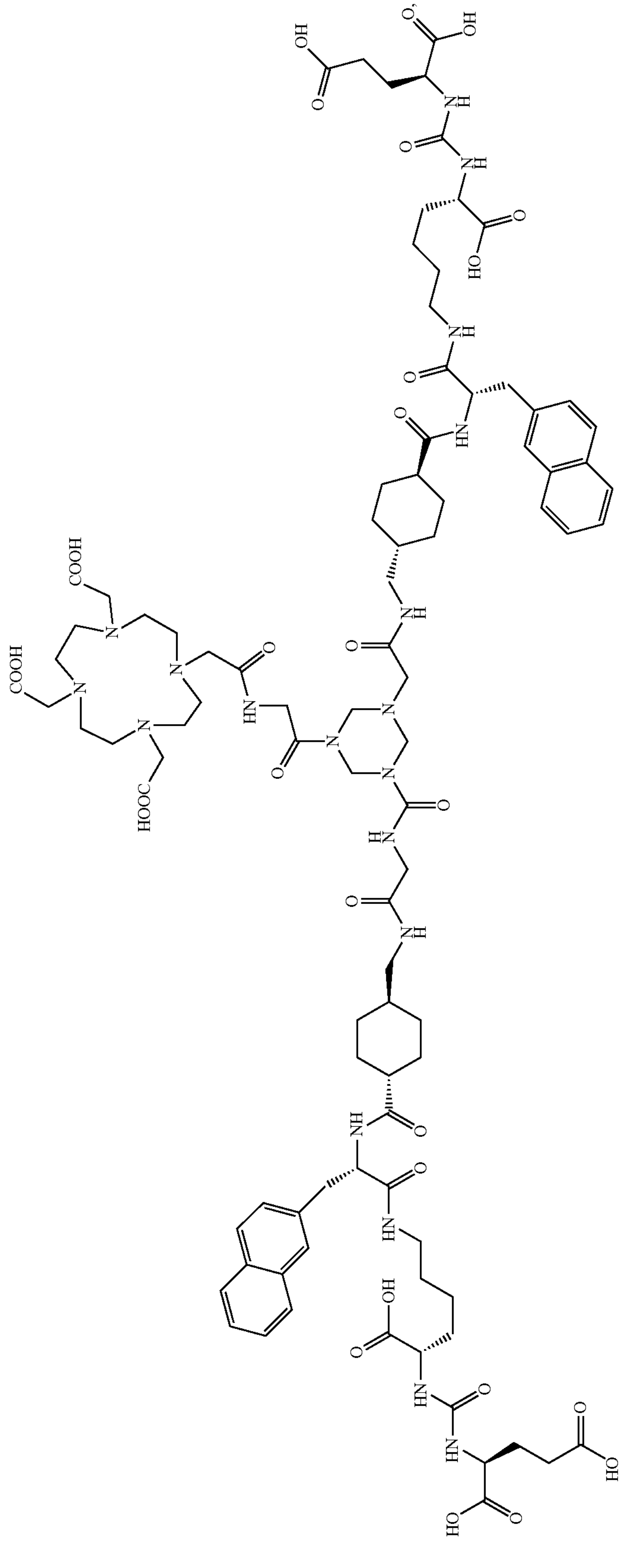

-continued
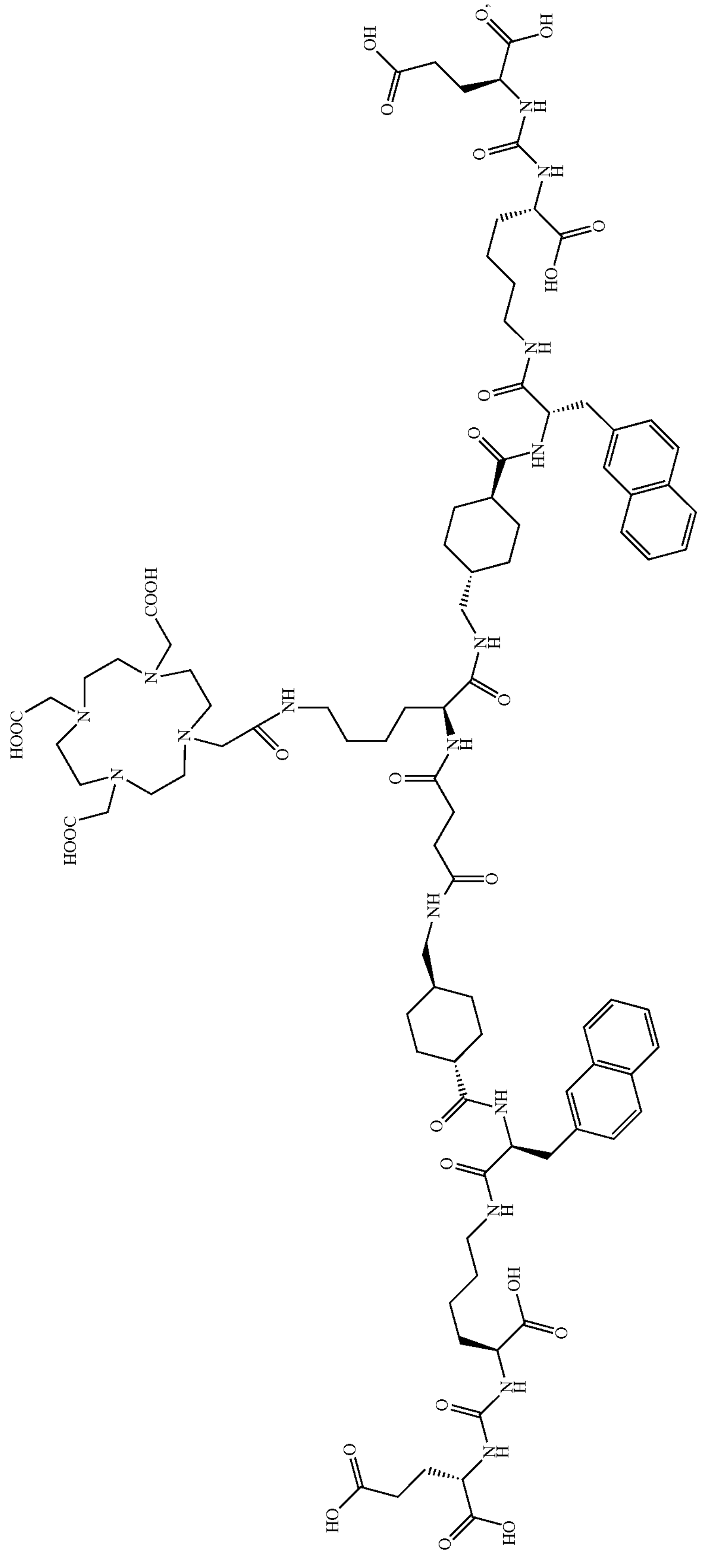

-continued
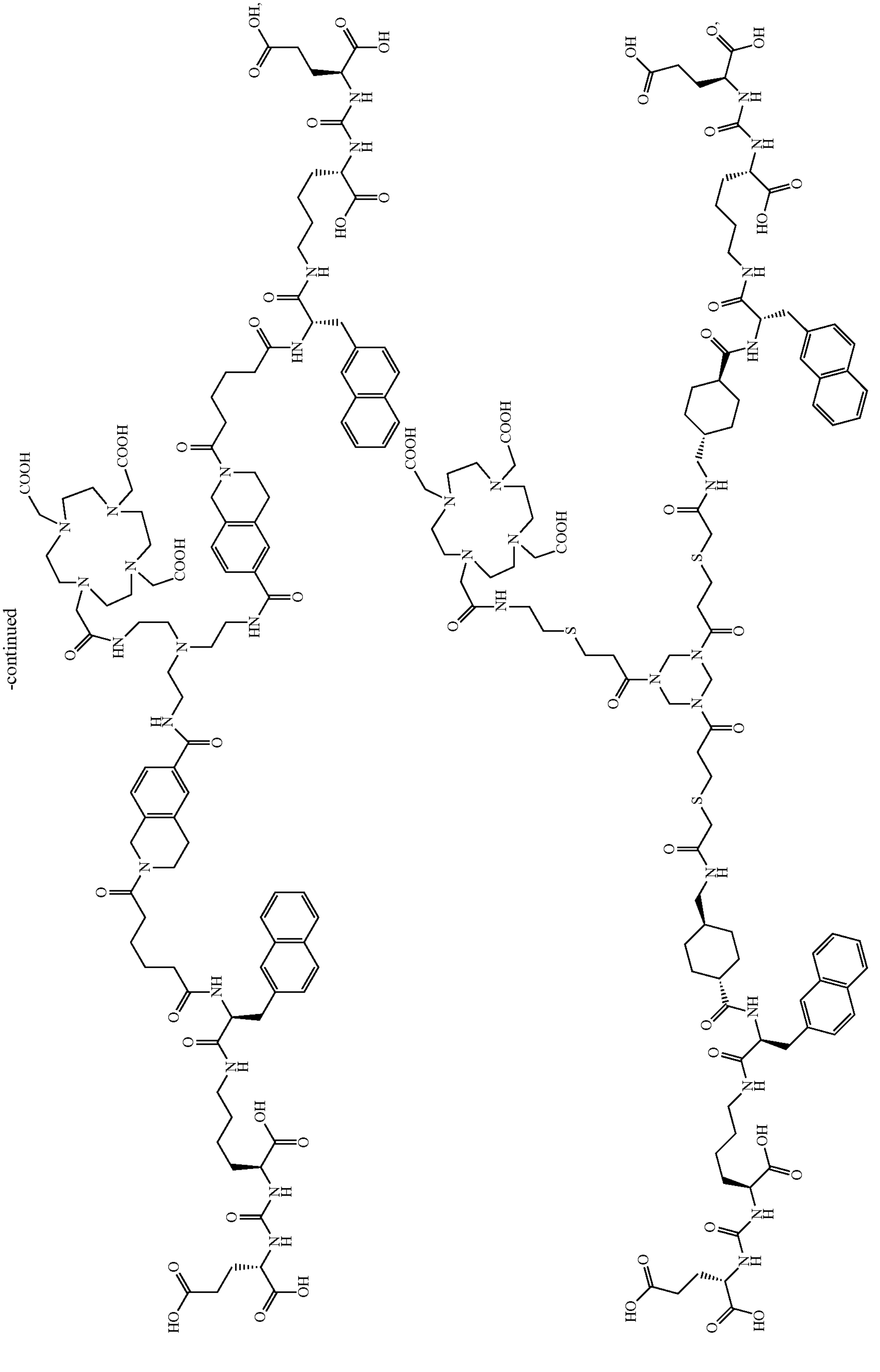

-continued
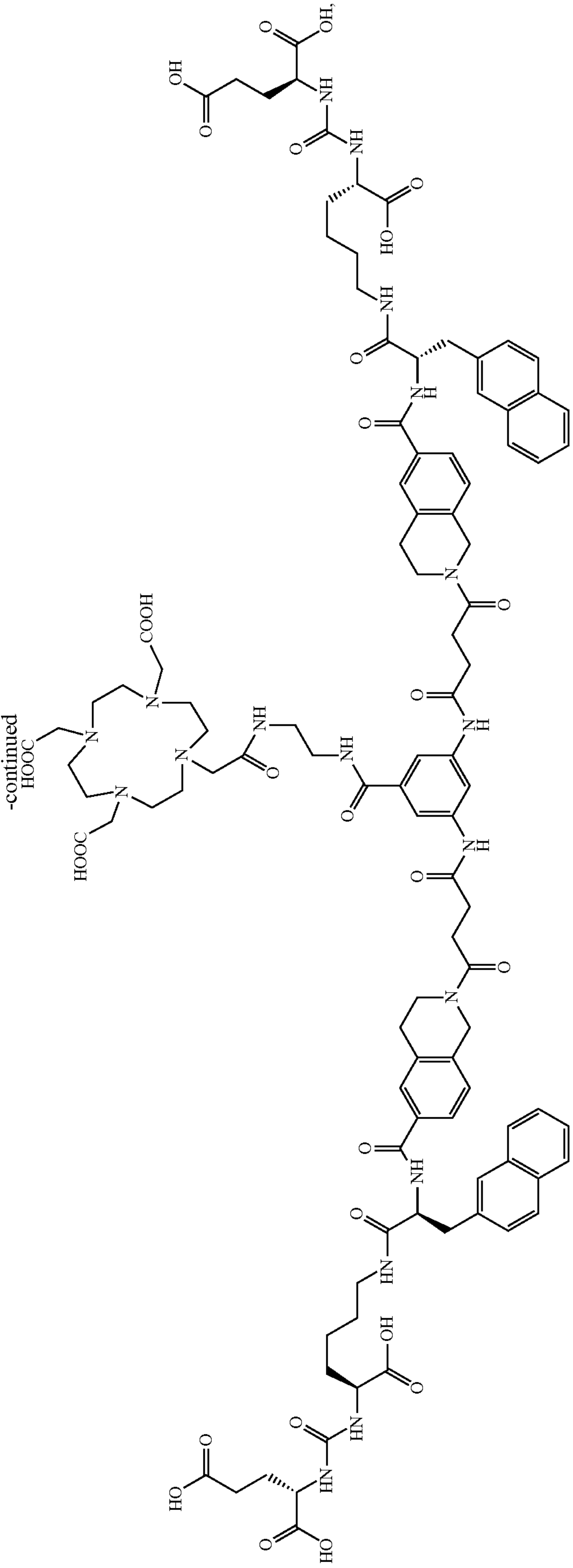
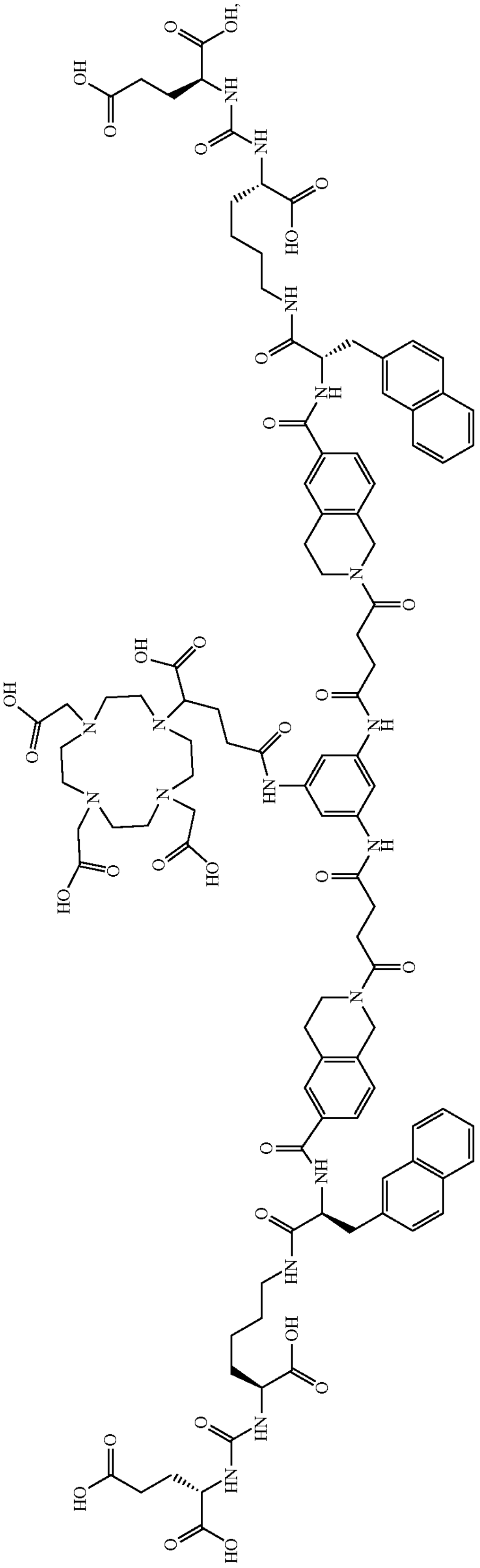

-continued
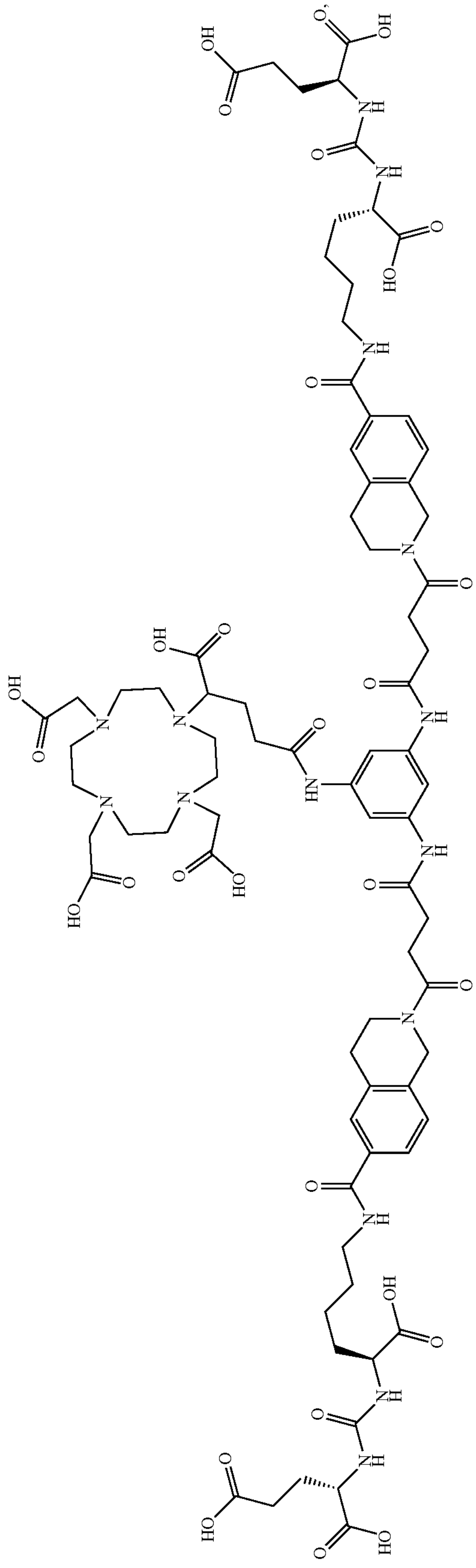

-continued
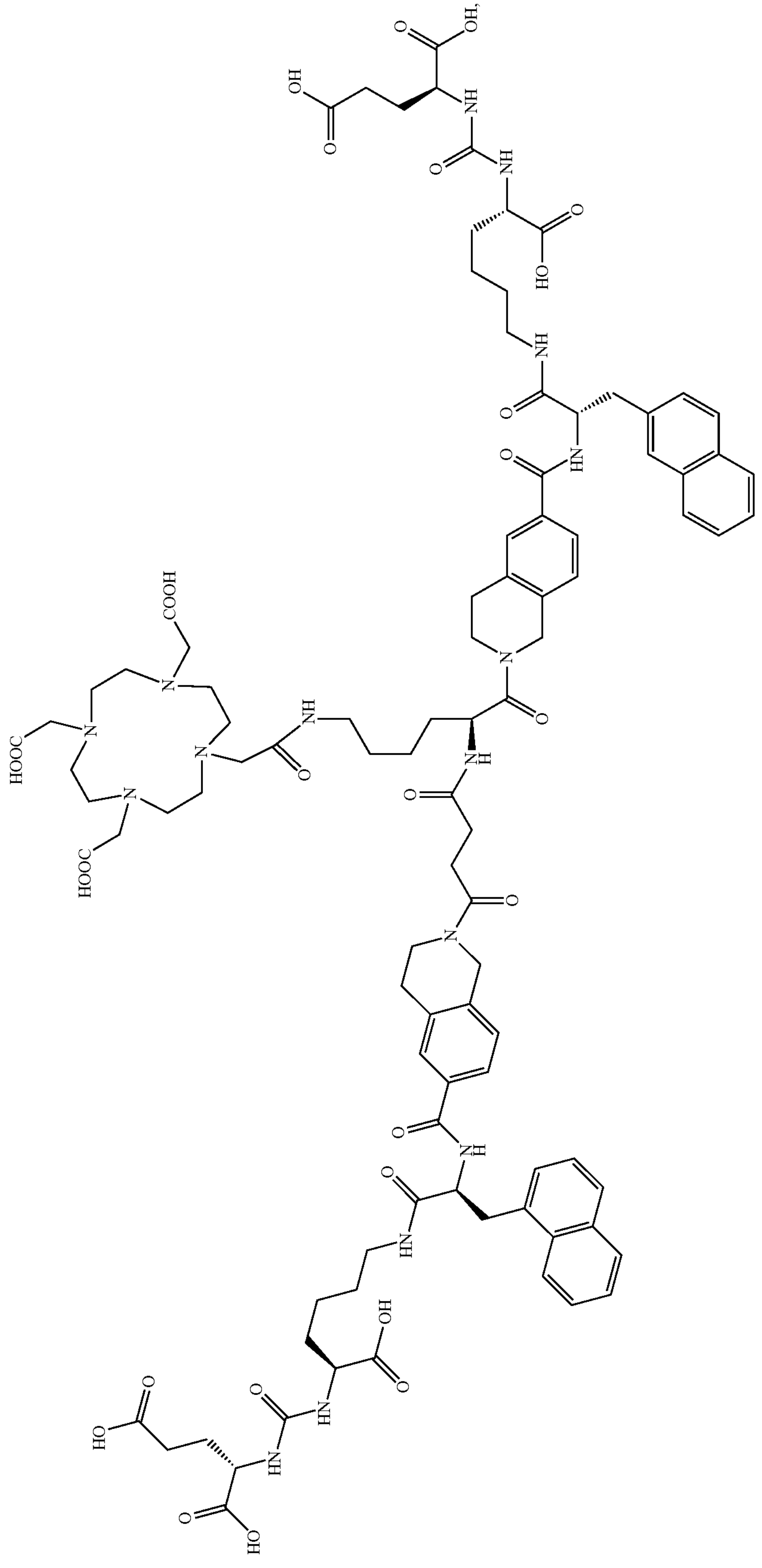

-continued
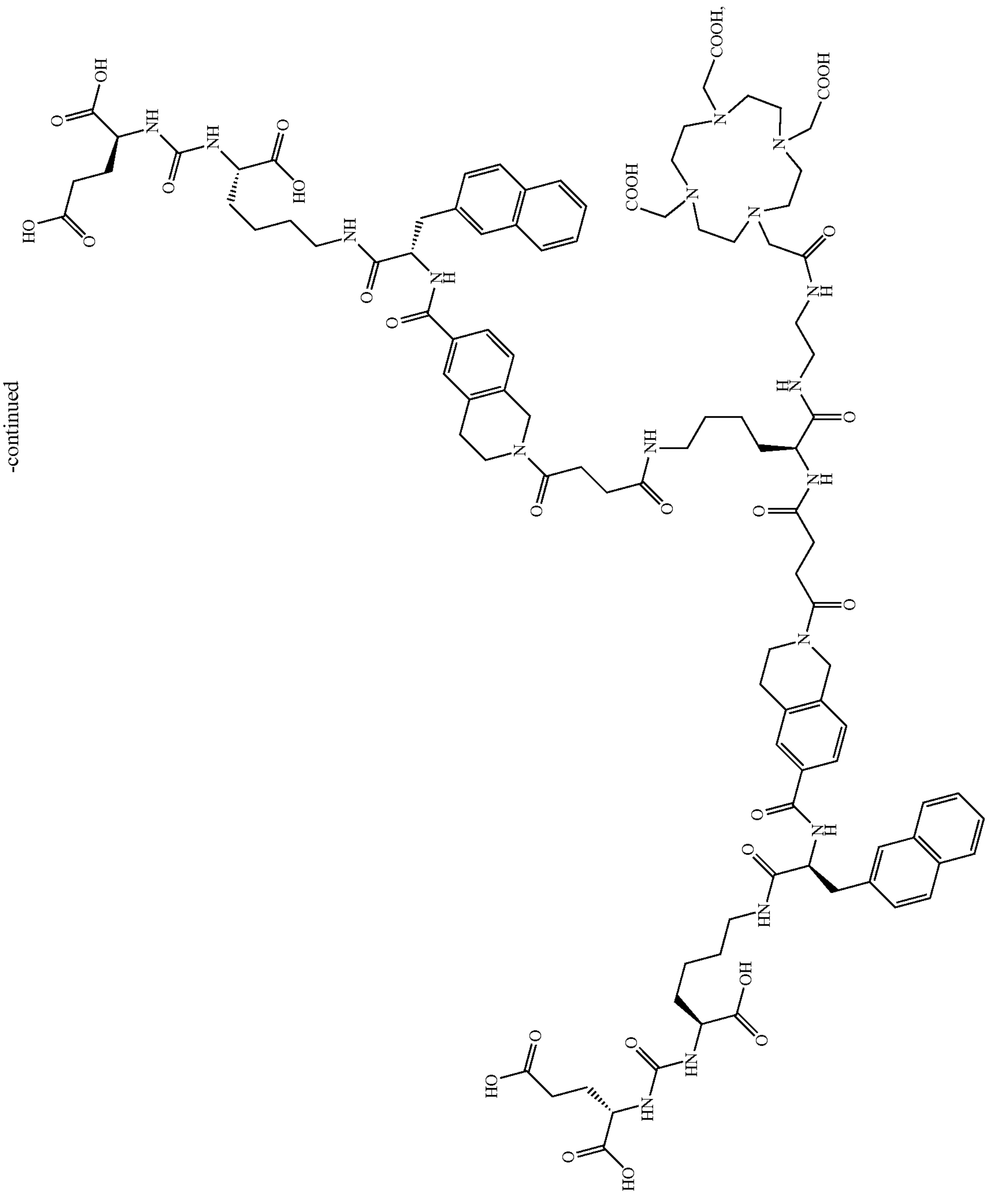

-continued
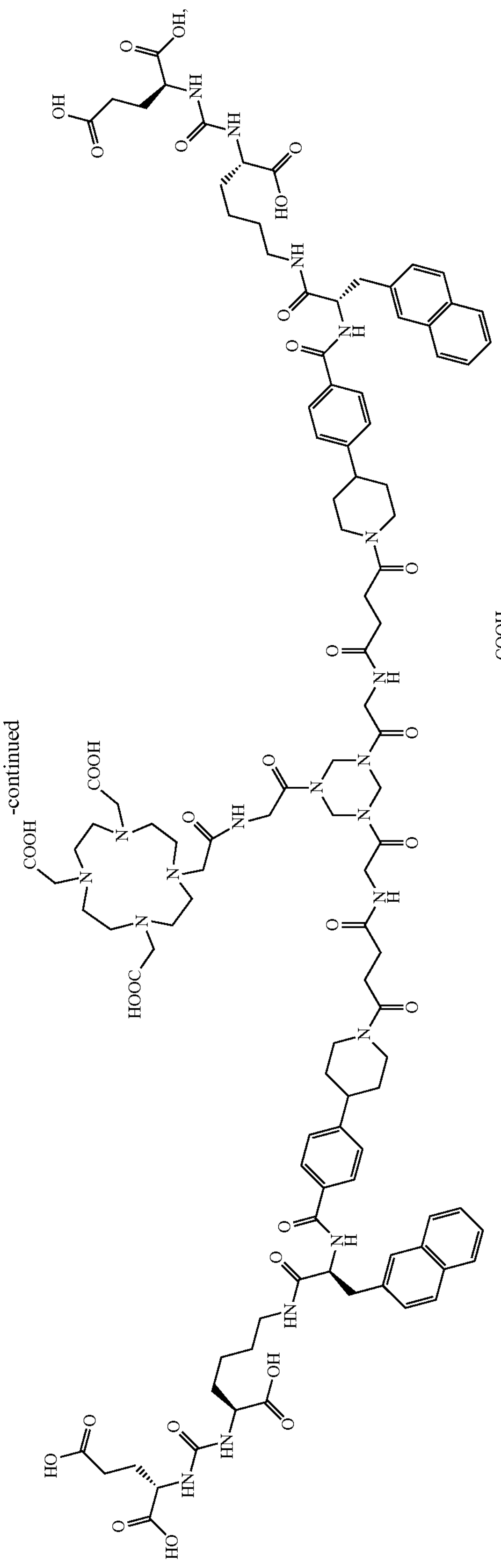
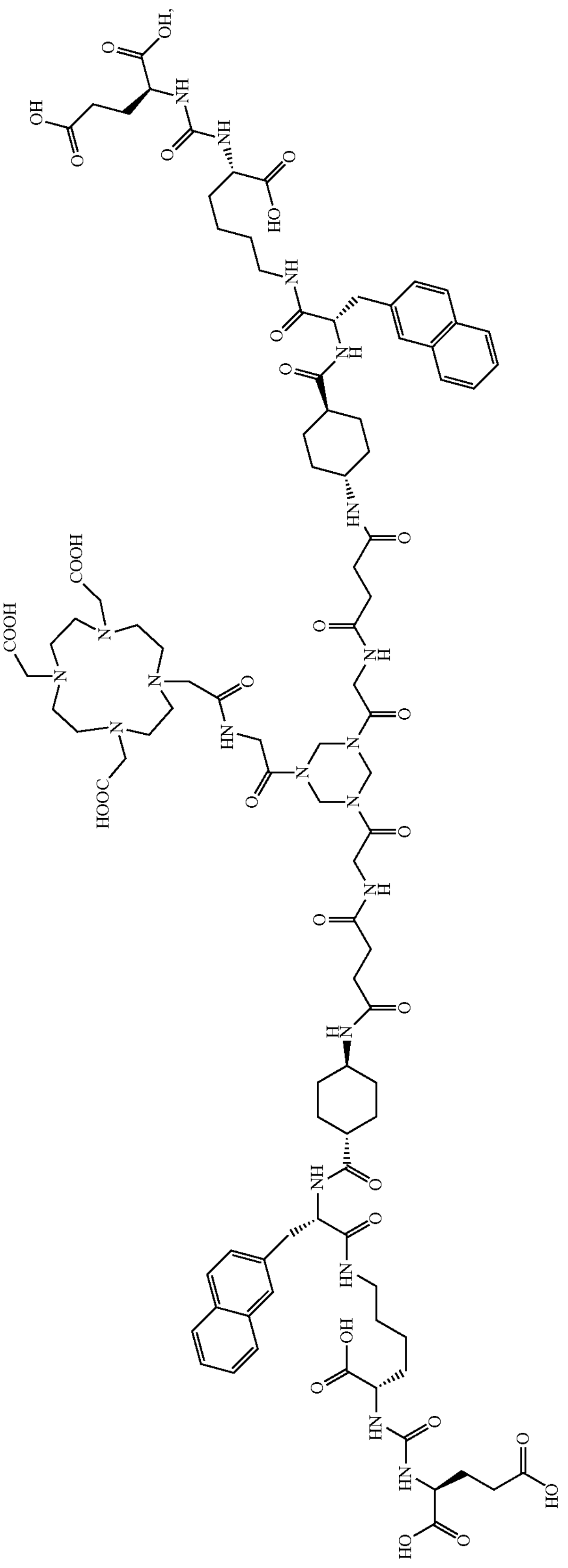

-continued
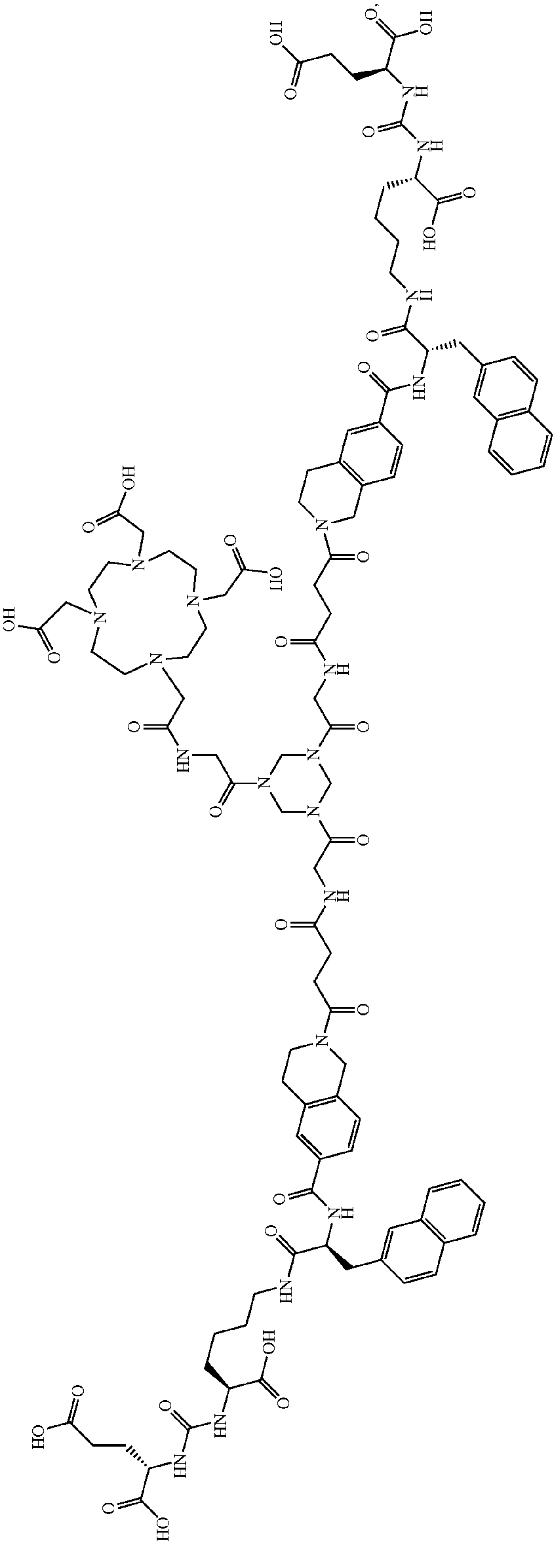

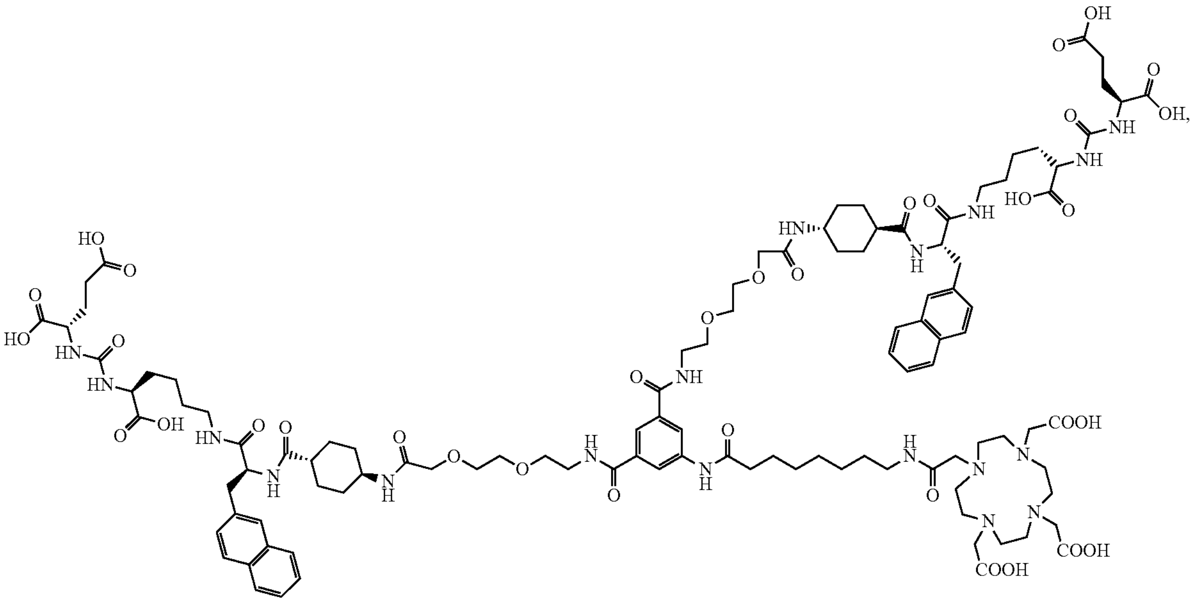
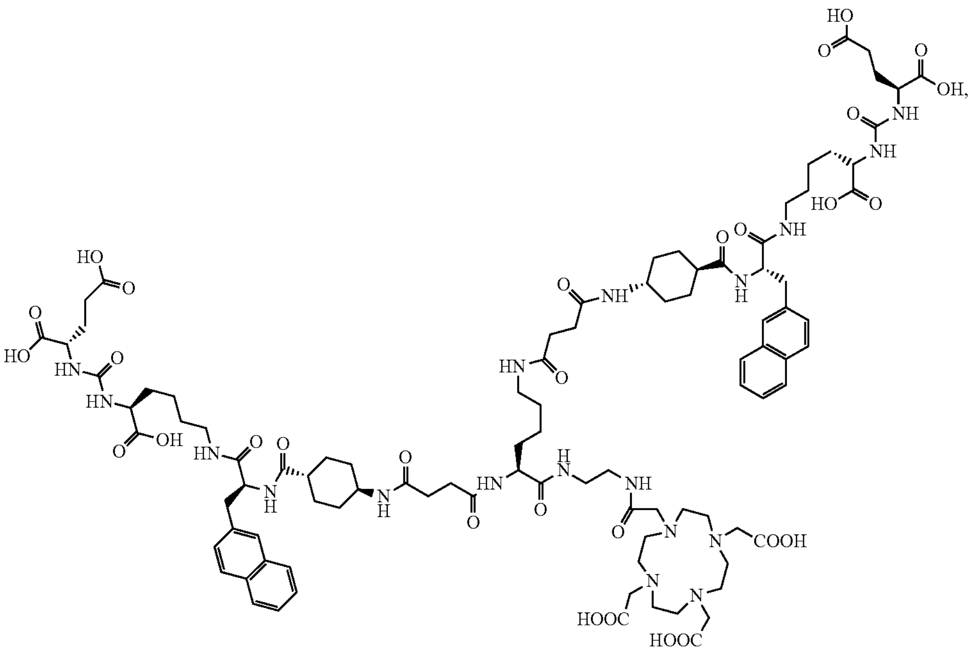

-continued
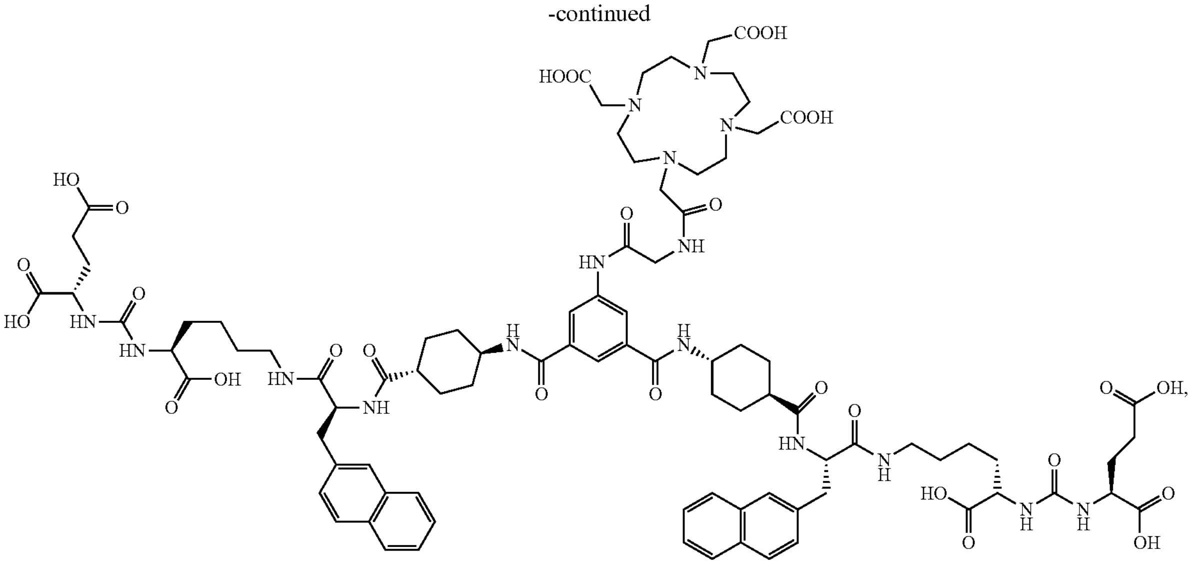
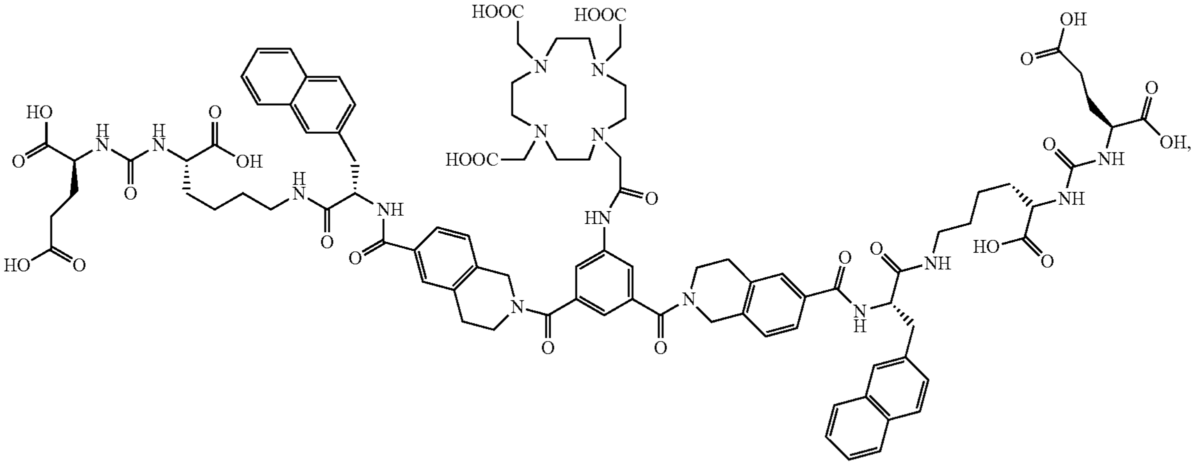
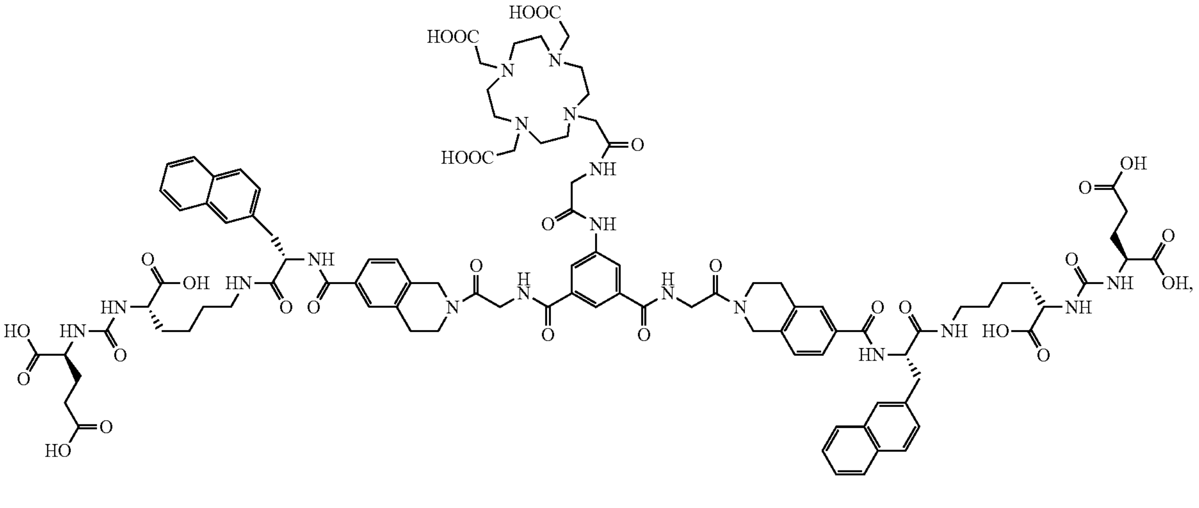

-continued
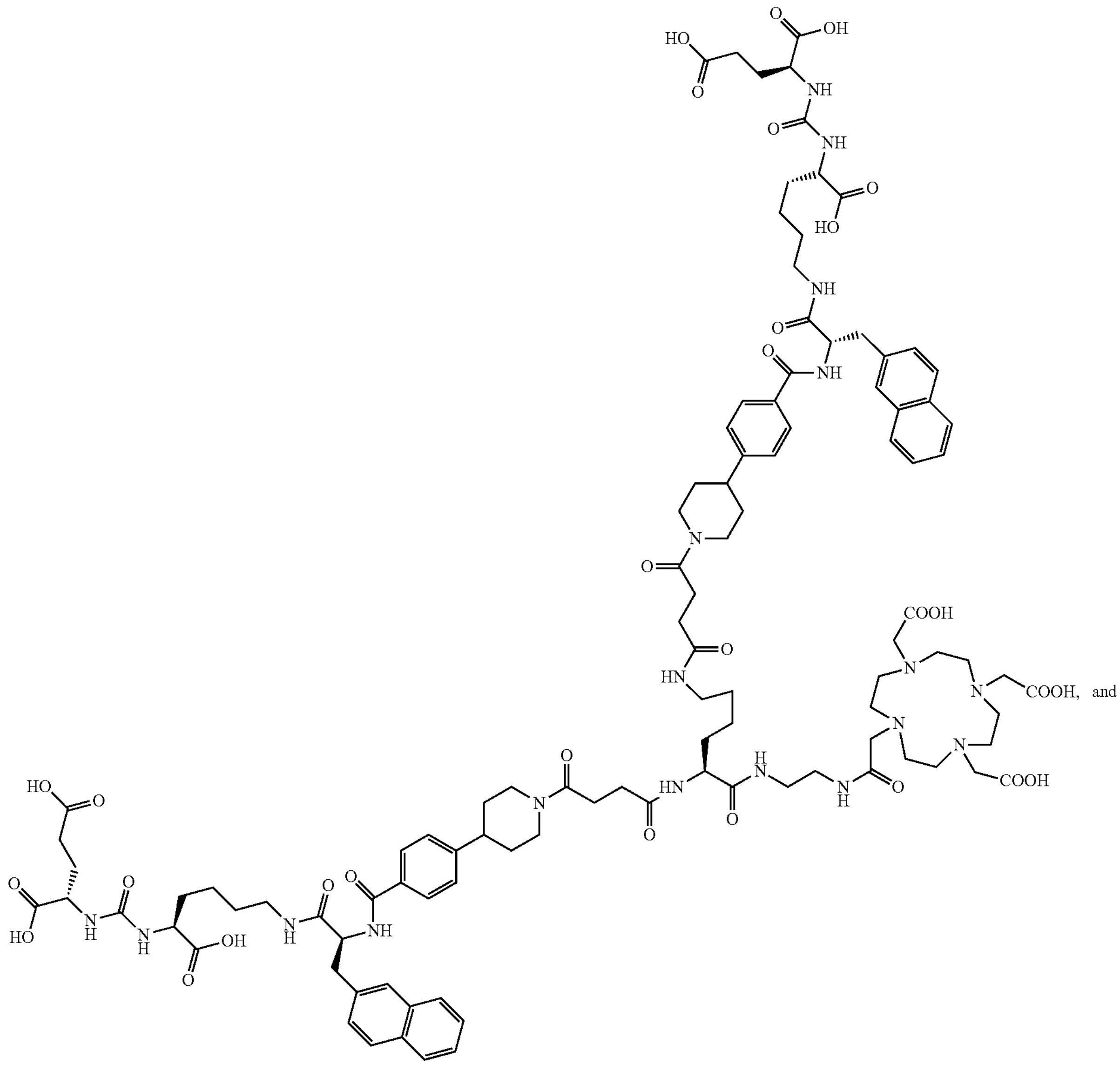
and

-continued
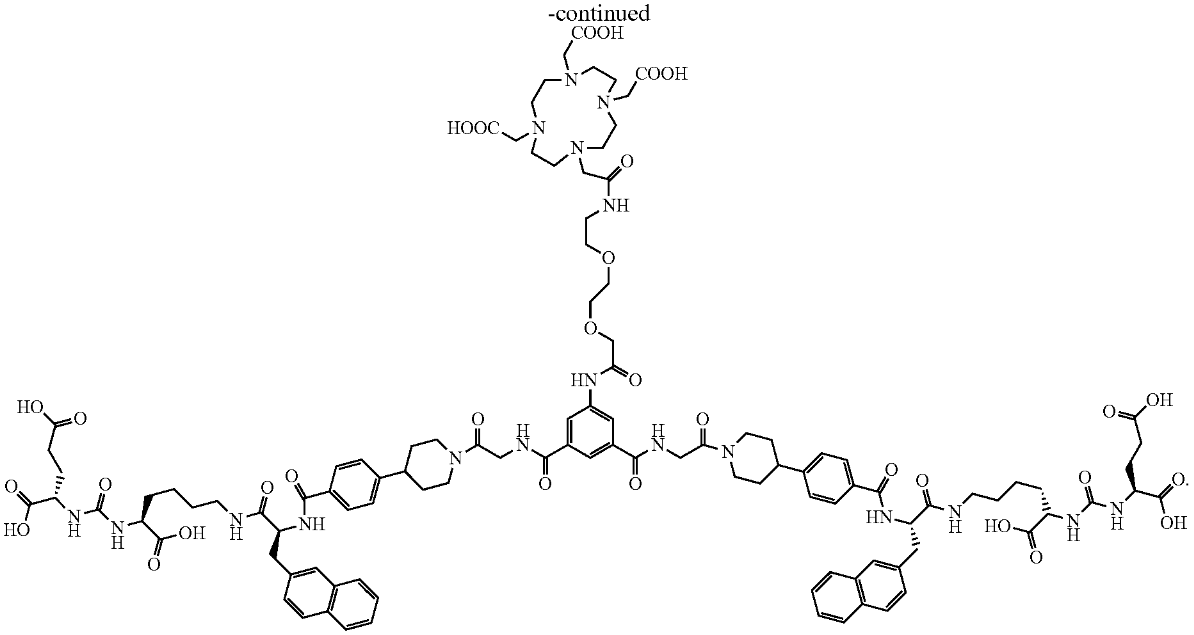
In one embodiment, the peptide urea derivative of formula I is a compound formed by chelation of compound A with $^{177}Lu^{3+}$, wherein the structure of compound A is any one of the following:

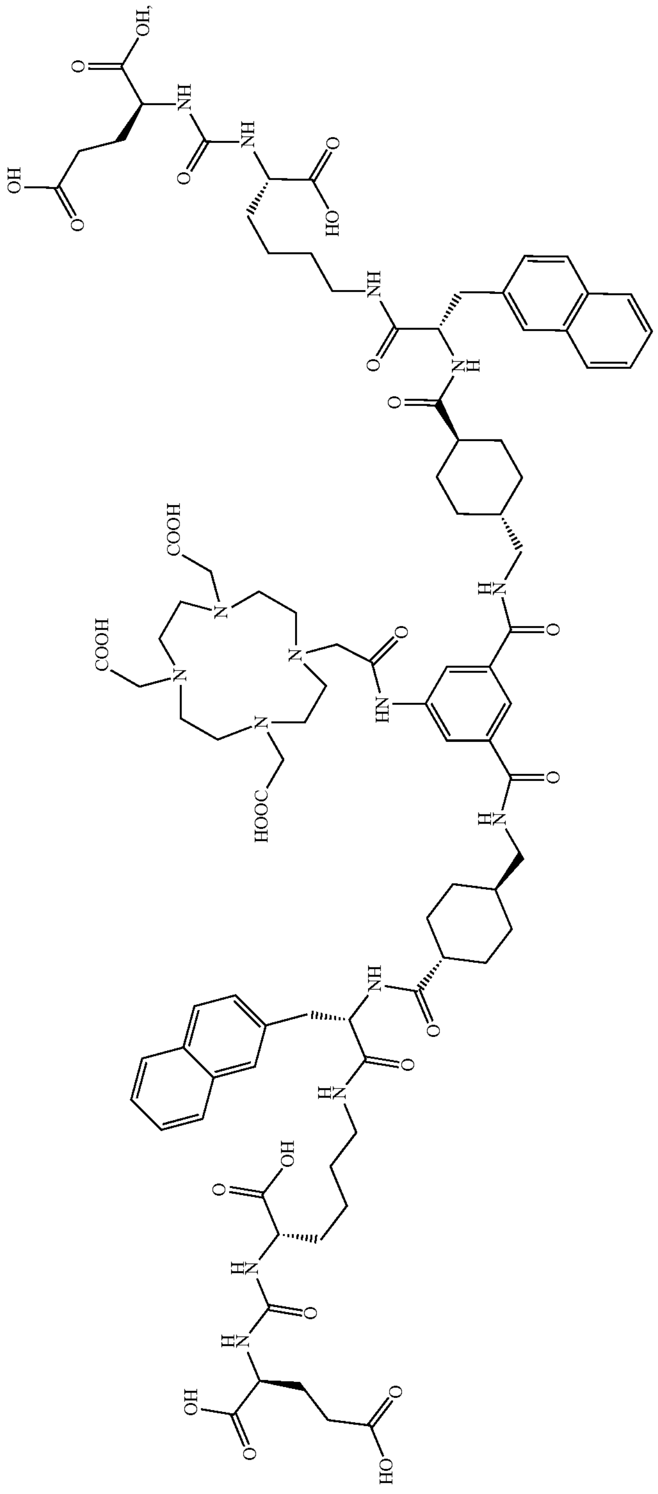

-continued
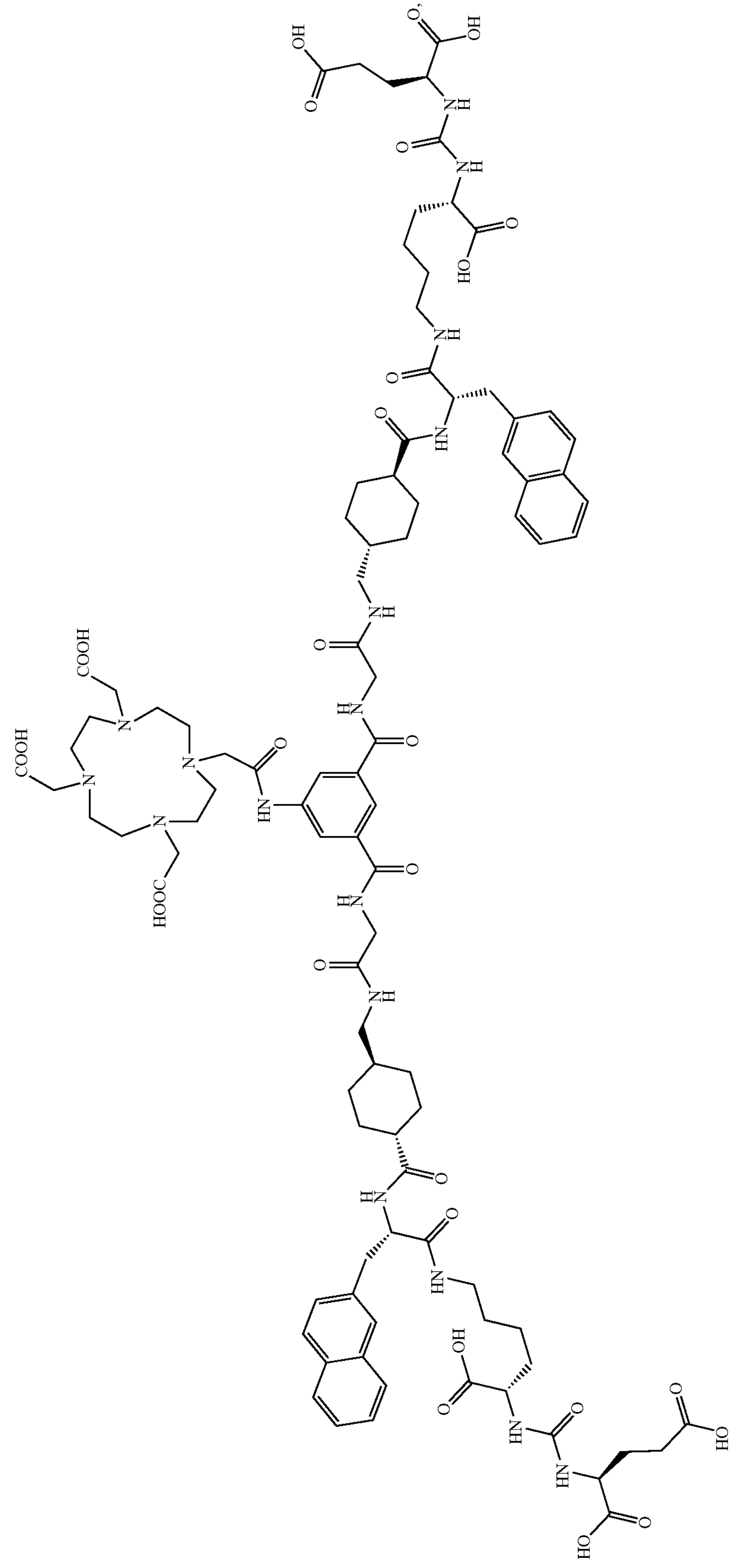

-continued
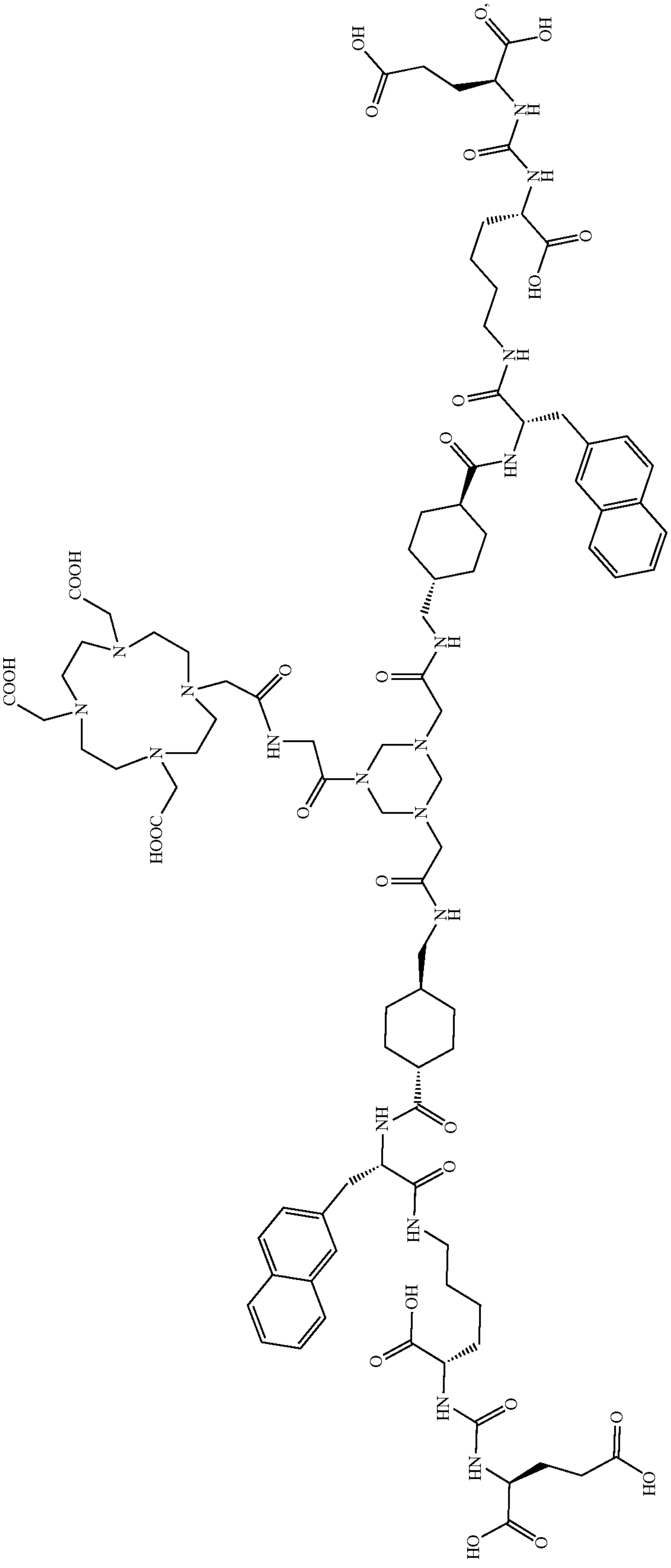

-continued
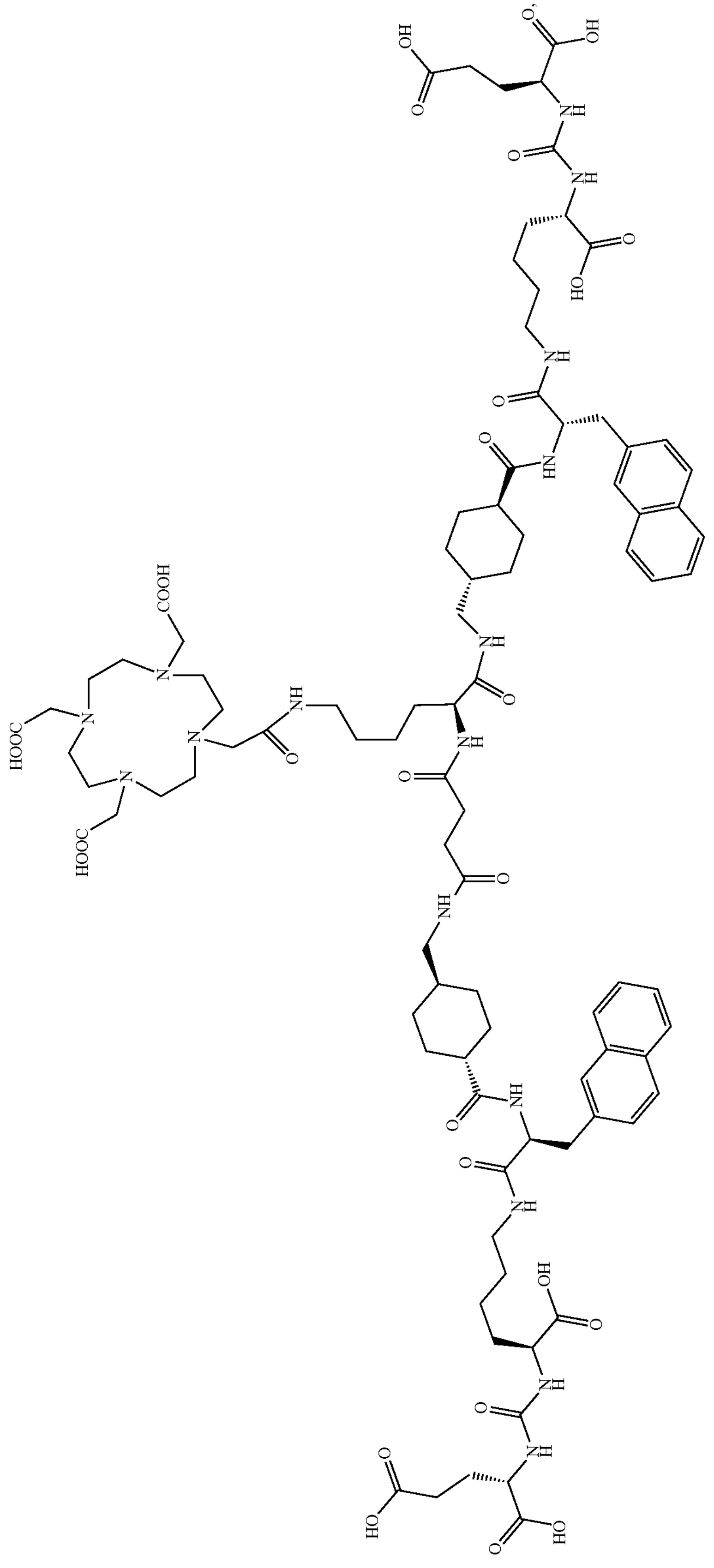

-continued
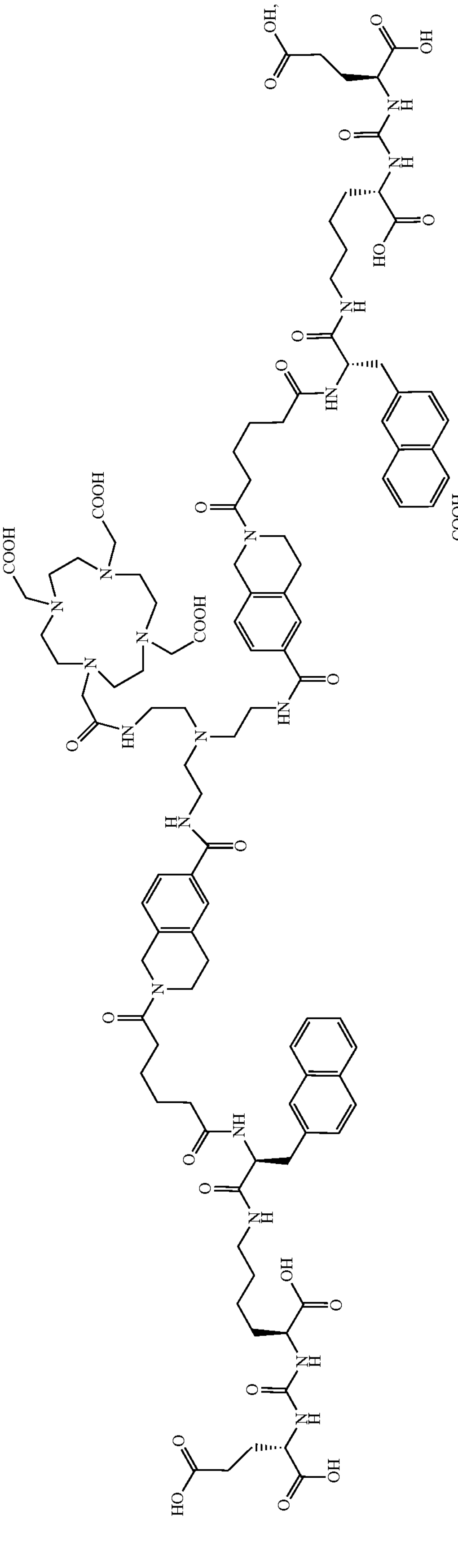
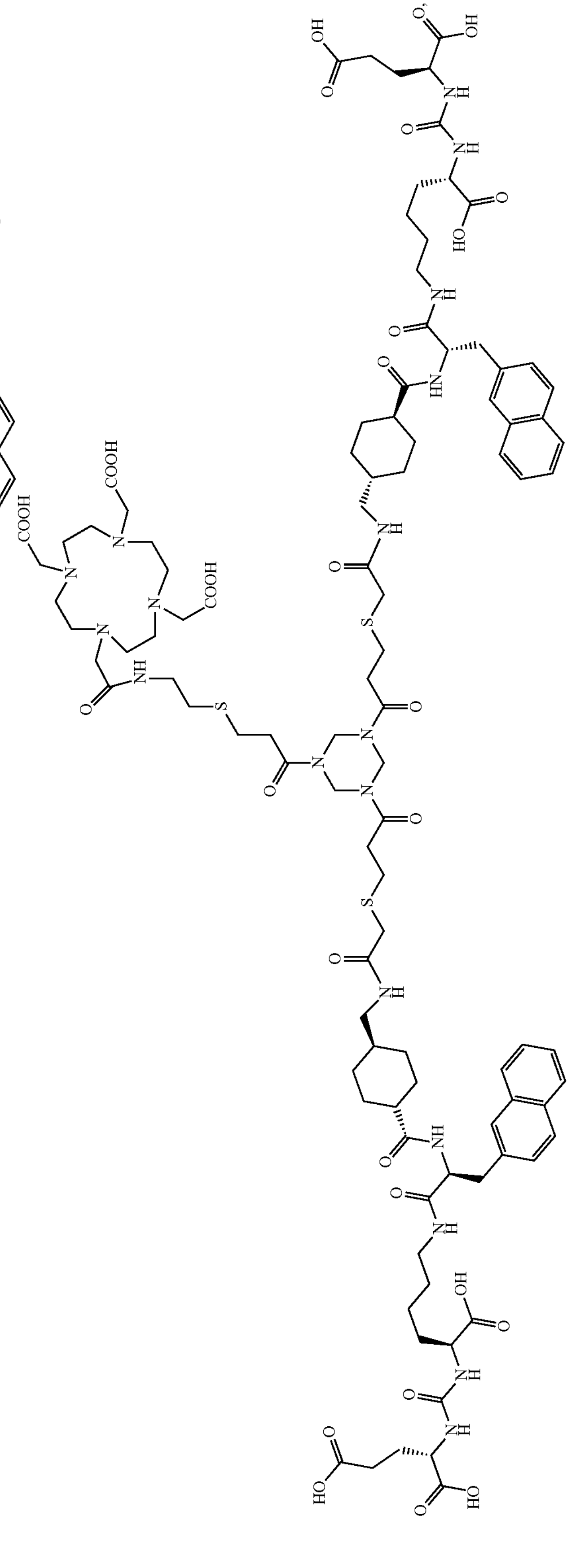

-continued
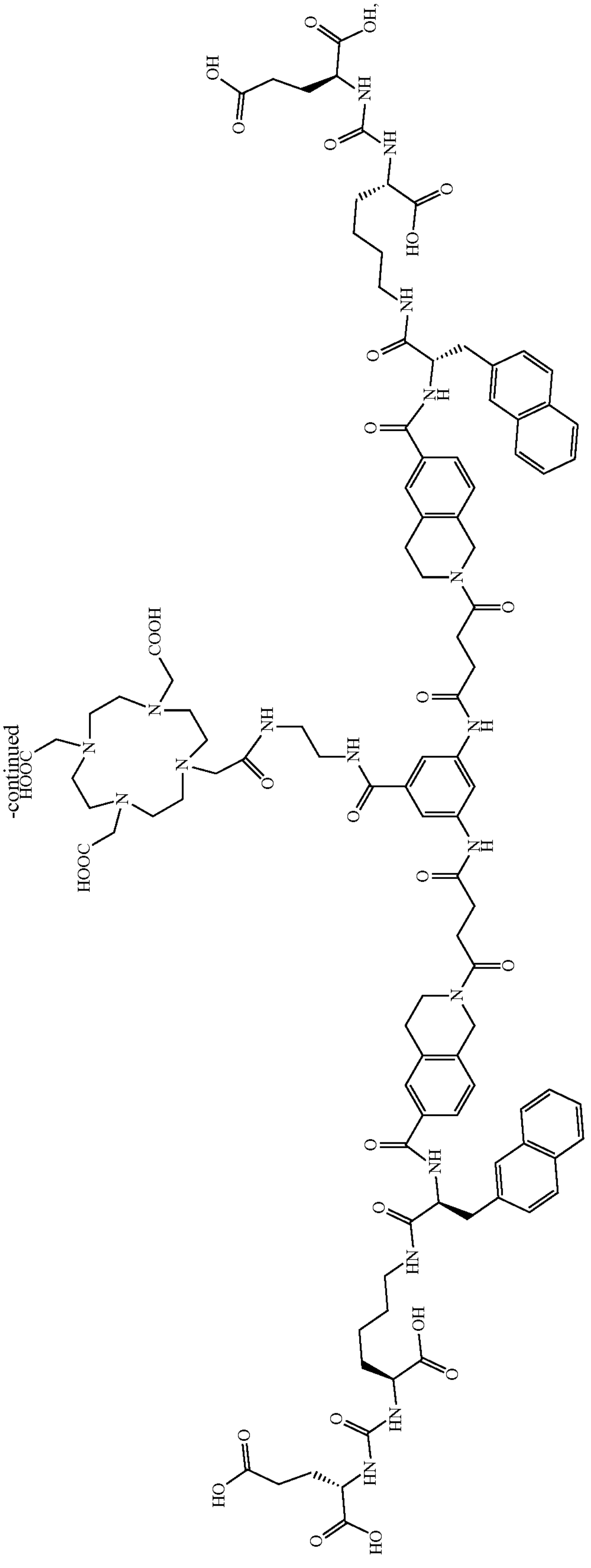
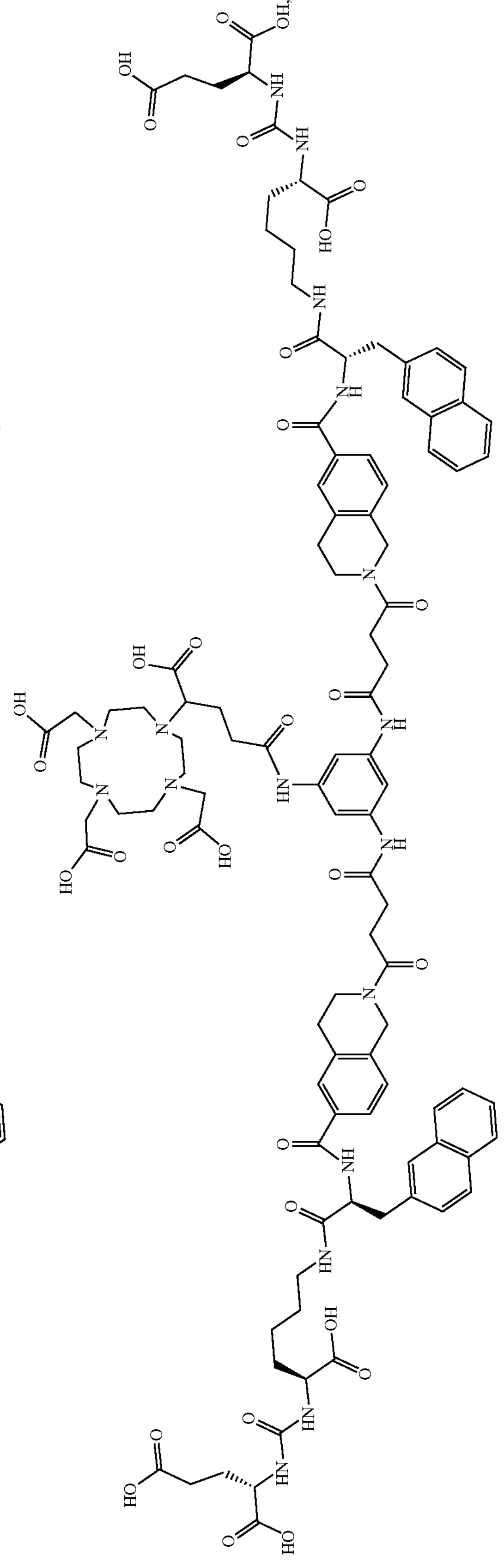

-continued
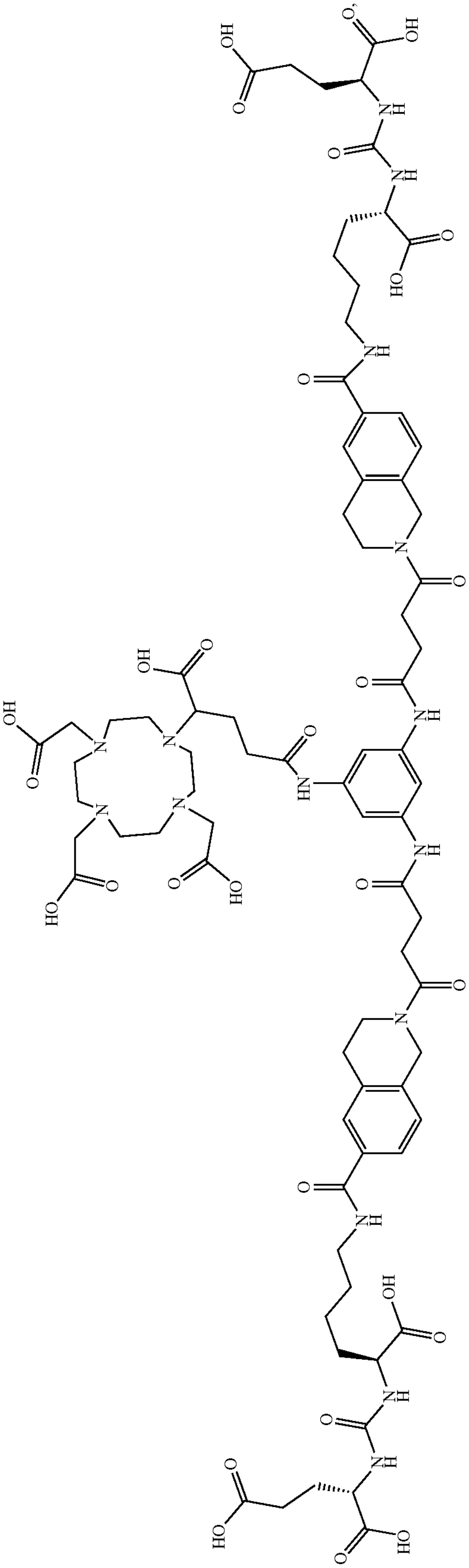

-continued
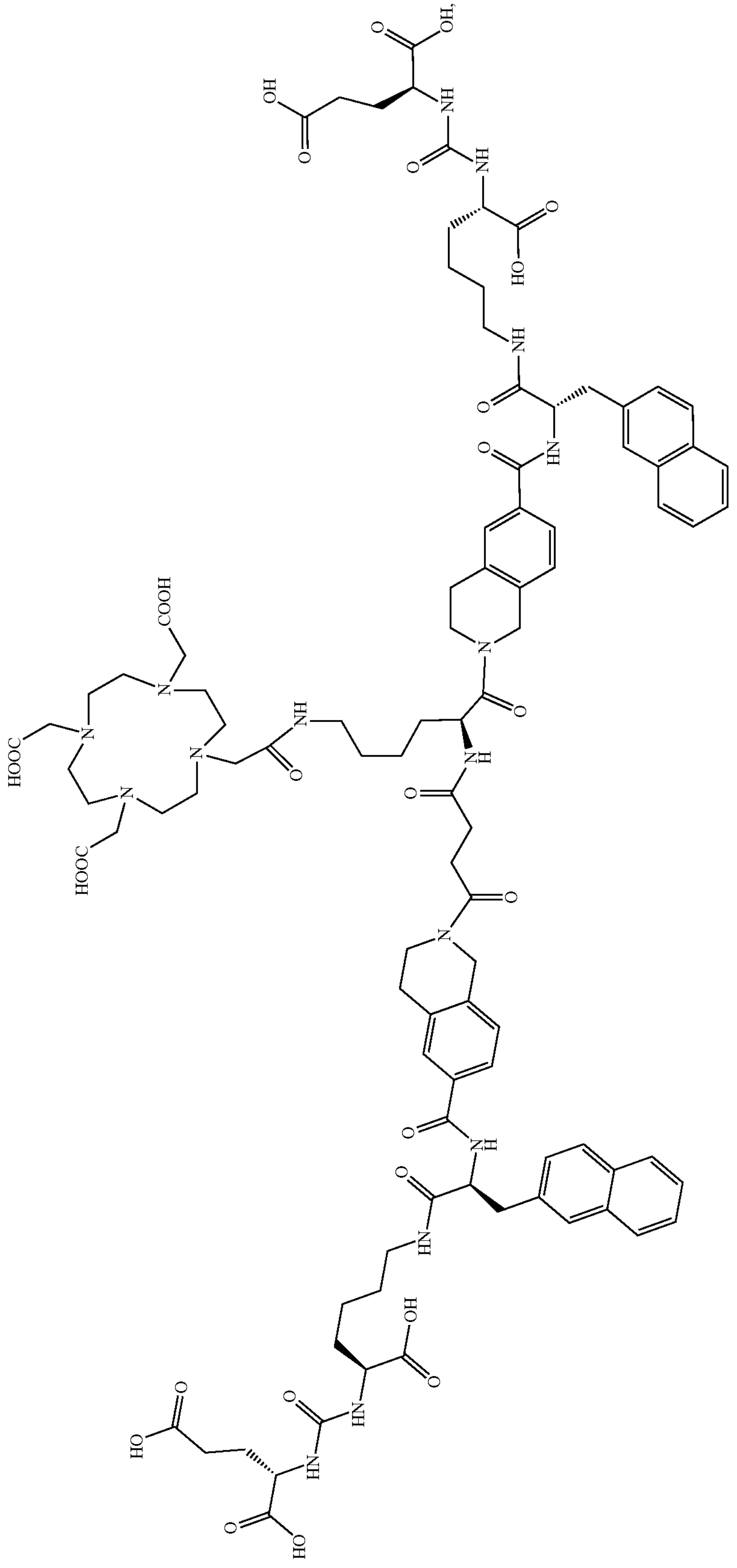

-continued
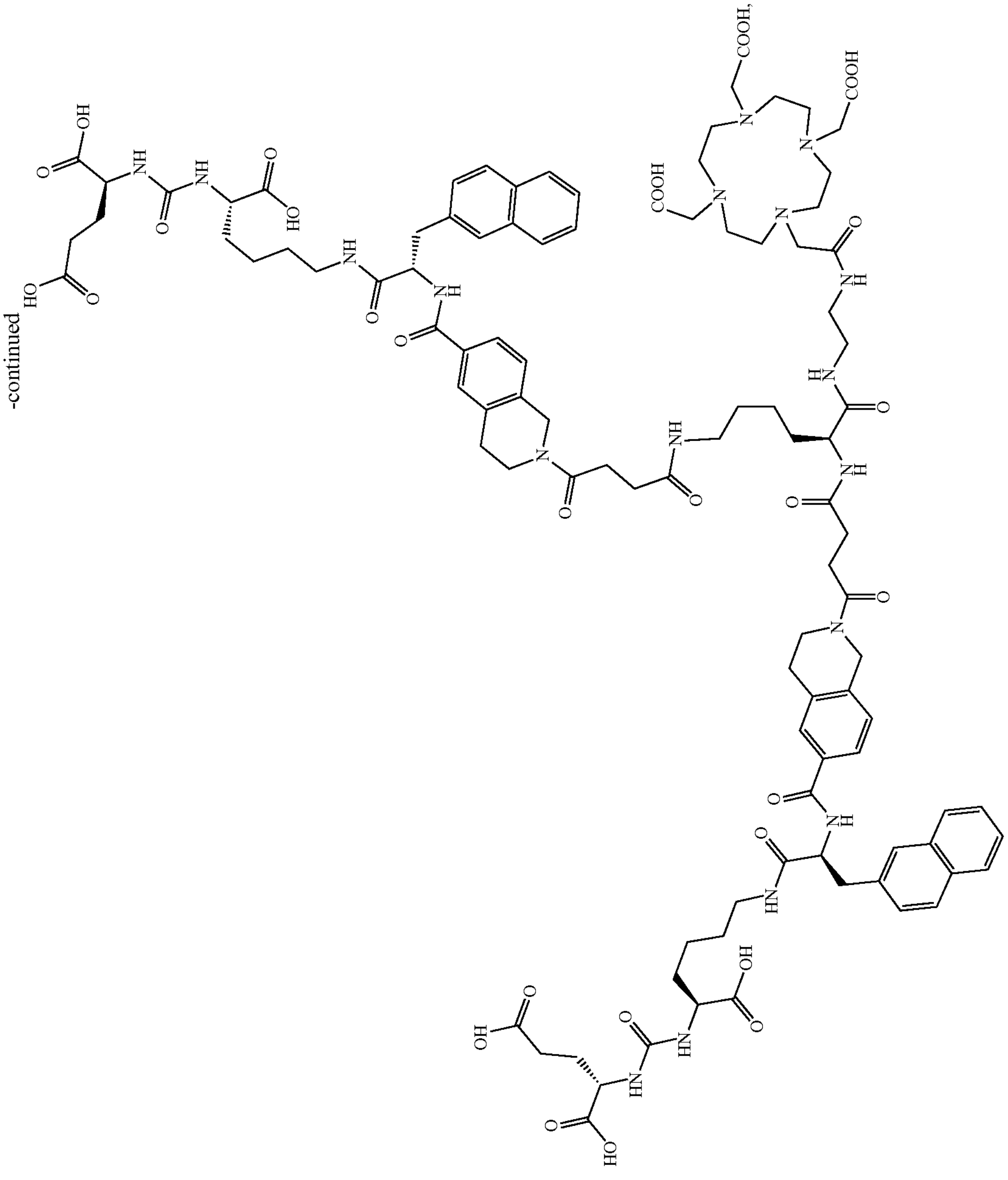

-continued
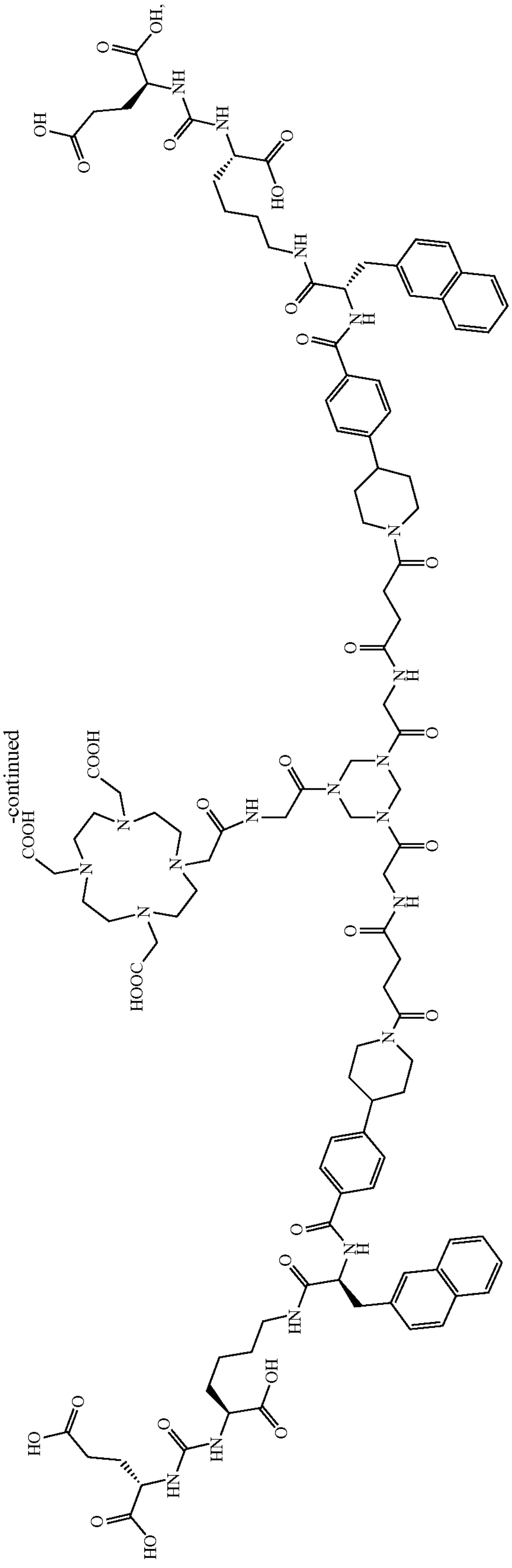
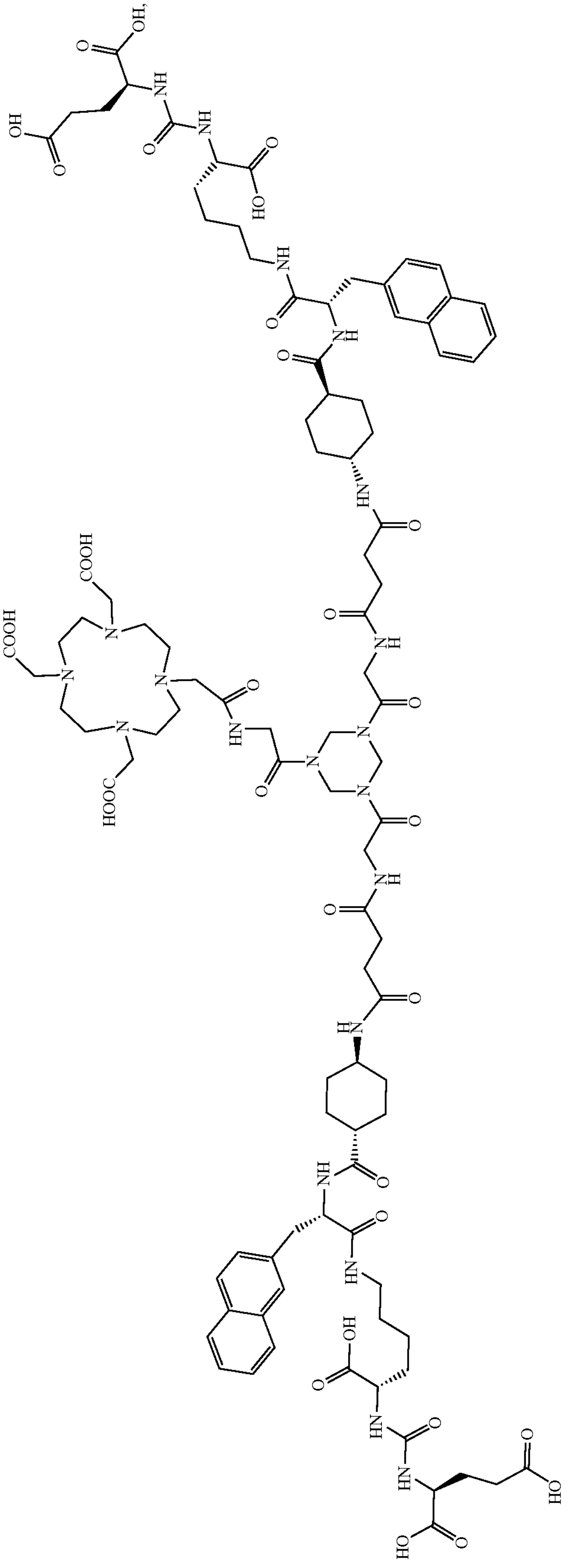

-continued
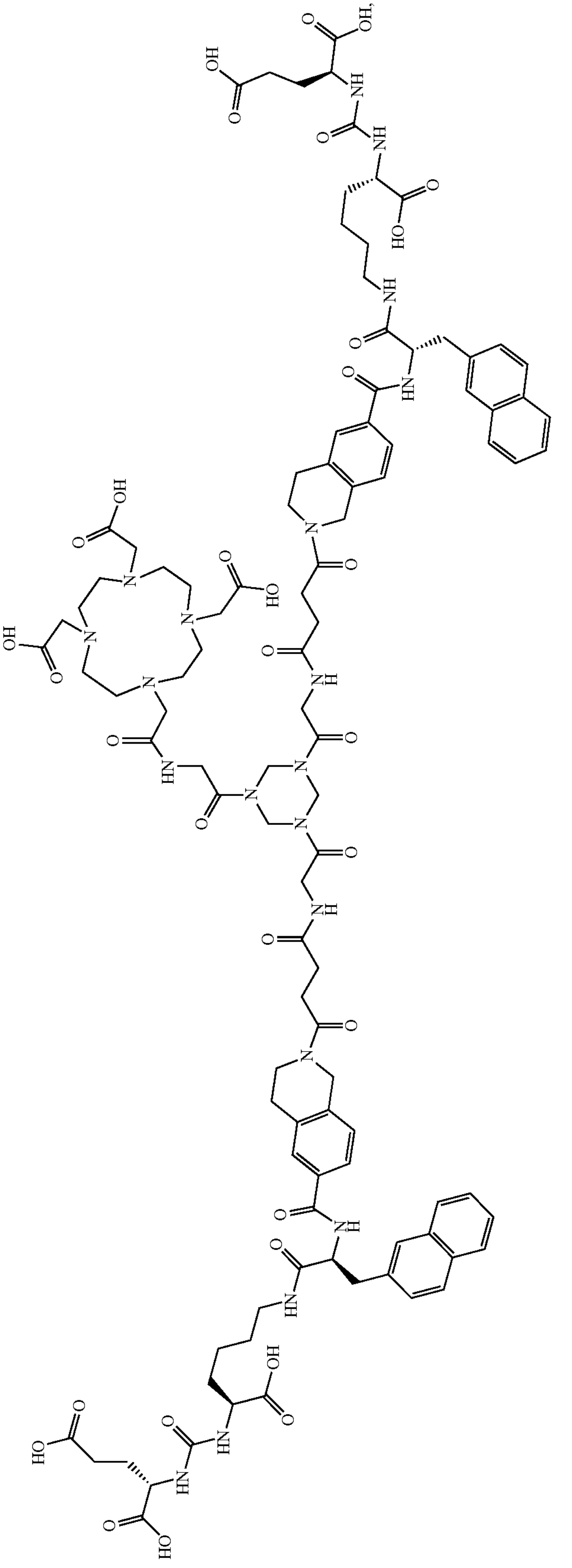

-continued
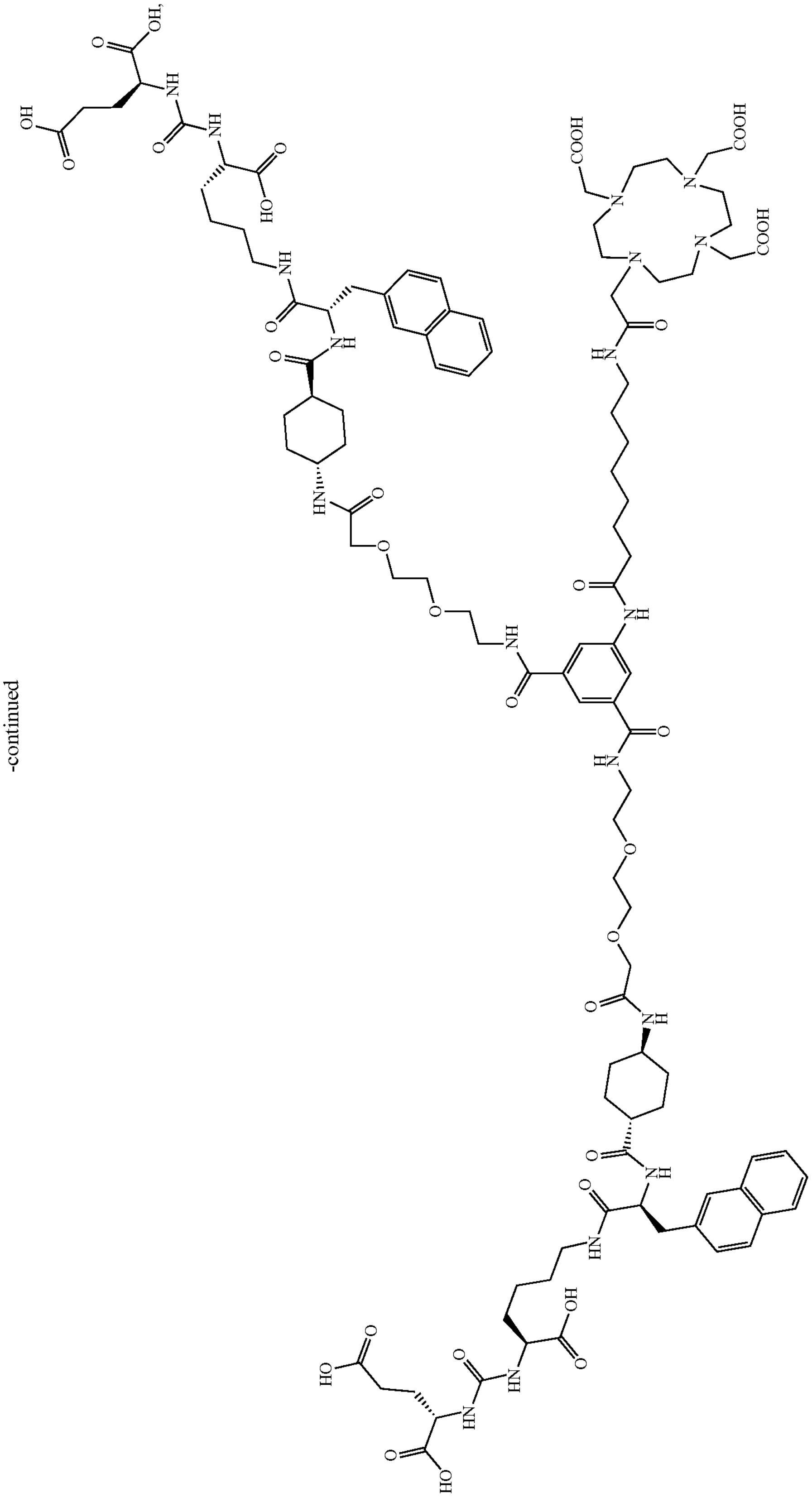

-continued
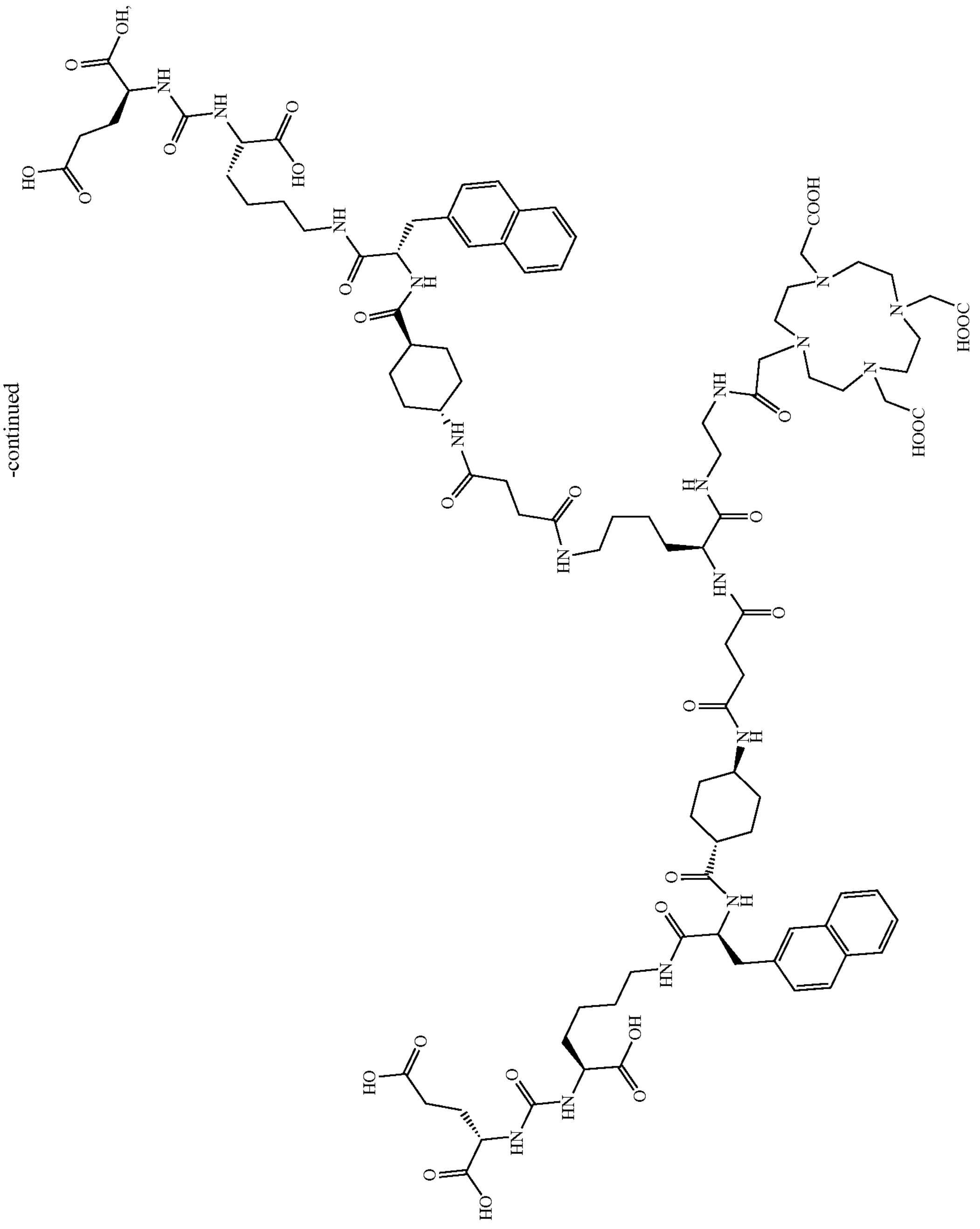

-continued
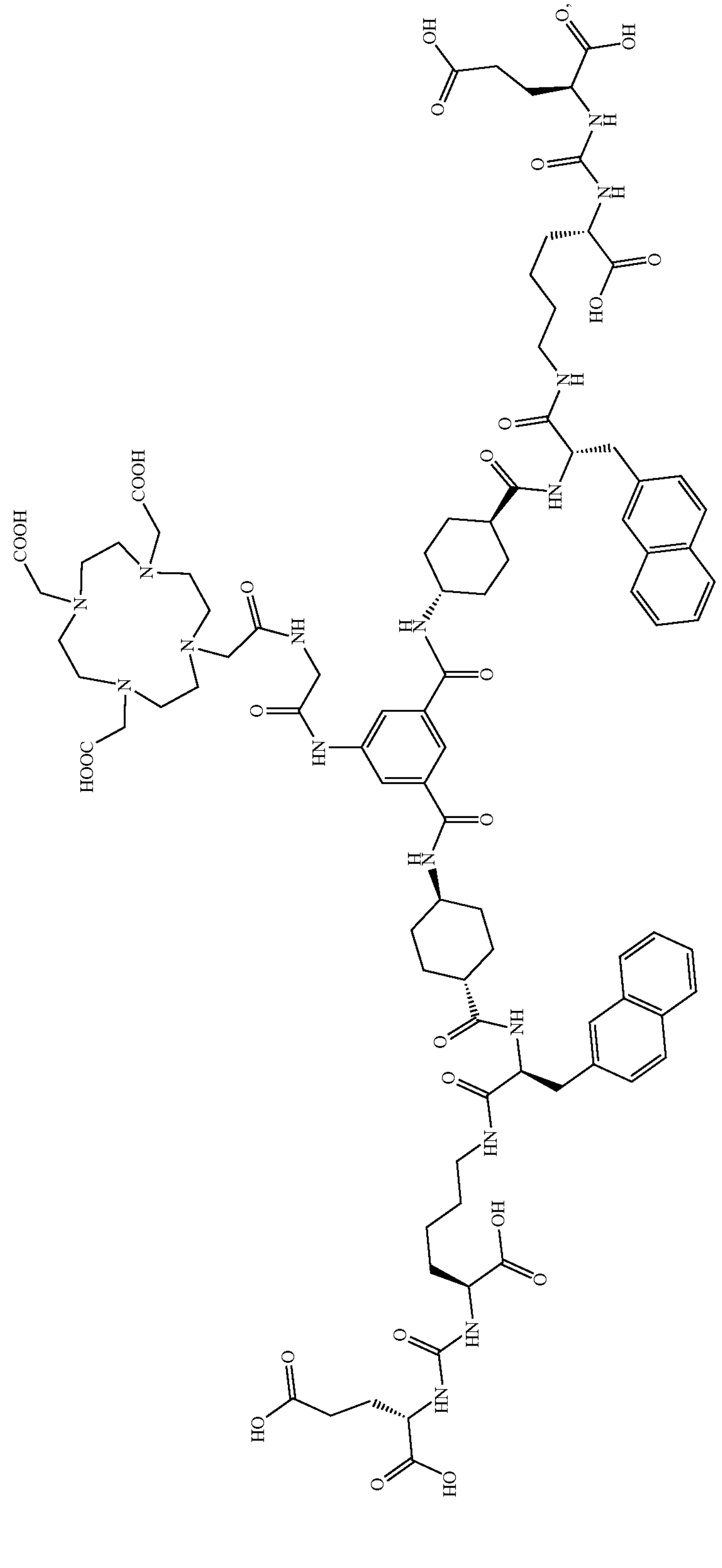

-continued
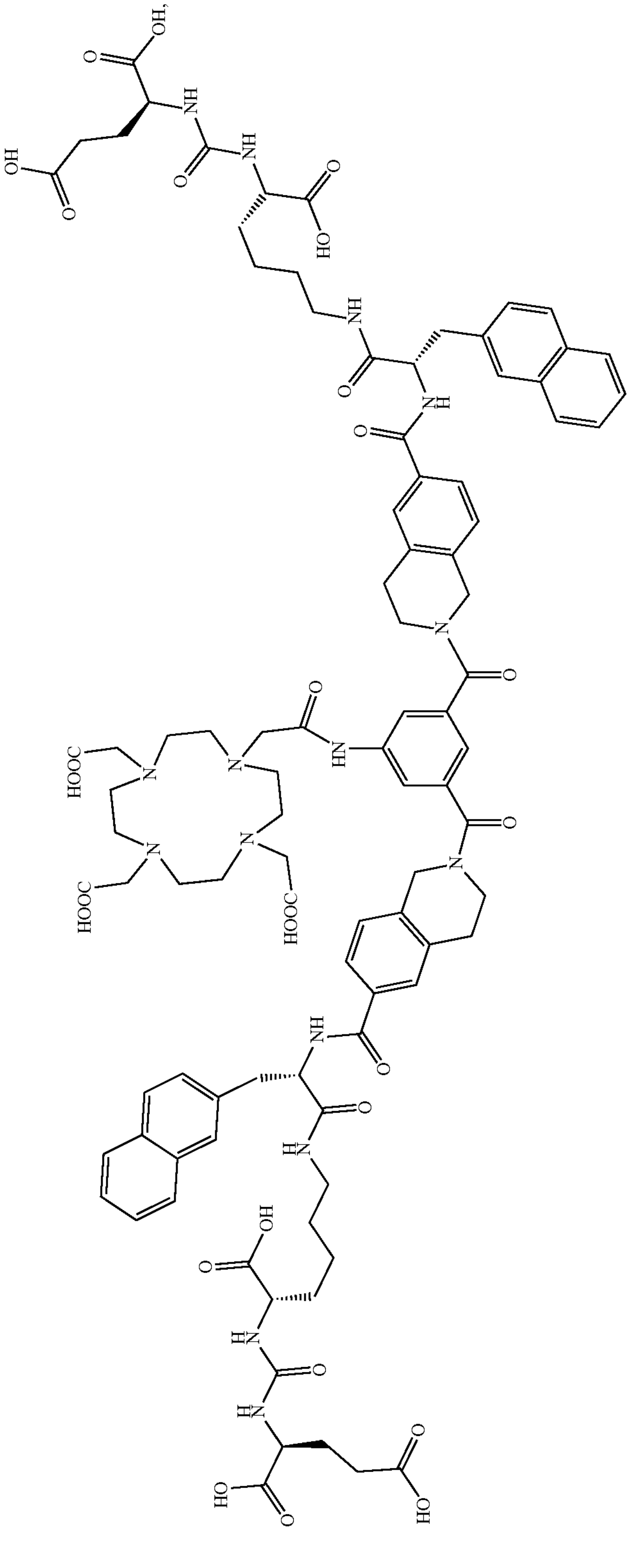

-continued
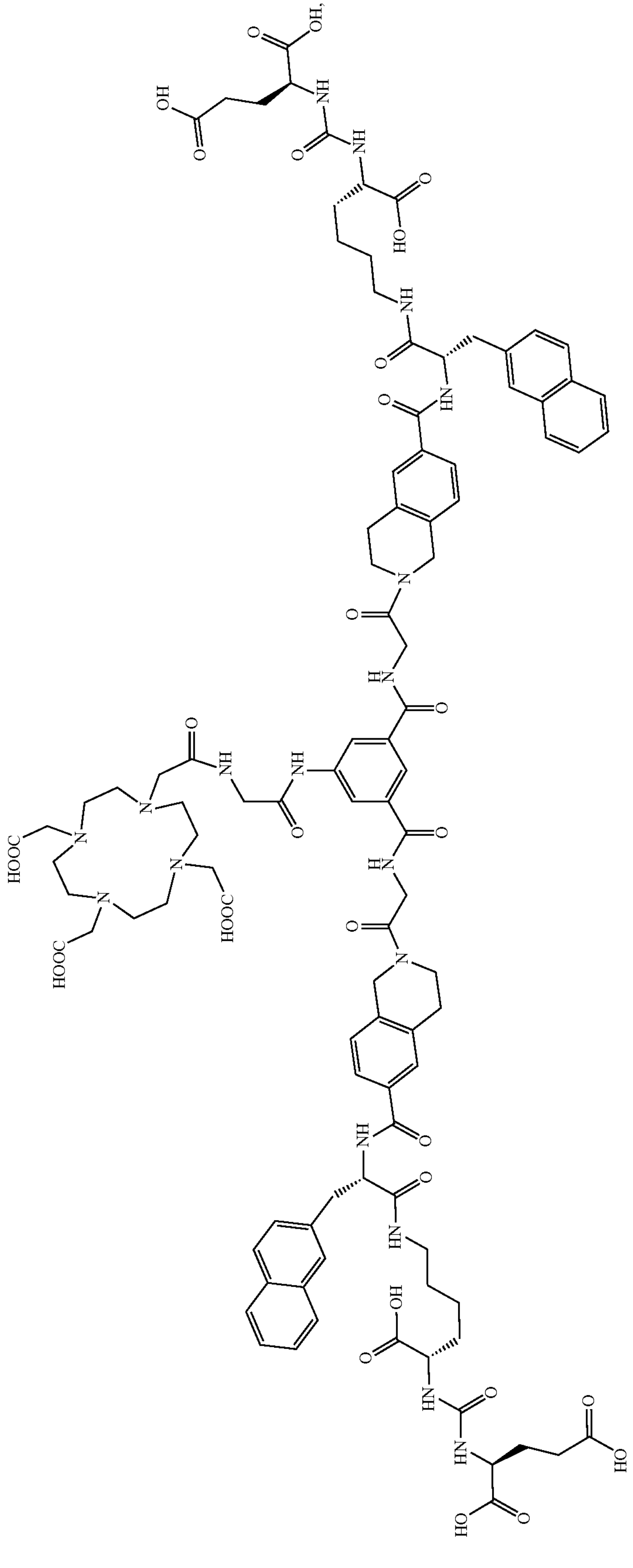

-continued
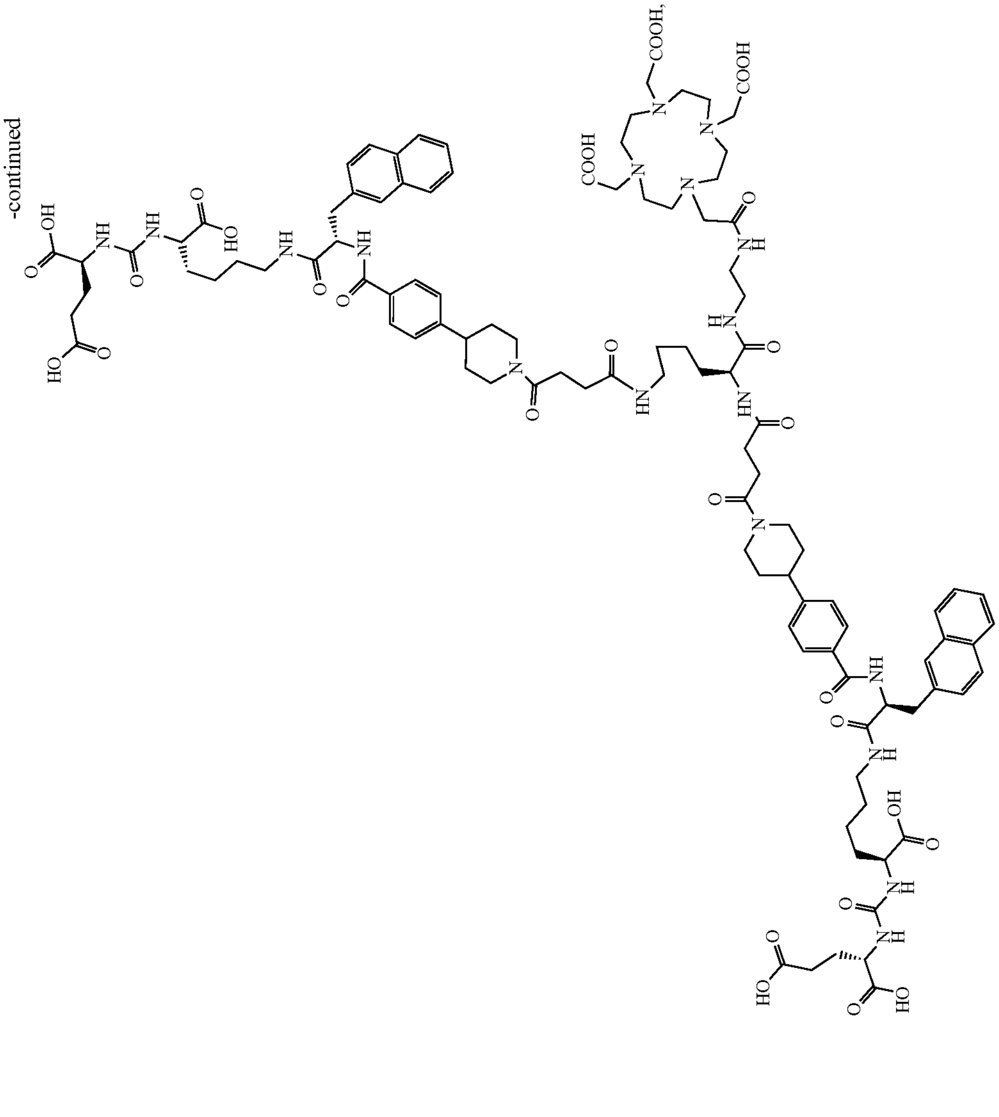
and

-continued
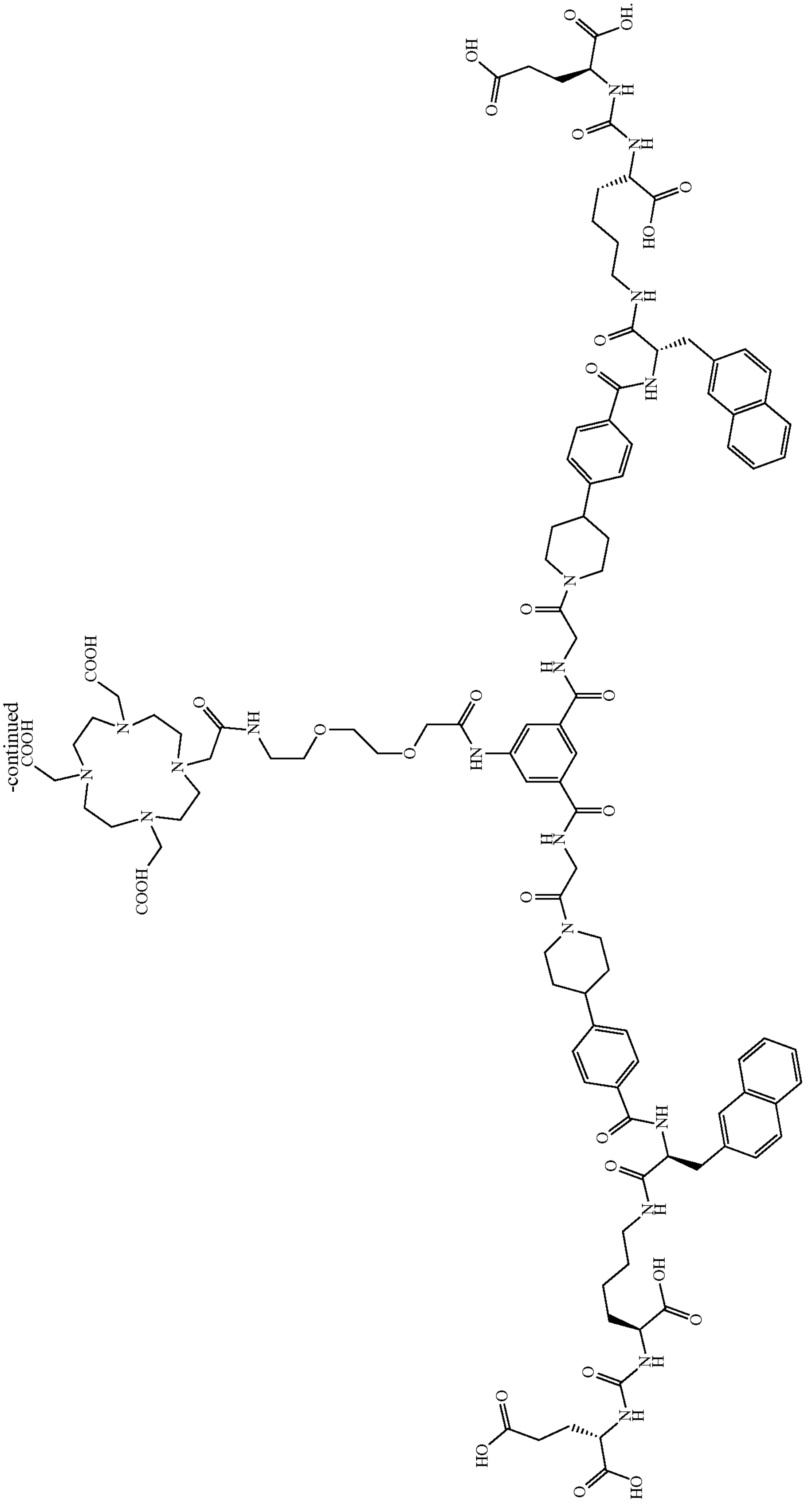

In one embodiment, the peptide urea derivative of formula I is a compound formed by chelation of compound A with $^{68}Ga^{3+}$, wherein the structure of compound A is any one of the following:

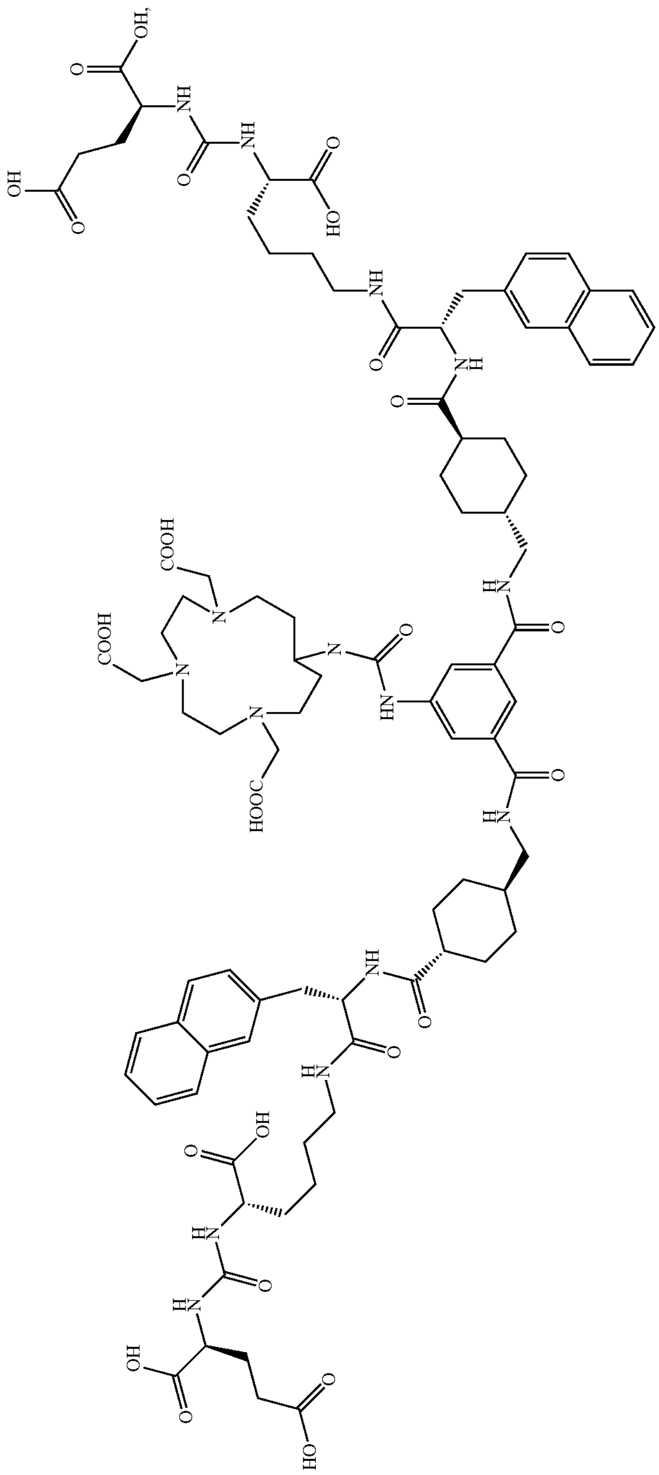

-continued
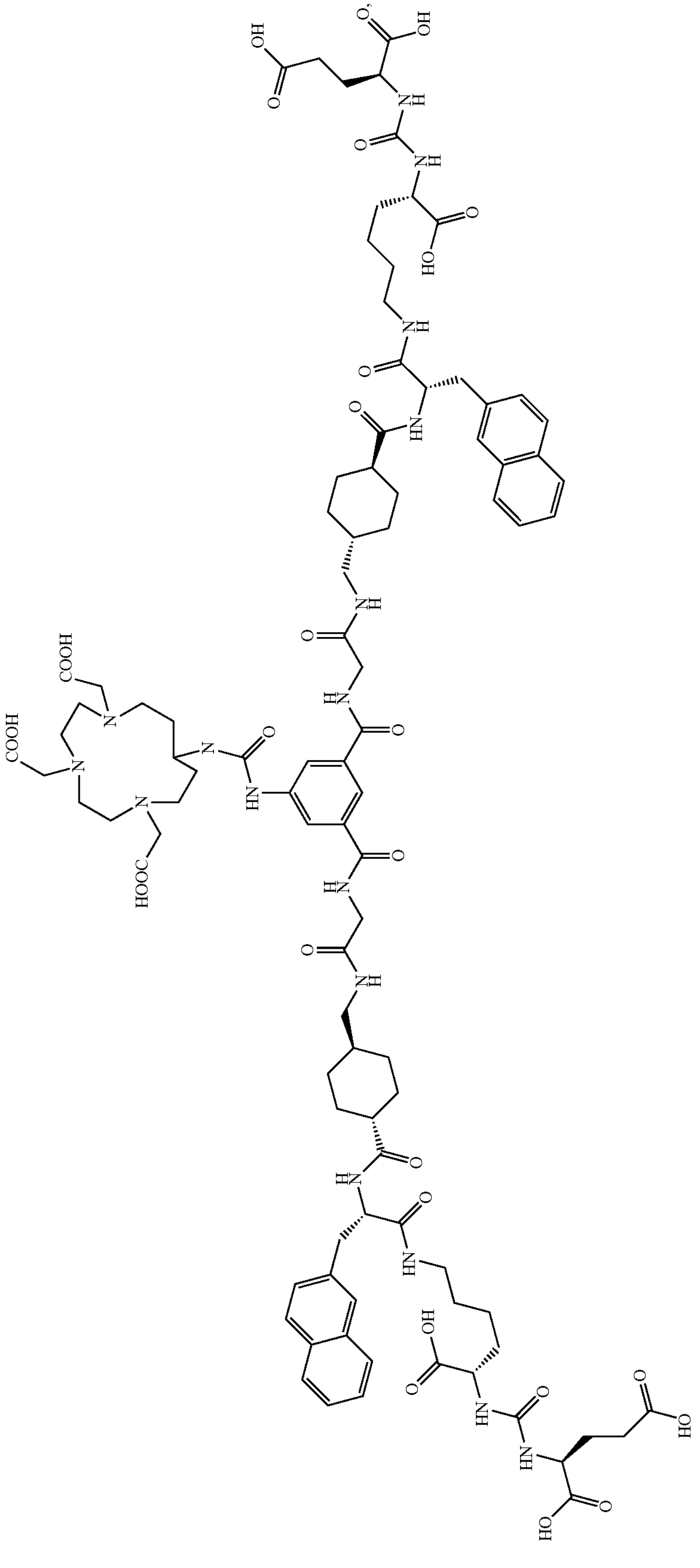

-continued
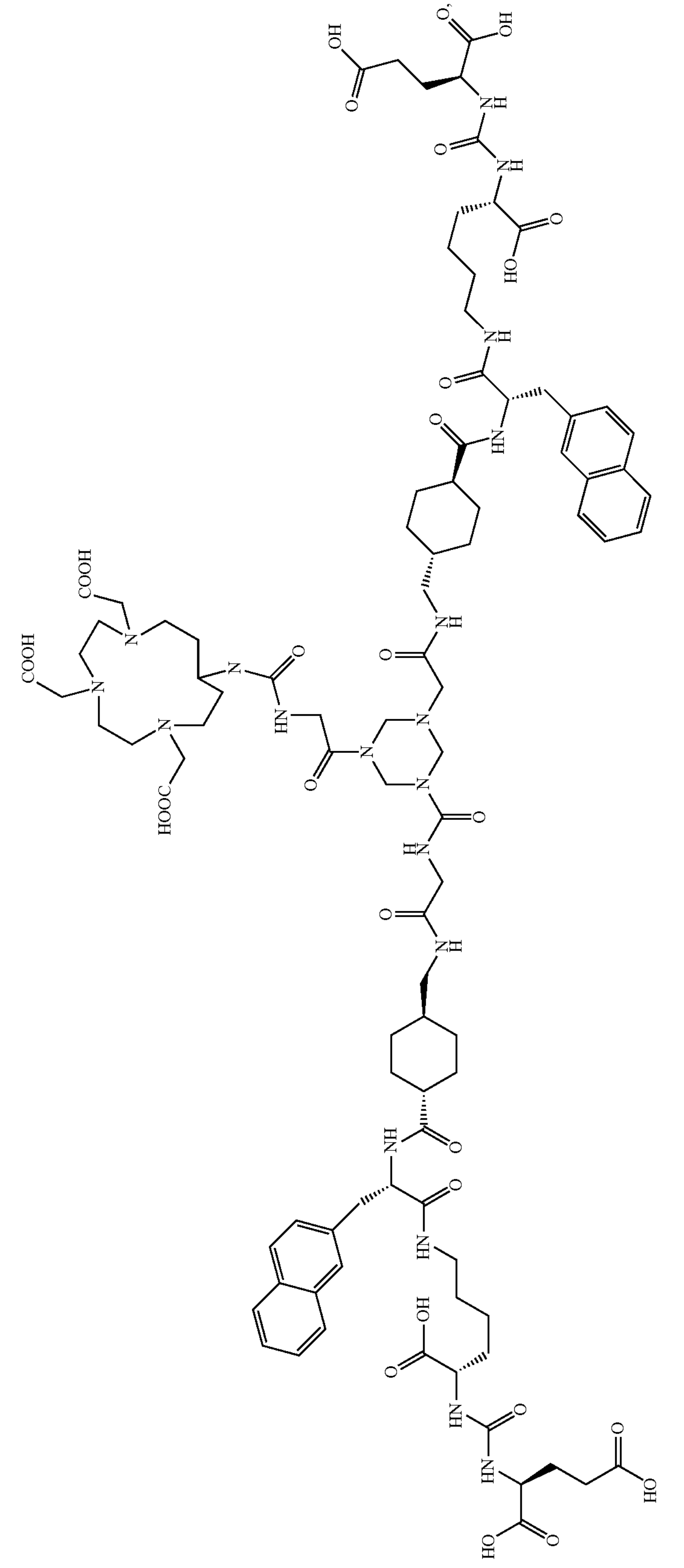

-continued
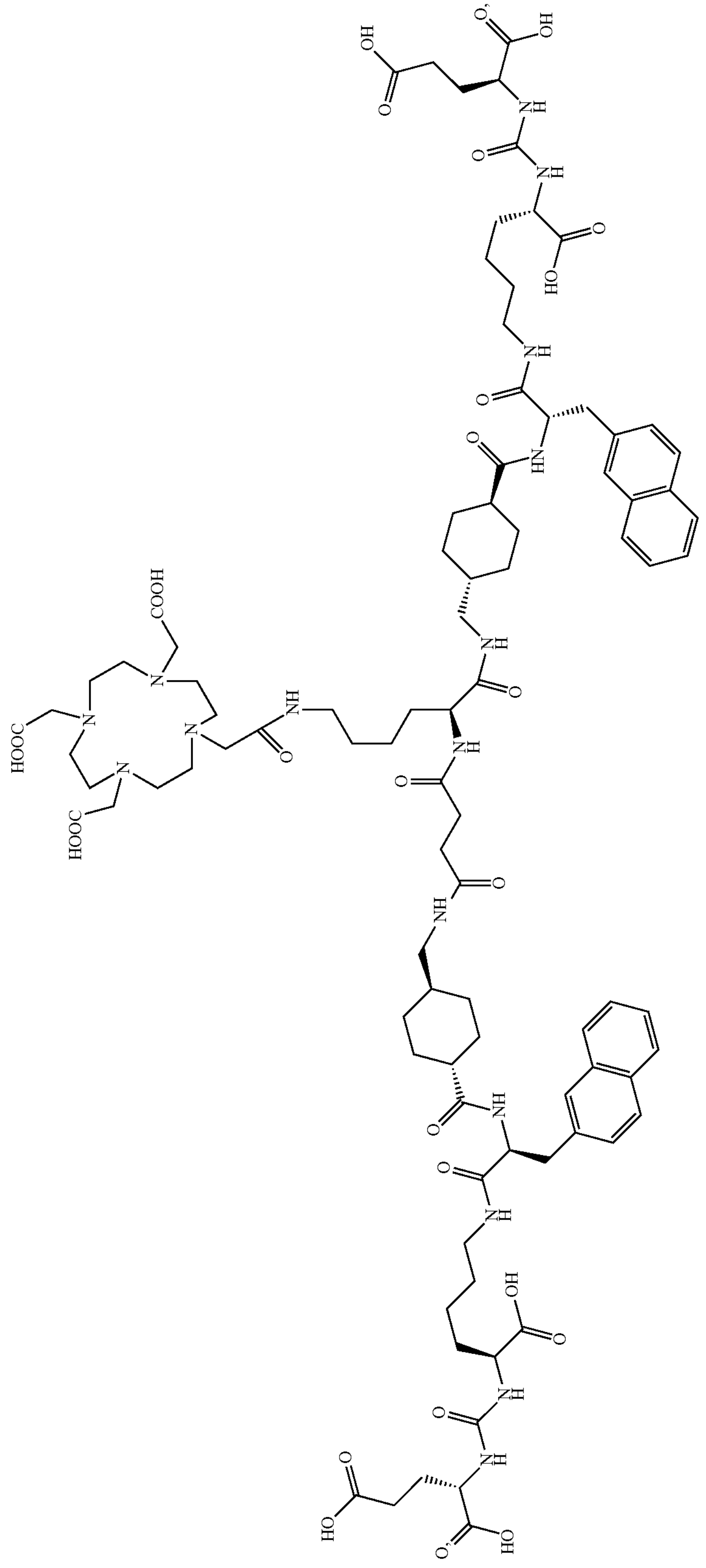

-continued
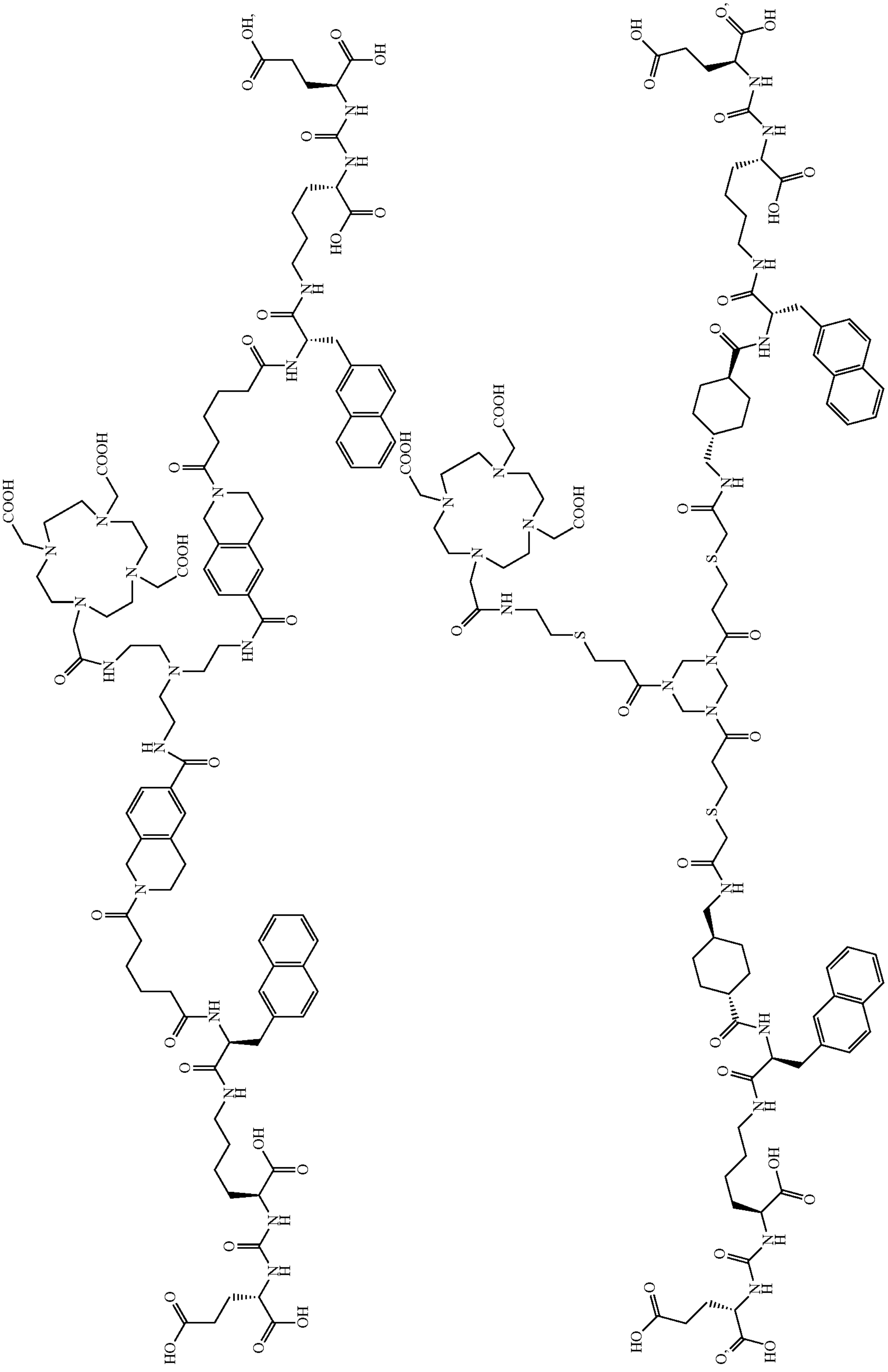

-continued
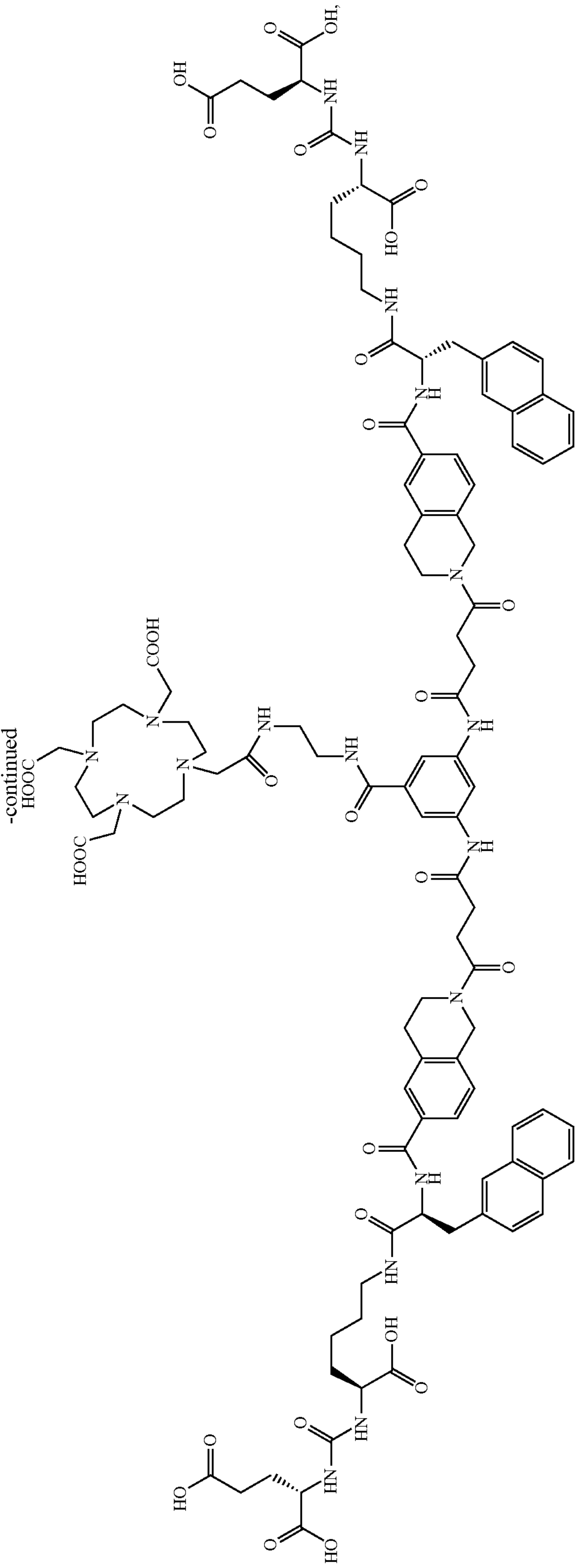
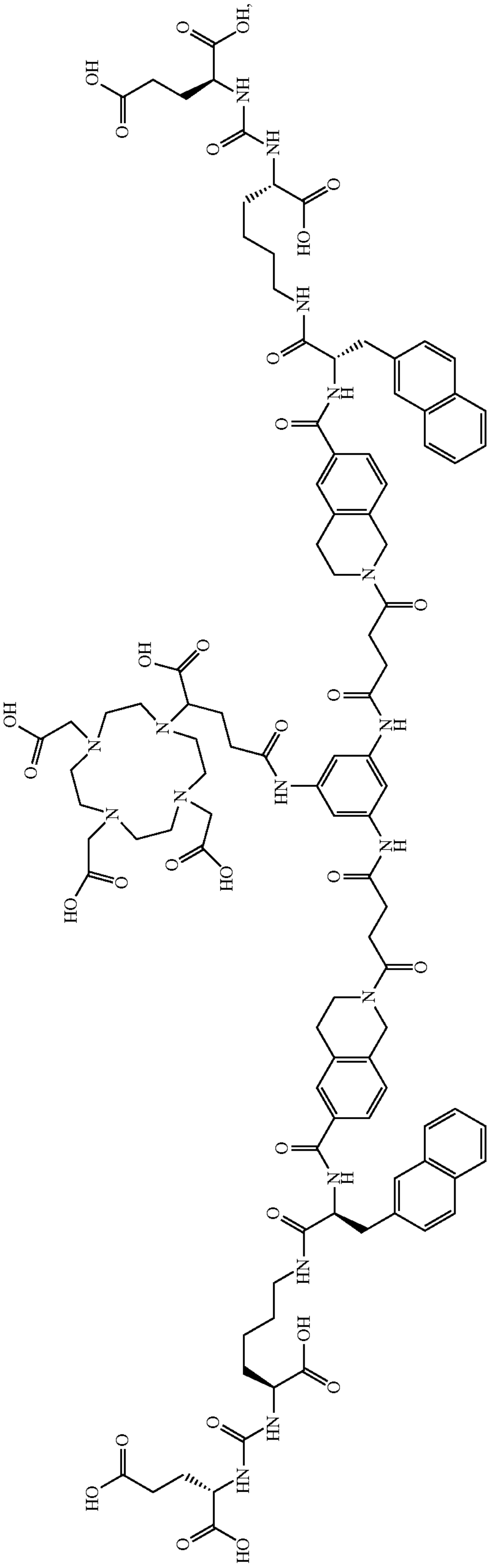

-continued
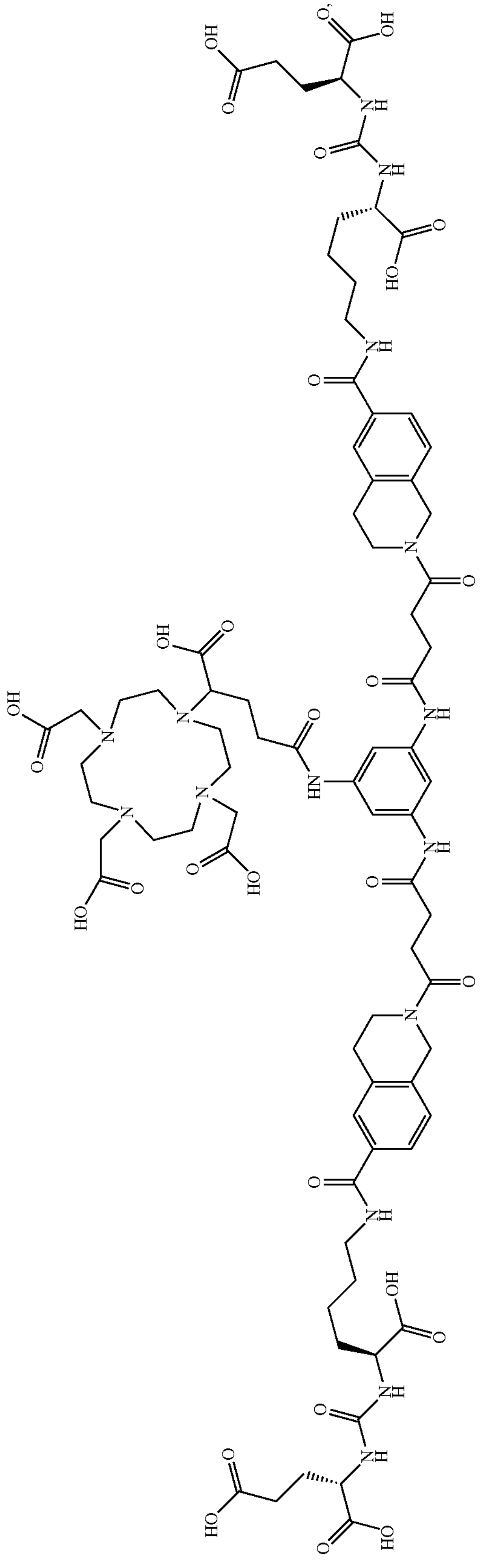

-continued
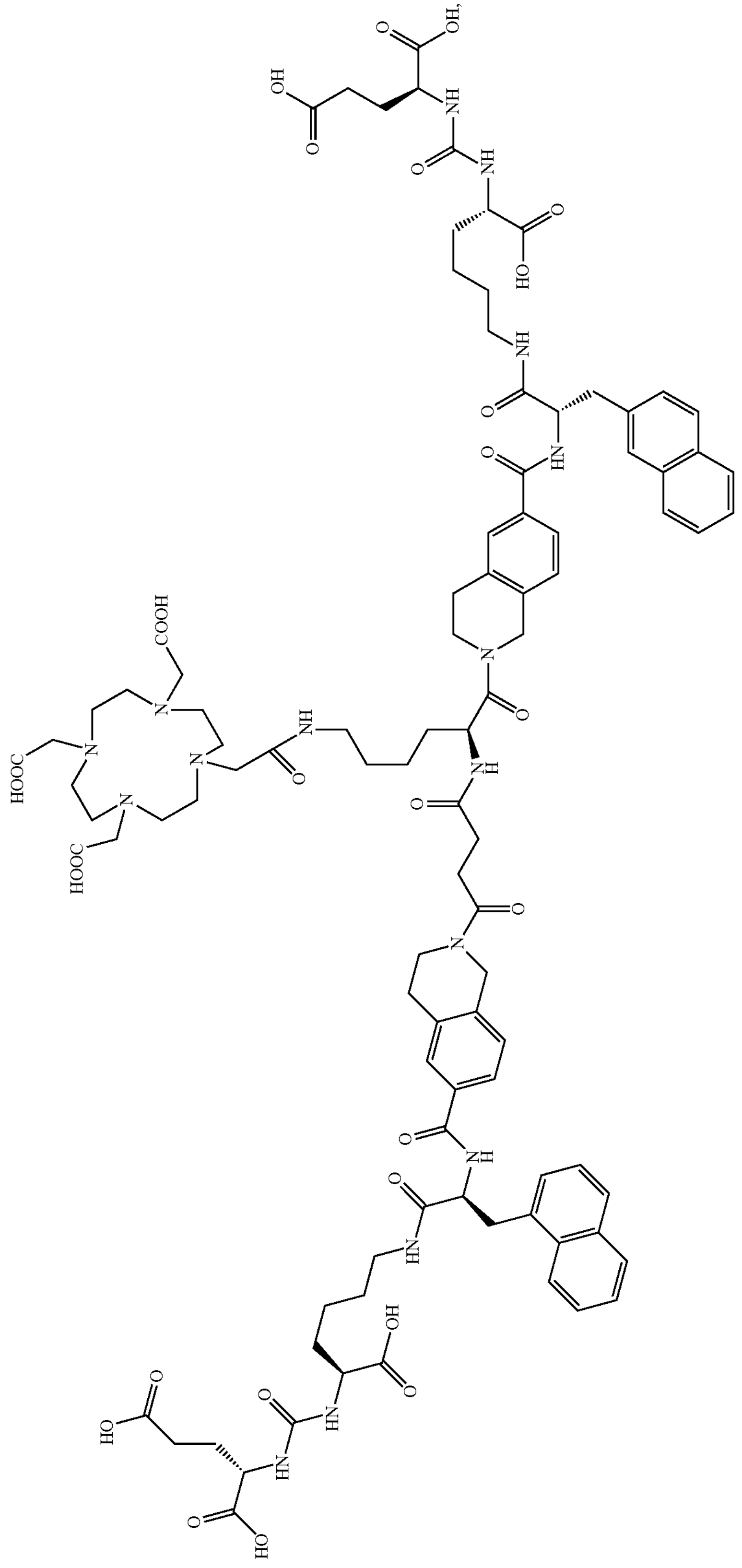

-continued
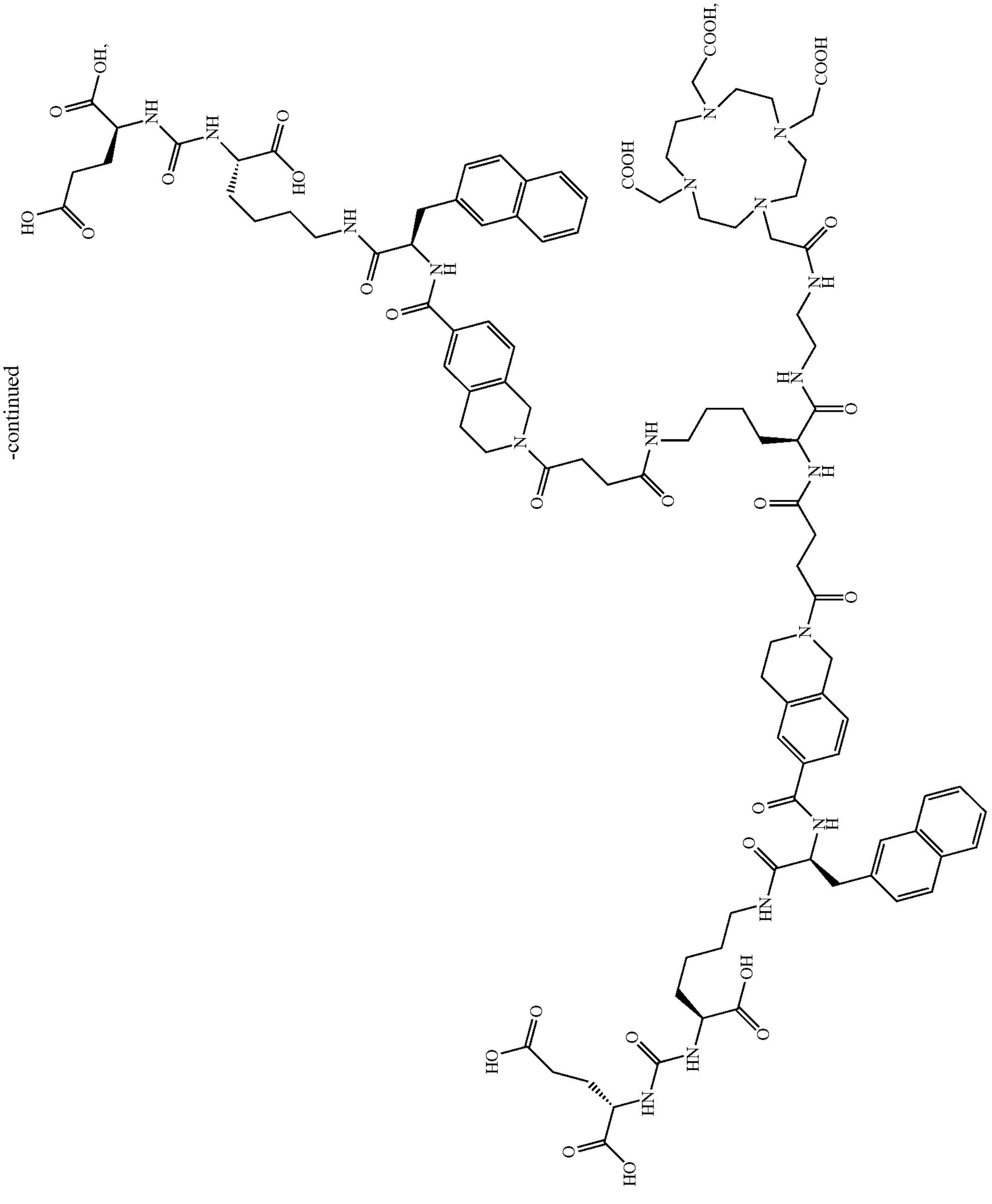

-continued
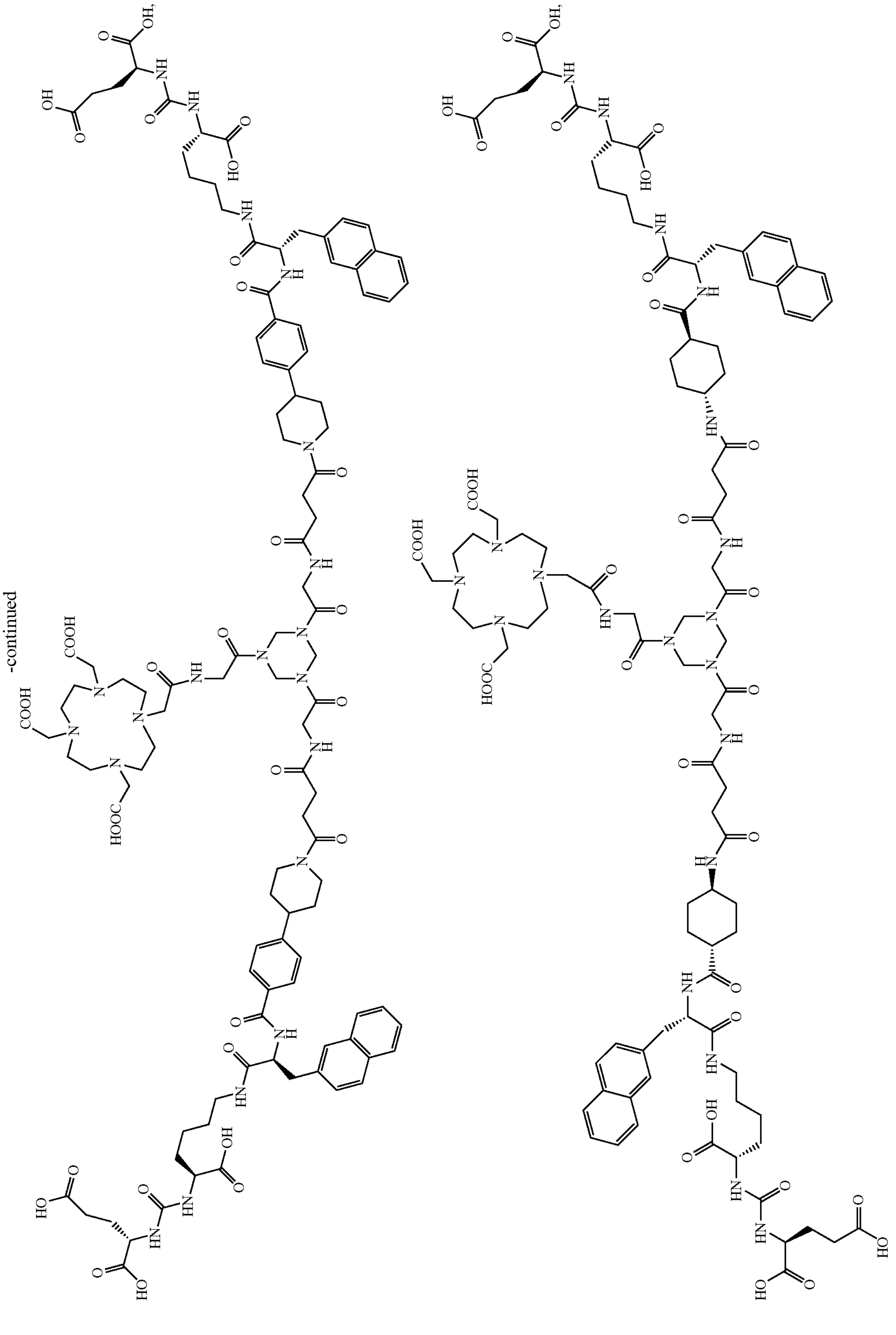

-continued
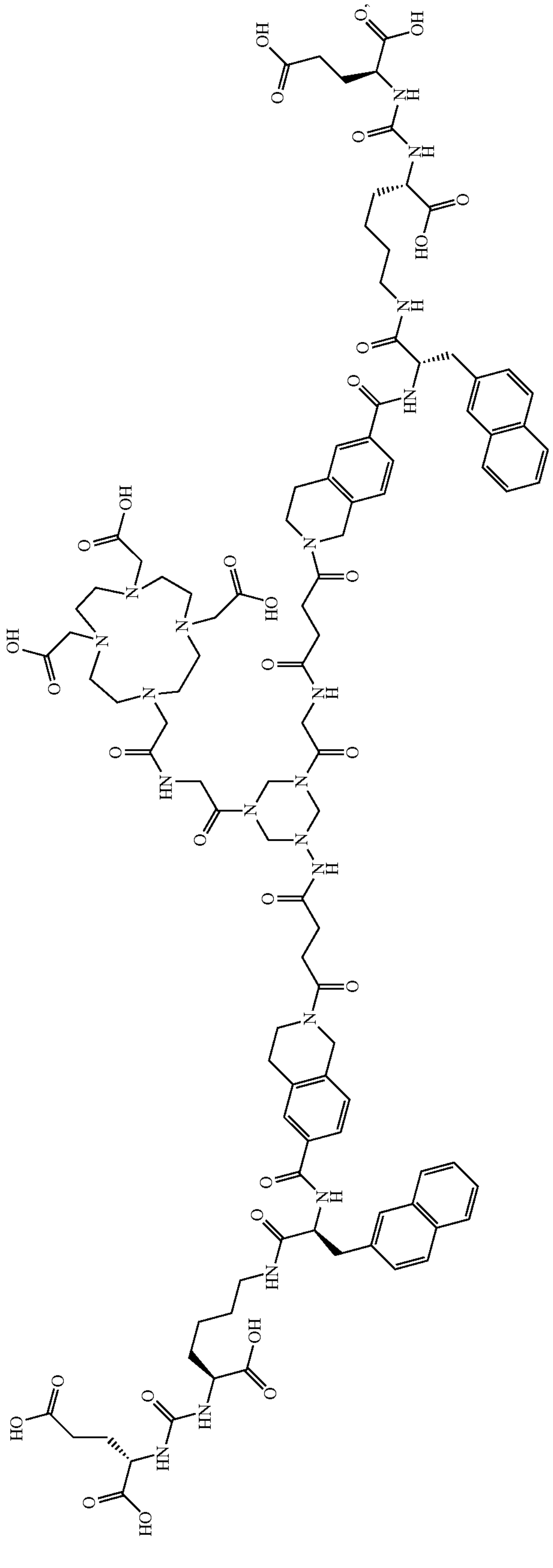

-continued
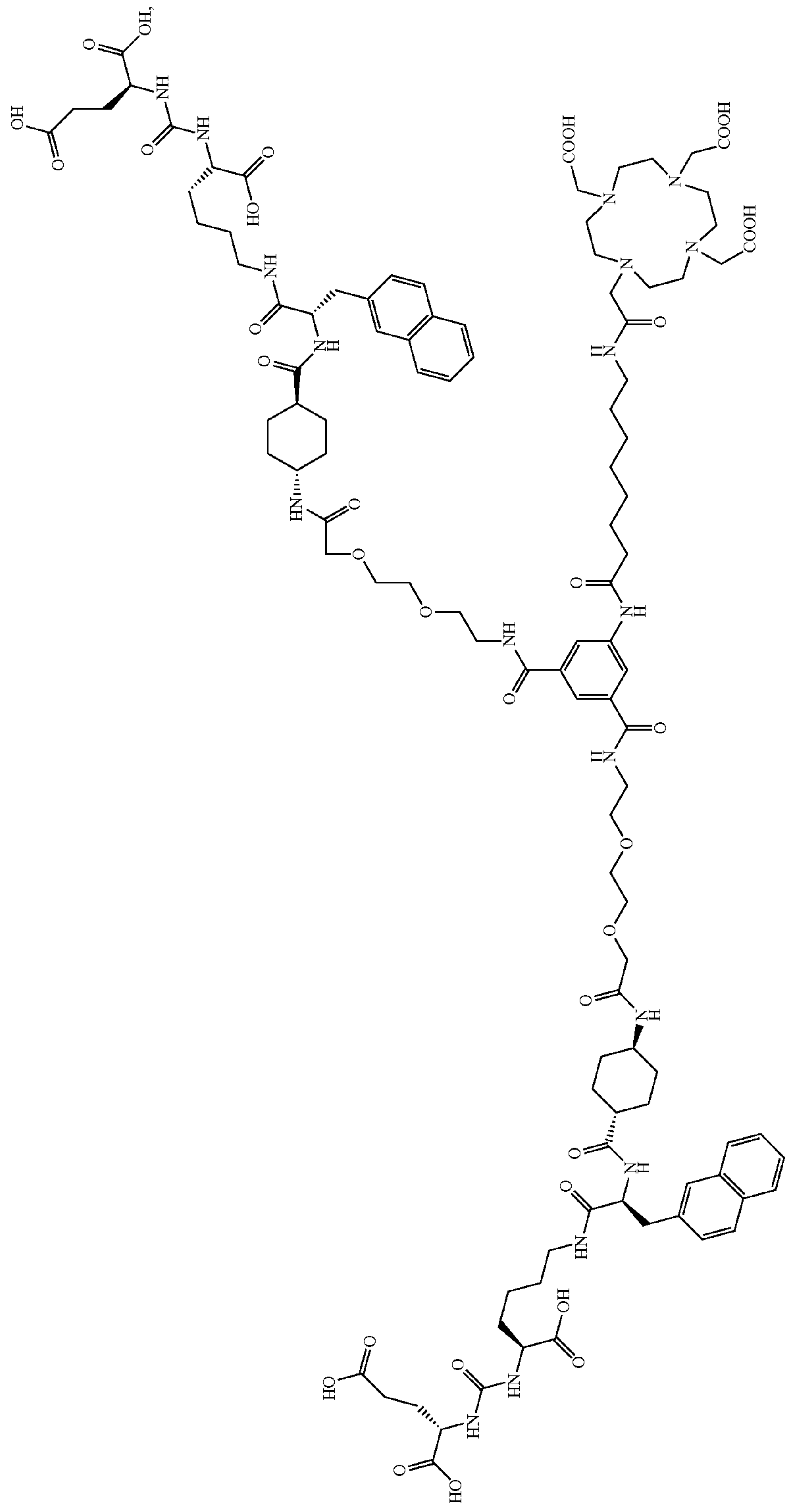

-continued
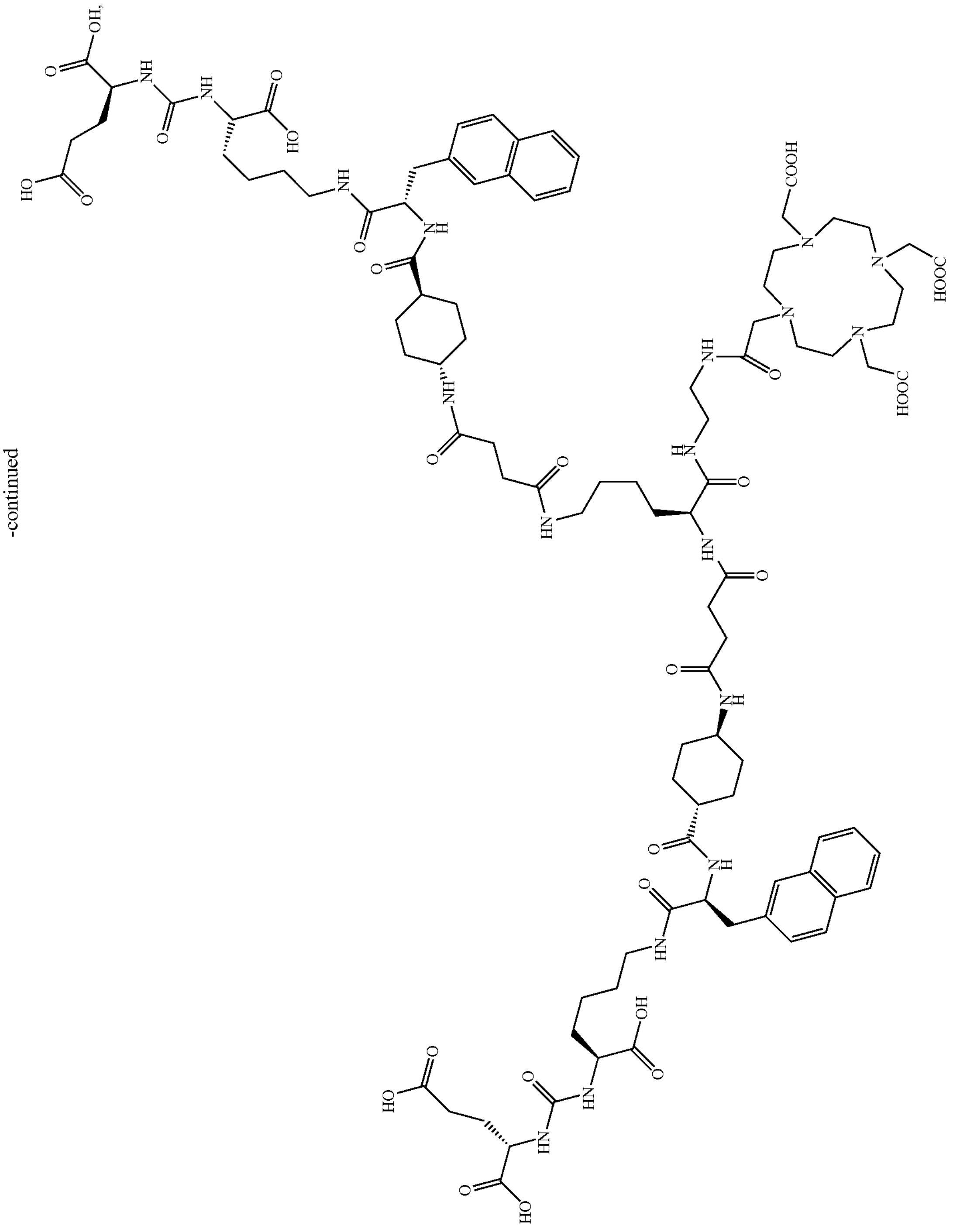

-continued
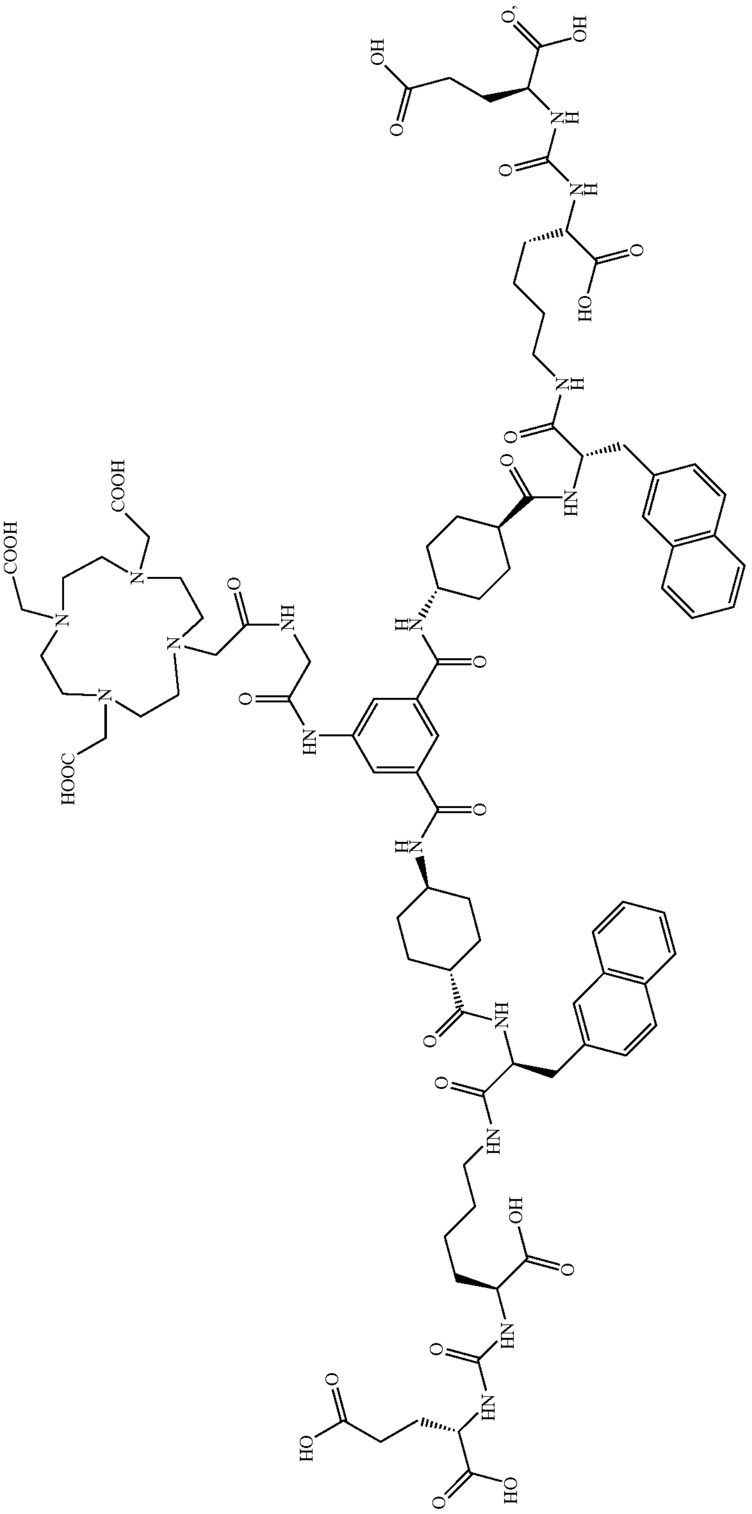

-continued
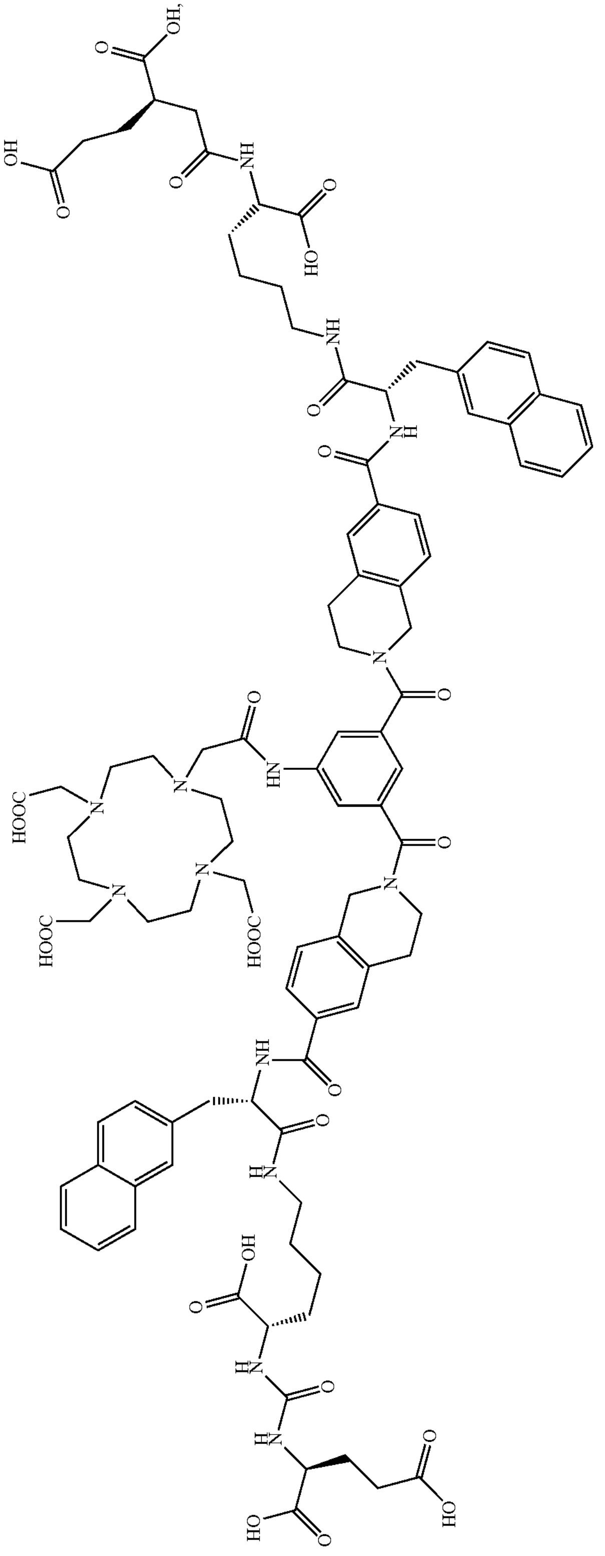

-continued
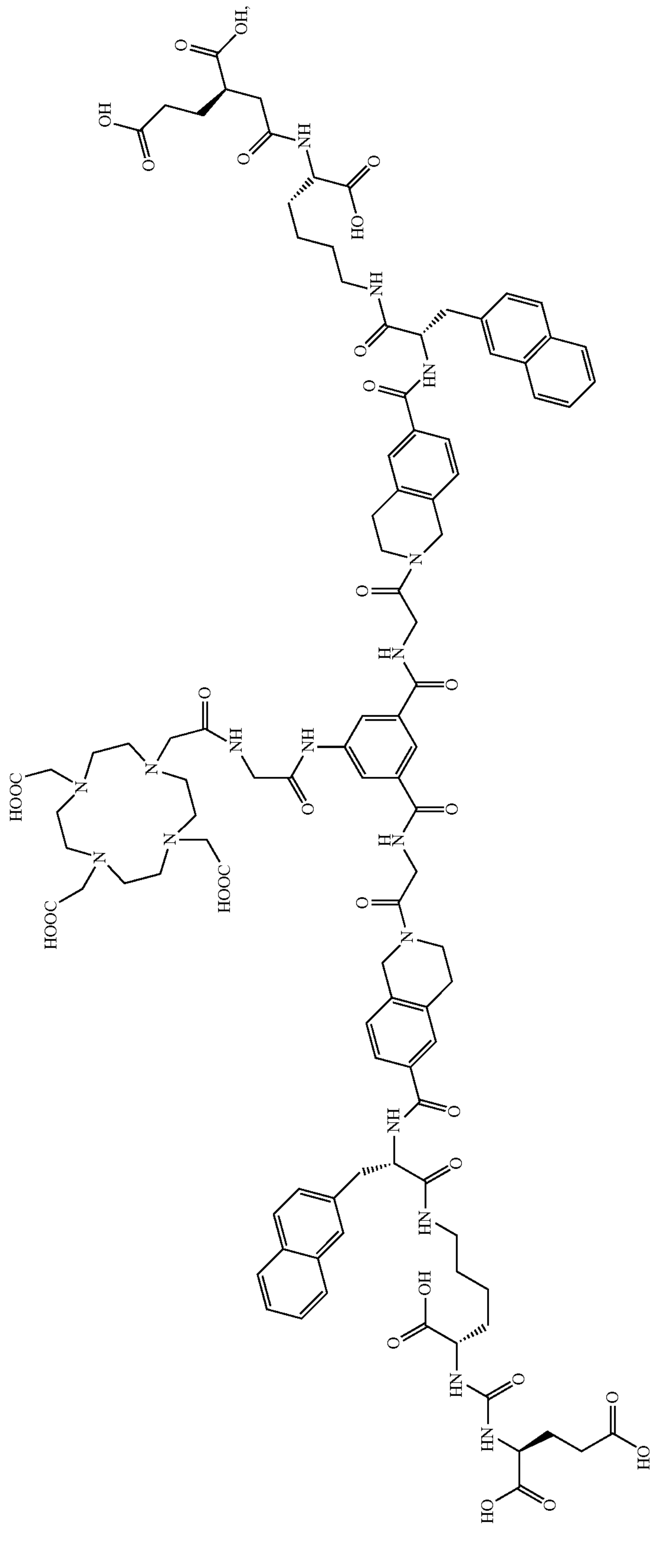

-continued
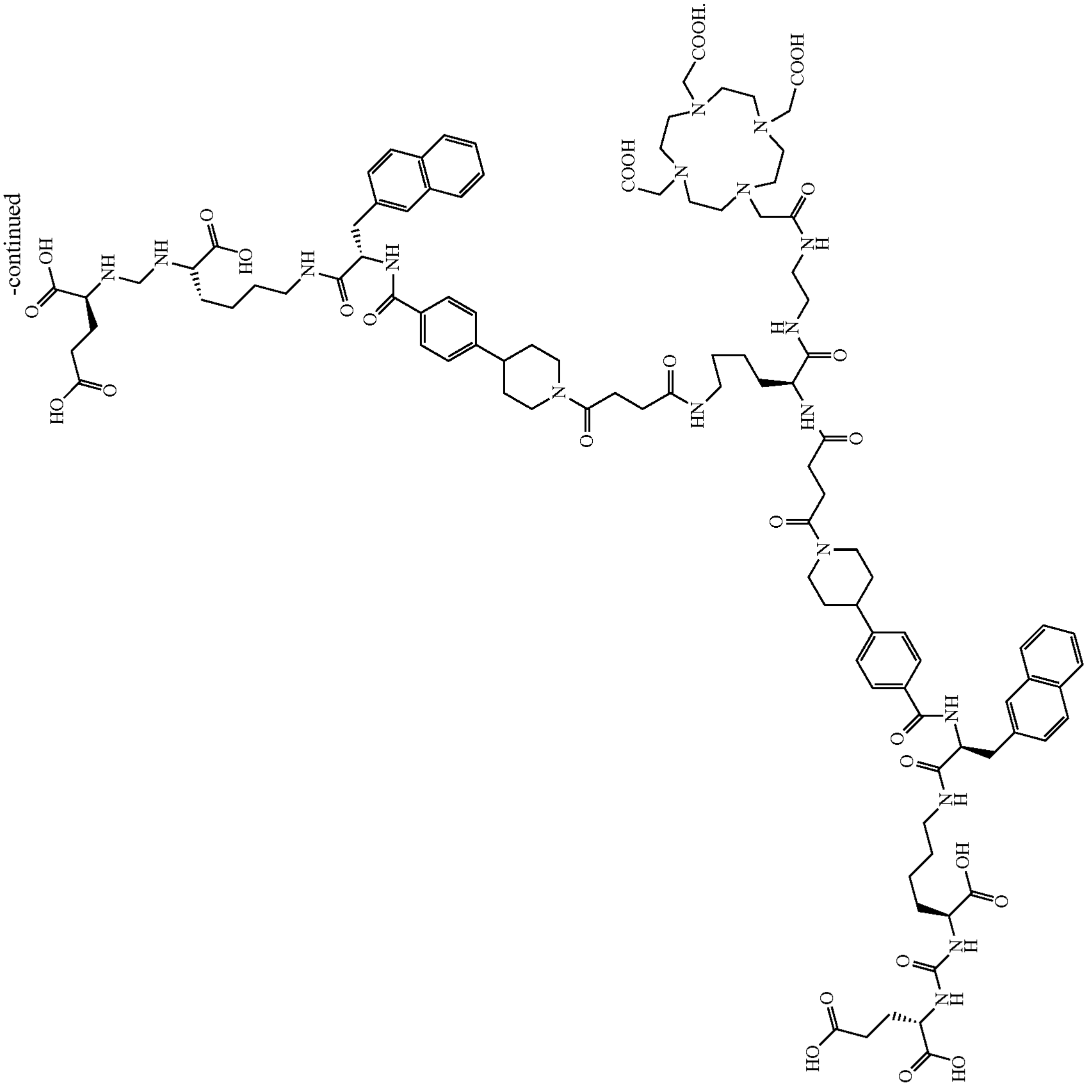

and 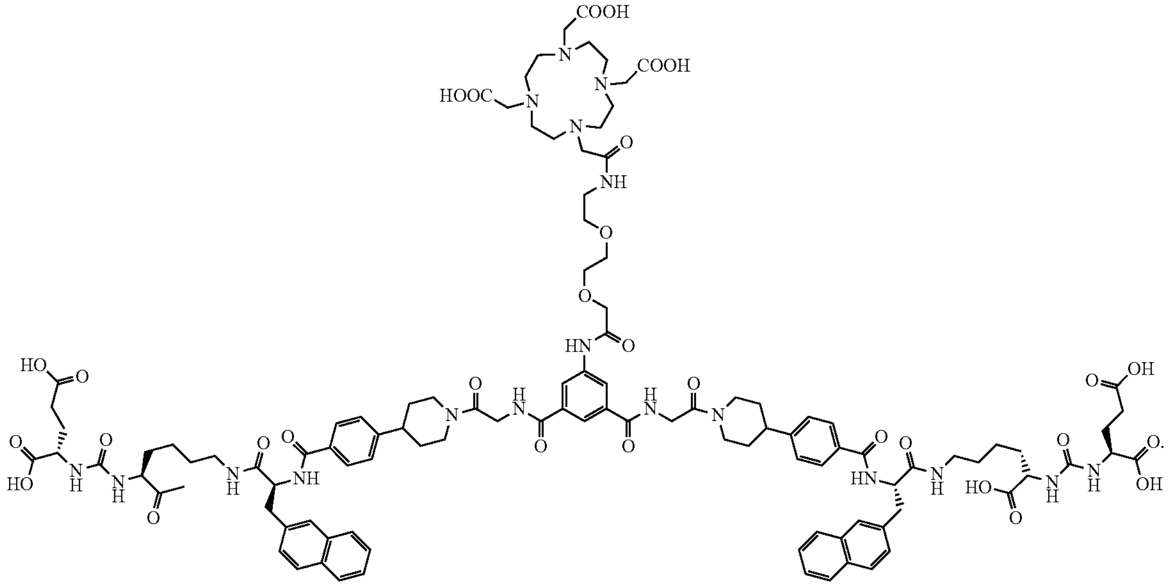

The present disclosure further provides a method for preparing the peptide urea derivative of formula I described above, comprising the following steps: chelating a radioactive metal ion with a compound of formula II;

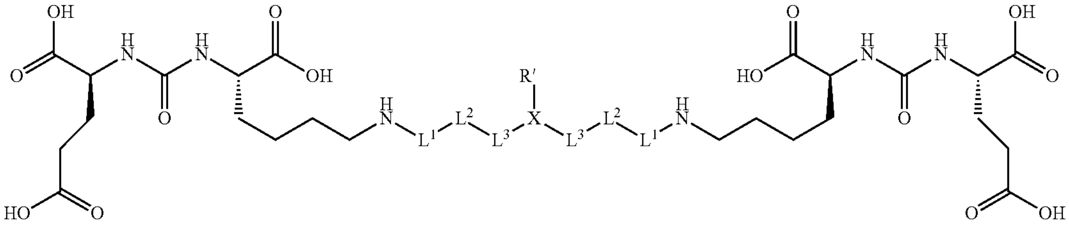
II wherein in the compound of formula II, R' is a group with metal ion chelating functionality.

The present disclosure further provides a compound of formula II,

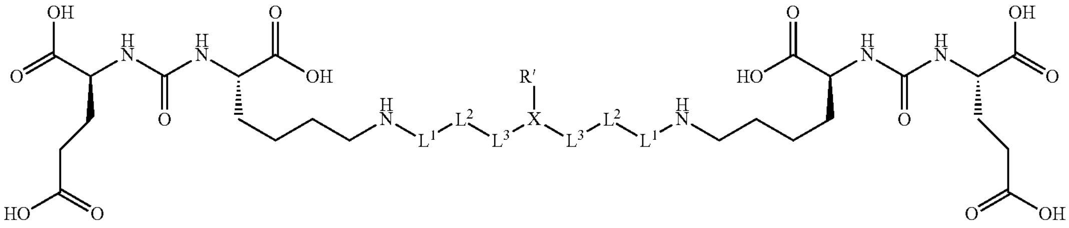
II wherein R' is a group with metal ion chelating functionality, and X, $L^1$, $L^2$, and $L^3$ are as defined above.

In the compound of formula II, the definition of the group with metal ion chelating functionality may be as defined above.

In the compound of formula II, the group with metal ion chelating functionality is not chelated with a metal ion.

The structure of the compound of formula II can be any one of the following:

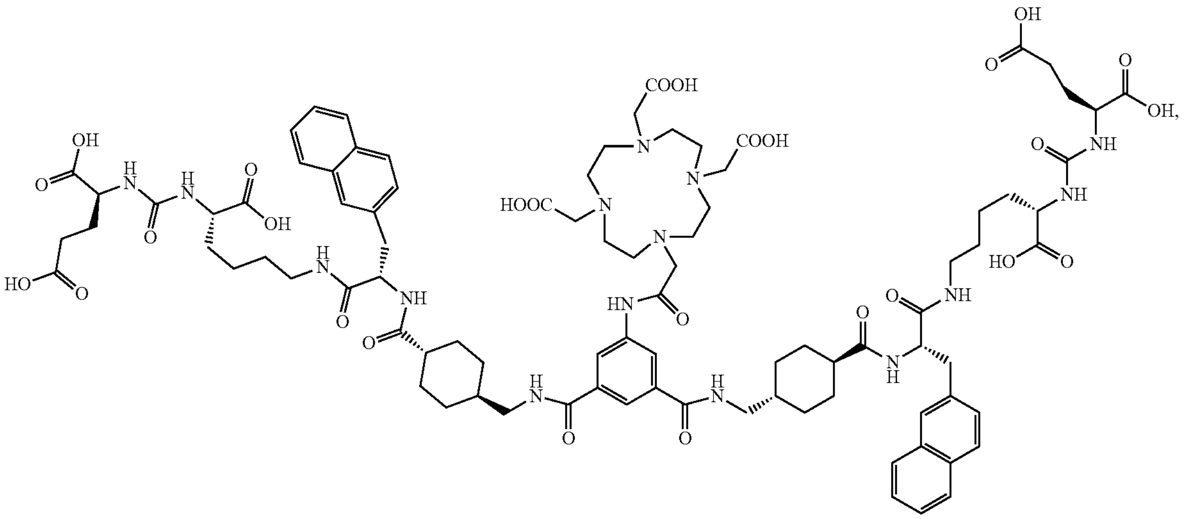

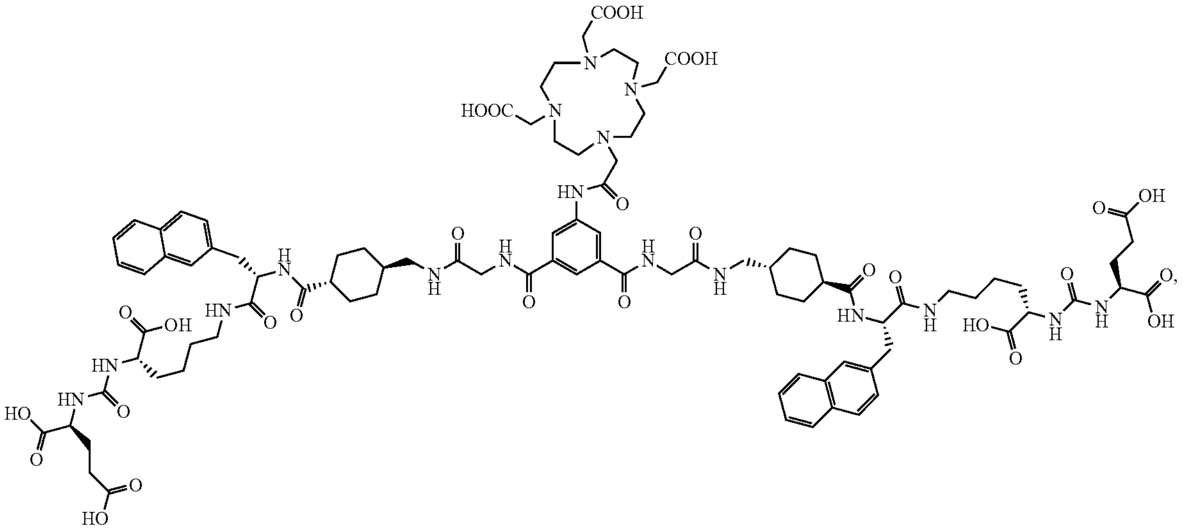 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CNC(=O)c2cc(NC(=O)CN3CCN(CC(=O)O)CCN(CC(=O)O)CCN(CC(=O)O)CC3)cc(C(=O)NCC(=O)NC[C@H]3CC[C@H](C(=O)N[C@@H](Cc4ccc5ccccc5c4)C(=O)NCCCC[C@H](NC(=O)N[C@@H](CCC(=O)O)C(=O)O)C(=O)O)CC3)c2)CC1)C(=O)O)C(=O)O]

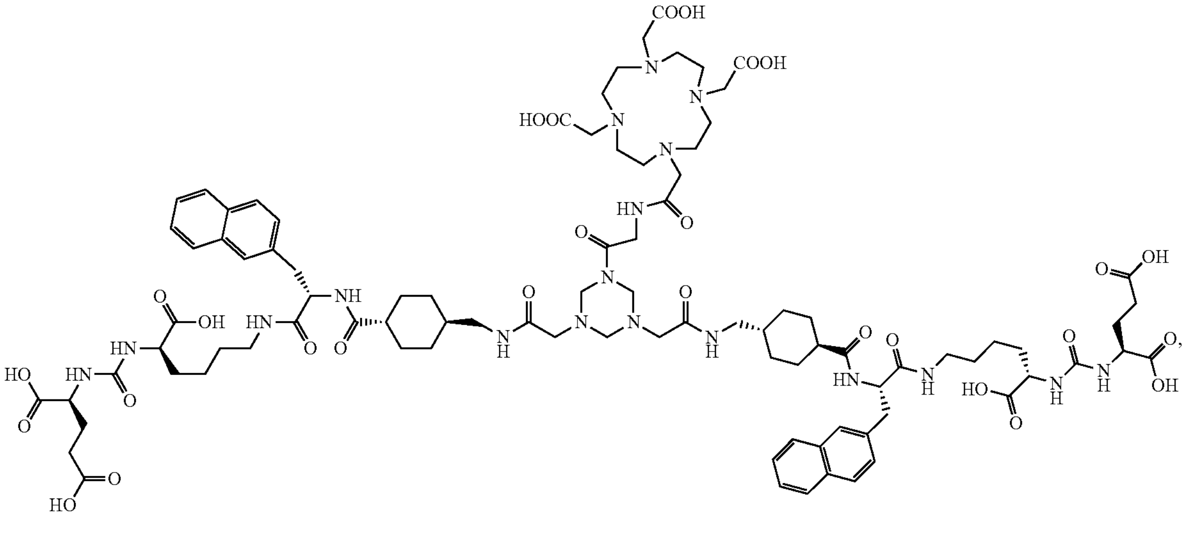

-continued
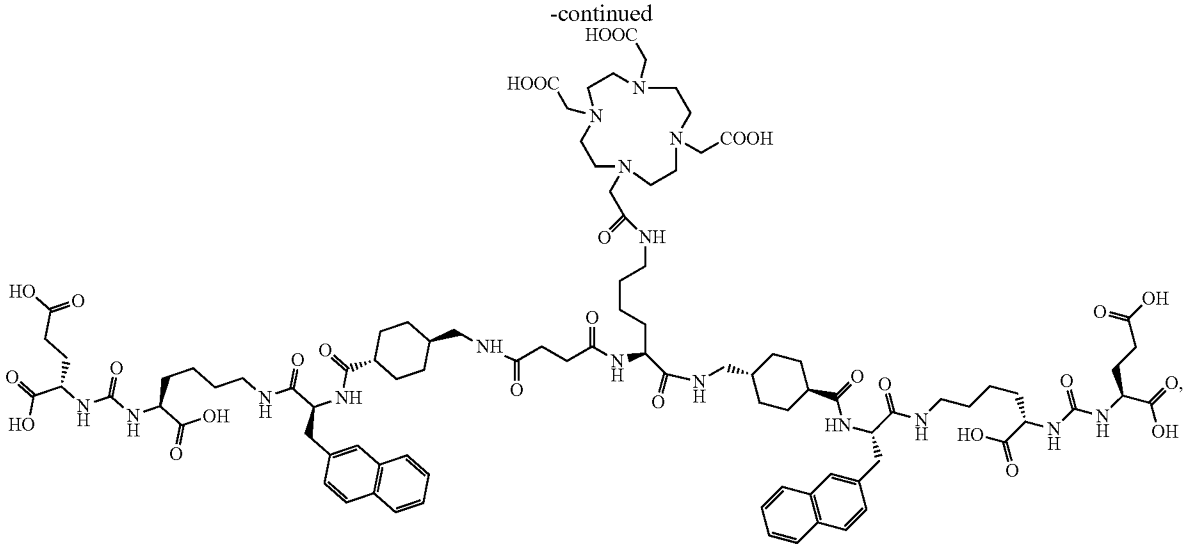
,
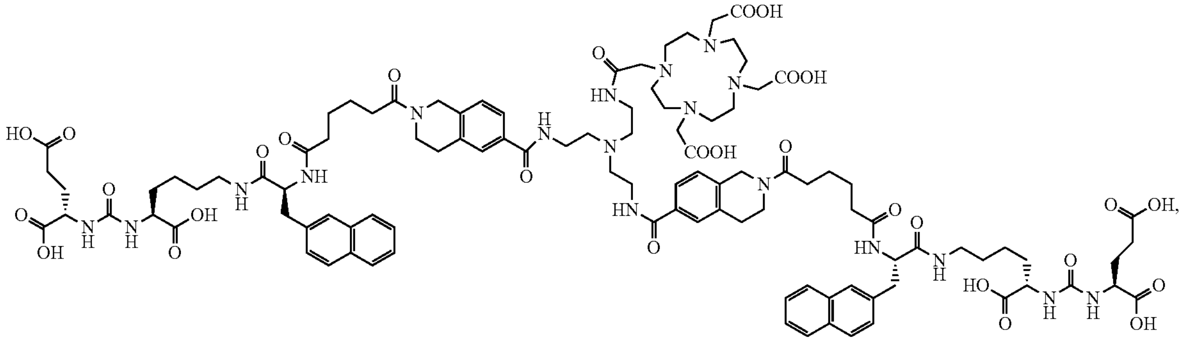
,
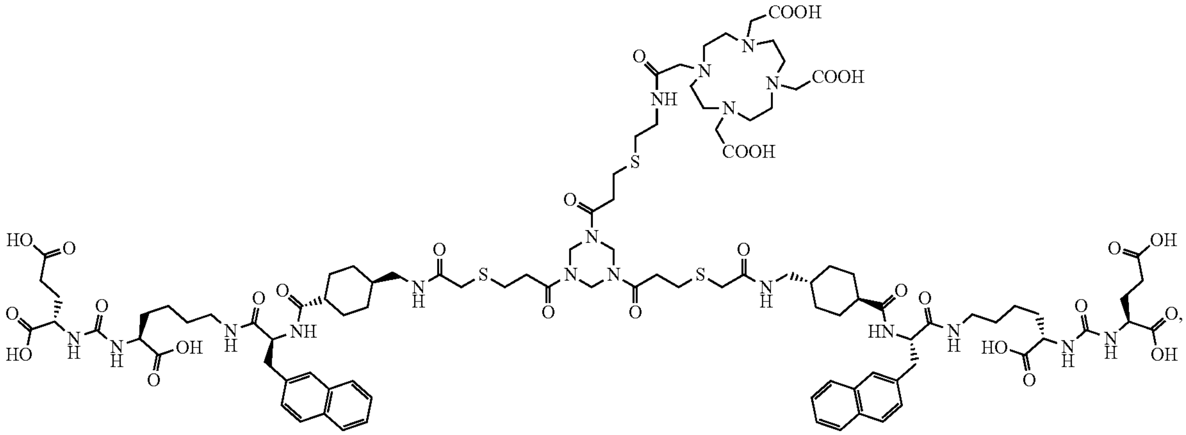
,
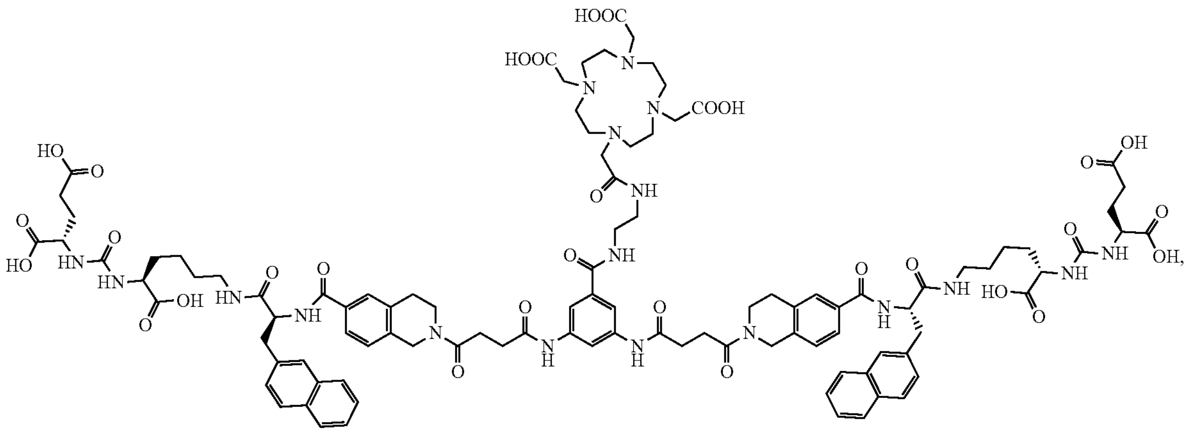
,

-continued
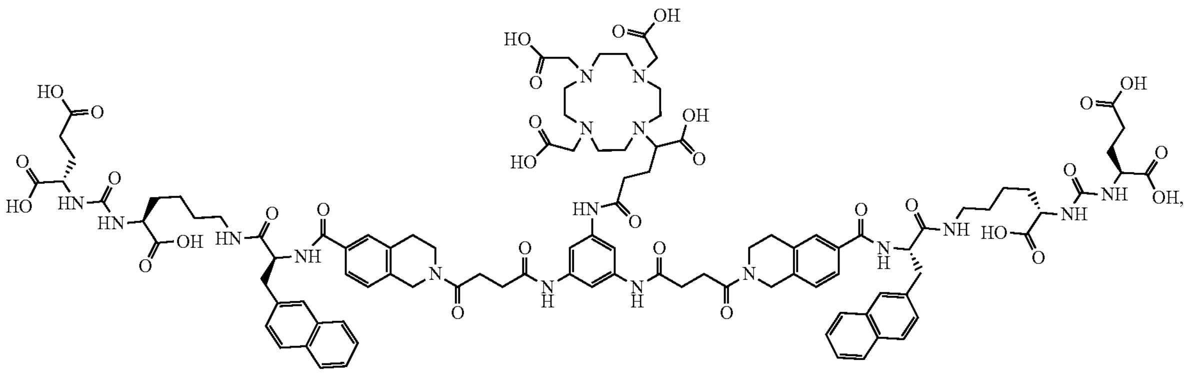
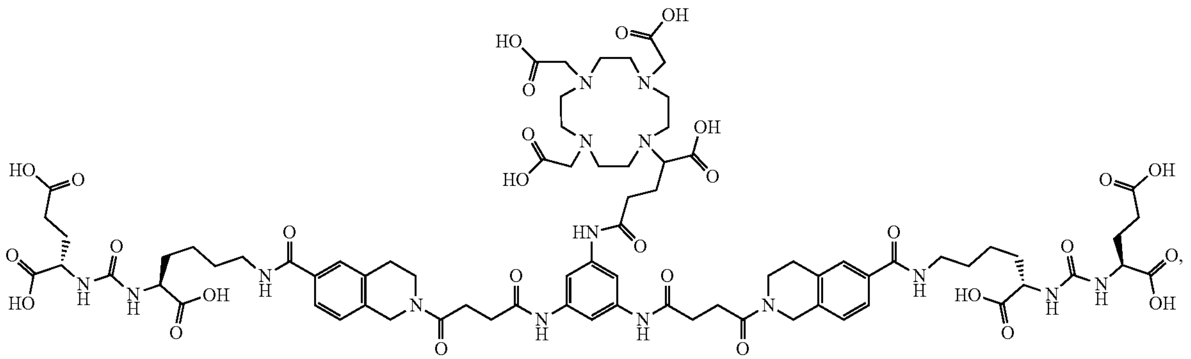
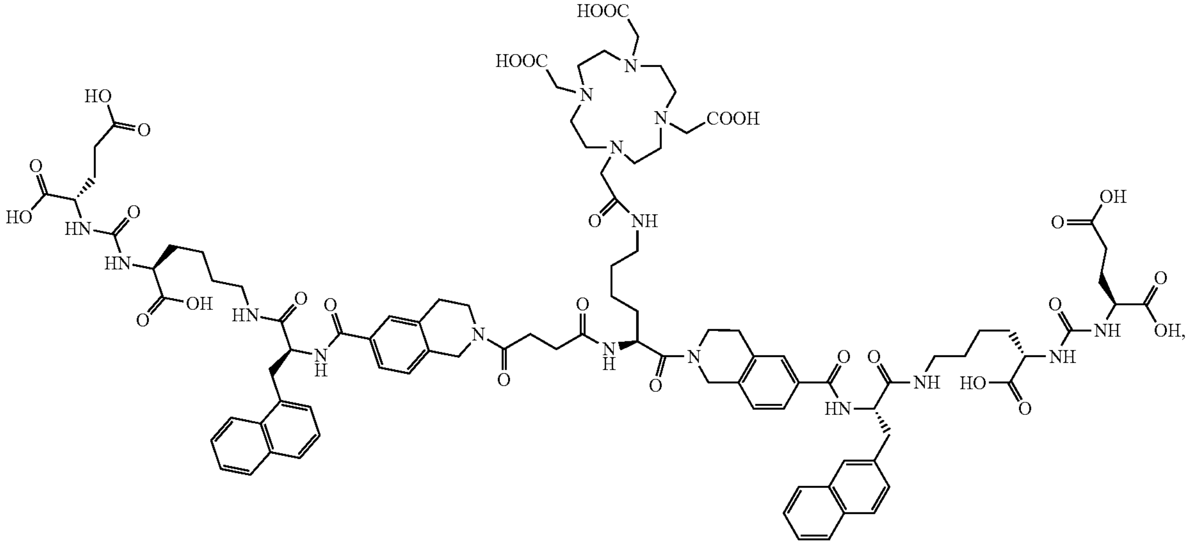

-continued
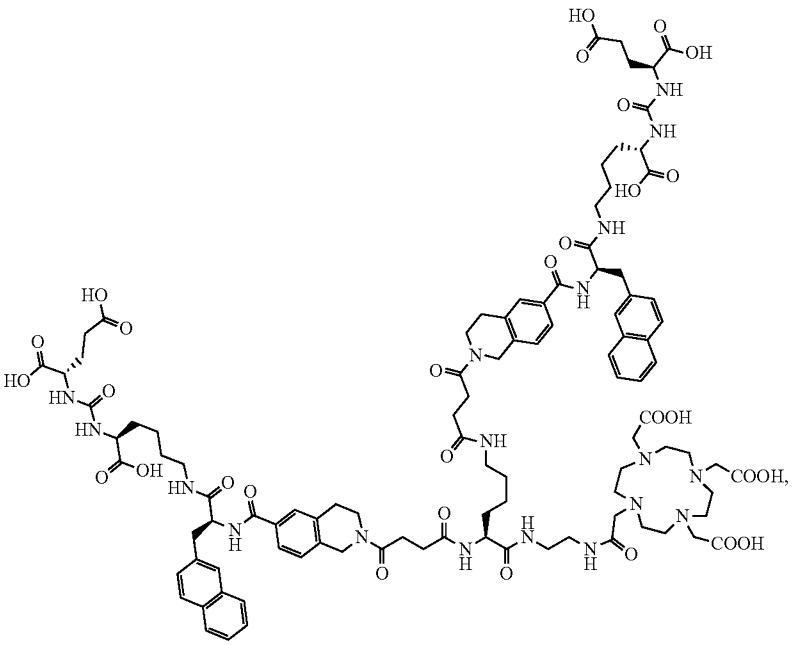
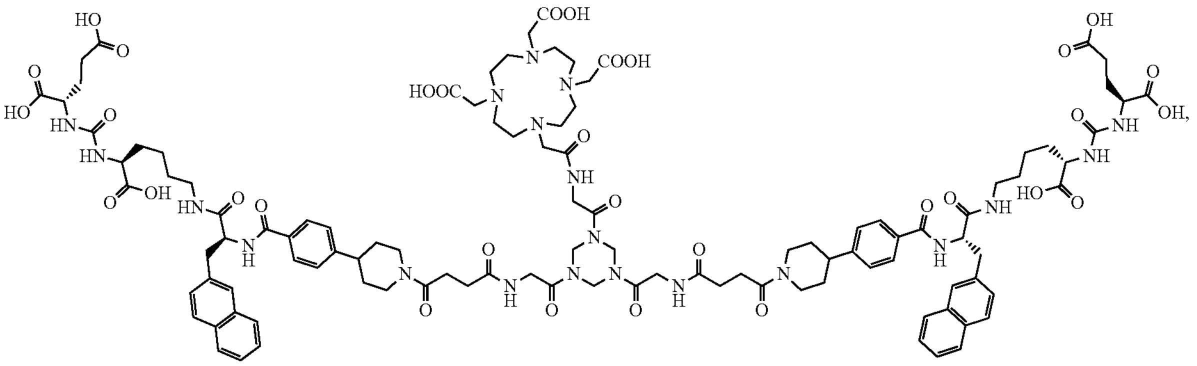
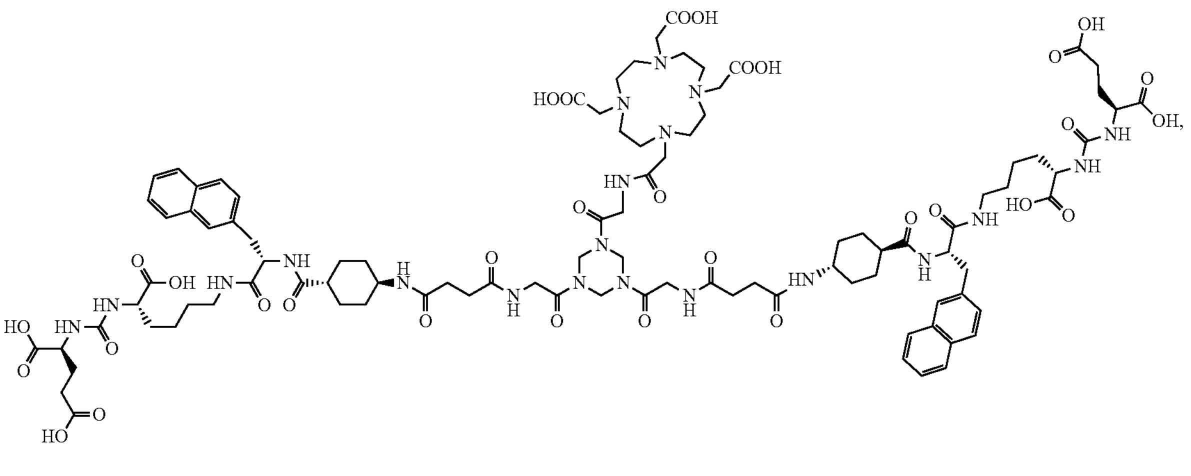

-continued
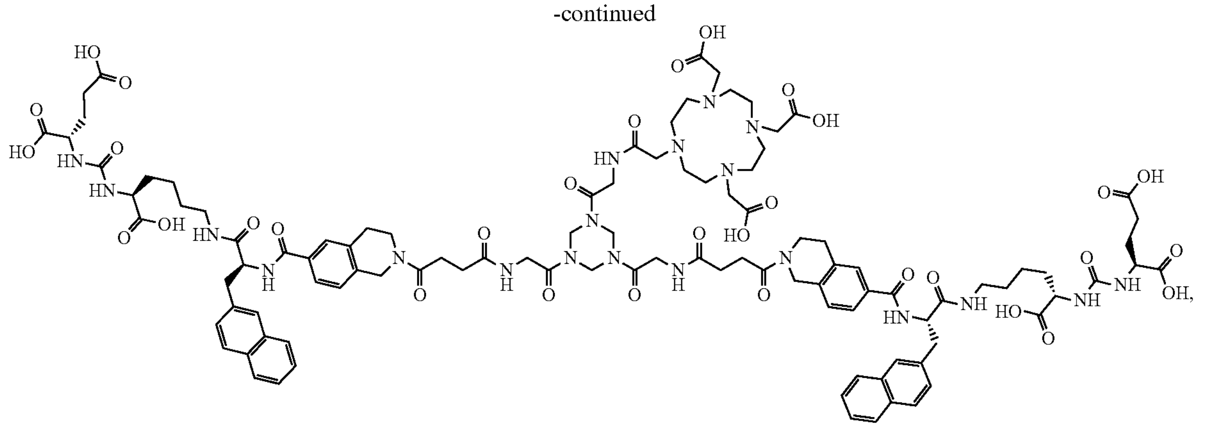
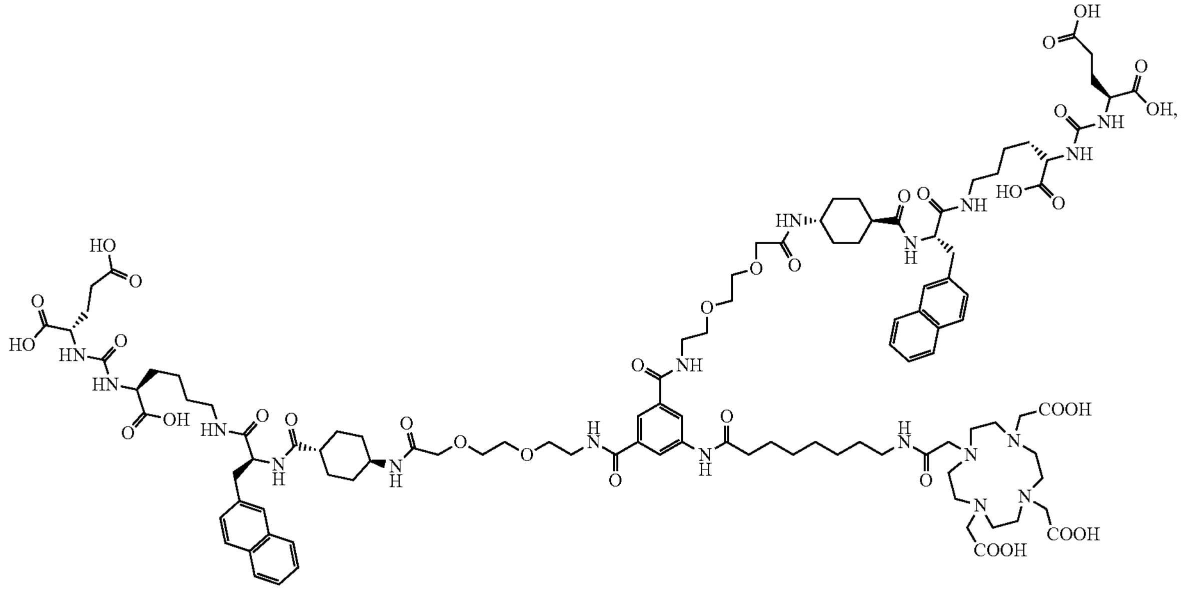
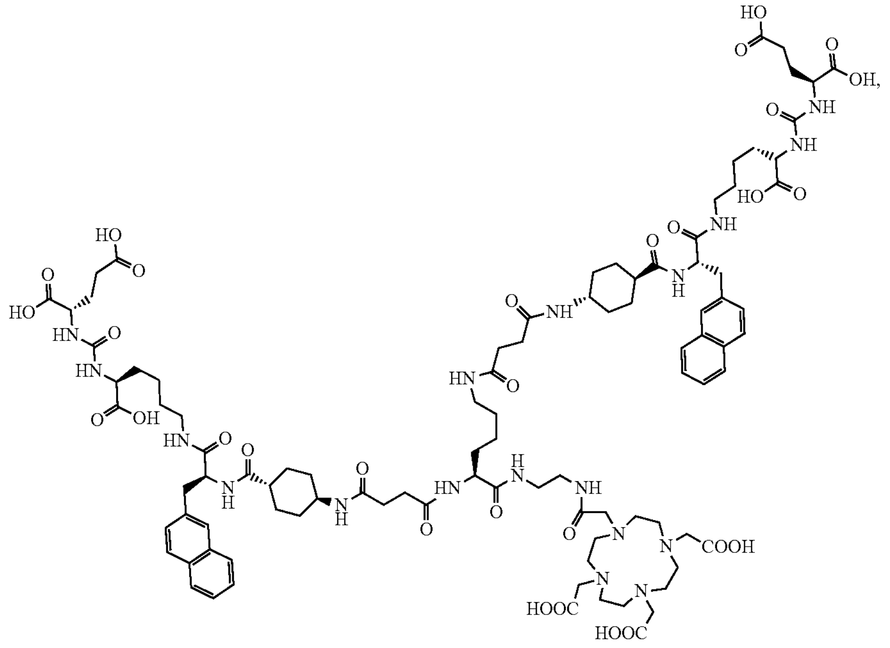

-continued
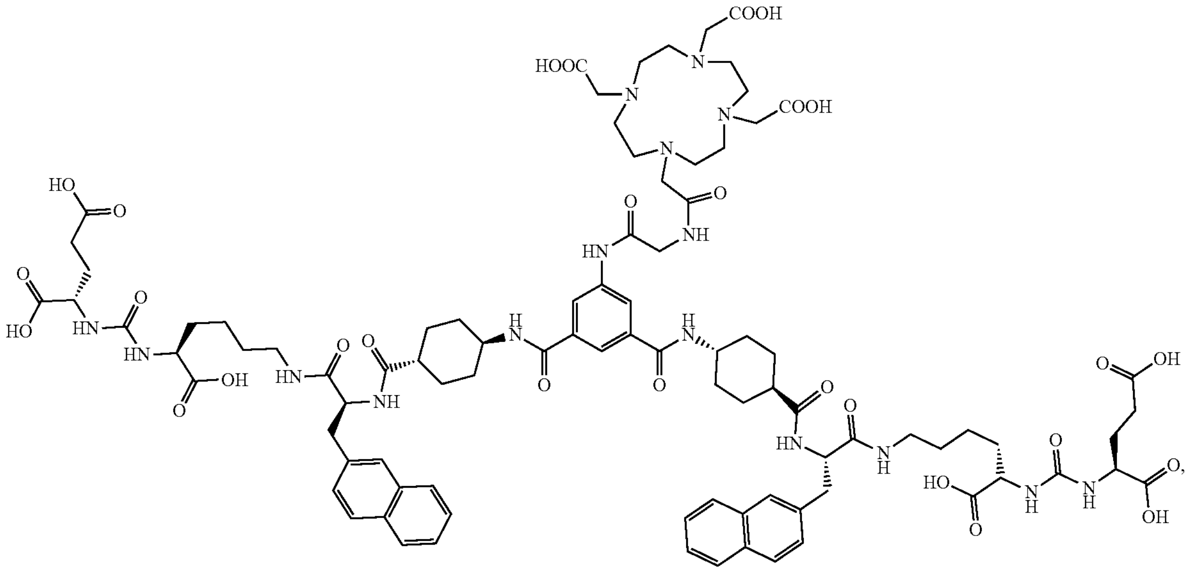
,
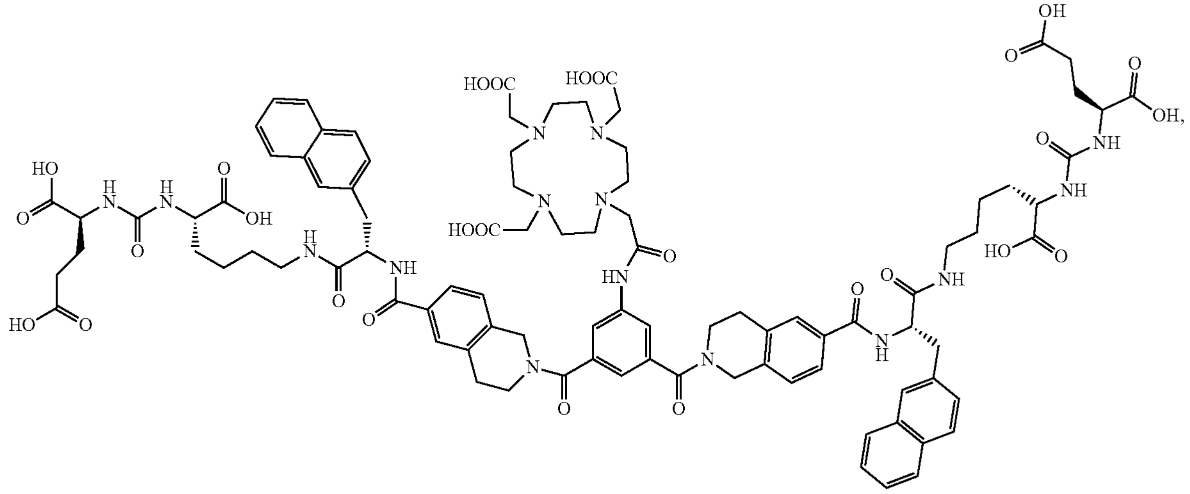
,
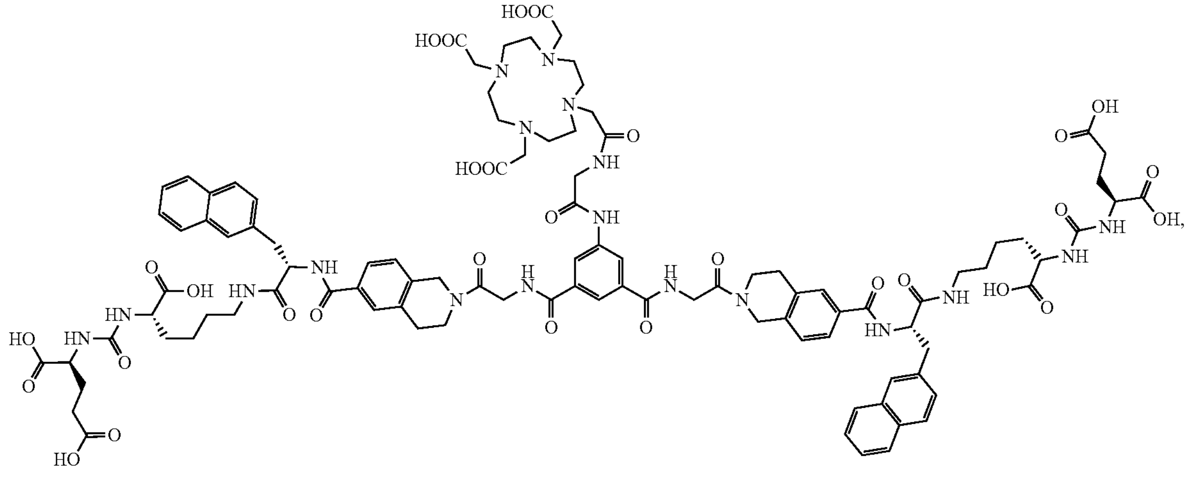
,

-continued
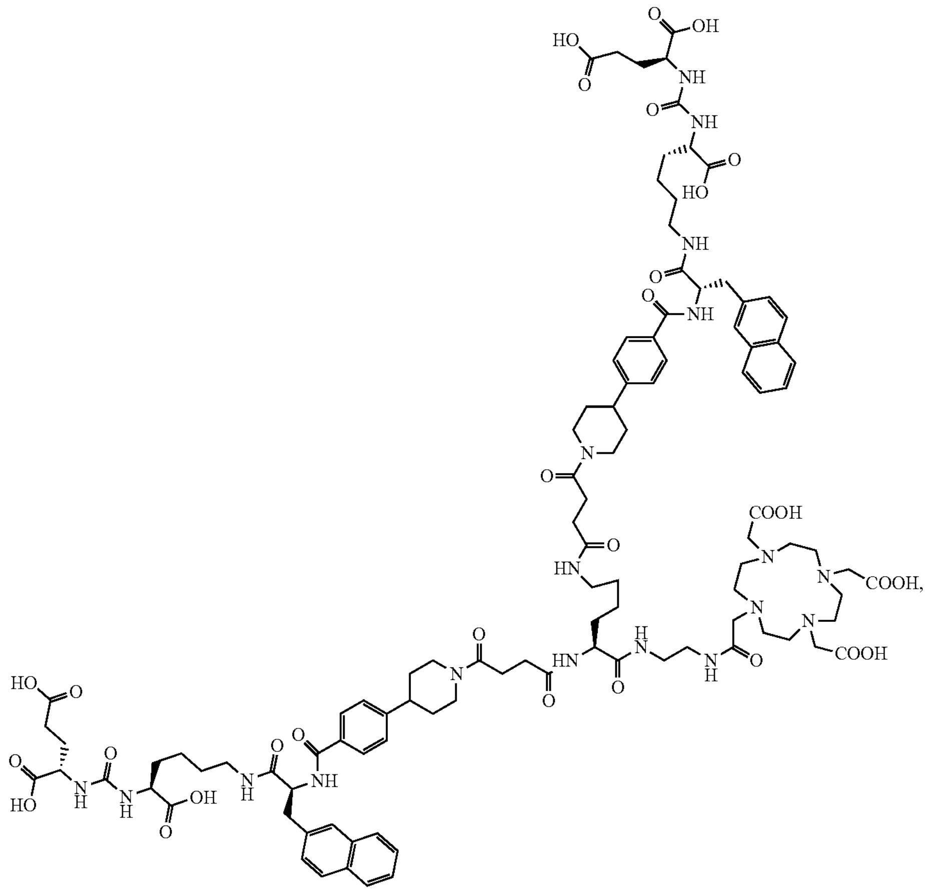
and
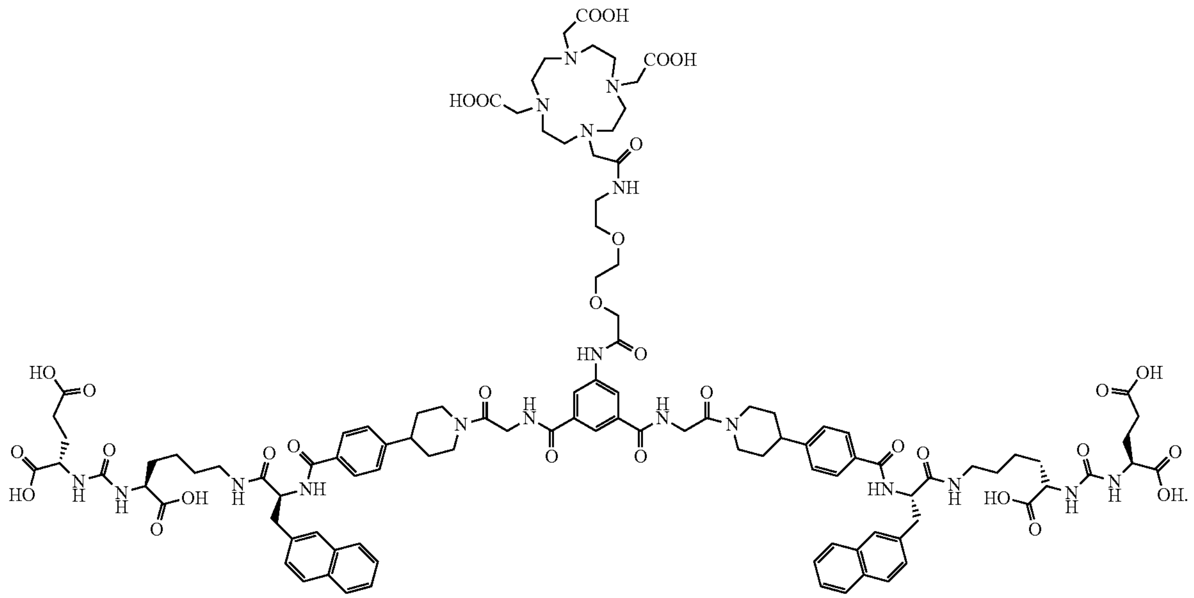

The present disclosure further provides one of the following compounds:
M4
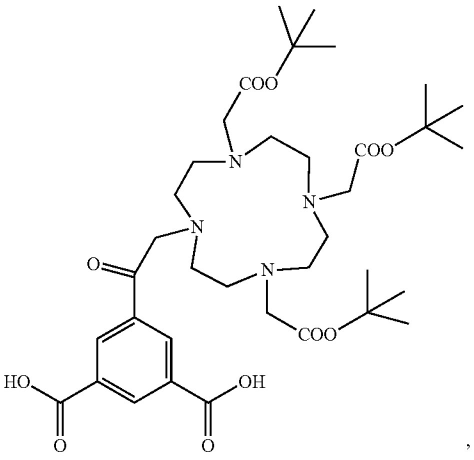
,
M5
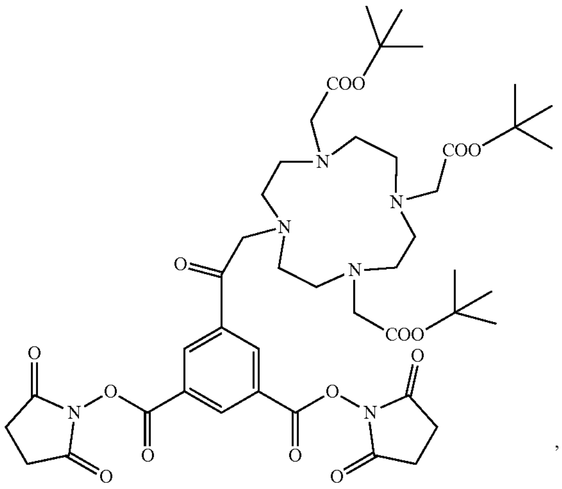
,
M7
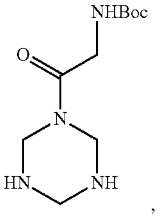
,
M8
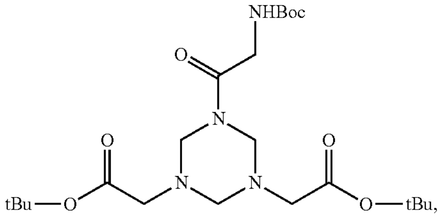
M9
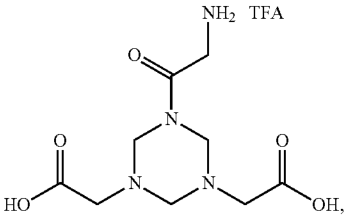
M10
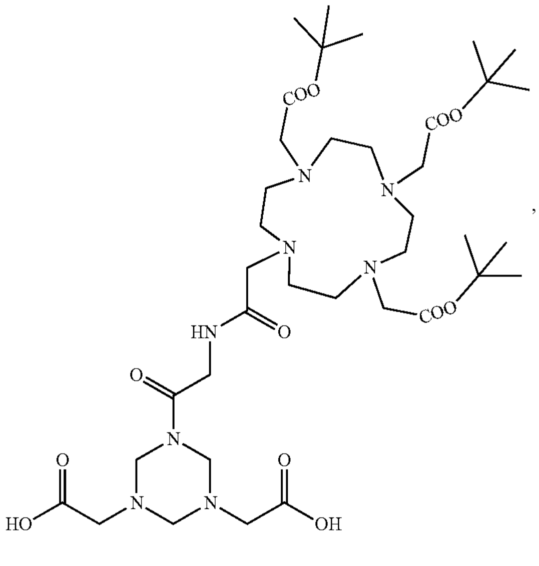
, -continued
M11
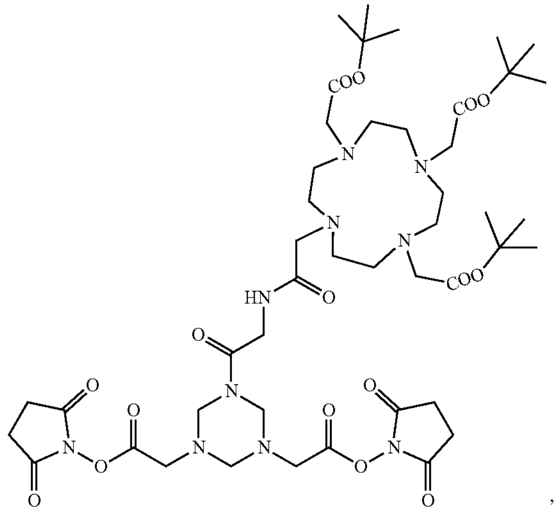
,
M12
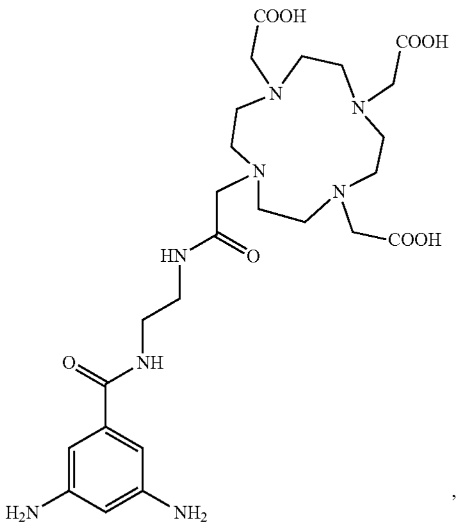
,
M13
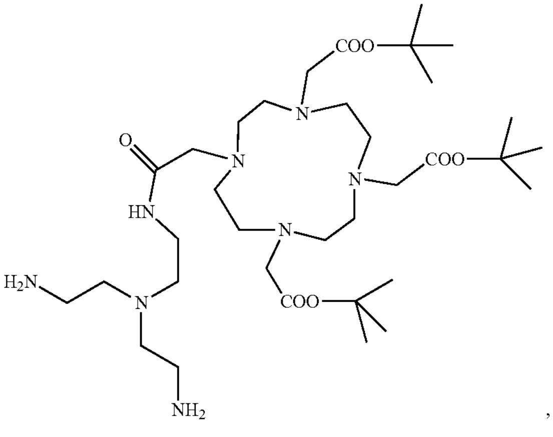
,
M 14
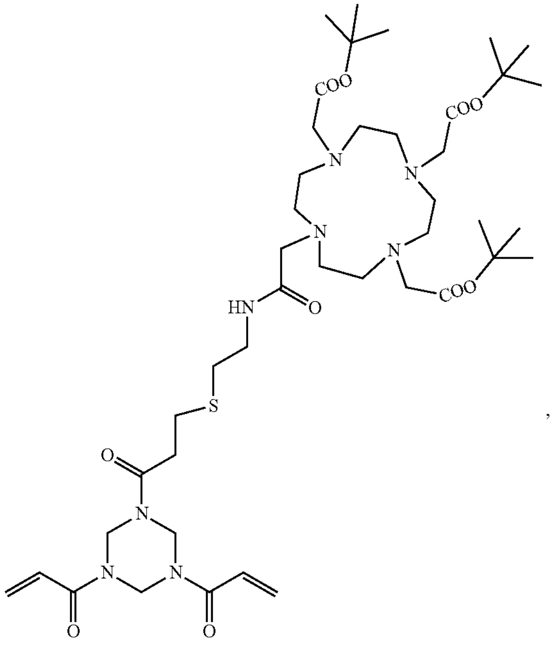
, -continued
M2a
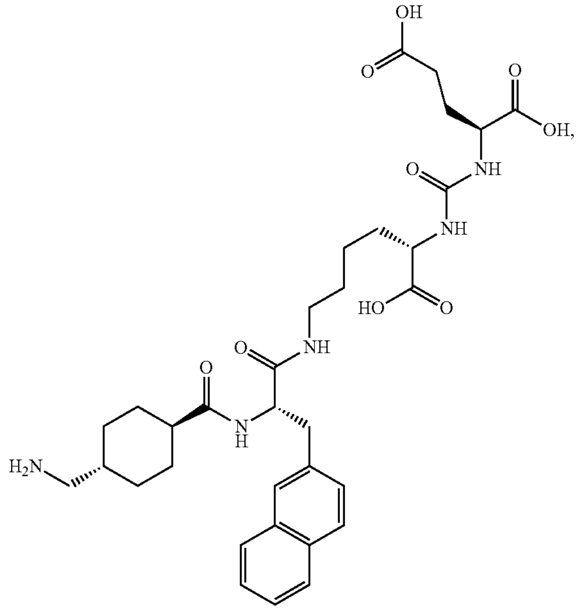
M3a
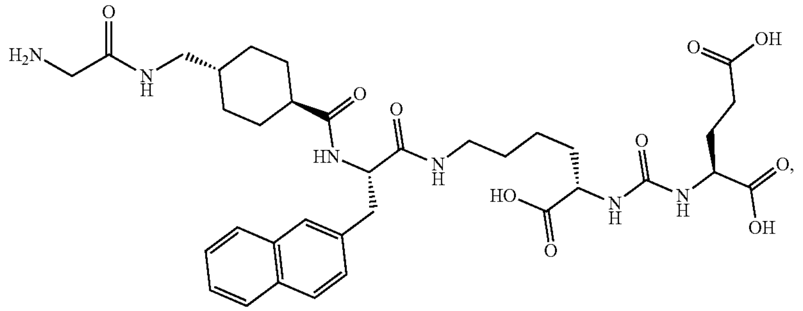
M3b
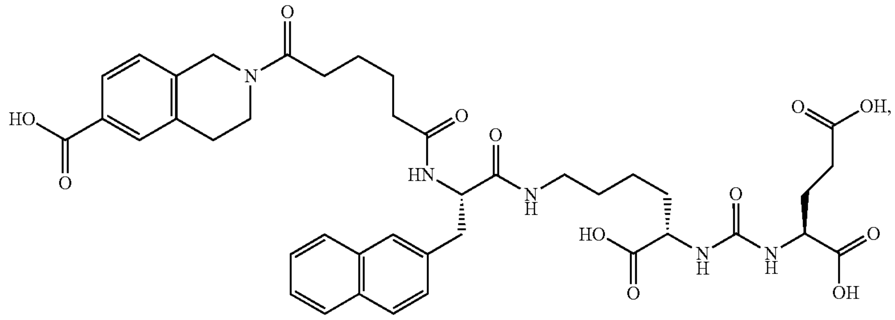
M3c
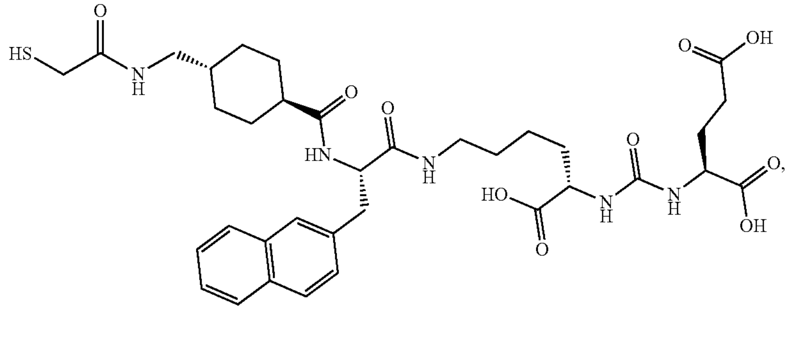

-continued
M3d
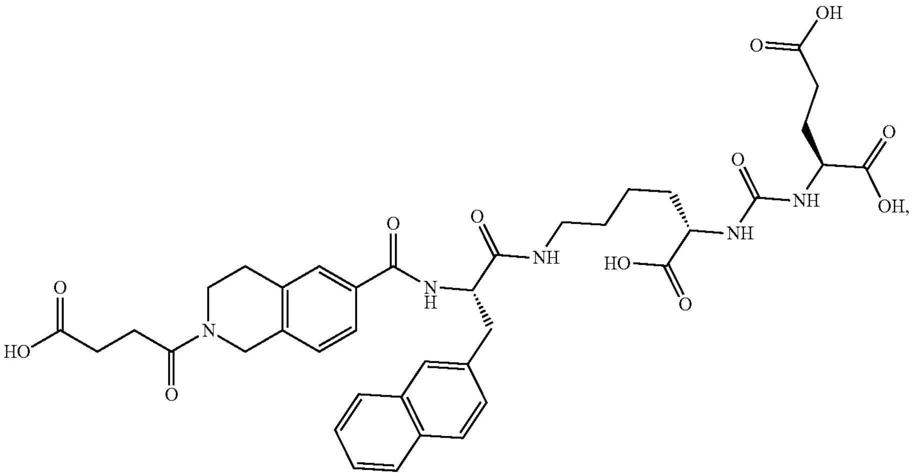
M3e
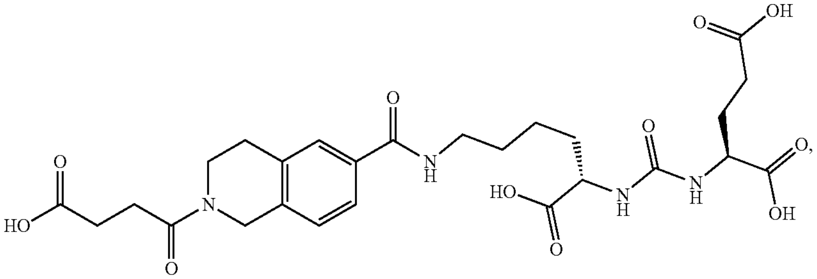
M3f
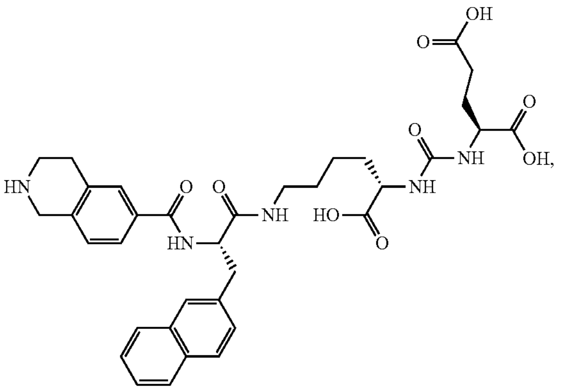
JH-04S10-01
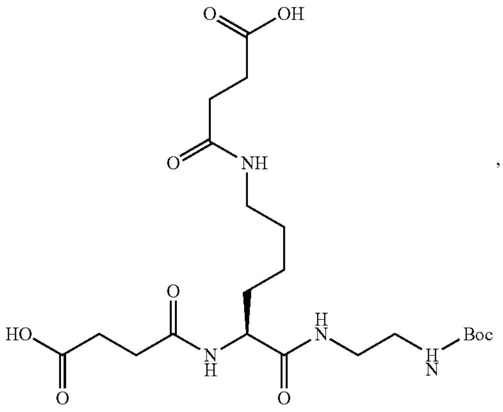
,
DB-11-01
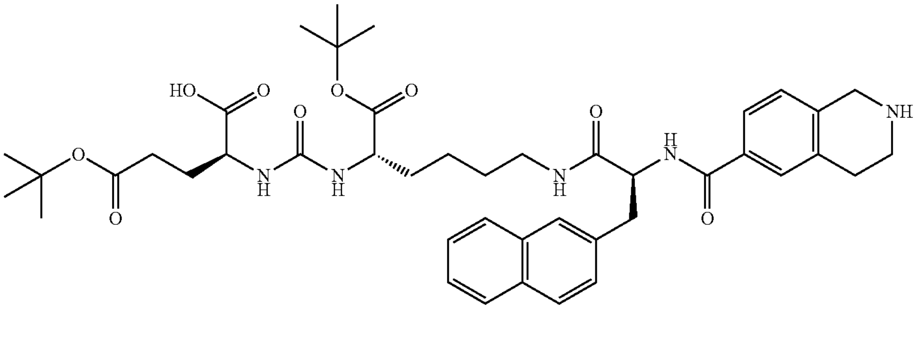

-continued
DB-11-02
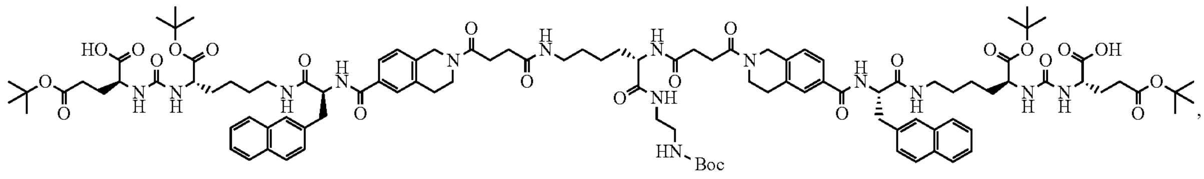
,
DB-11-03
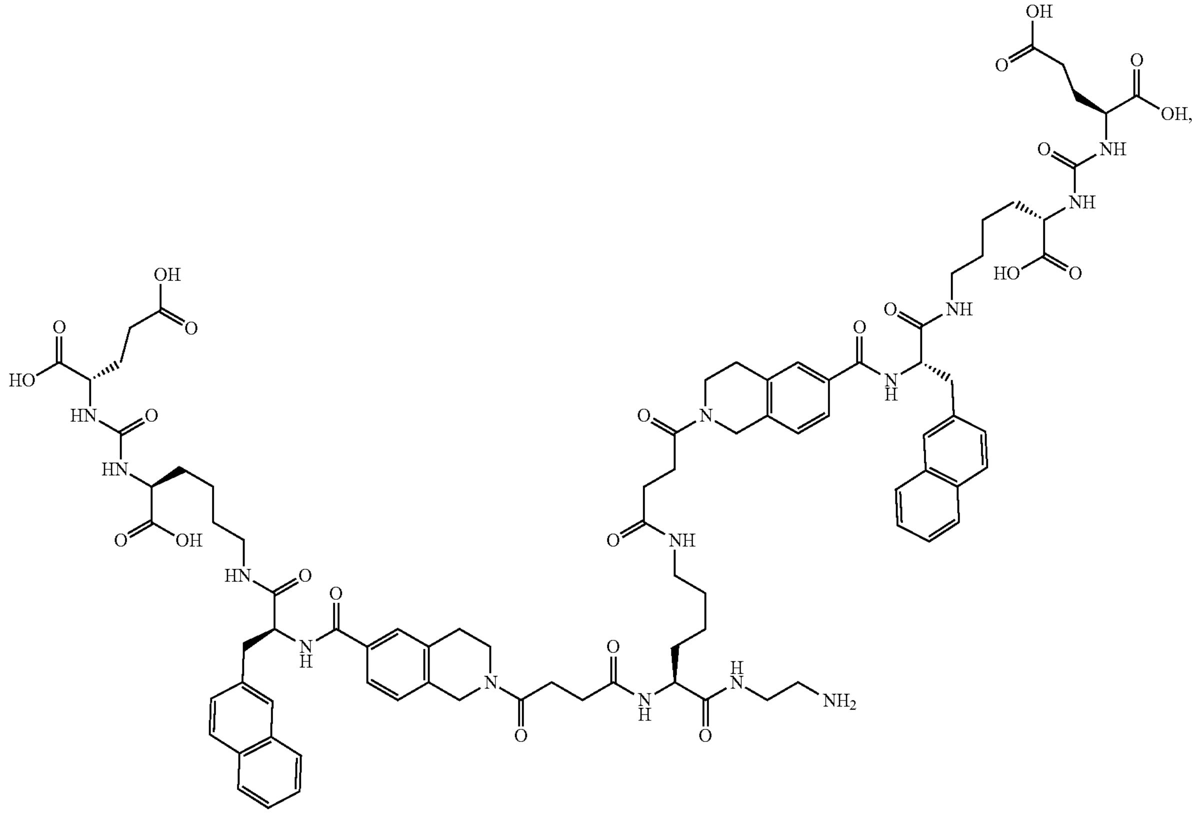
DB-A1
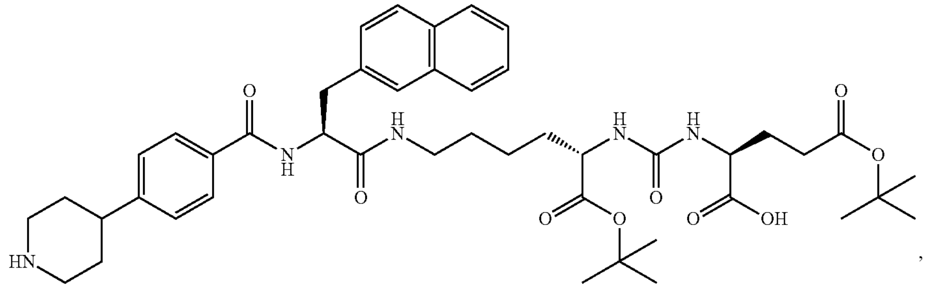
,
DB-A2
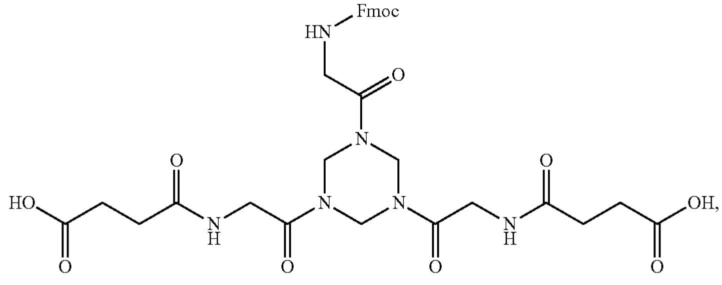

-continued

DB-A3

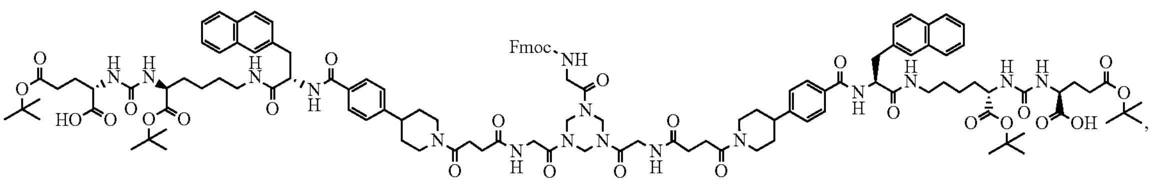

and

DB-A5

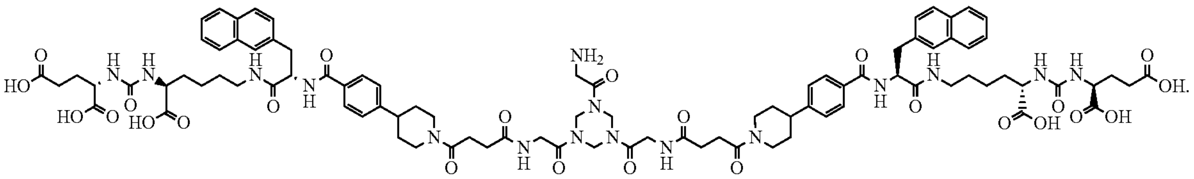

The present disclosure further provides a pharmaceutical composition comprising substance X and a pharmaceutical excipient; the substance X is the peptide urea derivative of formula I, the pharmaceutically acceptable salt thereof, the solvate thereof, or the solvate of the pharmaceutically acceptable salt thereof as above.

In one embodiment, the pharmaceutical composition may be a pharmaceutical composition for the treatment or diagnosis of prostate cancer.

In one embodiment, the pharmaceutical composition may be a pharmaceutical composition for imaging prostate cancer.

In one embodiment, the prostate cancer is castration-resistant prostate cancer.

In one embodiment, the prostate cancer is metastatic castration-resistant prostate cancer.

In one embodiment, the prostate cancer is PSMA-positive prostate cancer. In one embodiment, the substance X is a therapeutically effective amount of substance X.

The present disclosure further provides a use of the substance X in the manufacture of a medicament; the substance X is the peptide urea derivative of formula I, the pharmaceutically acceptable salt thereof, the solvate thereof, or the solvate of the pharmaceutically acceptable salt thereof as above;

The medicament is a medicament for the treatment or diagnosis of prostate cancer, or the medicament is a medicament for imaging prostate cancer.

In one embodiment, the medicament is a medicament for the treatment of prostate cancer, and the radioactive metal ion is a radioactive metal ion that emits γ ray.

In one embodiment, the medicament is a medicament for the treatment of prostate cancer, and the radioactive metal ion is $^{177}Lu^{3+}$.

In one embodiment, the medicament is a medicament for the diagnosis of prostate cancer, and the radioactive metal ion is a radioactive metal ion that emits α or β ray.

In one embodiment, the medicament is a medicament for the diagnosis of prostate cancer, and the radioactive metal ion is $^{68}Ga^{3+}$ or $^{64}Cu^{2+}$.

In one embodiment, the prostate cancer is castration-resistant prostate cancer.

In one embodiment, the prostate cancer is metastatic castration-resistant prostate cancer.

In one embodiment, the prostate cancer is PSMA-positive prostate cancer.

The term “pharmaceutically acceptable salt” refers to salts formed from the reaction of a compound with a pharmaceutically acceptable acid or base (relatively non-toxic, safe, and suitable for patient use). When the compound contains a relatively acidic functional group, base addition salts can be obtained by contacting the free form of the compound with an adequate amount of a pharmaceutically acceptable base in a suitable inert solvent. A pharmaceutically acceptable base addition salt includes, but is not limited to, sodium salts, potassium salts, calcium salts, aluminum salts, magnesium salts, bismuth salts, ammonium salts and the like. When the compound contains a relatively basic functional group, acid addition salts can be obtained by contacting the free form of the compound with an adequate amount of a pharmaceutically acceptable acid in a suitable inert solvent. A pharmaceutically acceptable acid addition salt includes, but is not limited to, hydrochloride, sulfate, methanesulfonate, acetate, trifluoromethanesulfonate and the like. For further details, refer to the Handbook of Pharmaceutical Salts: Properties, Selection, and Use (P. Heinrich Stahl, 2002).

The term “solvate” refers to a substance formed by the crystallization of a compound with a solvent (including but not limited to water, ethanol, etc.). The solvate can be a classified into stoichiometric solvate and a non-stoichiometric solvate.

The term “solvate of the pharmaceutically acceptable salt” refers to substances formed by the combination of the compound with a pharmaceutically acceptable acid or base and a solvent (including but not limited to water, ethanol, etc.), wherein the pharmaceutically acceptable salt has the same meaning as described above, and the solvent can be stoichiometric or non-stoichiometric. The solvate of the pharmaceutically acceptable salt includes, but is not limited to, hydrochloride monohydrate.

The term “alkyl” refers to a straight or branched chain alkyl group having a specified number of carbon atoms (e.g., $C_1$ to $C_6$). The alkyl includes, but is not limited to, methyl, ethyl, n-propyl, isopropyl, n-butyl, tert-butyl, isobutyl, sec-butyl, n-pentyl, n-hexyl, n-heptyl, n-octyl, etc.

The term “cycloalkyl” or “carbocycle” refers to a saturated cyclic group consisting only of carbon atoms with a specified number of carbon atoms (e.g., $C_3$ to $C_6$), and can be monocyclic, bridged, or spirocyclic. Cycloalkyl includes, but is not limited to, cyclopropyl, cyclobutyl, cyclopentyl, cyclohexyl, etc.

The term “aryl” or “aromatic ring” refers to a cyclic group consisting only of carbon atoms with a specified number of carbon atoms (e.g., $C_6$ to $C_{10}$), and can be a monocyclic ring or a fused ring, and at least one ring is aromatic (in accordance with Huckel’s rule). The aryl are attached to other moieties in the molecule through aromatic rings or non-aromatic rings. The aryl includes, but is not limited to, phenyl, naphthyl,

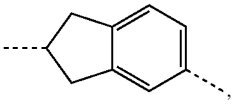

etc.

The “ ” in a structural moiety means that the structural moiety is attached to other moieties in the molecule through this site.

The term “pharmaceutical excipient” refers to the excipient and additive used in the production of drugs and preparation of prescriptions, and is all substances other than active ingredients included in pharmaceutical preparations. For details, see the *Pharmacopoeia of the People’s Republic of China* (2020 edition) or *Handbook of Pharmaceutical Excipients* (Raymond C Rowe, 2009).

The term “therapeutically effective amount” refers to the quantity of the compound is sufficient to effectively treat a disease when administered to a patient. The therapeutically effective amount will vary based on the compound, the type and severity of the disease, the age of the patient, and other factors, but can be adjusted by those skilled in the art as needed.

The term “patient” refers to any animal, preferably a mammal, most preferably a human, that has been or is about to be treated. The mammal includes, but is not limited to, a cattle, horse, sheep, pig, cat, dog, mouse, rat, rabbit, guinea pig, monkey, human, etc.

The term “treatment” refers to any of the following: (1) alleviating one or more than one biological manifestation of a disease; (2) interfering with one or more than one point in the biological cascade that causes the disease; (3) slowing the progression of one or more than one biological manifestation of a disease.

The term “prevention” refers to reducing the risk of developing a disease.

The following abbreviations are used in the present disclosure:

DMF refers to N,N-Dimethylformamide.

DMAP refers to 4-Dimethylaminopyridine.

Fmoc refers to 9-Fluorenylmethoxycarbonyl protecting group.

H-Glu (OtBu)-OH refers to L-Glutamic acid-5-tert-butyl ester.

Lys refers to L-Lysine.

ivDde refers to 1-(4,4-Dimethyl-2,6-dioxocyclohexylidene)ethyl.

The above preferred conditions can be combined arbitrarily to obtain preferred embodiments of the present disclosure without violating common knowledge in the art.

The reagents and raw materials used in the present disclosure are all commercially available.

The positive advancement of the present disclosure lies in: the derivative can be used for preoperative imaging diagnosis and grading of PSMA positive prostate cancer, can also be used for treatment of various types and stages of prostate cancer, achieving the integration of diagnosis and treatment, with a wide application prospect.

DETAILED DESCRIPTION OF THE PREFERRED EMBODIMENT

Figure 1:
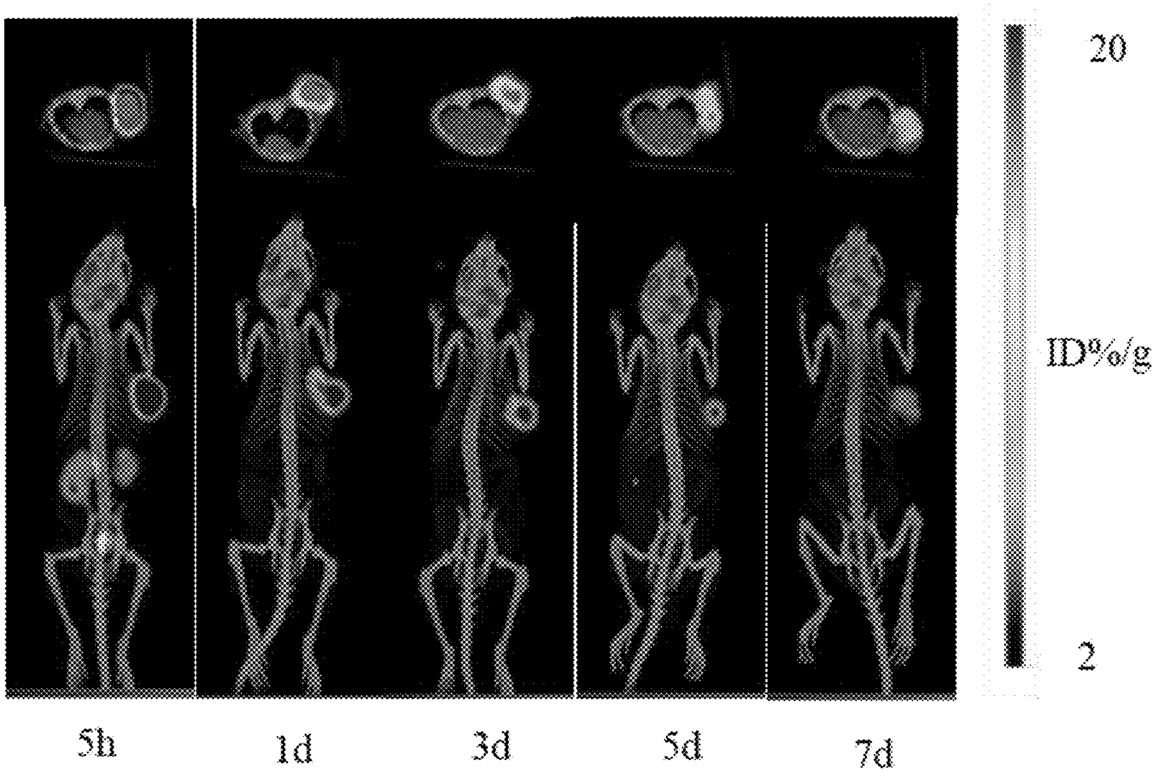
FIG. 1 shows the Micro-SPECT/CT imaging images of DB-01 in mouse 1 at different times.

The present disclosure will be described in detail below by way of examples, but the scope of the present disclosure is not limited thereto. Experimental methods that do not indicate specific conditions in the following examples should be selected according to conventional methods and conditions, or according to product specifications.

Example 1: Synthesis of Compound M1

M1

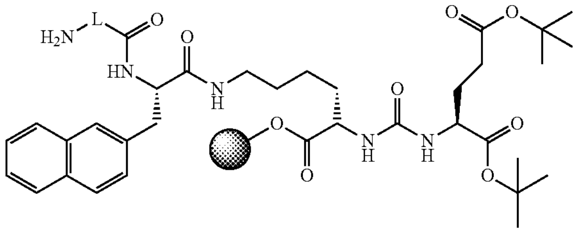

General synthetic method A: Fmoc-Lys (ivDde)-Wang resin (0.3 mmol/g) was used as the starting material and added to a reaction vessel. A solution of 25% piperidine/DMF (v/v) was then added, and the mixture was stirred for 30 minutes. The reaction mixture was monitored by ninhydrin test, which showed a deep blue color. The reaction mixture was then filtered under reduced pressure and washed five times with DMF, and the N-terminal Fmoc protecting group is removed to make the N-terminal a free amino group. Using DMF as the solvent, N,N'-disuccinimidyl carbonate (1 equivalent), N,N-diisopropylethylamine (DIPEA, 2 equivalents), and 4-dimethylaminopyridine (DMAP, 2 equivalents) were added in a ratio of 1:2:2, and the reaction was allowed to proceed for 1 hour under nitrogen atmosphere. Subsequently, H-Glu (OtBu)-OH (1.1 equivalents) was added, and the mixture was stirred for 24 hours. The Dde protecting group on the side chain of Lys was removed using a 2% hydrazine hydrate/DMF solution. Fmoc-2-Nal-OH/HOBt/DIC (3 equivalents) was then added to graft with the resin to introduce the 2-Nal amino acid residue. The Fmoc protecting group was again removed by treating with 25% hexahydropiperidine/DMF (v/v) to make the N-terminus of 2-Nal a free amino group. Subsequently, Fmoc-L-COOH/HOBt/DIC (3 equivalents) was graft the resin to introduce the L amino acid residue. Finally, the Fmoc protecting group was removed again using 25% hexahydropiperidine/DMF (v/v) to obtain a free amino group at the N-terminus, resulting in the synthesis of compound M1.

This method serves as a general synthesis method for compound M1, wherein Lis any corresponding group at the relevant position in DB-01 to DB-10.

Example 2: Synthesis of Compound M2

M2

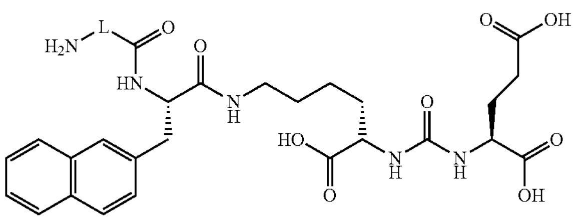

General synthetic method B: Using compound M1 as the starting material, the target polypeptide was cleaved from the resin of compound M2 and the side-chain protecting groups were removed by using a cleavage reagent (trifluoroacetic acid:$H_2O$:triisopropylsilane=90:5:5, v/v) (the cleavage reaction was performed at 30° C. for 3 hours). The filtrate was then added to a large volume of cold anhydrous ether to precipitate the polypeptide. The mixture was centrifuged. And the resulting polypeptide precipitate was washed several times with ether and then dried, obtaining the polypeptide product M2.

Example 3: Synthesis of Compound M3

M3

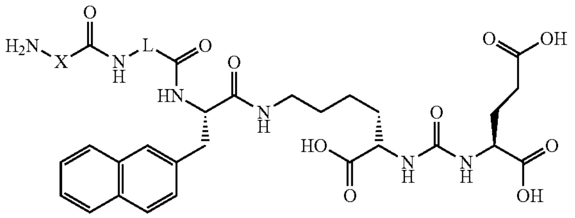

General synthetic method C: Using M1 as the starting material, the general synthetic method A was employed to couple the amino acid FmocNHXCOOH, and the Fmoc protecting group was then removed to obtain a free amino group at the N-terminus of X. Subsequently, a cleavage reagent (trifluoroacetic acid: $H_2O$: triisopropylsilane=90:5:5, v/v) was used to cleave the target polypeptide from the resin of compound M3 and to remove the side-chain protecting groups. This cleavage was performed at 30° C. for 3 hours. The filtrate was then added to a large volume of cold anhydrous ether to precipitate the polypeptide. The mixture was centrifuged. And the resulting polypeptide precipitate was washed several times with ether and then dried, obtaining the crude polypeptide product M3.

This method serves as a general synthesis procedure for compound M3, wherein X represents the corresponding group at the relevant position in DB-01 to DB-10.

Example 4: Synthesis of Compound M5

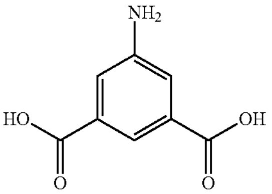

+

-continued

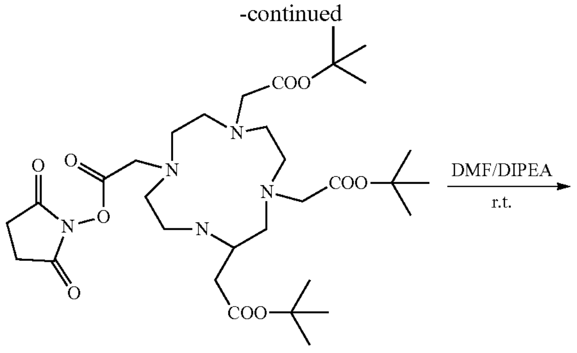

-continued

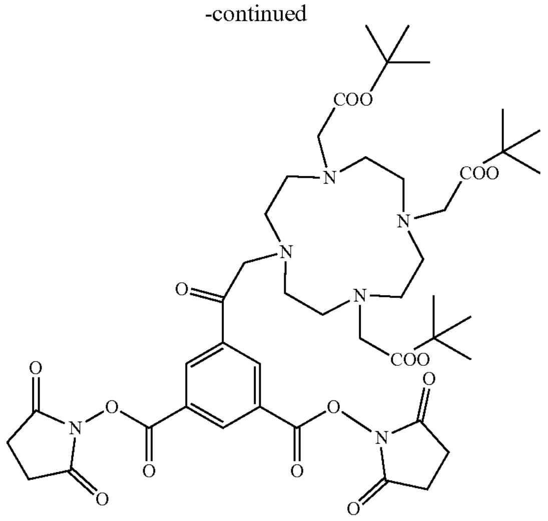

M5

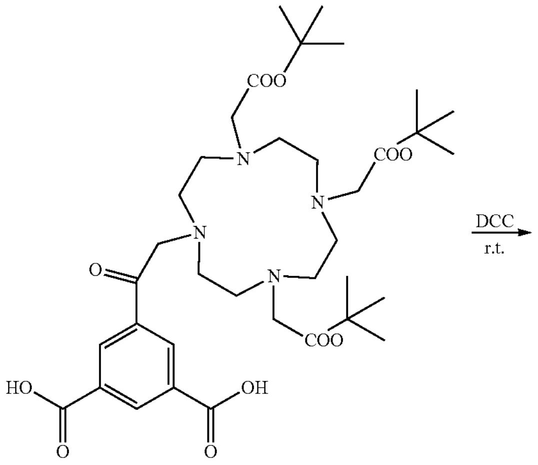

M4

General synthetic method D: 3,5-Dicarboxyaniline (1.0 equivalent) was dissolved in 50 mL of DMF, followed by the addition of DIPEA (1.5 equivalents). NHS-activated DOTA ester (1.1 equivalents) was then added, and the reaction mixture was stirred at room temperature overnight. The reaction mixture was poured into water and extracted with ethyl acetate (3x30 mL). The mixed organic extracts were washed with saturated NaCl solution (30 mL), dried over $Na_2SO_4$, filtered, and concentrated to remove the solvent. The residue was purified by column chromatography ($SiO_2$, 5-10% MeOH/DCM) to obtain M4 (0.8 equivalents, 80%). M4 (0.5 equivalents), DMAP (0.1 equivalents), and N-hydroxysuccinimide (1.1 equivalents) were dissolved in 20 mL of DMF and reacted overnight. The reaction mixture was diluted with 100 mL of ethyl acetate and washed with saturated $NaHCO_3$ solution (35 mL). The organic phase was washed with saturated NaCl solution, dried over $Na_2SO_4$, filtered, and concentrated to obtain M5. MS (ESI): 916. The crude M5 was used directly in the next reaction step.

Example 5: Synthesis of Compound M6

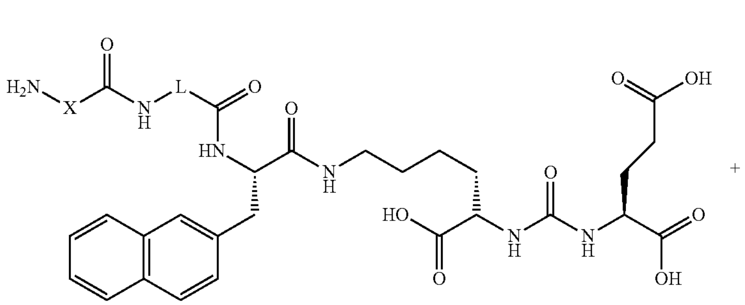

M3

-continued

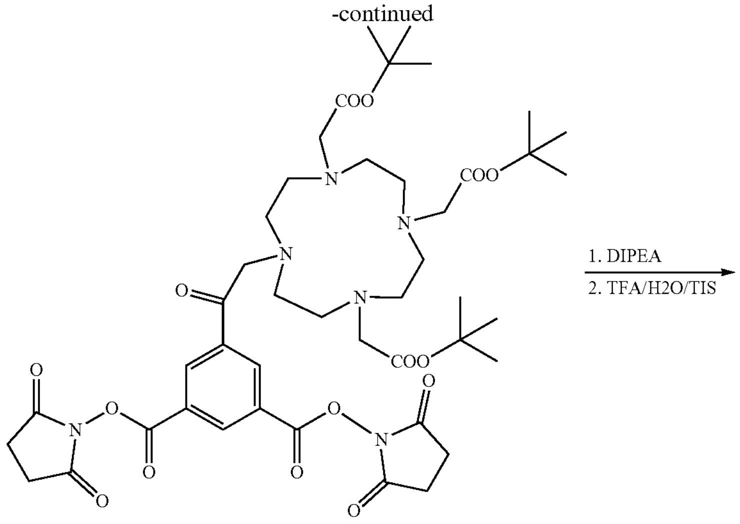

M5

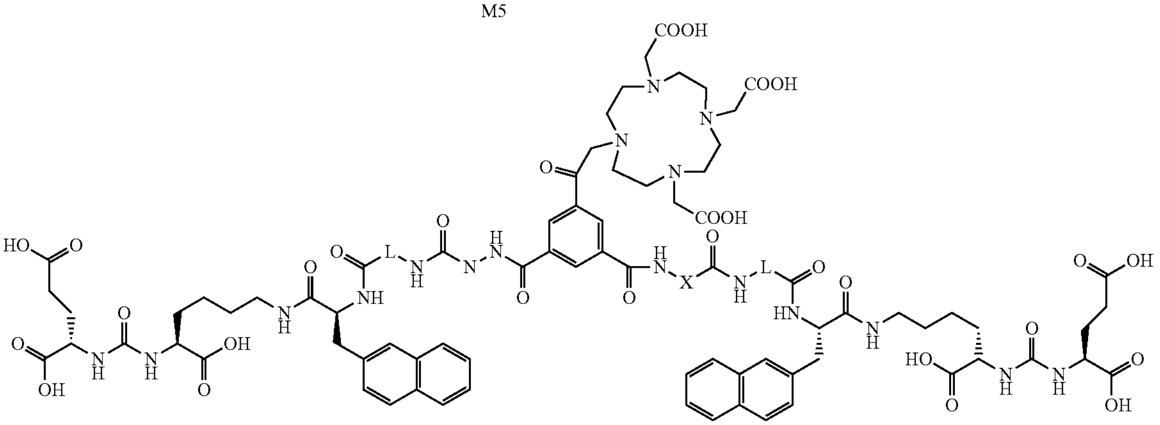

M6

General synthetic method E: M5 (0.01 equivalents), M3 (0.02 equivalents), and DIPEA (0.025 equivalents) were dissolved in DMF (10 mL). The reaction was carried out overnight. The solvent was then removed under vacuum, and the residue was treated with a cleavage reagent (trifluoroacetic acid: $H_2O$: triisopropylsilane=90:5:5, v/v) at 30° C. with stirring for 3 hours. The reaction mixture was poured into a large volume of cold anhydrous ether, and the resulting precipitate was filtered and washed with cold anhydrous ether. The precipitate was dried and then purified by preparative liquid chromatography (C18 column, A: 100% water/0.1% TFA, B: 100% acetonitrile/0.1% TFA). The fractions containing the desired product were combined and freeze-dried to obtain the product M6.

Example 6: Synthesis of Compound M11

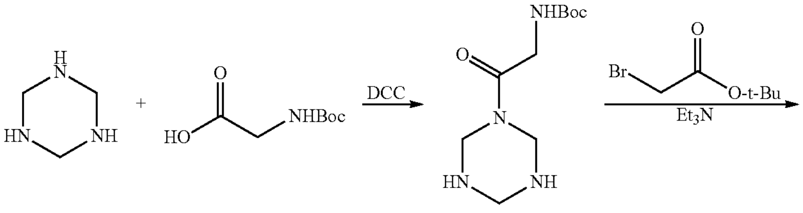

M7

-continued
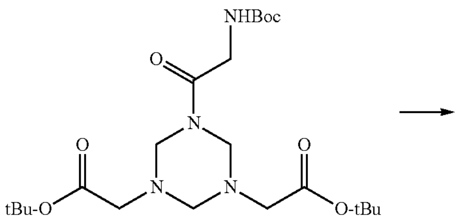
M8
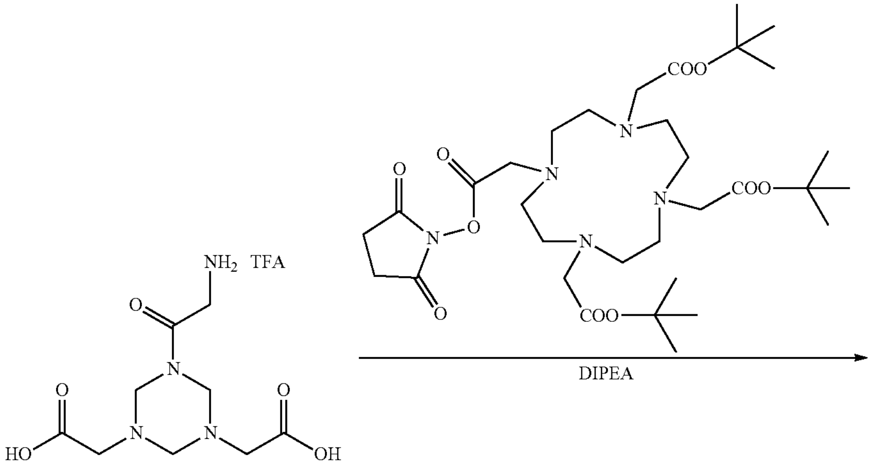
M9
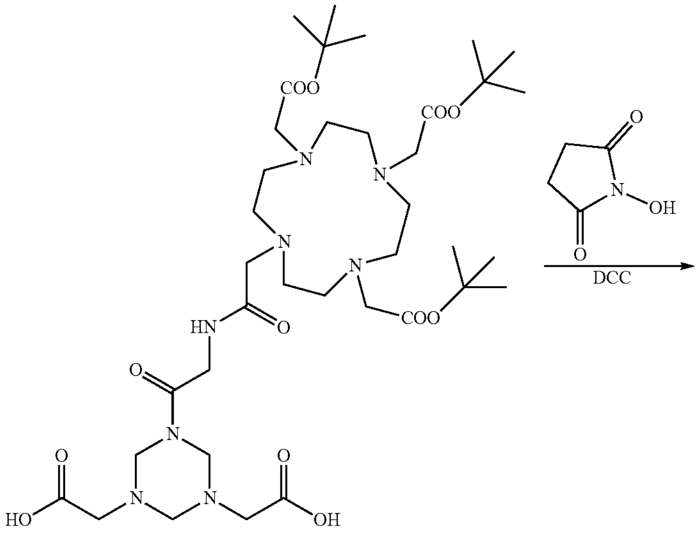
M10

-continued

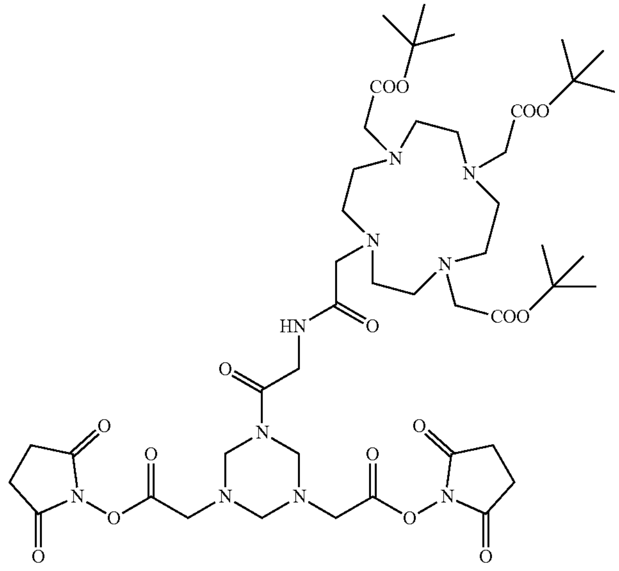

M11

Synthesis of Compound M11

N-Boc-Glycine (1.0 equivalent) and DCC (1.3 equivalents) were added to THF (100 mL) and stirred at room temperature for 30 minutes. 1,3,5-Triazinane (1.1 equivalents) was then added, and the reaction mixture was stirred overnight. The mixture was concentrated, and the residue was purified by column chromatography ($SiO_2$, 5-10% MeOH/DCM) to obtain M7 (0.8 equivalents). MS (ESI): 245 $(M+1)^+$.

M7 (1.0 equivalent), tert-butyl 2-bromoacetate (2.1 equivalents), and triethylamine (2.5 equivalents) were dissolved in DMF (100 mL) and stirred at room temperature overnight. The mixture was concentrated, and the residue was purified by column chromatography ($SiO_2$, 5-10% MeOH/DCM) to obtain M8 (0.75 equivalents). MS (ESI): 473 $(M+1)^+$.

M8 (1.0 equivalent) was mixed with a DCM solution of TFA (TFA:DCM:TIS=9:1:0.1) and stirred at room temperature for 6 hours. The mixture was concentrated, washed with anhydrous ether, and filtered. The resulting solid (M9) was dried under vacuum and used directly in the next reaction step.

M9 (0.5 equivalents), DIPEA (0.5 equivalents), and NHS-activated DOTA ester (0.55 equivalents) were dissolved in DMF (50 mL). The general synthetic method D was employed to obtain M10 (0.5 equivalents). MS (ESI): 816 $(M+1)^+$.

M10 (0.5 equivalents), DMAP (0.1 equivalents), and N-hydroxysuccinimide (1.05 equivalents) were dissolved in DMF (20 mL). The general synthetic method D was employed to obtain M11 (0.48 equivalents). MS (ESI): 1010 $(M+1)^+$.

Example 7: Synthesis of Compound M12

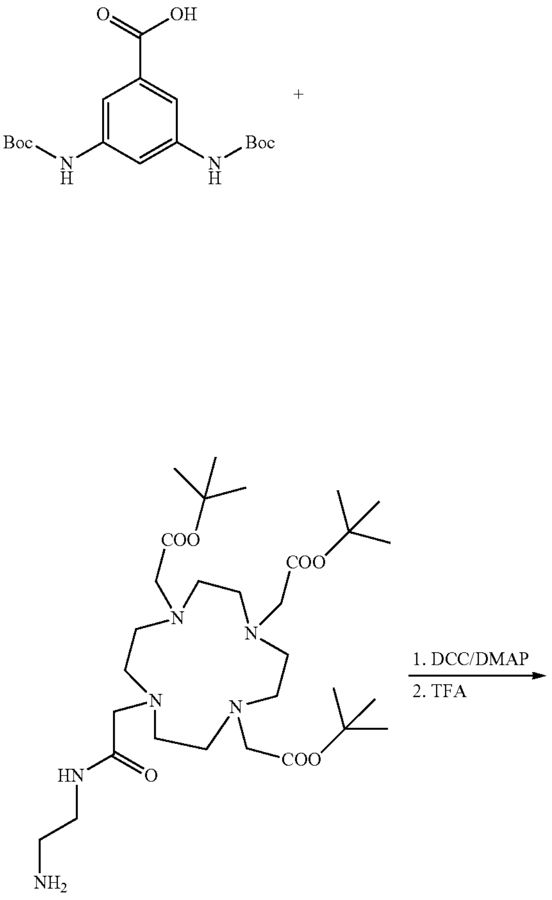

-continued

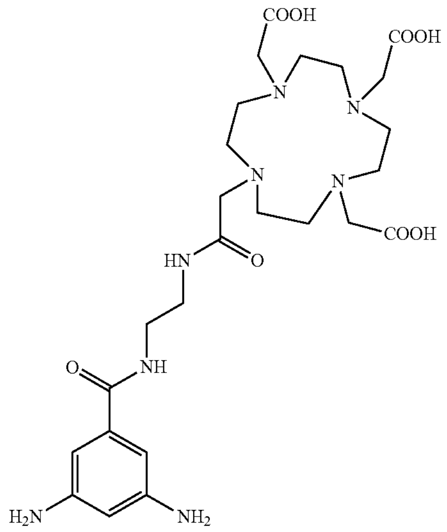

M12

-continued

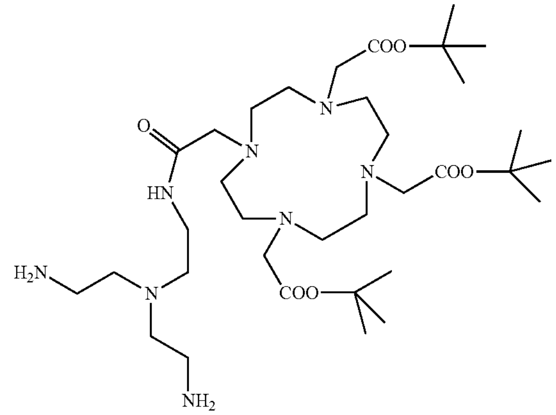

M13

3,5-bis-BOC-aminobenzoic acid (0.5 equivalents), DCC (0.55 equivalents), and DMAP (0.1 equivalents) were dissolved in 100 mL of DMF and stirred at room temperature for 30 minutes. Subsequently, the DOTA derivative (0.5 equivalents) was added, and the reaction mixture was stirred overnight at room temperature. The mixture was then concentrated and filtered. The filtrate was concentrated, and the residue was mixed with a DCM solution of TFA (TFA:DCM:TIS=9:1:0.1). The mixture was stirred at room temperature for 2 hours, concentrated, washed with anhydrous ether, and filtered. The resulting solid (M12) was dried under vacuum to obtain M12. MS (ESI): 581 $(M+1)^+$. M12 was used directly in the next reaction step without purification. The next reaction step is the preparation of DB-07.

Example 8: Synthesis of Compound M13

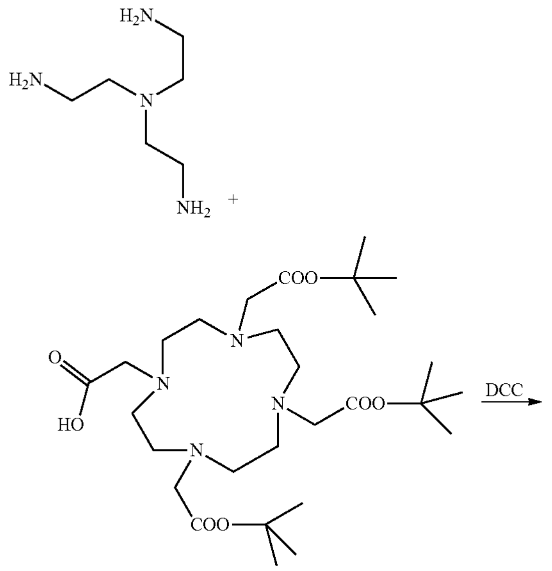

DOTA derivative (0.15 equivalents), DCC (0.15 equivalents), and DMAP (0.05 equivalents) were dissolved in DMF (20 mL) and stirred for 30 minutes. Subsequently, tris(2-aminoethyl)amine (0.5 equivalents) was added, and the reaction mixture was stirred overnight. The mixture was then concentrated, diluted with DCM, filtered, and concentrated to obtain the crude product M13. This crude product was used directly in the next reaction step. MS (ESI): 701 $(M+1)^+$.

Example 9: Synthesis of Compound M14 (General Synthetic Method F)

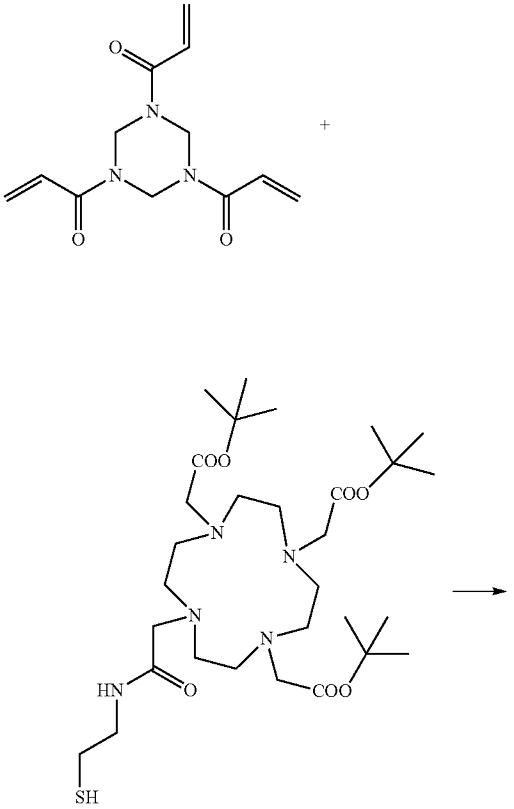

-continued

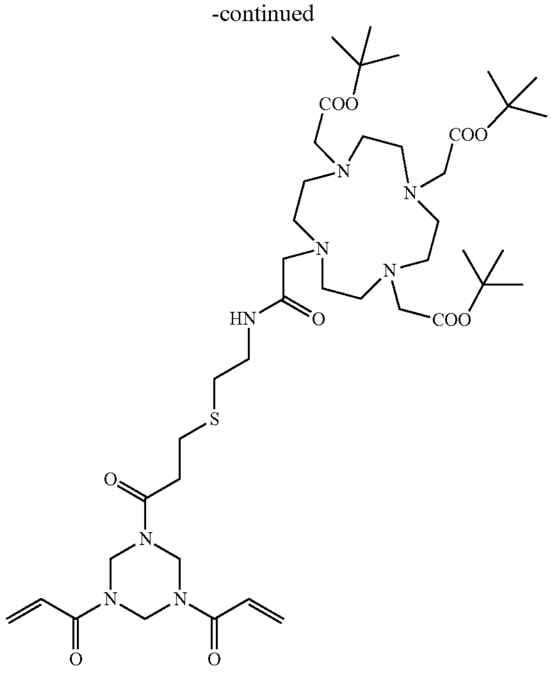

M14

1,3,5-Triacryloylhexahydro-1,3,5-triazine (0.5 equivalents) and M3c (0.15 equivalents) were stirred in DMF overnight. The mixture was then concentrated, and the residue was diluted with cold ether. The precipitate was filtered, washed with cold ether, and dried to obtain M14. MS (ESI): 882 $(M+1)^+$.

Example 10: Synthesis of Compounds

Synthesis of M2a

M2a

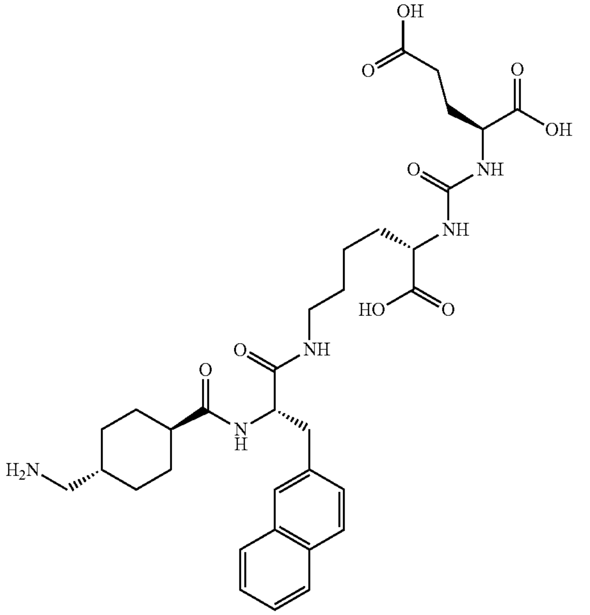

Compound M2a was synthesized using the general synthetic methods A and B. MS (ESI): 656 $(M+1)^+$.

Synthesis of M3a

M3a

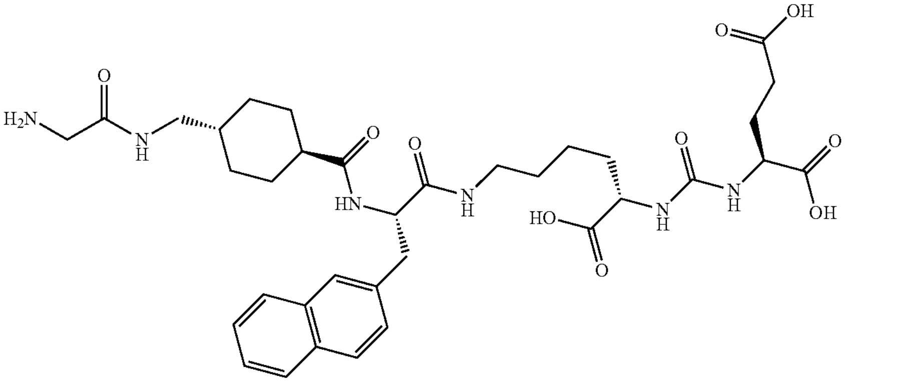

Compound M3a was synthesized using the general synthetic methods A and C. MS (ESI): 713 $(M+1)^+$.
Synthesis of M3b
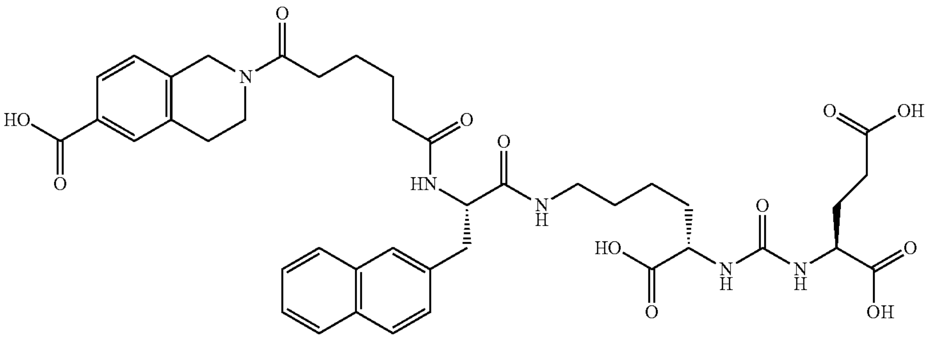
M3b
Compound M3b was synthesized using the general synthetic method A and the corresponding method C. MS (ESI): 804 $(M+1)^+$.
Synthesis of M3c
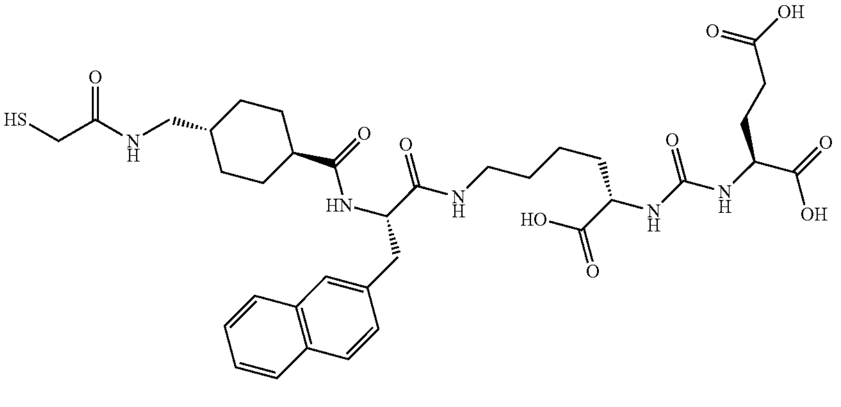
M3c Compound M3c was synthesized using the general synthetic methods A and C. MS (ESI): 730 $(M+1)^+$.
Synthesis of M3d
M3d
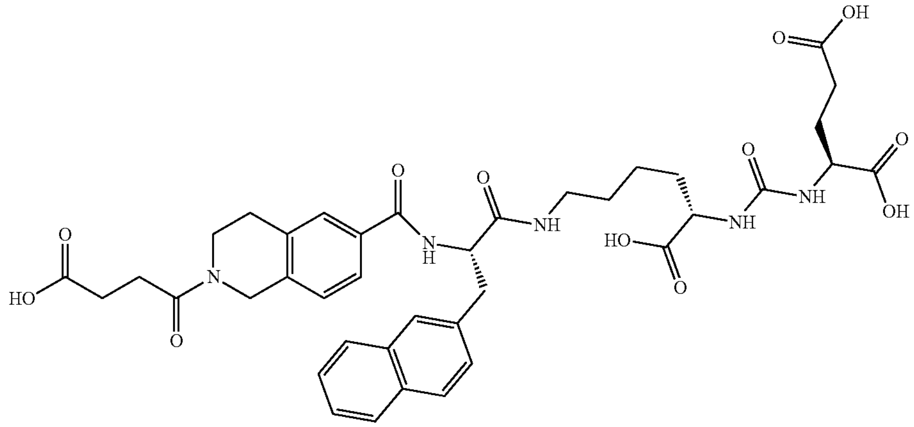
Compound M3d was synthesized using the general synthetic methods A and C. MS (ESI): 776 $(M+1)^+$.
Synthesis of M3e
M3e
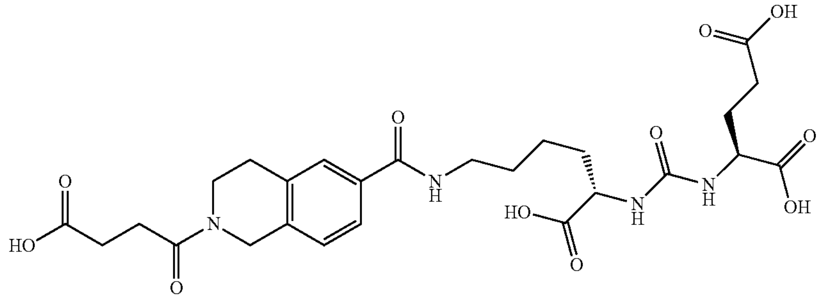

Compound M3e was synthesized using the general synthetic methods A and C. MS (ESI): 579 (M+1)$^+$.
Synthesis of M3f
M3f
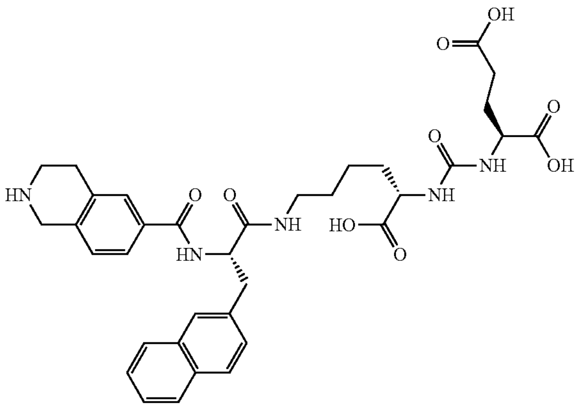
Compound M3f was synthesized using the general synthetic methods A and B. MS (ESI): 676 (M+1)$^+$.
Example 11: Synthesis of DB-01
DB-01
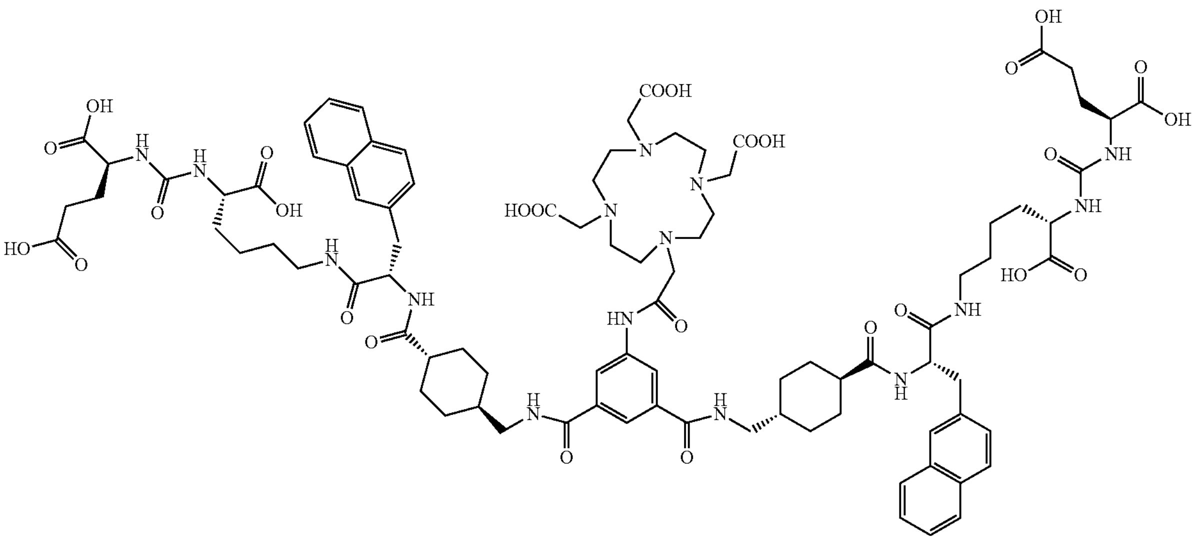

DB-01 was prepared from M5 and M2a according to the general synthetic method D. MS (ESI): 1844 (M+1)$^+$.
Example 12: Synthesis of DB-02
DB-02
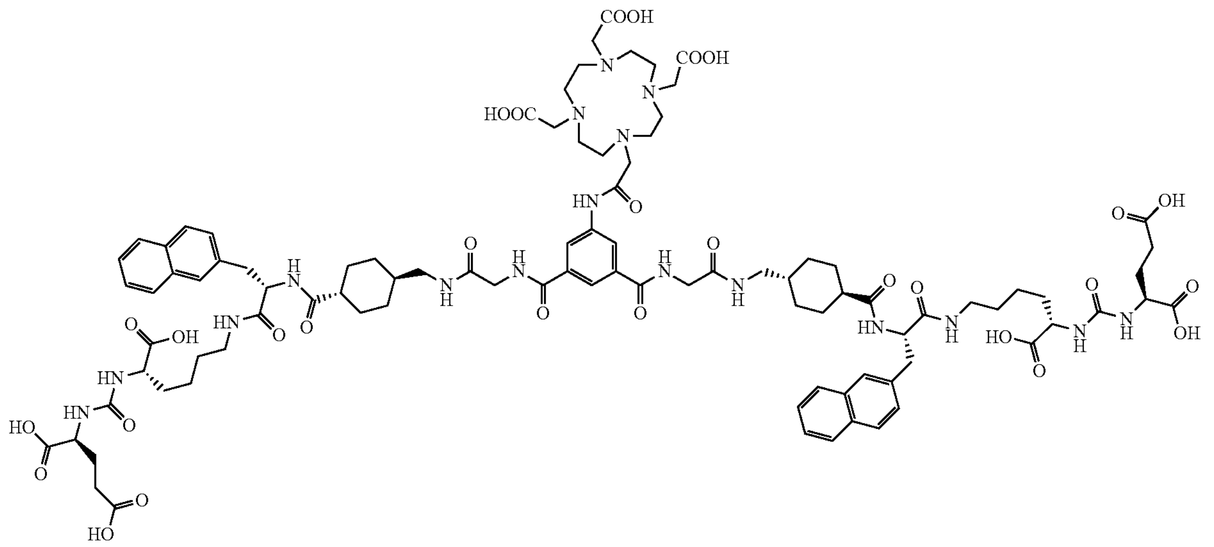 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CNC(=O)c2cc(NC(=O)NC3CCN(CC(=O)O)CCN(CC(=O)O)CCN(CC(=O)O)CC3)cc(C(=O)NCC(=O)NC[C@H]3CC[C@H](C(=O)N[C@@H](Cc4ccc5ccccc5c4)C(=O)NCCCC[C@H](NC(=O)N[C@@H](CCC(=O)O)C(=O)O)C(=O)O)CC3)c2)CC1)C(=O)O)C(=O)O]
DB-02 was prepared from M5 and M3a according to the general synthetic method D. MS (ESI): 1844 (M+1)$^+$.
Example 13: Synthesis of DB-03
DB-03
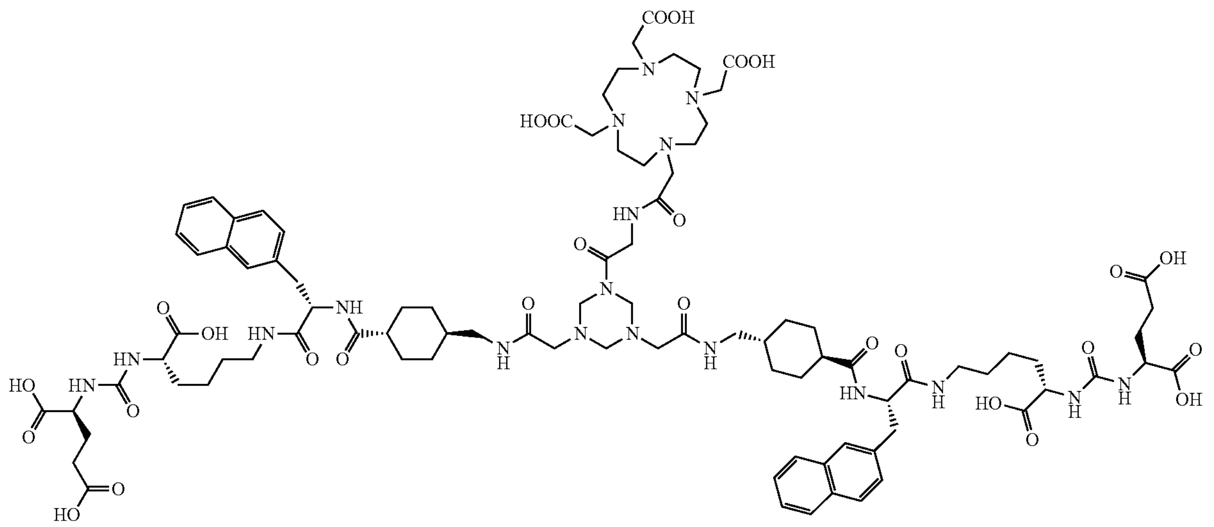

DB-03 was prepared from M11 and M3a according to the general synthetic method E. MS (ESI): 1923 $(M+1)^+$.

Example 14: Synthesis of DB-04

DB-04

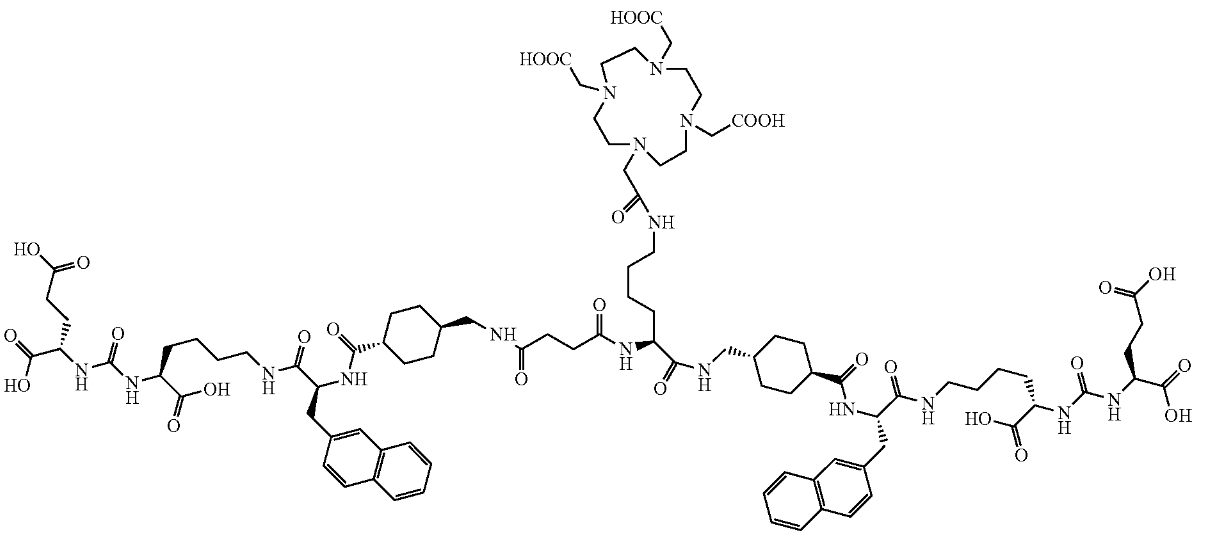 [SMILES: O=C(O)CC[C@H](NC(=O)N[C@@H](CCCCNC(=O)[C@H](Cc1ccc2ccccc2c1)NC(=O)[C@H]1CC[C@H](CNC(=O)CCC(=O)N[C@@H](CCCCNC(=O)CN2CCN(CC(=O)O)CCN(CC(=O)O)CCN(CC(=O)O)CC2)C(=O)NC[C@H]2CC[C@H](C(=O)N[C@@H](Cc3ccc4ccccc4c3)C(=O)NCCCC[C@H](NC(=O)N[C@@H](CCC(=O)O)C(=O)O)C(=O)O)CC2)CC1)C(=O)O)C(=O)O]

Compound DB-04 is synthesized according to the following route: first, the lysine derivative and M2a were used to prepare M15 according to synthetic method E. After removing the Boc protecting group on the nitrogen atom of M15 with TFA, M16 was obtained by reacting M15 with a DOTA derivative according to synthetic method E. Following the removal of the Fmoc protecting group from M16, it was coupled with M3d. Subsequently, the Boc protecting group on DOTA was removed using TFA to obtain the crude product DB-04. The crude product was then purified by preparative liquid chromatography and lyophilized to obtain the pure DB-04. MS (ESI): 1909 $(M+1)^+$.

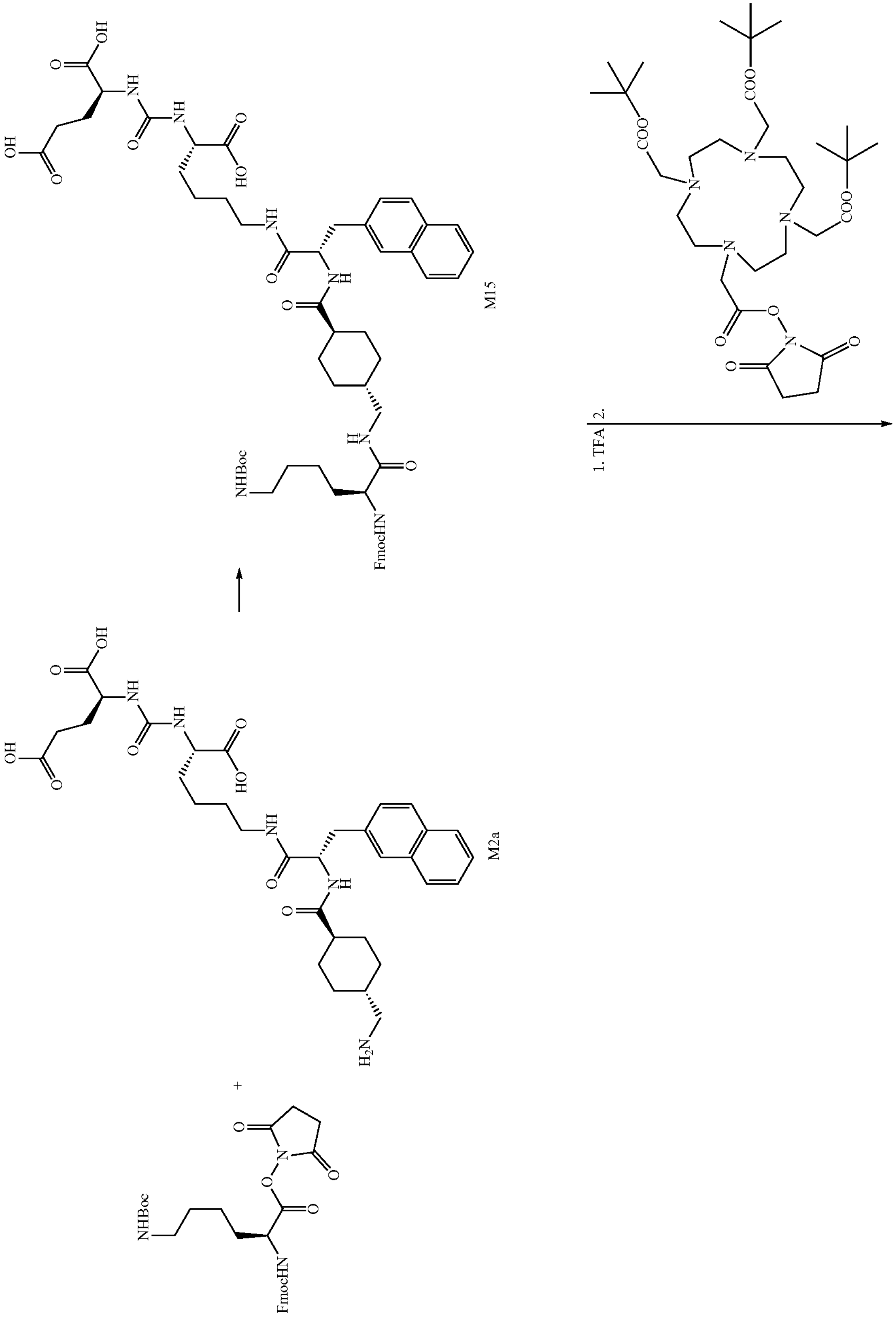
M2a
M15

-continued
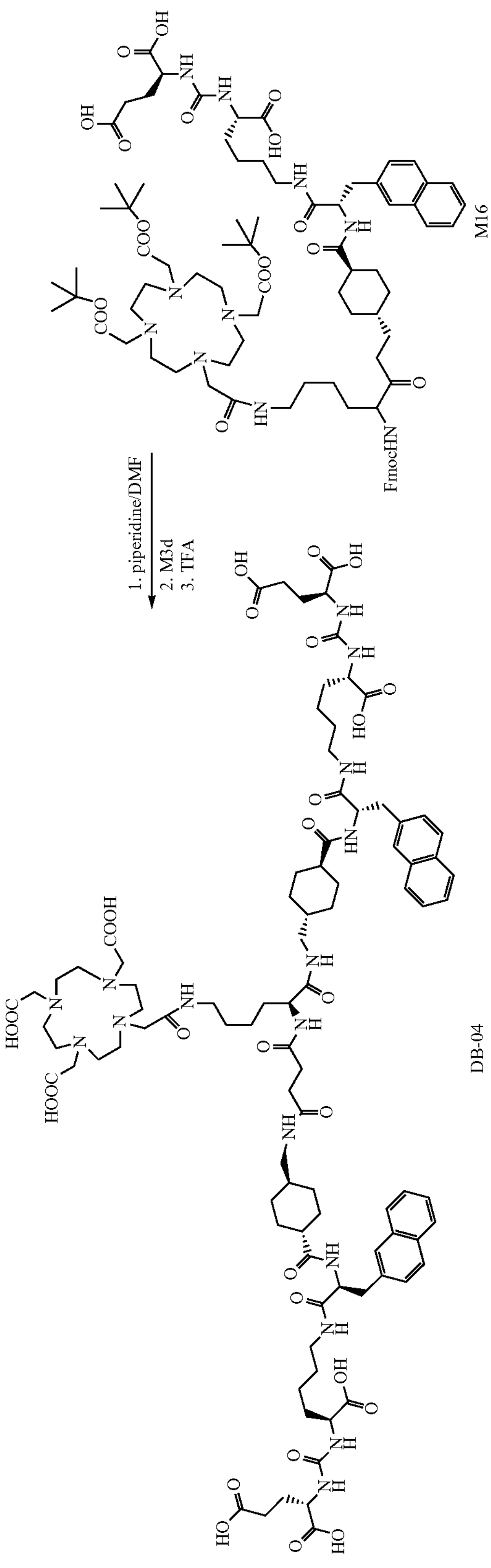
M16
DB-04

Example 15: Synthesis of DB-05
DB-05
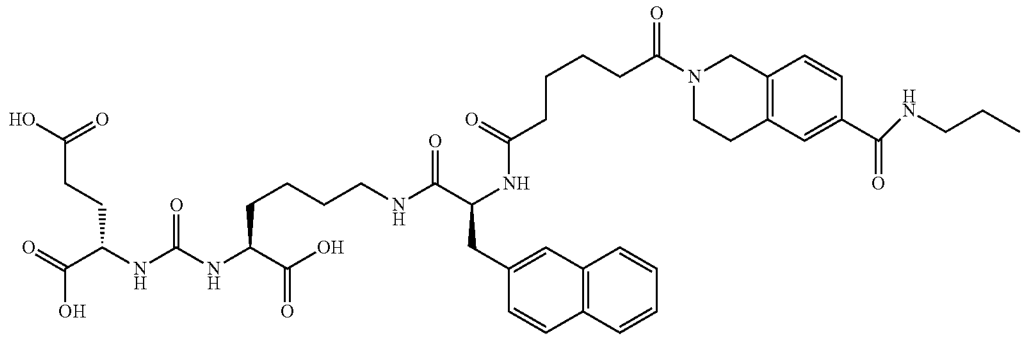
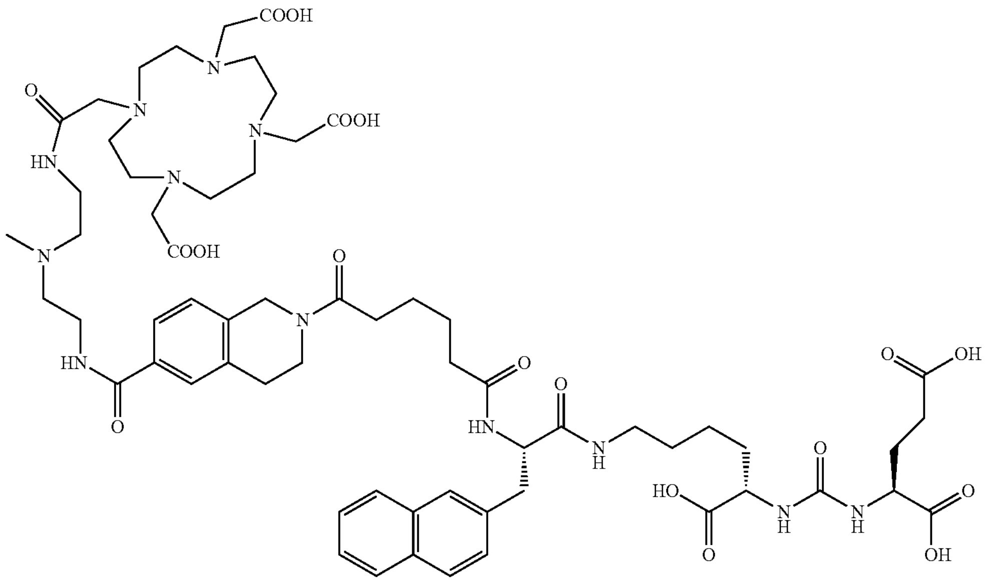

DB-05 was prepared by coupling M13 with M3b. MS (ESI): 2105 (M+1).

Example 16: Synthesis of DB-06

DB-06
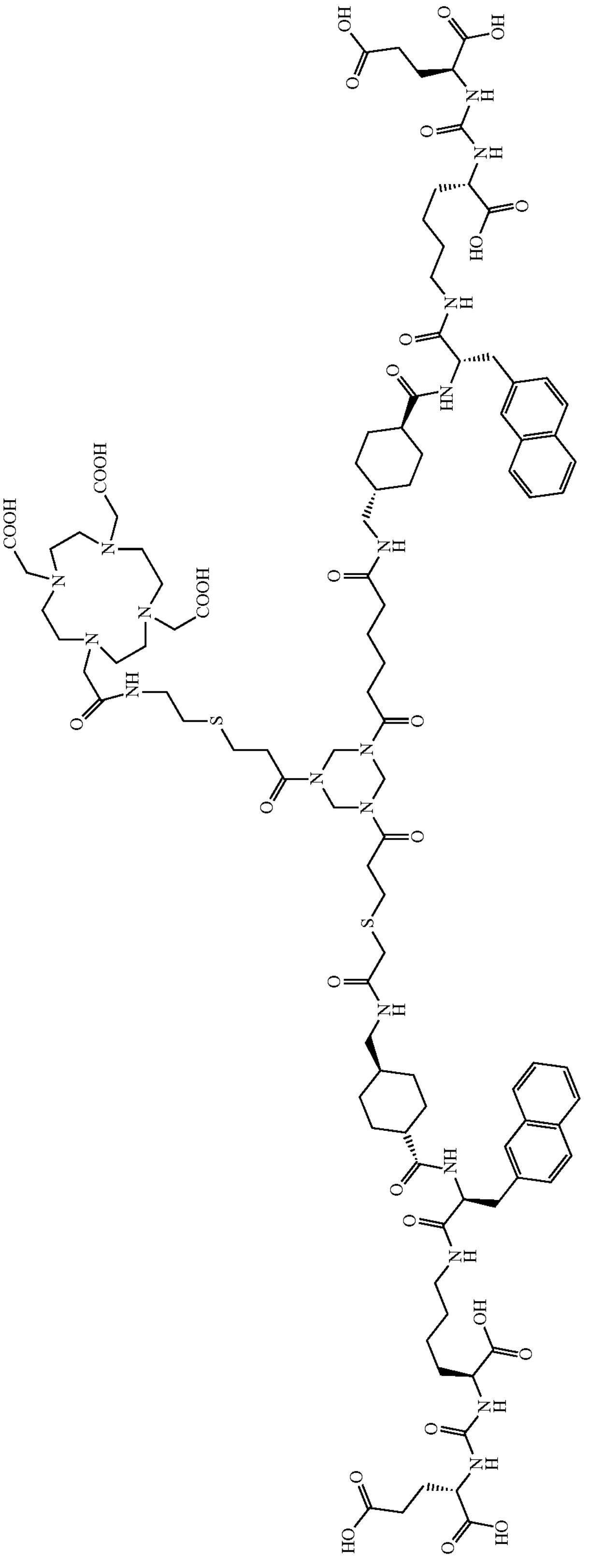

DB-06 was prepared from M14 and M3c according to the general synthetic method F. MS (ESI): 2173 $(M+1)^+$.

Example 17: Synthesis of DB-07

DB-07
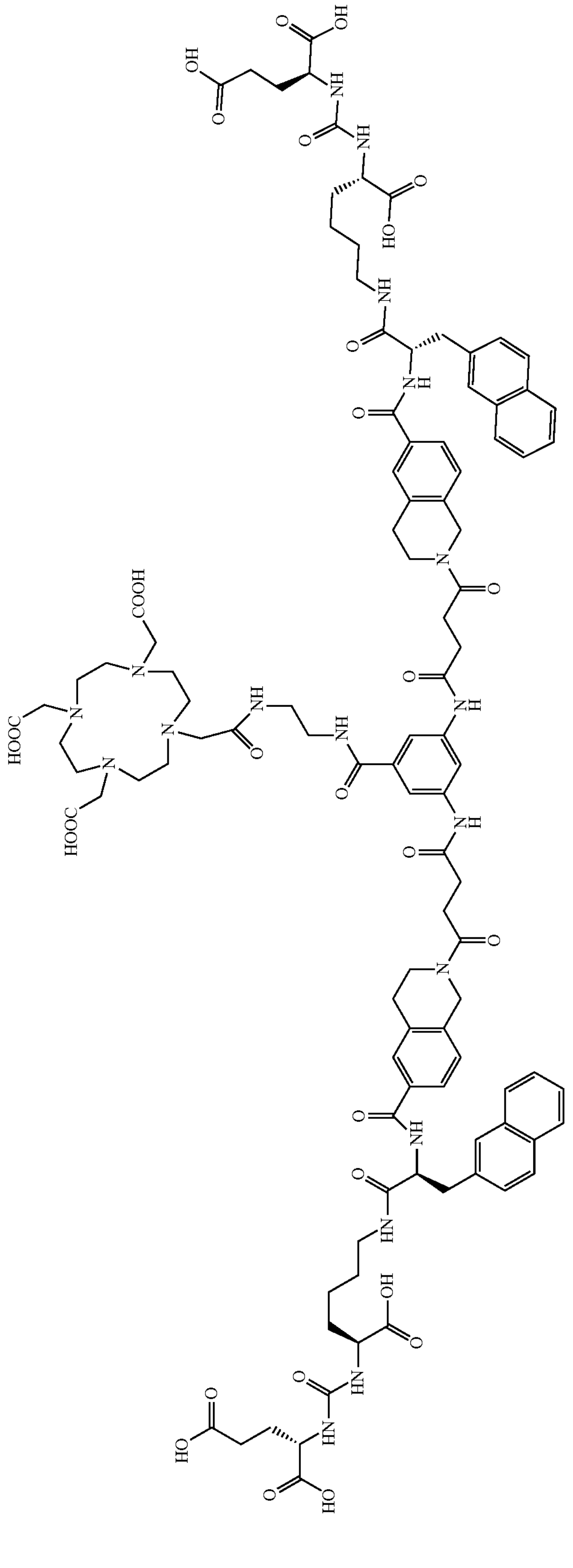

DB-07 was prepared by coupling M12 with M3d. MS (ESI): 2097 $(M+1)^+$.

Example 18: Synthesis of DB-08

DB-08
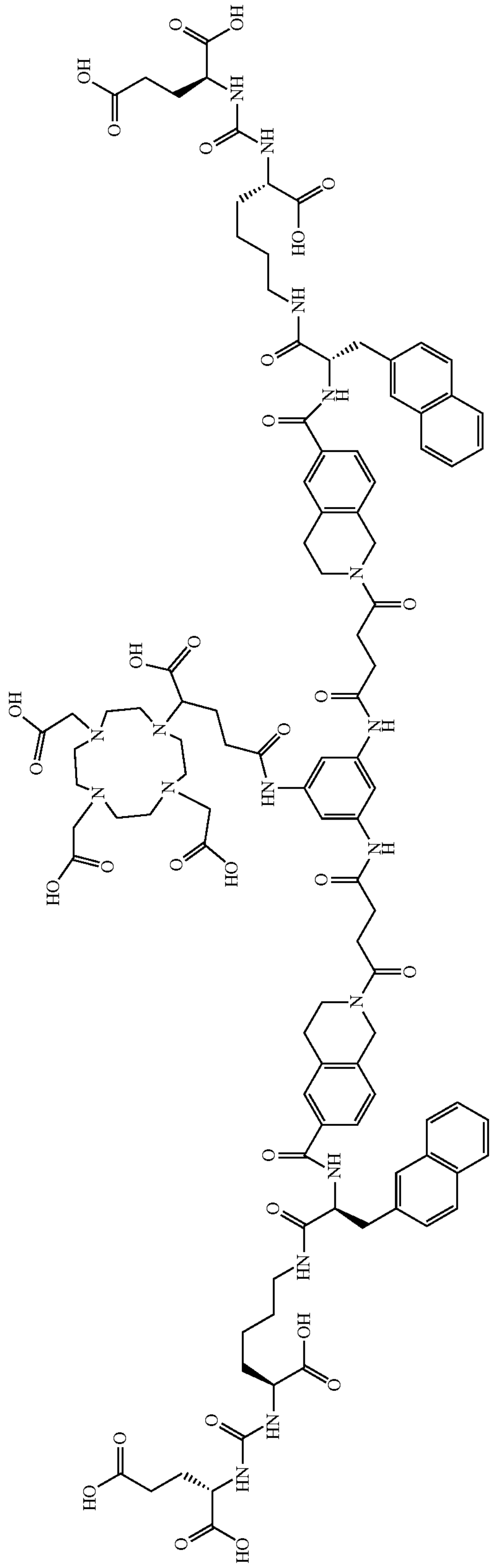

DB-08 was prepared using the method for synthesizing DB-07. MS (ESI): 2098 $(M+1)^+$.

Example 19: Synthesis of DB-09

DB-09
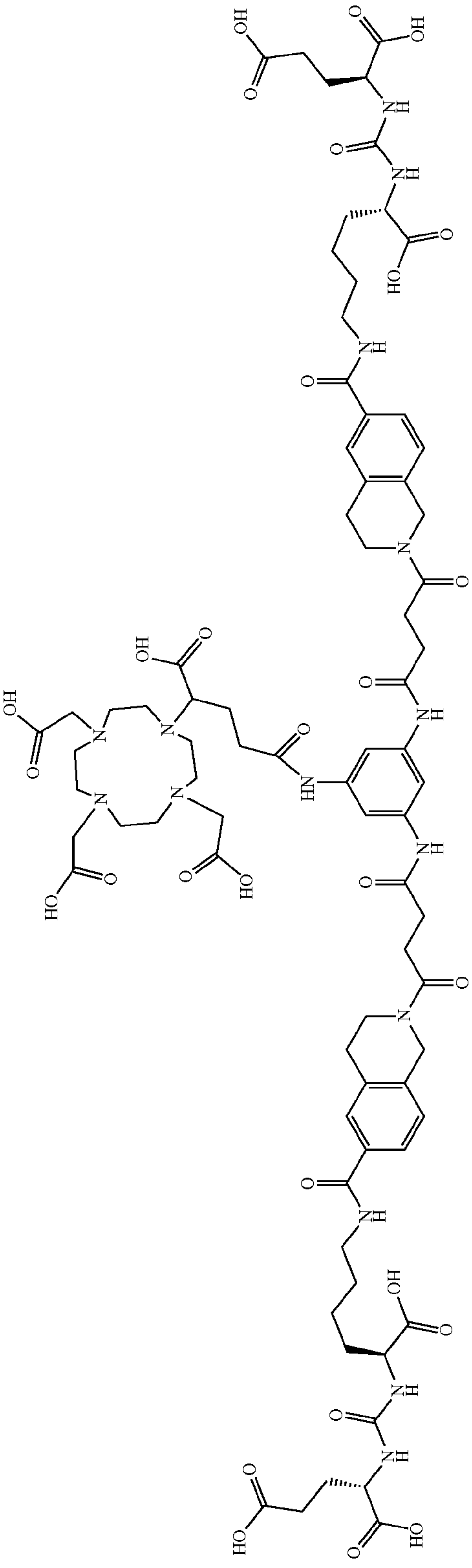

DB-09 was prepared using the method for synthesizing DB-08. MS (ESI): 1703 $(M+1)^+$.

Example 20: Synthesis of DB-010

DB-10
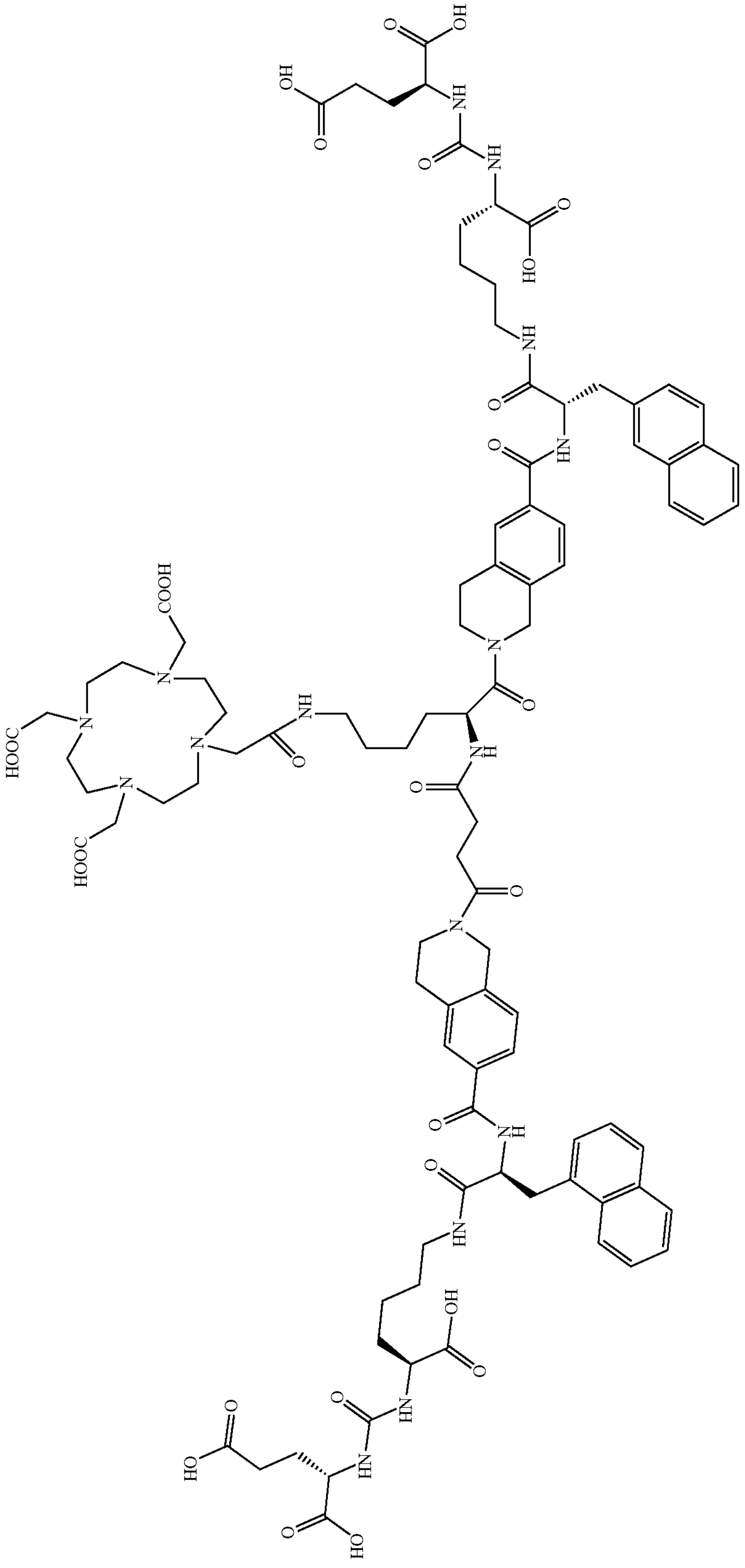

DB-10 was prepared using the method for synthesizing DB-04. MS (ESI): 1949 $(M+1)^+$.

Example 21 Synthesis of Metal Complex $^{177}$Lu-DB-01

177Lu-DB-01

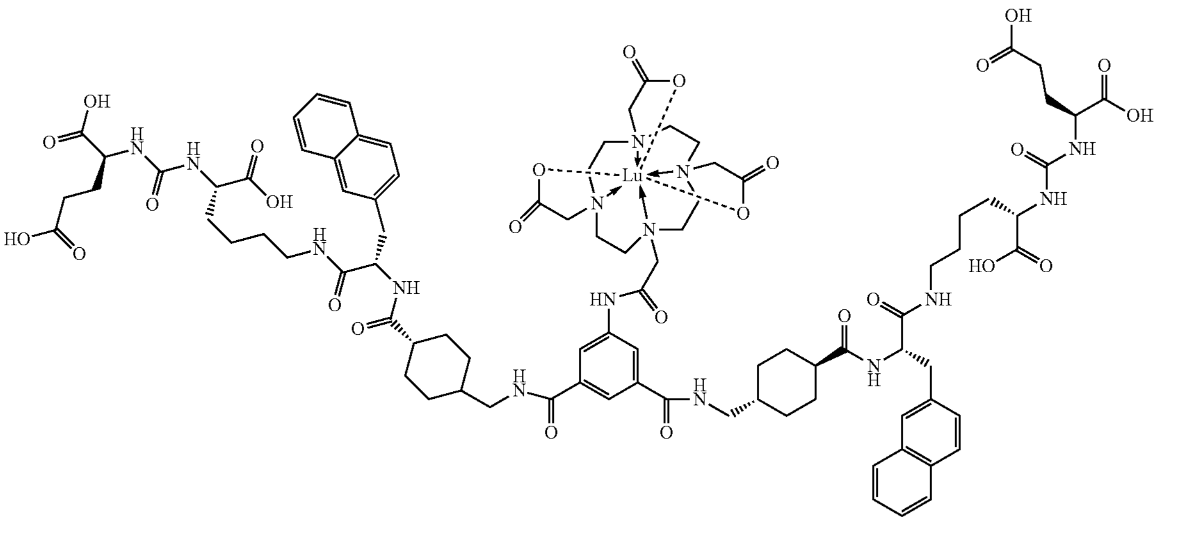

1) Sodium acetate (4.1 g) was weighed and dissolved in 45 mL of ultrapure water. The pH was adjusted to 4.0 using glacial acetic acid, and the solution was then diluted with ultrapure water to a final volume of 50 mL, resulting in a 1M sodium acetate solution. The temperature-controlled heating block was preheated to 95° C.

2) The precursor compound DB-01 (1 mg) was weighed and dissolved in 1000 μL of the sodium acetate respectively. After the compound was fully dissolved, a 1 μg/μL precursor solution was obtained. A solution of the precursor (10 μL, 10 μg) was diluted with 240 μL of sodium acetate solution. Subsequently, 250 μCi of $^{177}LuCl_3$ solution was added and mixed thoroughly. The mixture was then placed on the heating block at 95° C. for 30 minutes and purified using a C18 Sep-Pak.

3) EDTA sodium salt (0.5 g) was weighed and dissolved in 50 mL of physiological saline to obtain a 1% sodium EDTA sodium salt solution. A sample of $^{177}LuCl_3$ solution (2 μL) was spotted on an instant thin-layer chromatography (ITLC) silica gel plate, 1 cm away from the bottom, and evaporated to dryness. Similarly, 2 μL of the post-reaction solution was spotted on another ITLC silica gel plate, 1 cm away from the bottom, and evaporated to dryness. The silica gel plates were developed using 0.5 mL of the 1% EDTA sodium salt solution as the developing solvent, with the bottom of the plate immersed no more than 5 mm into the solvent in a glass tube. The tube was sealed with a rubber stopper, and when the plates were developed until the solvent front reached 9-10 cm., the plates were taken out and evaporated to dryness. The γ-scanner was used to scan the plates, and the radiochemical purity and labeling rate were calculated by comparing the peak areas of the $^{177}LuCl_3$ solution and the post-reaction solution.

As shown in Table 1, the $^{177}LuCl_3$ solution develops to the top of the silica gel plate in the developing solvent.

TABLE 1

Region: $^{177}$Lu Detector: PMT

| Name | Start (mm) | End (mm) | Rf value (RF) | Area (Counts) | % ROI (%) | % Total proportion (%) |
|---|---|---|---|---|---|---|
| Region 1 | 79.6 | 97.8 | 0.988 | 2384 | 100.00 | 99.33 |
| 1 Peak | | | | 2384 | 100.00 | 99.33 |

Total area: 2401 counts

Average background: 0 counts

As shown in Table 2, the labeled compound $^{177}$Lu-DB-01 develops only to the bottom of the silica gel plate in the developing solvent, with a radiochemical purity of 99.1% and a labeling rate of 100%.

TABLE 2

Region: $^{177}$Lu Detector: PMT

| Name | Start (mm) | End (mm) | Rf value (RF) | Area (Counts) | % ROI (%) | % Total proportion (%) |
|---|---|---|---|---|---|---|
| Region 1 | 10.6 | 30.8 | 0.163 | 2485 | 100.00 | 99.48 |
| 1 Peak | | | | 2485 | 100.00 | 99.48 |

Total area: 2498 counts

Average background: 0 counts

Example 22: Synthesis of DB-11

DB-11

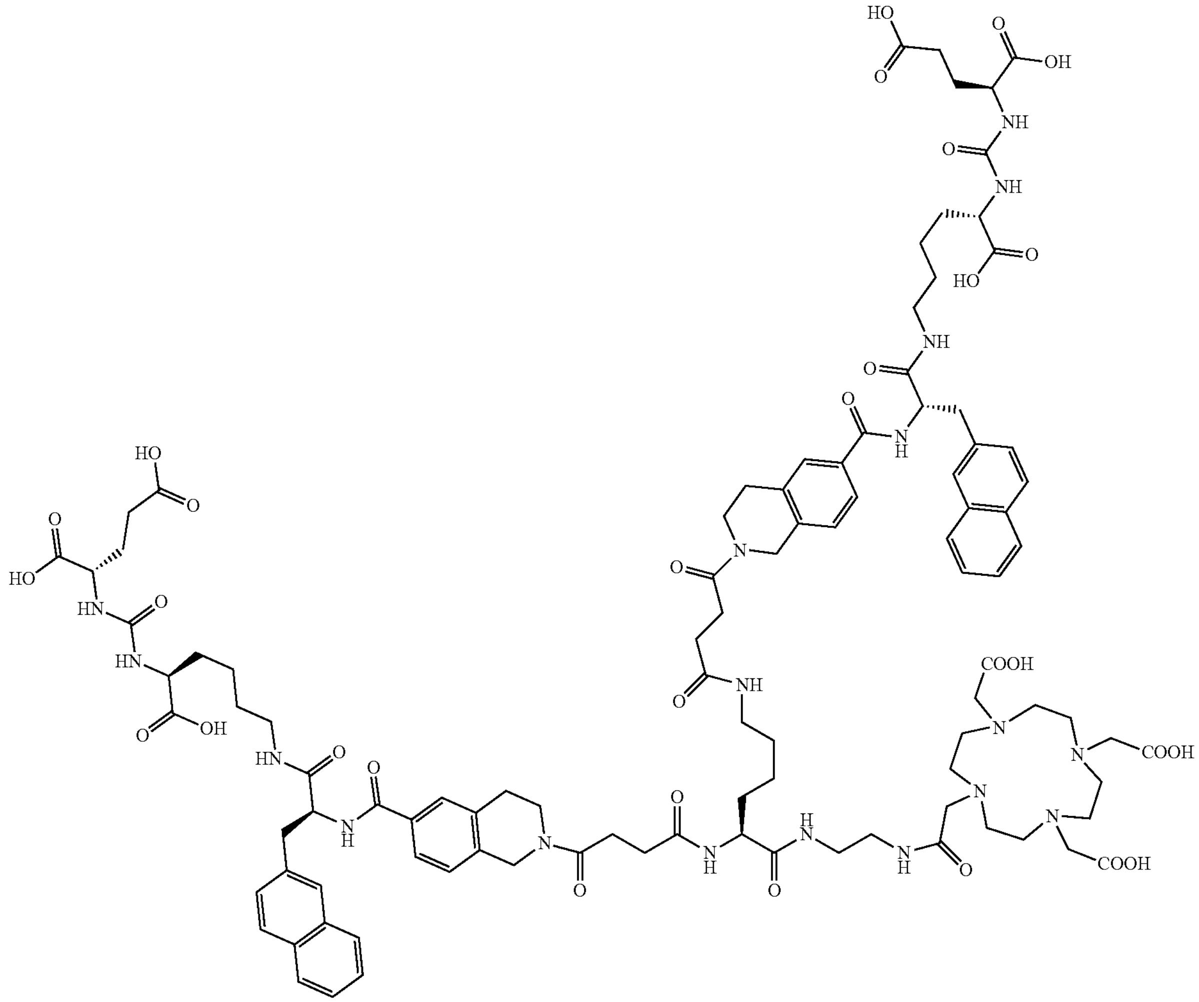

DB-11 was synthesized using the following general synthetic method: Through a series of condensation reactions, including solid-phase synthesis, the intermediates JH-04S10-01 (MS: $[M+H]^+$=489.61) and DB-11-01 (MS: $[M+H]^+$=788.50) were obtained. DB-11-02 (MS: $[M/2+H]^+$= 1015.43) was obtained by the condensation of JH-04S10-01 and DB-11-01, which was deprotected to obtain DB-11-03 (MS: $[M/2+H]^+$=852.81). This intermediate was then reacted with DOTA-NHS to obtain the final product, compound DB-11. HPLC: 98.54%, RT: 8.23; MS: $[M/2+H]^+$= 1046.36.

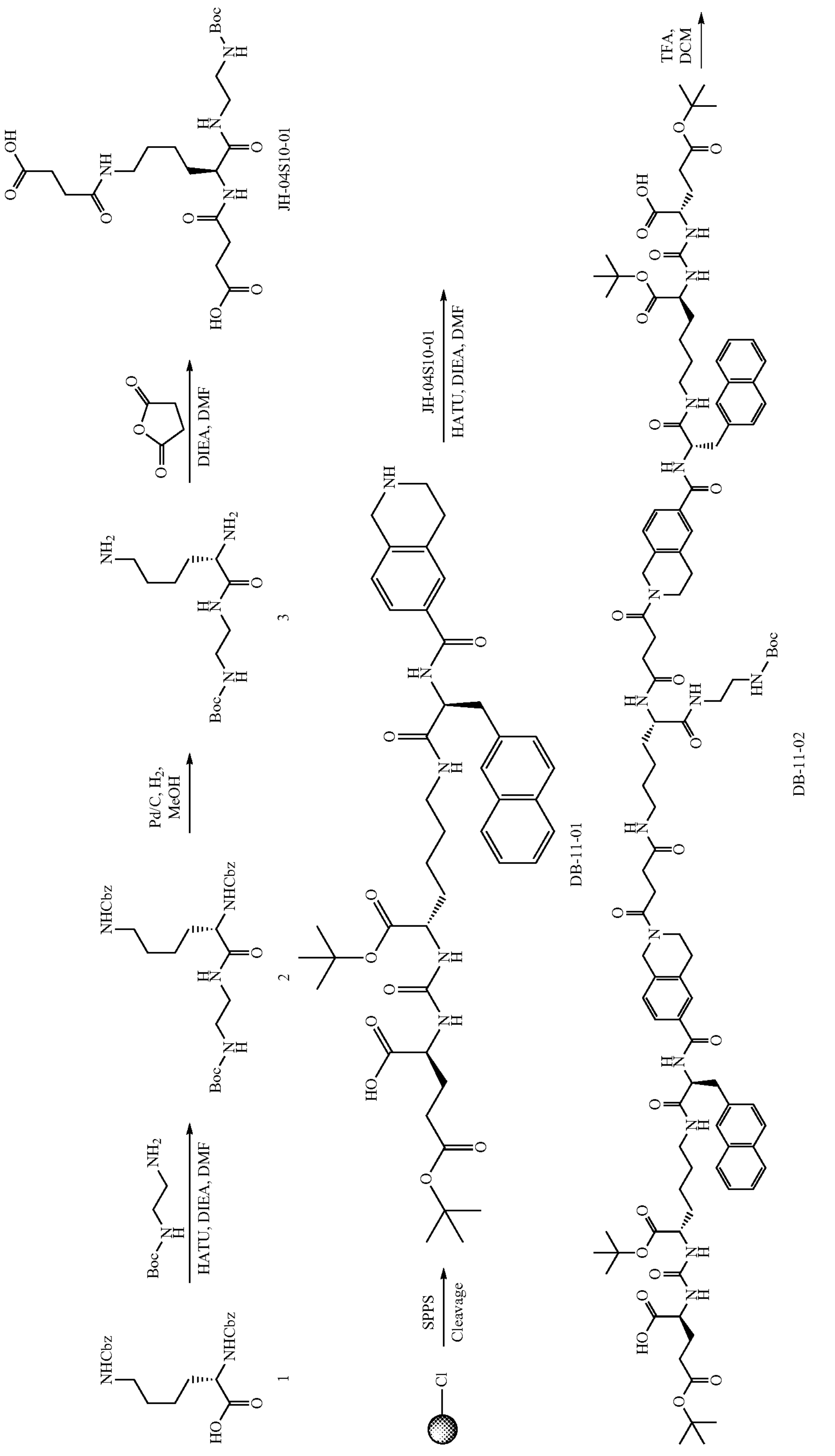
1
2
3
JH-04S10-01
DB-11-01
DB-11-02

-continued
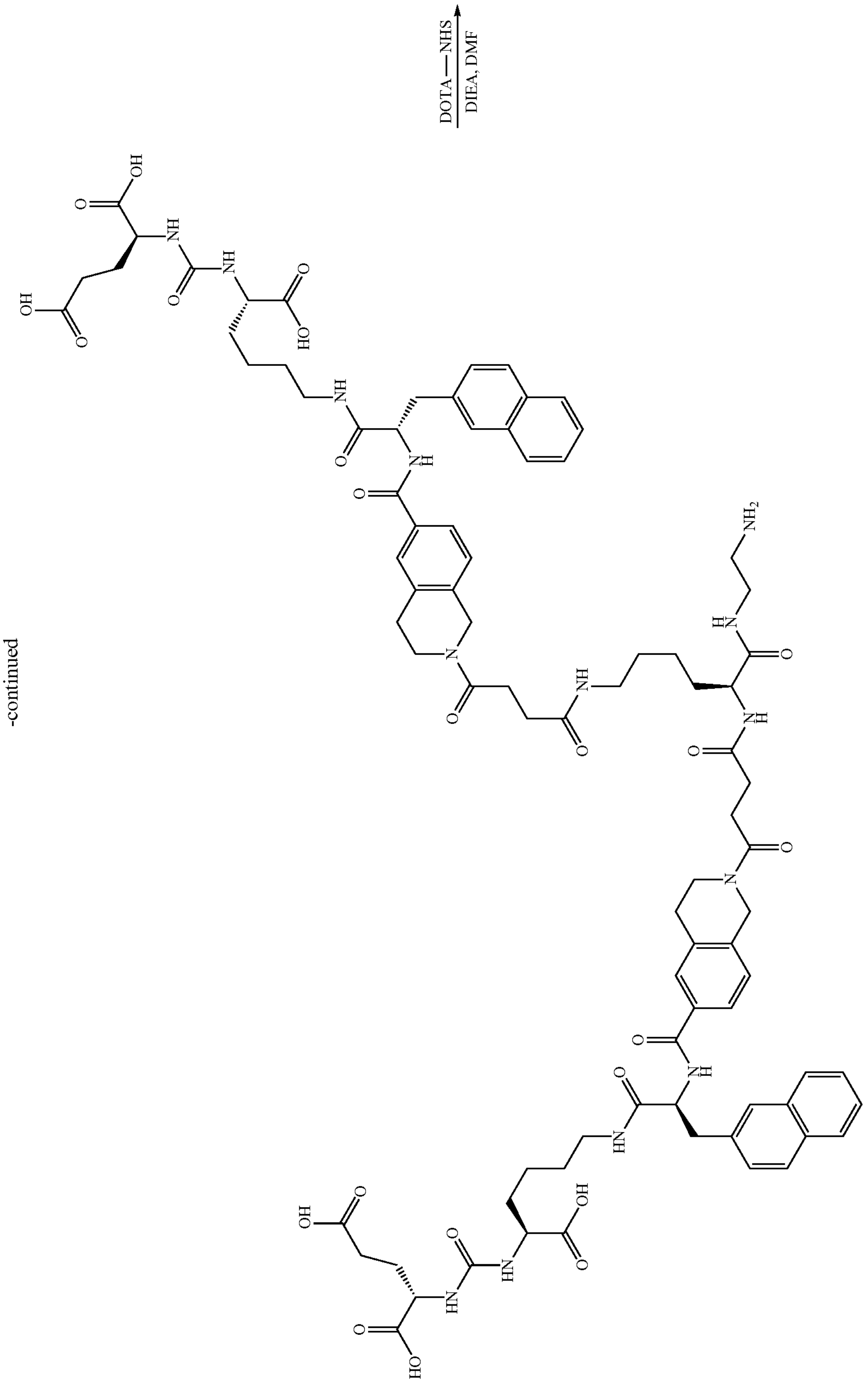
DB-11-03

-continued
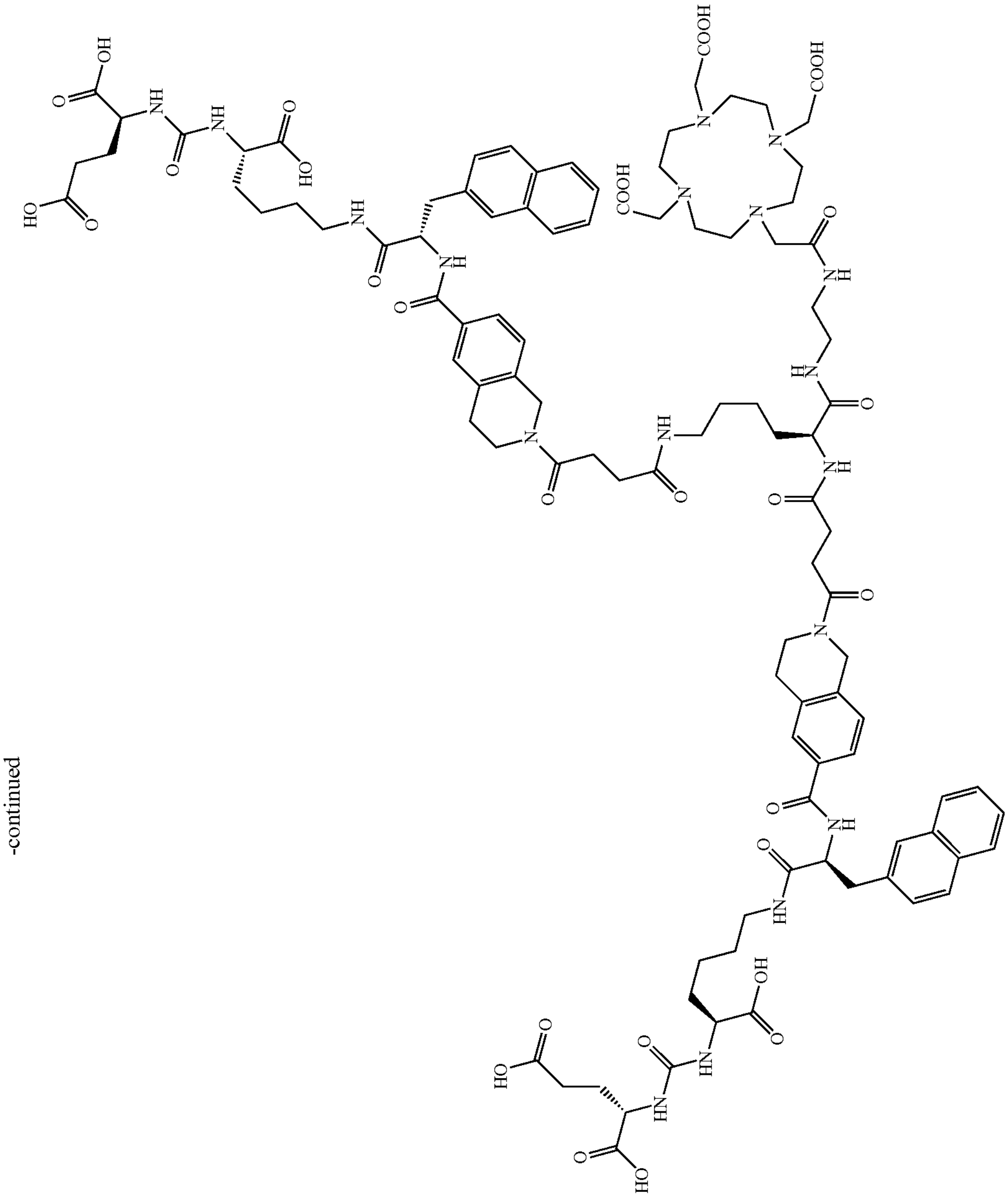
DB-11

Example 23: Synthesis of DB-12

DB-12
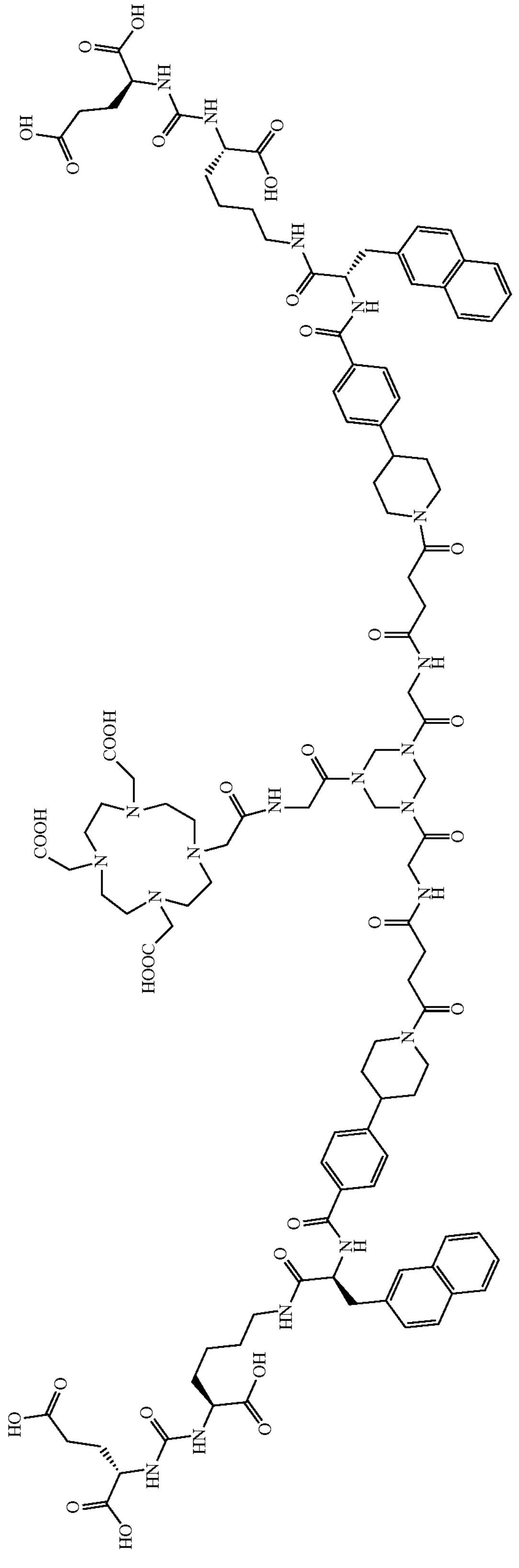

DB-12 was synthesized using the following general method. DB-A1 (MS: $[M+H]^+$=816.83) and DB-A2 (MS: $[M+H]^+$=681.73), both obtained via solid-phase synthesis, were coupled to obtain DB-A3 (MS: $[M/2+H]^+$=1139.49). After two deprotection steps, the intermediate DB-A5 (MS: $[M/2+H]^+$=916.21) was reacted with DOTA-NHS to obtain DB-12. HPLC: 95.58%, RT: 10.963; MS: $[M/2+H]^+$=1109.90.

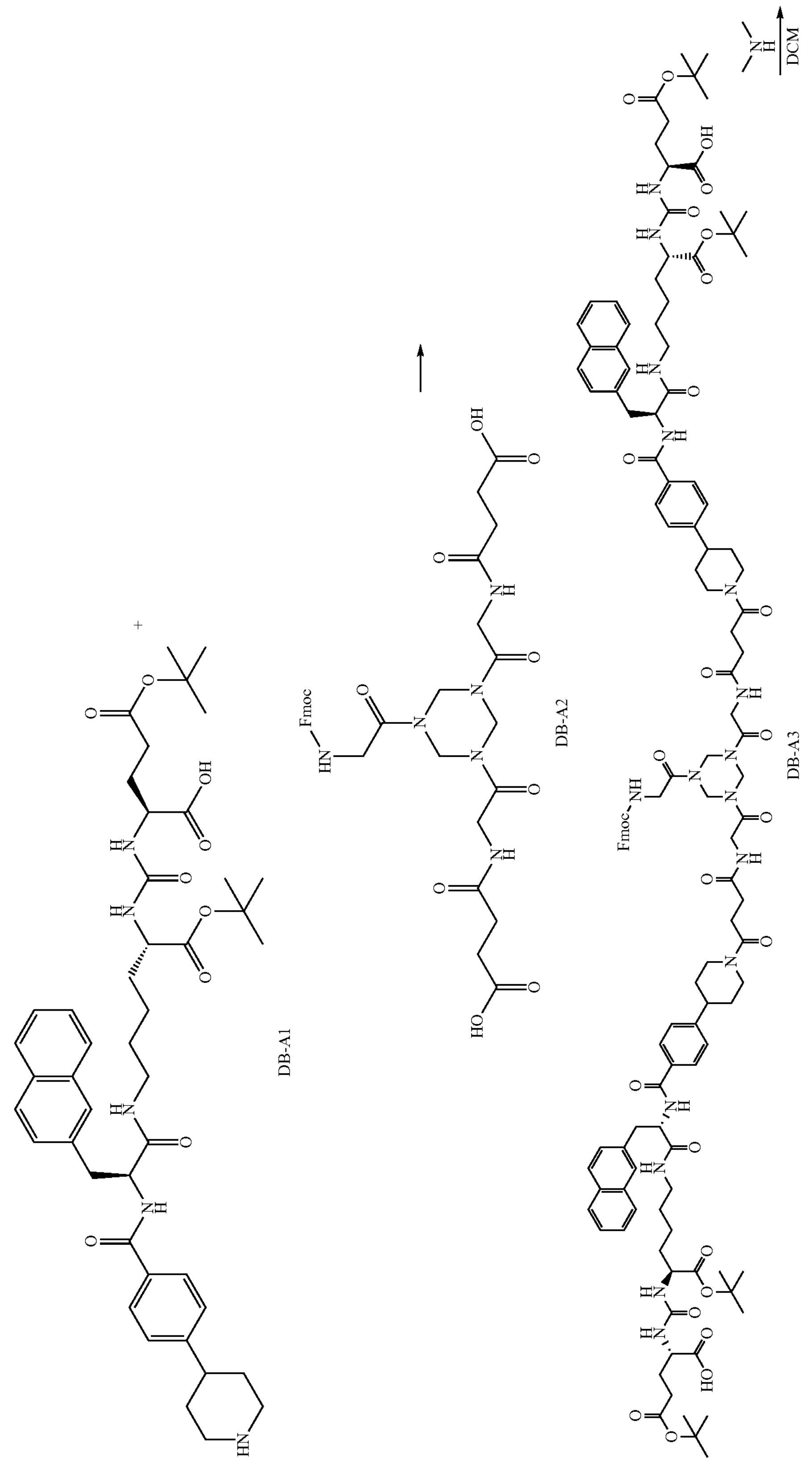
DB-A1
DB-A2
DB-A3

-continued
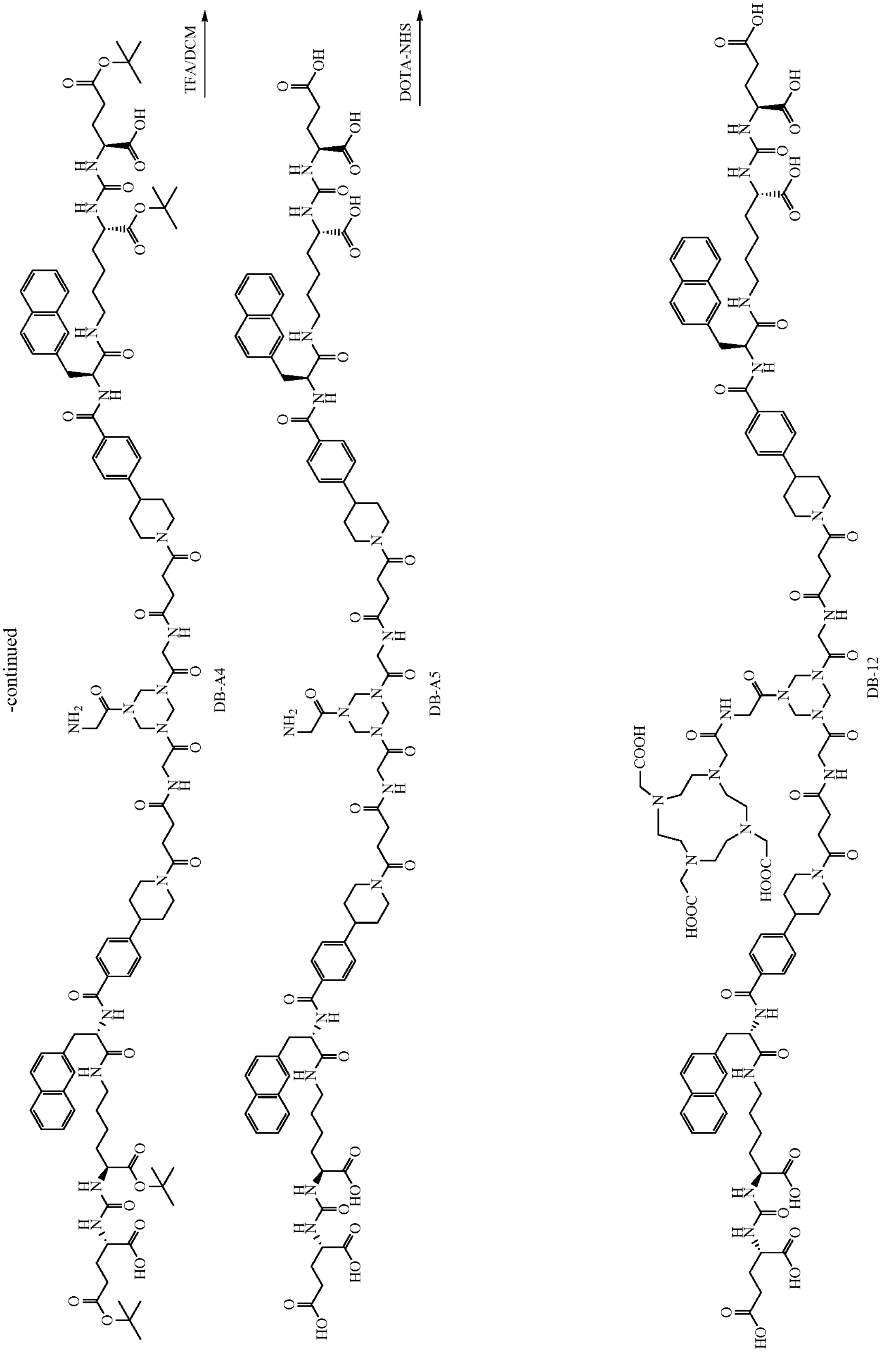
DB-A4
DB-A5
DB-12

Example 24: Synthesis of DB-13

DB-13
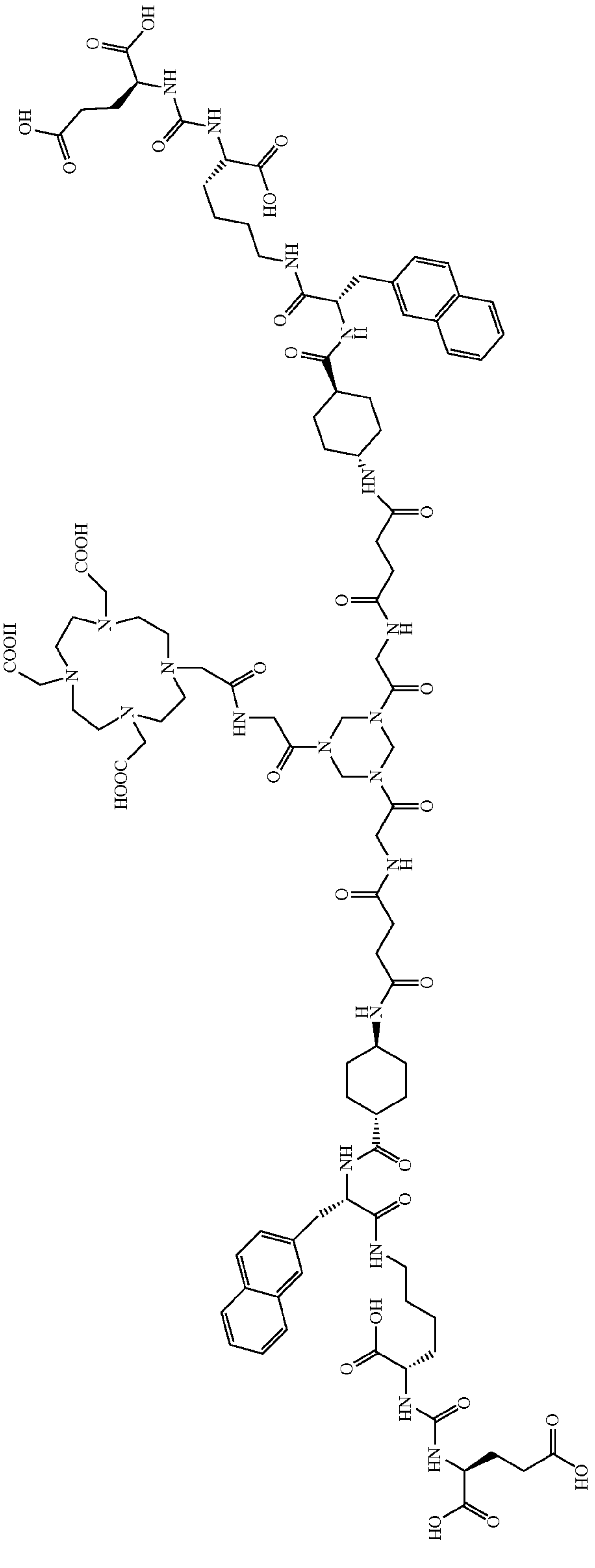

DB-13 was synthesized with reference to the general synthetic method used for DB-12. HPLC: 97.73%, RT: 9.214; MS: $[M/2+H]^+$=1047.34.

Example 25: Synthesis of DB-14

DB-14
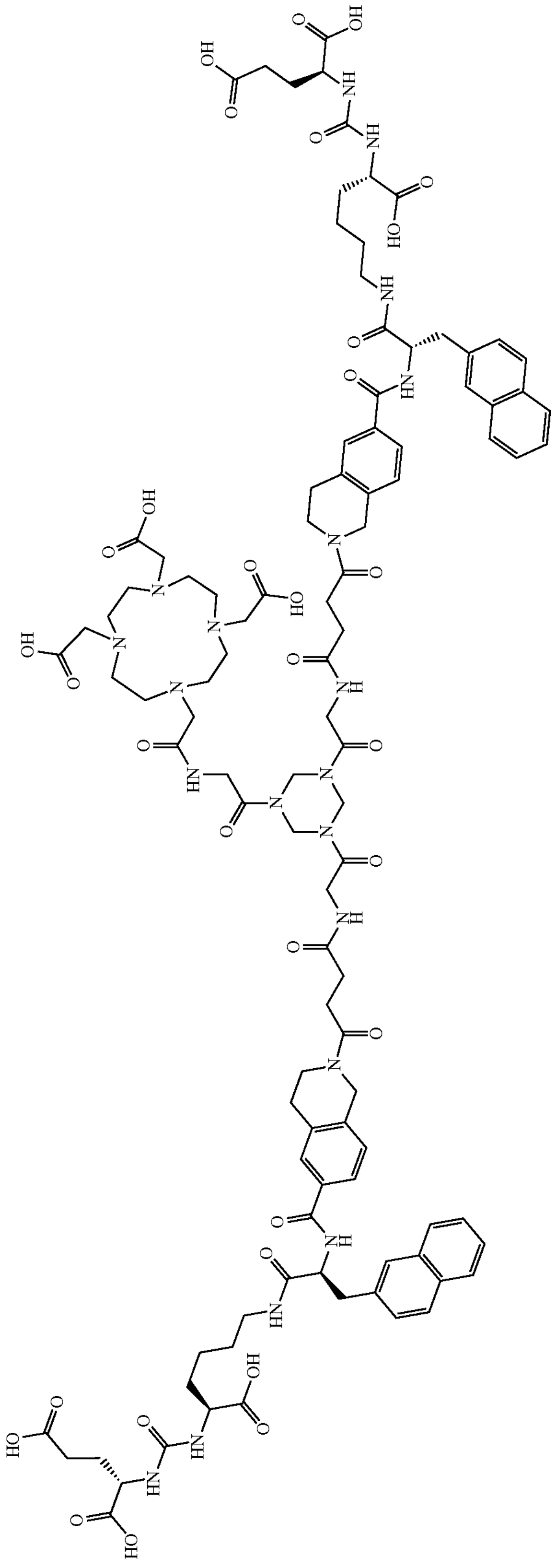

DB-14 was synthesized with reference to the general synthetic method used for DB-12. HPLC: 95.8%, RT: 9.52; MS: $[M/2+H]^+$=1047.34.

Example 26: Synthesis of DB-15

DB-15
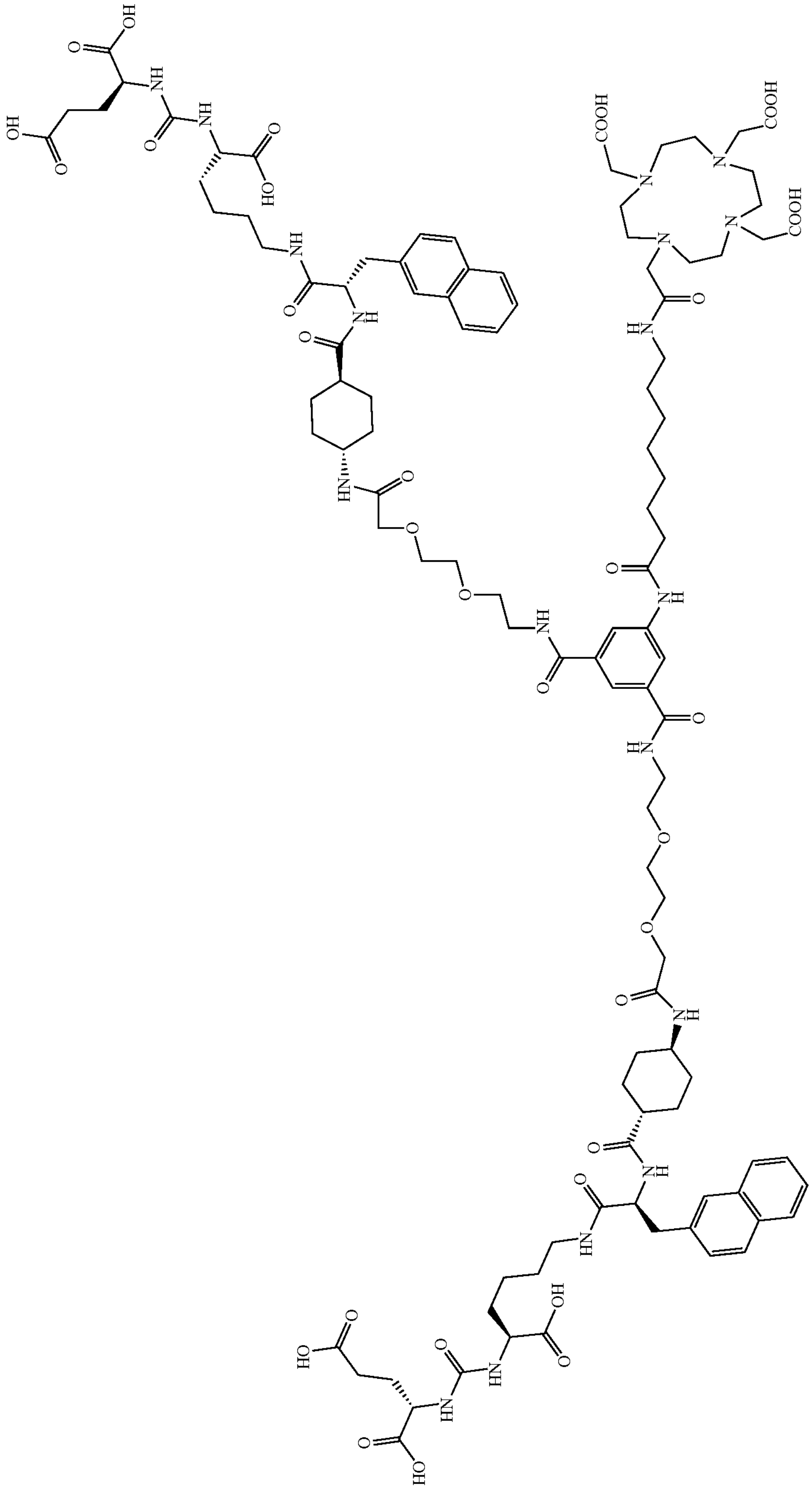

DB-15 was synthesized with reference to the general synthetic methods D and E. HPLC: 95.8%, RT: 12.34; MS: $[M/2+H]^{+}$=1124.59.
Example 27: Synthesis of DB-16
DB-16
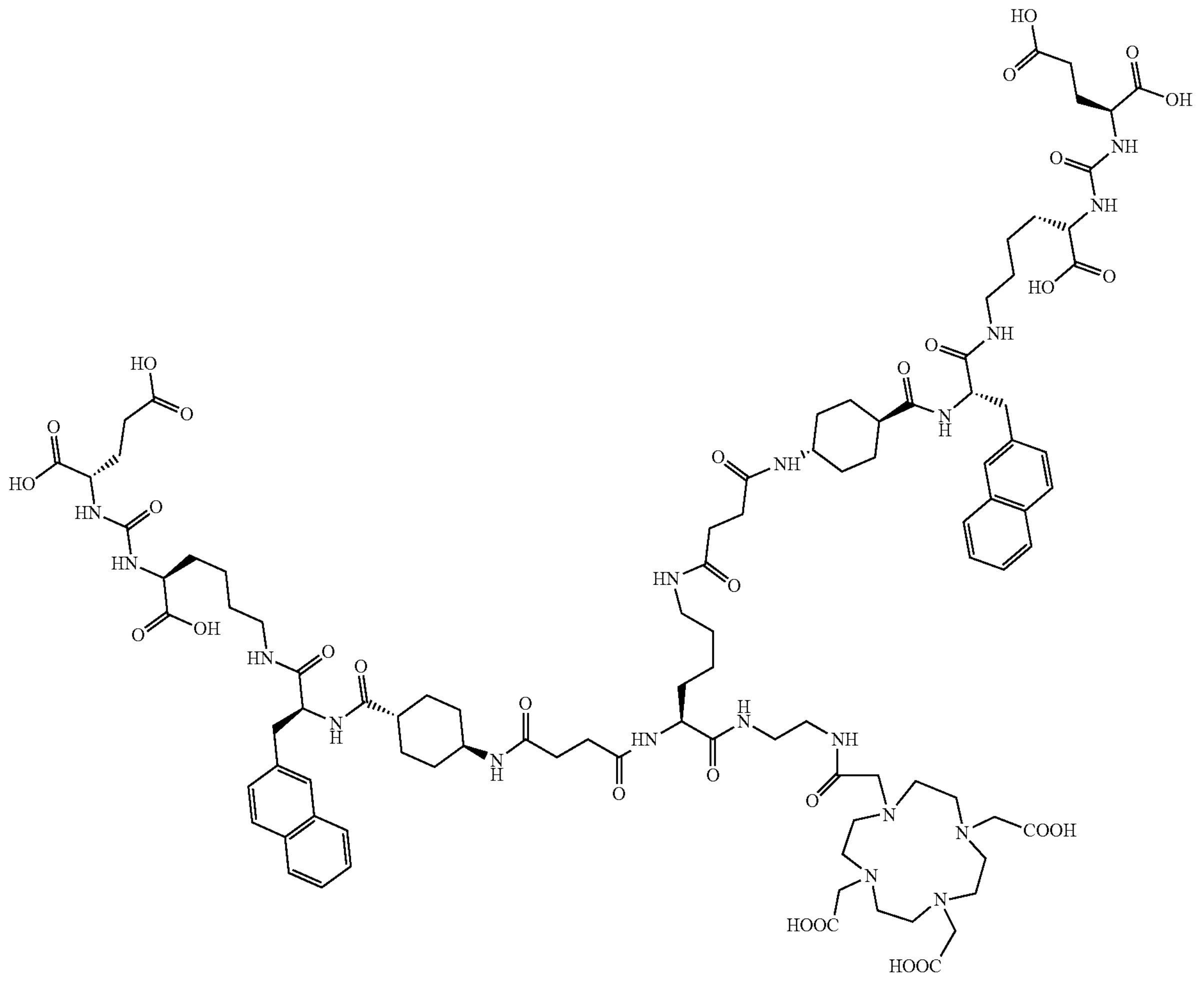

DB-16 was synthesized with reference to the general synthetic method used for DB-11. HPLC: 96.62%, RT: 9.543; MS: $[M/2+H]^+$=1012.36.
Example 28: Synthesis of DB-17
DB-17
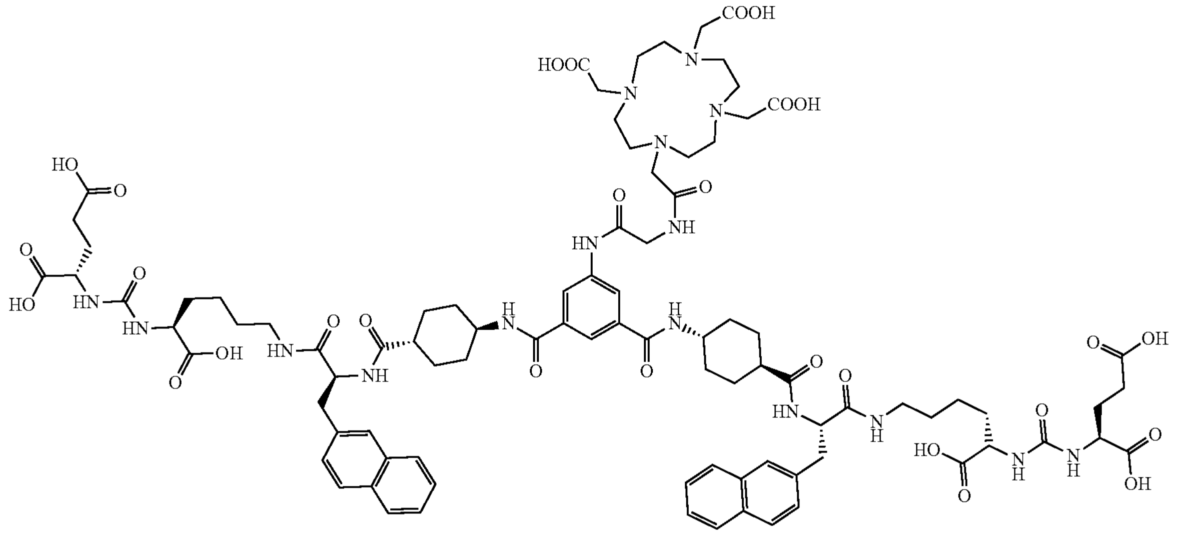
DB-17 was synthesized with reference to the general synthetic methods D and E. HPLC: 99.24%, RT: 10.423; MS: $[M/2+H]^+$=937.27.
Example 29: Synthesis of DB-18
DB-18
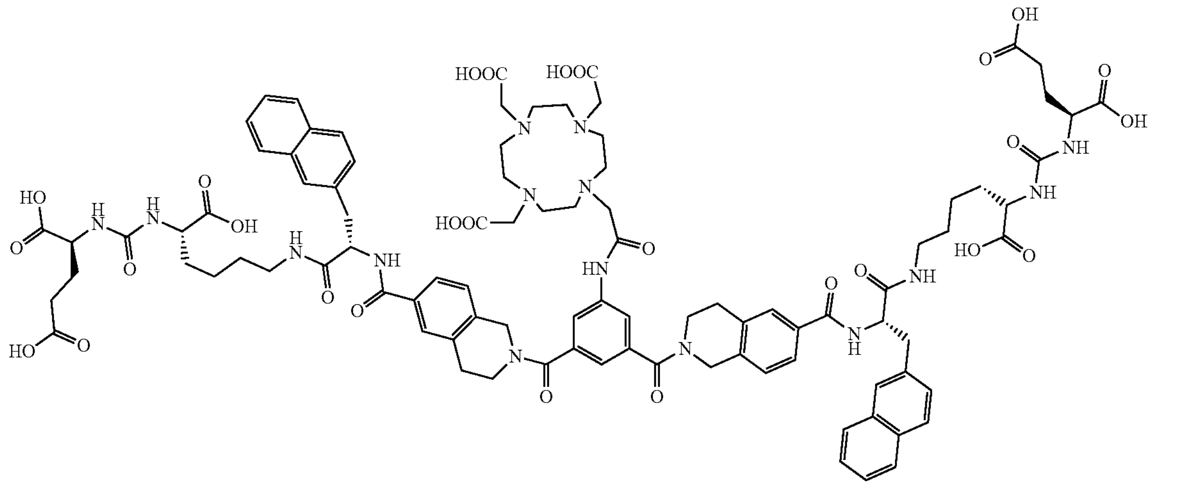

DB-18 was synthesized the general synthetic methods D and E. HPLC: 95.64%, RT: 7.78; MS: $[(M-1)/3-1]^+$= 626.37.

Example 30: Synthesis of DB-19

DB-19
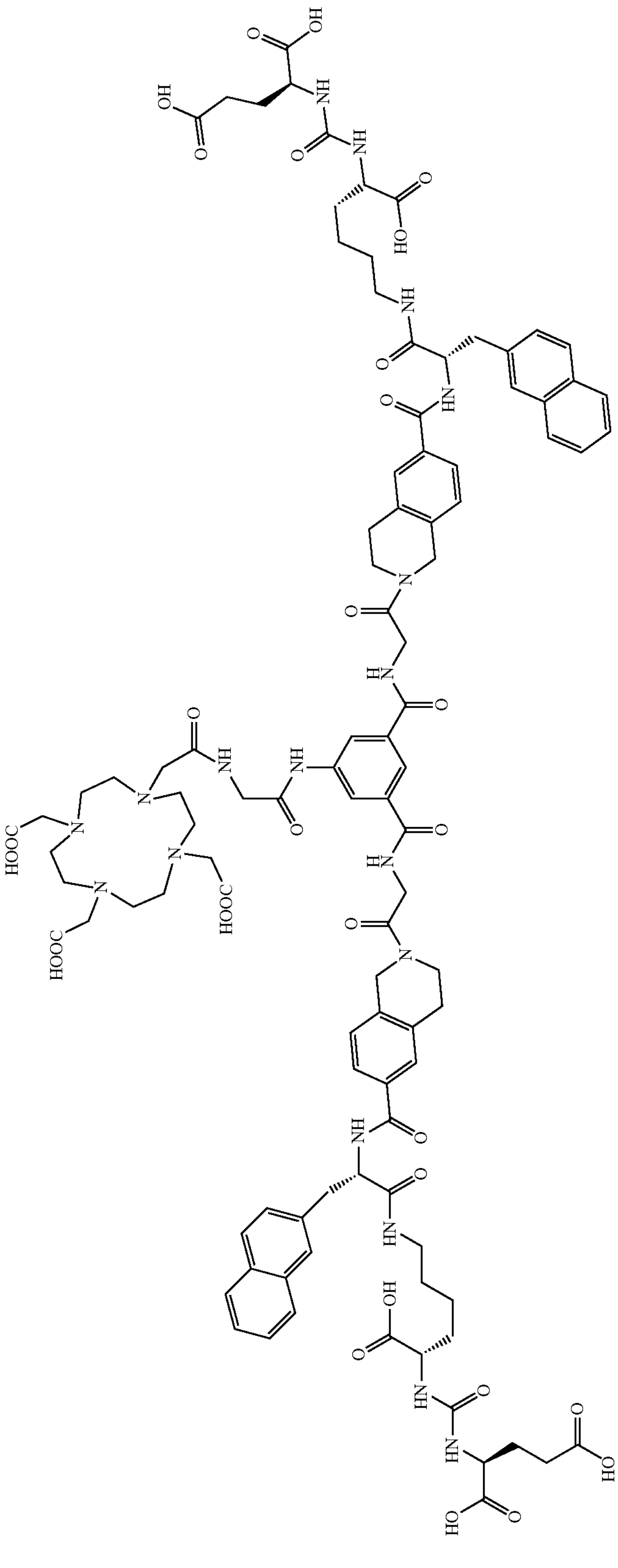

DB-19 was synthesized the general synthetic methods D and E. HPLC: 97.73%, RT: 9.10; MS: $[M/2+H]^+$=1028.17.
Example 31: Synthesis of DB-20
DB-20
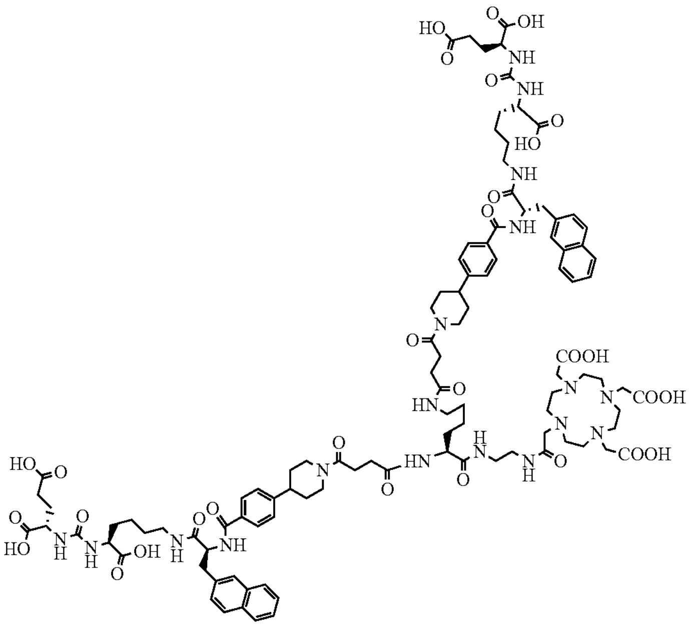
DB-20 was synthesized the general synthetic method used for DB-11. HPLC: 98.95%, RT: 11.294; MS: $[M/2+H]^+$= 1074.49.
Example 32: Synthesis of DB-21
DB-21
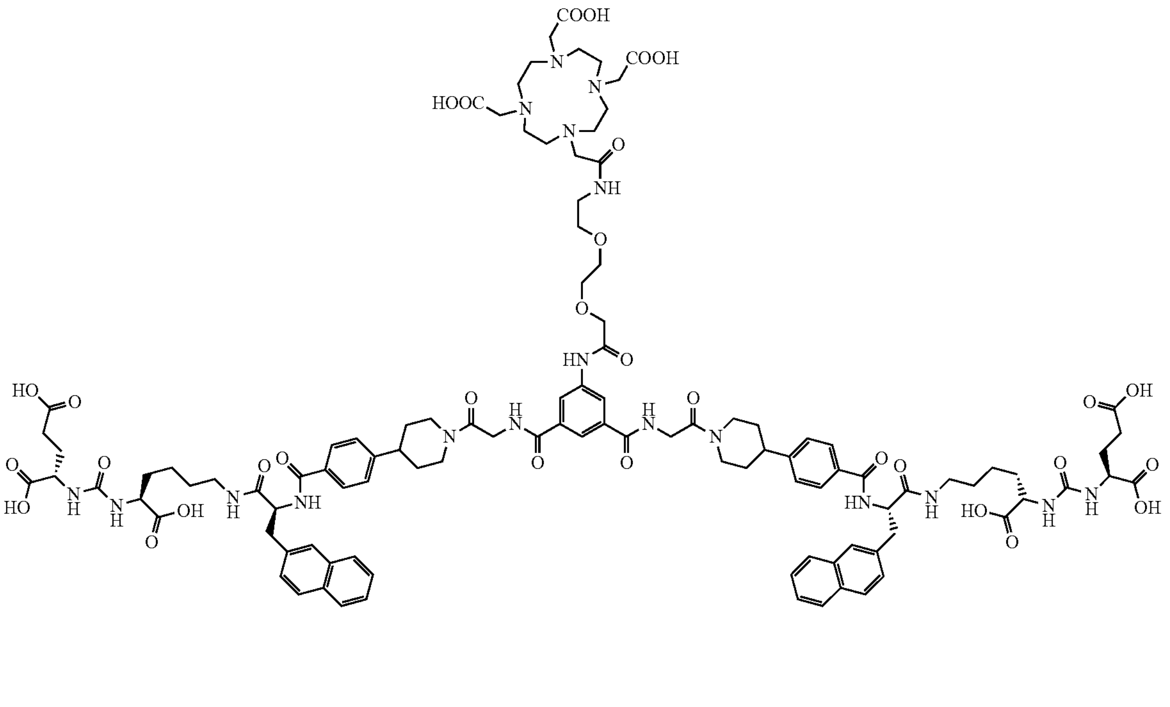

DB-21 was synthesized with reference to the general synthetic methods D and E. HPLC: 98.01%, RT: 12.446; MS: $[M/2+H]^+$=1100.24.

The structure of the reference compound used in the following effect examples is as follows:

PSMA-617

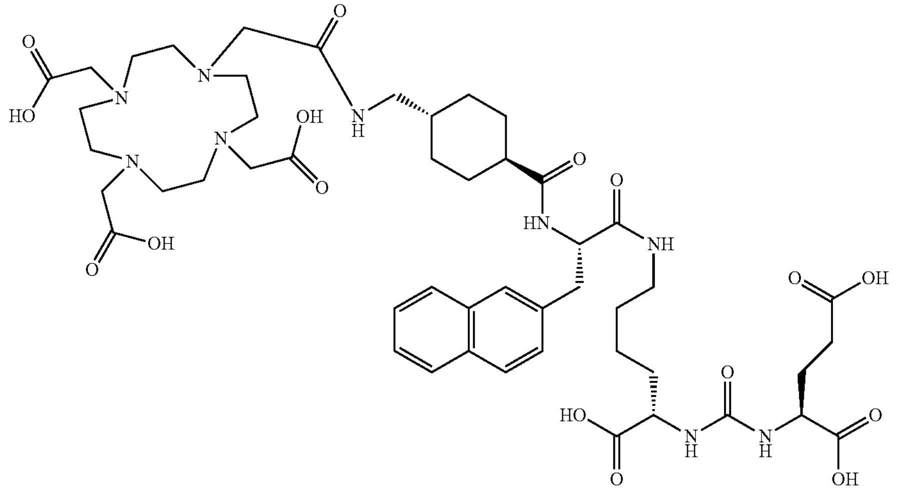

E-3

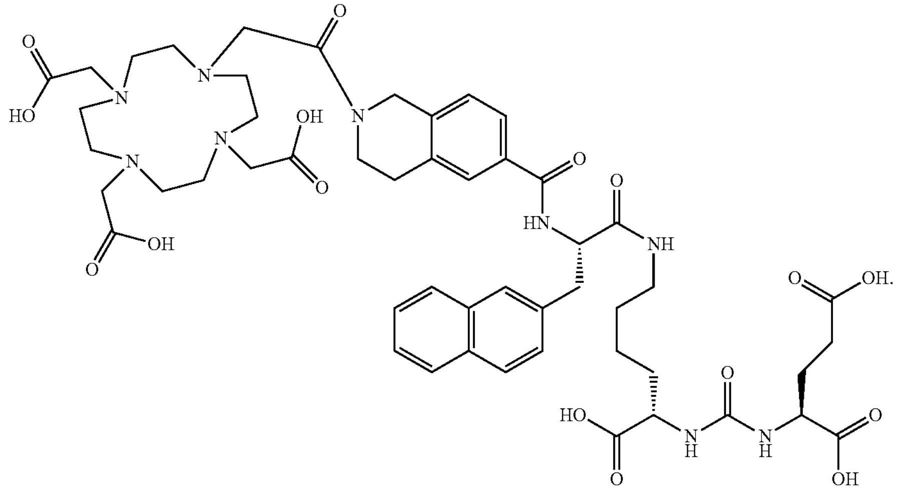

Effect Example 1: Determination of Binding Affinity and Dissociation Constant of PSMA-Targeting Candidate Molecules The dissociation constant was determined using the Biacore 8K (GE Healthcare) following the manufacturer's instructions. In brief, PSMA-bio protein, diluted in PBS pH 7.4 with 1 mM TCEP, 0.05% Tween 20, and 2% DMSO buffer, was immobilized on the flow cell of an SA sensor chip. Using PBS pH 7.4, 1 mM TCEP, 0.05% Tween 20, and 2% DMSO as the running buffer, five serial dilutions of the PSMA-targeting candidate molecules were injected into the flow cell at a rate of 30 μL/min, with a binding time of 90 seconds. The buffer flow was maintained for 1800 seconds to allow dissociation. The KD values for the interaction between the candidate small molecules and the PSMA protein were evaluated using Biacore 8K evaluation software 1.0 and a 1:1 binding model.

The results are shown in Table 3. The binding affinity of DB-01 was slightly higher than that of PSMA-617.

TABLE 3

Binding kinetics and affinity of candidate molecules with PSMA protein determined by Biacore 8K

| Molecule Number | Protein | KD(M) | ka (1/Ms) | kd (1/s) |
|---|---|---|---|---|
| PSMA-617 | hPSMA-biotin | 4.83E−10 | 1.01E+05 | 4.88E−05 |
| DB-01 | hPSMA-biotin | 1.20E−10 | 2.22E+05 | 2.65E−05 |

Effect Example 2: Micro-SPECT/CT Scanning Imaging Study in Mouse Transplanted with Human Prostate Cancer Cell Line 22RV1

Human prostate cancer cell line 22RV1 cells were subcutaneously injected into the axilla of nude mouse to establish a prostate cancer tumor model. Approximately 3.7 MBq (100 μCi/200 μL) of the $^{177}$Lu-labeled compound [$^{177}$Lu]DB-01 was administered via intravenous injection. SPECT/

CT images were acquired using the U-SPECT+/CT (MI Labs) at 3rd hour, 5th hour, 24th hour, 72nd hour, 120th hour and 168th hour post-injection, and the resulting SPECT/CT images were quantitatively analyzed.

Table 4 presents the uptake in various organs of mouse at the $3^{rd}$ hour, $5^{th}$ hour, $24^{th}$ hour, $72^{nd}$ hour, $120^{th}$ hour, and $168^{th}$ hour post-injection of [$^{177}$Lu] DB-01. The results are expressed as the quantitative percentage of the injected dose (% ID)/g, based on Micro-SPECT/CT quantitative analysis.

As shown in Table 4, [$^{177}$Lu] DB-01 was rapidly excreted through the kidneys and bladder in the early stages post-injection.

In the case of [$^{177}$Lu] DB-01, its uptake in tumors increased over time. According to calculations, the uptake in tumor at 180 minutes was 13.55±3.85% ID/g, with a significantly prolonged tumor retention time, still showing 7.85±1.16% ID/g at 168 hours. Additionally, the [$^{177}$Lu] DB-01 compound exhibited a reduction in renal uptake starting from the 5th hour, followed by rapid excretion from the body.

TABLE 4

Uptake of [$^{177}$Lu] DB-01 in various organs of mouse over time (% ID/g)

| Time | Tumor (22Rv1) | Kidney | Bladder | Liver | Muscle |
|---|---|---|---|---|---|
| 3 hr | 21.25 ± 4.38 | 43.00 ± 7.38 | 65.50 ± 36.65 | 2.75 ± 0.90 | 1.97 ± 0.71 |
| 5 hr | 21.28 ± 0.42 | 19.29 ± 2.77 | 140.36 ± 10.51 | 1.56 ± 0.15 | 1.10 ± 0.56 |
| 24 hr | 15.51 ± 2.65 | 1.32 ± 0.63 | 0.61 ± 0.00 | 0.91 ± 0.45 | 0.51 ± 0.17 |
| 72 hr | 12.41 ± 0.95 | 1.38 ± 0.29 | 1.03 ± 0.62 | 0.90 ± 0.42 | 0.81 ± 0.23 |
| 120 hr | 8.90 ± 0.48 | 0.77 ± 0.62 | 0.92 ± 0.06 | 0.99 ± 0.22 | 0.43 ± 0.17 |
| 168 hr | 7.85 ± 1.16 | 1.53 ± 0.46 | 1.01 ± 0.38 | 1.04 ± 0.26 | 0.65 ± 0.34 |

Figure 2:
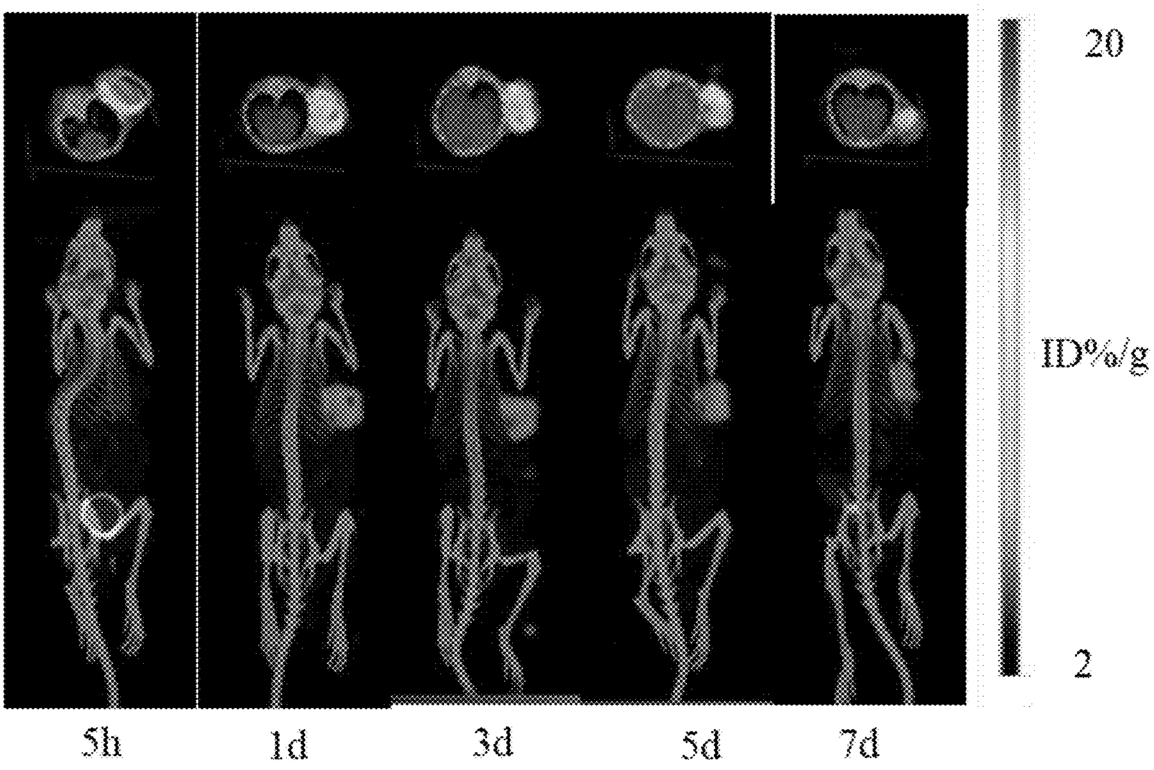
FIG. 2 shows the Micro-SPECT/CT imaging images of DB-01 in mouse 2 at different times.
Figure 3:
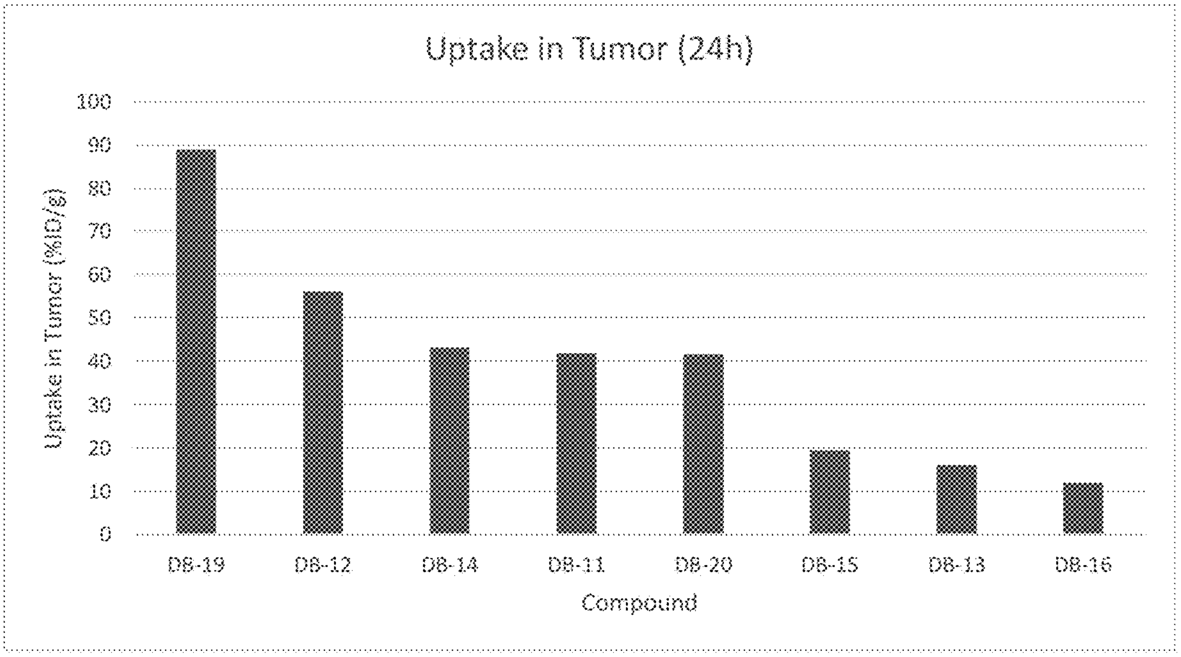
FIG. 3 shows the uptake of different DB compounds in the tumor samples of mouse 24 hours after administration in effect example 4.
Figure 4:
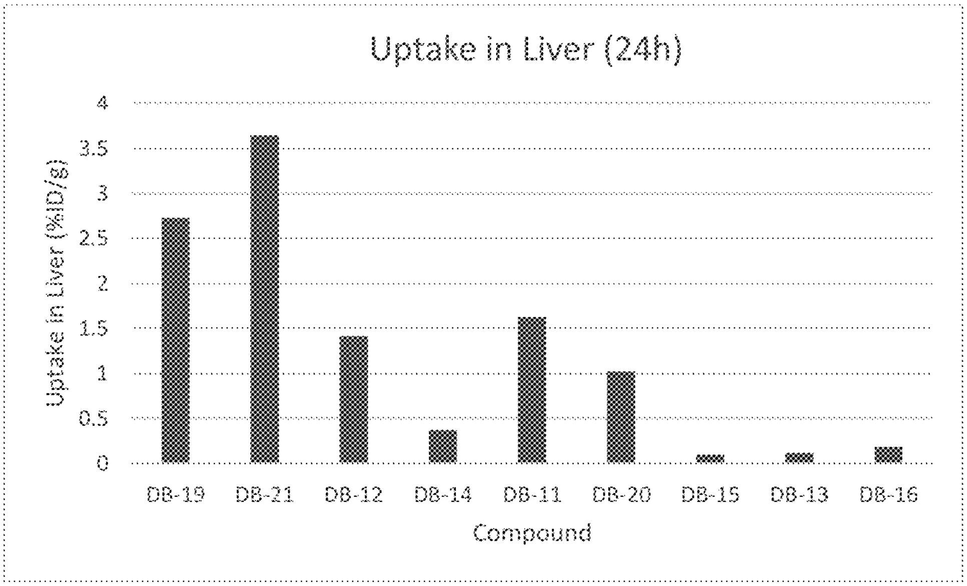
FIG. 4 shows the uptake of different DB compounds in the liver samples of mouse 24 hours after administration in effect example 4.
Figure 5:
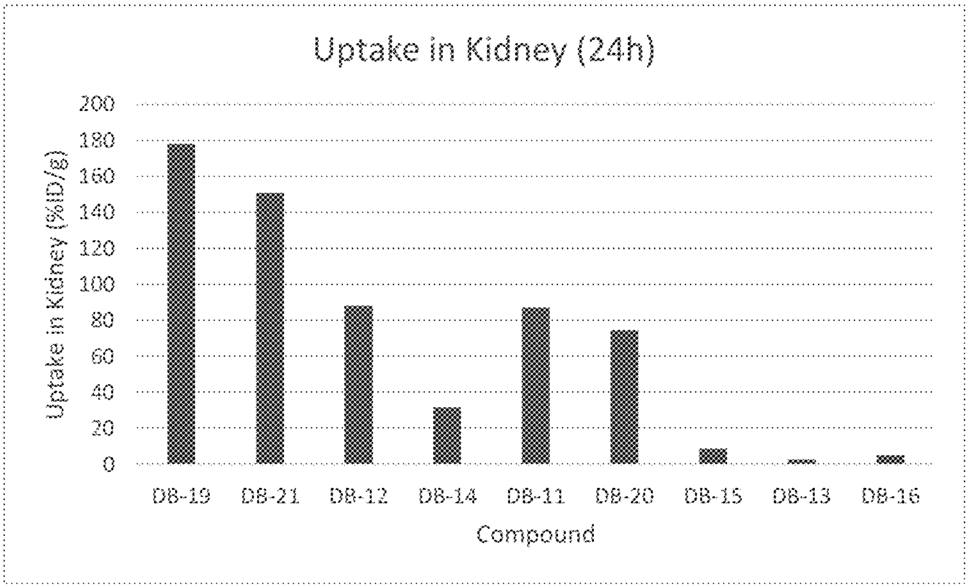
FIG. 5 shows the uptake of different DB compounds in the kidney samples of mouse 24 hours after administration in effect example 4.
Figure 6:
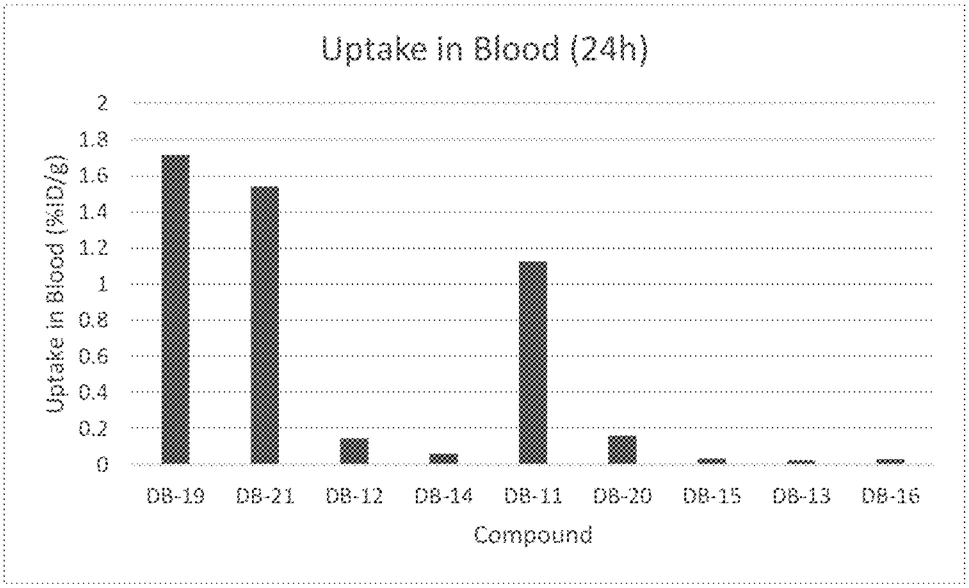
FIG. 6 shows the uptake of different DB compounds in the blood samples of mouse 24 hours after administration in effect example 4.
Figure 7:
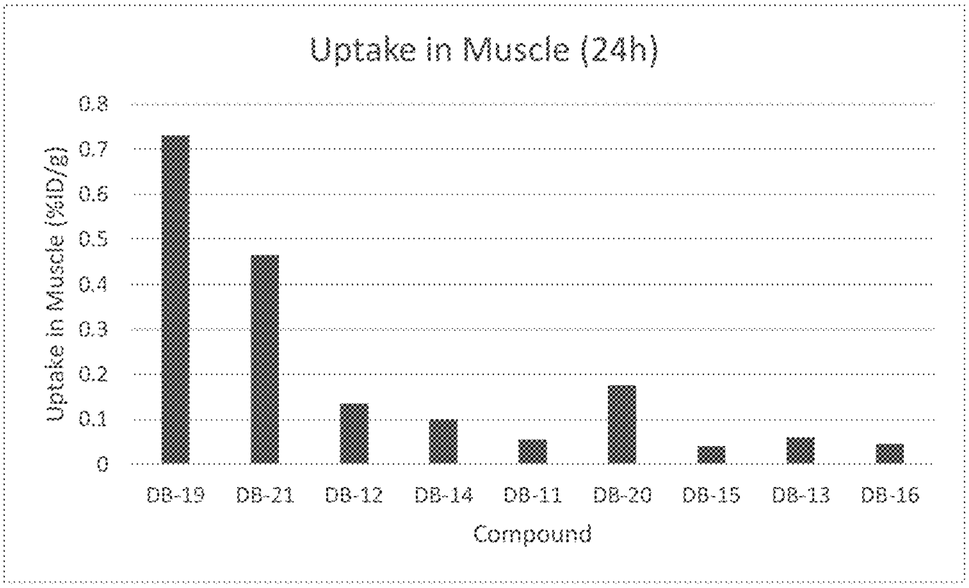
FIG. 7 shows the uptake of different DB compounds in the muscle samples of mouse 24 hours after administration in effect example 4.

From Table 4, along with FIG. 1 and FIG. 2, it can be observed that after the administration of $^{177}$Lu-DB-01 into mouse, it is rapidly distributed to various organs and target sites. The primary metabolic pathway is through excretion via urine. After 5 hours post-administration, the concentration of the radiopharmaceutical in the tumor reaches its peak, followed by a gradual decline. After 24 hours, the accumulation of the radiopharmaceutical significantly decreases in other organs, except for its concentration in the tumor. Even after 7 days, a substantial amount of the radiopharmaceutical remains in the tumor. The results indicate that the compound disclosed in this patent application not only exhibits better PSMA cell affinity compared to the reference compound PSMA-617 but also possesses superior pharmacokinetics, making it a more promising candidate for theranostic radiopharmaceuticals.

Effect Example 3: Testing the Affinity of DB Compounds to PSMA Protein Using Biacore The affinity of DB compounds to PSMA protein was tested using the Biacore 8K (Cytiva) instrument to detect ligand binding to PSMA protein (Sino Biological). PSMA protein was captured on an SA chip. Before fixing the ligand (flow paths 1 and 2, flow rate of 10 μL/min), PSMA protein (10 μg/mL, flow rate of 5 μL/min, injection time of 600 s) was fixed on flow path 2 using a flow buffer. The sensor surface was adjusted by continuously injecting 1 M NaCl three times in 50 mM NaOH. After each ligand injection, additional cleaning was performed using isopropanol in 1 M NaCl and 50 mM NaOH (flow paths 1 and 2, flow rate of 10 μL/min, injection time of 60 s).

All compounds were dissolved in 100% DMSO and diluted to 10 mM, then further diluted to the appropriate highest concentration in the analysis buffer (PBS, PH 7.4, 1 mM TCEP (tris-(2-hydroxyethyl) phosphine), 0.05% P20, 2% DMSO). The analysis was conducted under the following conditions: 15° C. analysis temperature; analysis steps=all set to LMW kinetics; cycle type=single cycle (90 s contact time, 1800 s dissociation time, 30 μL/min flow rate, flow paths 1 and 2); detection in flow=path 2-1. Data evaluation was performed using Biacore Insight Evaluation Software, fitting the data to a 1:1 binding model.

Biacore results are shown in Table 5: pKD=−Log KD, wherein KD is the binding affinity of the compound to PSMA protein measured by Biacore. It is expressed by Kd (M)=Kd (1/s)/Ka (1/Ms). A indicates pKD>8; B indicates 7<pKD<8; C indicates 6<pKD<7; D indicates pKD<6.

TABLE 5

Biacore test results

| Compound | pKD |
|---|---|
| DB-1 | A |
| DB-2 | A |
| DB-11 | A |
| DB-12 | A |
| DB-13 | A |
| DB-14 | A |
| DB-15 | A |
| DB-16 | A |
| DB-17 | A |
| DB-18 | A |
| DB-19 | A |
| DB-20 | A |
| DB-21 | A |
| E-3 | A |
| PSMA-617 | A |

Effect Example 4: 177Lu Labeling and Animal Biodistribution Experiment

Distribution in PSMA-positive tumor-bearing mouse tissues: Tumor-bearing animals (purchased from Shanghai Alamo Pharmaceutical Technology Co., Ltd.) were subcutaneously inoculated with $3\times10^6$ 22rv1 cells (in 50% Matrigel, Corning) into the right shoulder region of 6-9 week old (Balb/c Nude) mouse. Once the tumors had grown to an appropriate size, $^{177}$Lu-radiolabeled DB compounds were injected into the mouse via the tail vein (approximately 1.85 MBq-3.7 MBq/mouse, specific activity: 22423.82 Kbq/μg). After administration, the animals were euthanized using carbon dioxide inhalation at 24 hours. The blood and organs (blood, liver, kidney, muscle, tumor) were collected.

Blood was collected through the abdominal aorta and 100 μL was immediately quantified into designated centrifuge tubes (weighed). After collection, the organs were washed twice with deionized water, dried, placed in pre-weighed tubes, and weighed again to calculate the sample weight. Samples were measured on the day of collection. All blood and tissue samples were measured for radioactivity using a gamma counter. The results are shown in FIGS. 3, 4, 5, 6, 7, and Table 6.

Following intravenous administration, the $^{177}$Lu-labeled DB compounds rapidly distributed to various organs in the tumor-bearing mouse. The uptake in non-target organs remained low and was quickly metabolized out of the body, with a rapid clearance rate from the blood, which was primarily excreted through the kidneys. At 24 hours post-administration, the uptake of the $^{177}$Lu-labeled compound in tumors remained at high levels, particularly DB-12 and DB-19, which exhibited exceptionally high uptake in PSMA-positive 22RV1 tumor cells.

TABLE 6

Biodistribution data of $^{177}$Lu-labeled compounds (n = 2)

| 24 h | E-3 | DB-19 | DB-21 | DB-12 | DB-14 | DB-11 | DB-20 | DB-15 | DB-13 | DB-16 |
|---|---|---|---|---|---|---|---|---|---|---|
| Tumor volume ($mm^3$) | 262.99 | 248 | 445.34 | 254.335 | 326.78 | 247.7 | 394.94 | 350.32 | 398.98 | 452.98 |
| Name | % ID/g | % ID/g | % ID/g | % ID/g | % ID/g | % ID/g | % ID/g | % ID/g | % ID/g | % ID/g |
| Blood | 0.02 | 1.715 | 1.54 | 0.145 | 0.06 | 1.125 | 0.160 | 0.035 | 0.025 | 0.03 |
| Tumor | 32.875 | 89.05 | 77.54 | 56.08 | 43.175 | 41.83 | 41.73 | 19.46 | 16.195 | 12.015 |
| Liver | 0.09 | 2.725 | 3.645 | 1.415 | 0.37 | 1.625 | 1.020 | 0.095 | 0.115 | 0.185 |
| Kidney | 2.01 | 177.885 | 150.54 | 88.175 | 31.72 | 87.105 | 74.455 | 8.76 | 2.890 | 5.135 |
| Muscle | 0.035 | 0.73 | 0.465 | 0.135 | 0.1 | 0.055 | 0.175 | 0.04 | 0.060 | 0.045 |

Effect Example 5: Competitive Binding (1) 22Rv1 cells in the logarithmic growth phase were prepared into a cell suspension, and the cell density was adjusted to $1\times10^4$ cells/mL. 1 mL of the cell suspension was seeded into each well of a 24-well cell culture plate. The cells were cultured overnight in a 37° C. incubator.

(2) The cell culture medium was aspirated, and the cells were washed once with PBS. Then, 975 μL of additive-free medium was added.

(3) To each well, 25 μL of a fixed concentration of radiolabeled PSMA-617 ligand (final concentration in the medium: 2 μCi/mL) and different concentrations (final concentrations in the medium: 1000 ng/ml, 100 ng/mL, 10 ng/mL, 1 ng/mL, 0.1 ng/mL, 0.01 ng/mL, 0.001 ng/mL, 0 ng/ml) of the unlabeled test blocking compounds DB-18, DB-19, DB-13, E-3 were added.

(4) The cells were incubated on ice for 2 hours.

(5) The cells were washed three times with ice-cold PBS.

(6) The cells were lysed with 0.5 mL of 1 M sodium hydroxide, and washed twice with 0.5 mL PBS. The sodium hydroxide (0.5 mL) and PBS (0.5 mL×2) solutions were collected for uptake counting.

Figure 8:
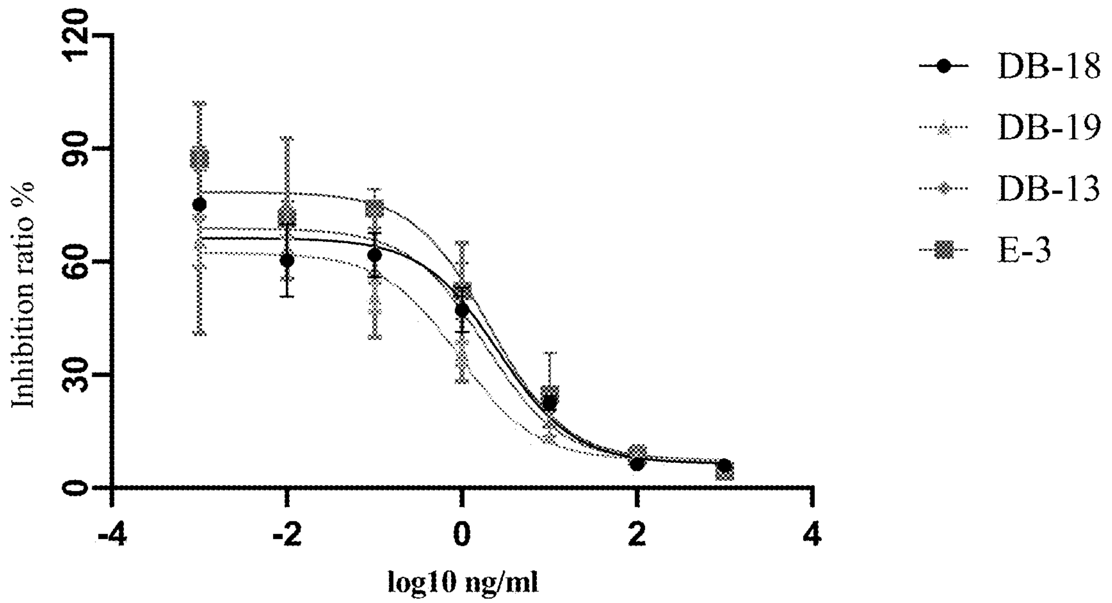
FIG. 8 shows the competitive binding of DB compounds and the reference compound on PSMA-expressing cells.

The experimental results are shown in FIG. 8. The results indicate that the $IC_{50}$ values for compounds E-3, DB-13, DB-18, and DB-19 are 2.06 nM, 1.83 nM, 2.58 nM, and 0.93 nM, respectively.

Effect Example 6: Cell Killing

A. LNCaP cells in the logarithmic growth phase were prepared into a cell suspension, and the cell density was adjusted to $1\times10^5$ cells/mL. 1 mL of the cell suspension was seeded into each well of a 24-well cell culture plate. The cells were cultured for 24 hours in a 37° C. incubator.

B. The $^{177}$Lu-labeled compound ($^{177}$Lu-E-3) was prepared in serum-containing culture medium at radioactive concentrations of 5, 15, and 45 μCi/mL (the unlabeled E-3 was prepared at a corresponding precursor concentration for 45 μCi/mL).

C. The experimental groups were treated with 1 mL/well of the above $^{177}$Lu-labeled compound solutions, while the control group was treated with 1 mL/well of serum-containing culture medium.

D. The cells were cultured in the incubator for 24 hours, after which the medium was entirely replaced with fresh culture medium.

E. On the fifth day, cell proliferation in each group was monitored using an enhanced CCK8 assay kit.

Figure 9:
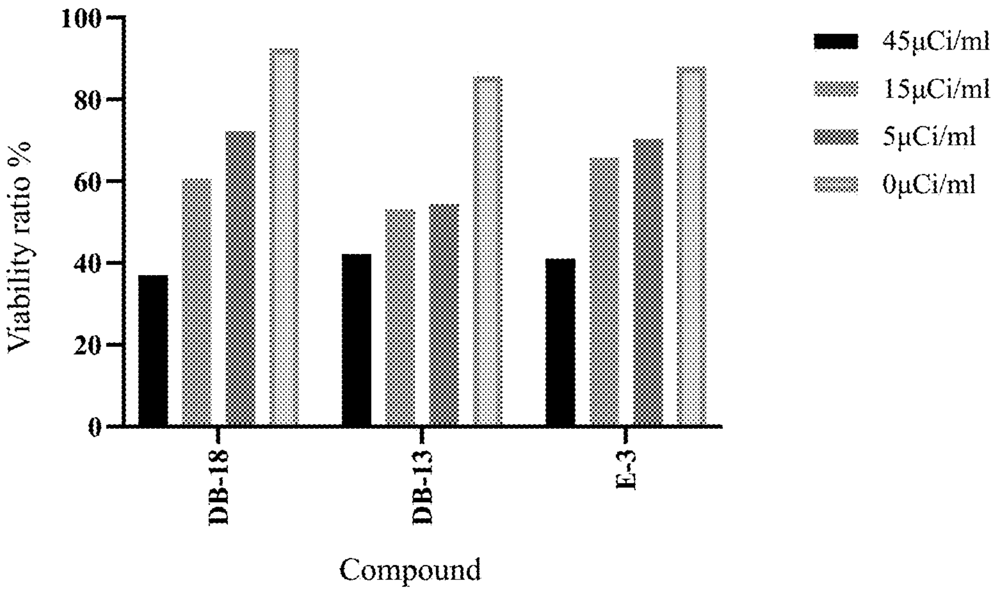
FIG. 9 shows the cytotoxicity assay of DB compounds and the reference compound on LNCaP cells.

The experimental results are shown in FIG. 9. The results indicate that at the tested doses, both compounds and the reference compound exhibited cell-killing effects with a dose-response relationship. At the equivalent dose of 45 μCi/mL, DB-13 demonstrated a stronger cell-killing effect, achieving a 67% cell-killing rate.

Effect Example 7: Determination of c Log P

Three EP tubes were prepared, each containing 0.1 mL of saturated n-octanol and 80 μL of ultrapure water. Then, 20 μL (approximately 1 MBq) of the $^{177}$Lu-labeled DB-13, DB-18, and DB-19 compound solutions were added to the respective tubes. After shaking evenly, the tubes were centrifuged at room temperature (2000 r/min, 5 minutes, centrifugation radius of 10 cm). From each tube, 100 μL was taken from both the lipid layer and the aqueous layer, and the radioactivity counts per minute for both phases were measured. The Log P values were calculated, and their mean values were taken as the final result.

Figure 10:
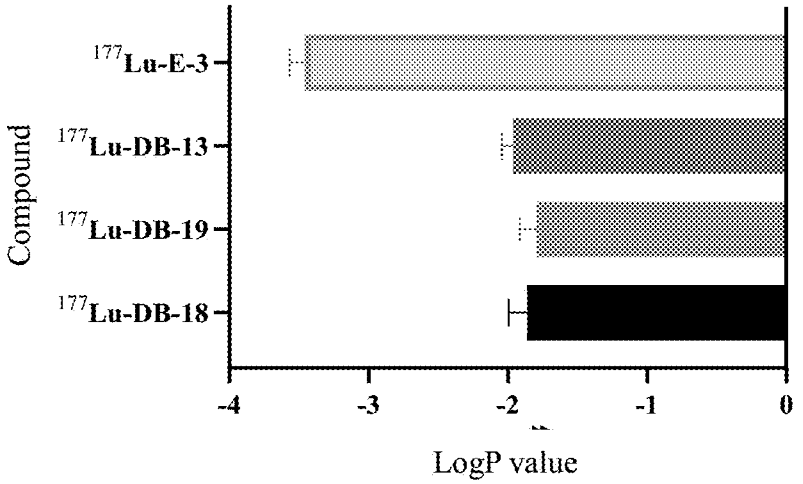
FIG. 10 shows the lipid-water partition coefficients of DB compounds and the reference compound.

The experimental results are shown in FIG. 10. The experimental Log P values for DB-13, DB-18, DB-19, and E-3 were −1.96, −1.86, −1.79, and −3.46, respectively. These results indicate that the tested compounds exhibit good water solubility.

Effect Example 8: Plasma Protein Binding (PPB) Test

The labeled compounds $^{177}$Lu-E-3, 177Lu-DB-13, 177Lu-DB-18, and $^{177}$Lu-DB-19 (1 μCi) were prepared in a reaction solution by adding 50 μL of PBS to achieve a concentration of 20 μCi/mL. 50 μL of the 20 μCi/mL reaction solution was added to 200 μL of plasma, repeated for 3 tubes. The mixture was mixed well and incubated at room temperature for 10 minutes, then added to ultrafiltration tubes and centrifuged at 13000 rpm for 45 minutes. Following this, 50 μL of normal saline was added and the samples were centrifuged again for 15 minutes. The upper chamber and the filtrate were respectively counted for radioactivity.

PPB=[(upper chamber counts−background counts]/(filtrate counts+upper chamber counts−2*background counts)]*100%.

Figure 11:
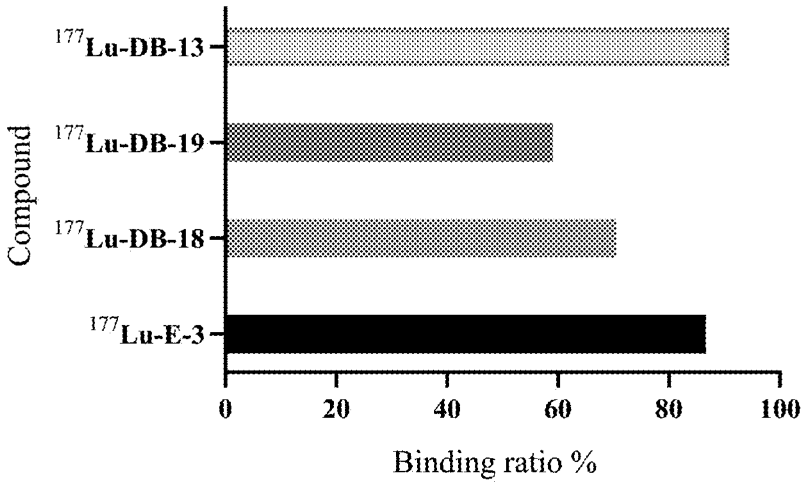
FIG. 11 shows the albumin binding ratio of DB compounds and the reference compound in rat plasma.

The experimental results are shown in FIG. 11. Compared with the reference compound, the synthesized compounds demonstrated the following plasma protein binding ratios: DB-13 exhibited a higher albumin binding ratio (DB-13: 90.84%, E-3:86.61%), while DB-18 and DB-19 exhibited lower albumin binding ratios than the reference compound, at 70.51% and 59.07%, respectively.

Effect Example 9: Treatment

Balb/c Nude mouse, approximately 6-8 weeks old, were subcutaneously inoculated with $3\times10^6$ 22rv1 cells (in 50% Matrigel, Corning) into the right scapular region. Once the tumors reached the required size for the experiment, the animals were randomly assigned into 11 experimental groups based on tumor volume, with 5 mouse per group. The body weight and tumor size of the animals were measured. On the day of grouping, treatments were administered as follows: control group (normal saline), group 1 ($^{177}$Lu-DB-13, 0.15 mCi/mouse), group 2 ($^{177}$Lu-DB-13, 0.45 mCi/mouse), group 3 ($^{177}$Lu-DB-13, 0.05 mCi/mouse), group 4 ($^{177}$Lu-B-11, 0.05 mCi/mouse), group 5 ($^{177}$Lu-DB-11, 0.15 mCi/mouse), group 6 ($^{177}$Lu-DB-11, 0.45 mCi/mouse), group 7 ($^{177}$Lu-PSMA-617, 0.15 mCi/mouse), group 8 ($^{177}$Lu-PSMA-617, 0.45 mCi/mouse), group 9 ($^{177}$Lu-DB-19, 0.05 mCi/mouse), group 10 ($^{177}$Lu-DB-19, 0.15 mCi/mouse), group 11 ($^{177}$Lu-DB-19, 0.45 mCi/mouse). After the start of treatment, general health and appearance were observed daily. Body weight and tumor size were measured at each sampling time point. Any abnormal observations during the study were recorded in the raw data.

Figure 12:
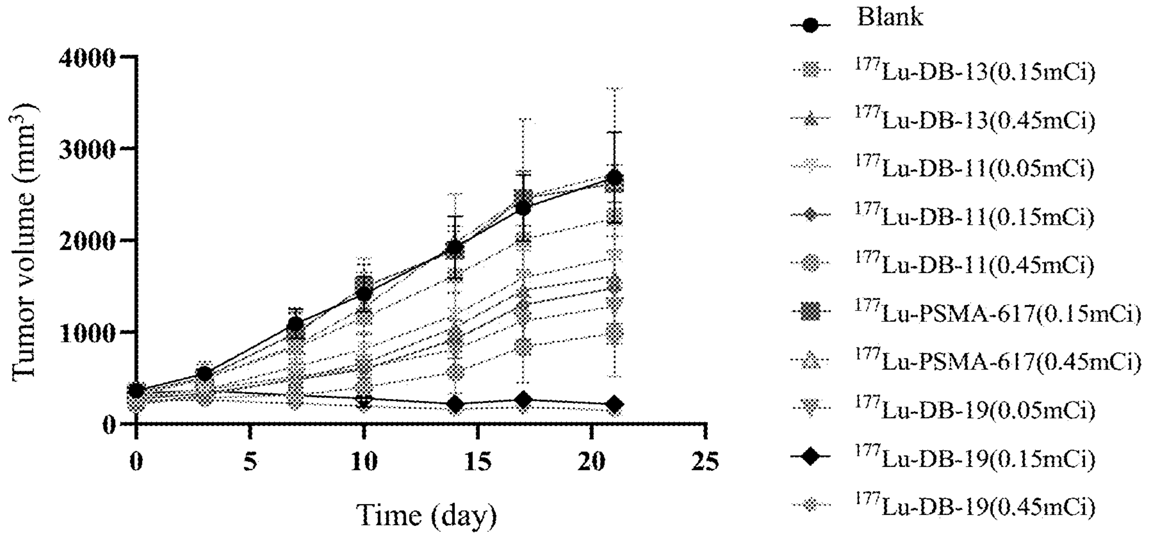
FIG. 12 shows the efficacy (tumor volume change) of DB compounds and the reference compound in the 22RV1 tumor-bearing mouse animal model.
Figure 13:
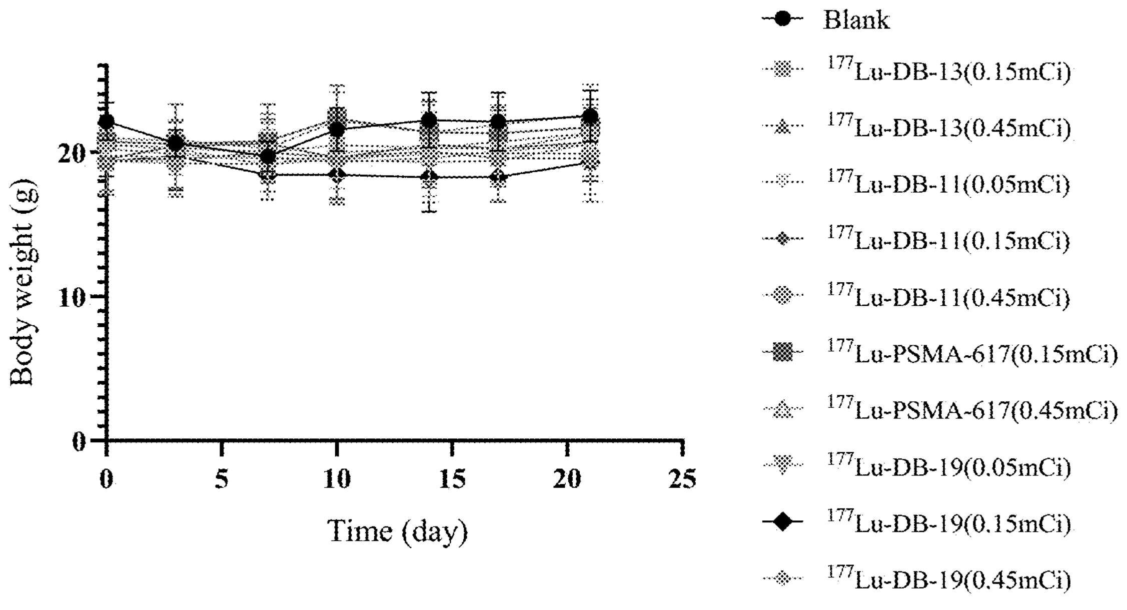
FIG. 13 shows the efficacy (body weight change) of DB compounds and the reference compound in the 22RV1 tumor-bearing mouse animal model.

The experimental results are shown in FIGS. 12, 13, and Table 7. The results indicate that, compared with PSMA-617, DB-19 exhibited superior tumor growth inhibition on tumor cells at two different doses (0.15 mCi and 0.45 mCi). DB-11 showed a certain degree of tumor growth inhibition at the high dose (0.45 mCi) after administration, but its inhibitory effect decreased over time, although it remained higher than that of PSMA-617.

TABLE 7

| | | Tumor volume ($mm^3$)[a] | | | |
|---|---|---|---|---|---|
| Group | Test compound | Before administration | $21^{st}$ day of group administration | T/C | P[b] |
| G1 | Blank | 362.73 ± 29.61 | 2,686.57 ± 494.02 | — | — |
| G2 | $^{177}$Lu-DB-13(0.15 mCi) | 329.30 ± 121.12 | 2,238.77 ± 347.83 | 83.33% | 0.3726 |
| G3 | $^{177}$Lu-DB-13(0.45 mCi) | 223.16 ± 21.81 | 1,609.45 ± 733.75 | 59.91% | 0.0018 |
| G4 | $^{177}$Lu-DB-11(0.05 mCi) | 283.53 ± 50.73 | 1,811.19 ± 238.09 | 67.42% | 0.0161 |
| G5 | 177Lu-DB-11(0.15 mCi) | 274.32 ± 21.78 | 1,480.32 ± 392.77 | 55.10% | 0.0002 |
| G6 | 177Lu-DB-11(0.45 mCi) | 219.81 ± 32.22 | 989.39 ± 472.70 | 36.83% | <0.0001 |
| G7 | 177Lu-PSMA-617(0.15 mCi) | 338.02 ± 33.41 | 2,616.99 ± 203.91 | 97.41% | 0.0296 |
| G8 | 177Lu-PSMA-617(0.45 mCi) | 309.34 ± 83.89 | 2,726.19 ± 926.52 | 101.47% | 0.0091 |
| G9 | 177Lu-DB-19(0.05 mCi) | 306.40 ± 108.56 | 1,280.09 ± 259.95 | 47.65% | <0.0001 |
| G10 | 177Lu-DB-19(0.15 mCi) | 335.89 ± 66.39 | 215.91 ± 73.98 | 8.04% | <0.0001 |
| G11 | 177Lu-DB-19(0.45 mCi) | 260.45 ± 50.47 | 147.14 ± 39.77 | 5.48% | <0.0001 |

Note:

[a]Mean ± standard error; [b]Statistical analysis of tumor volume between treatment groups and control group on the $28^{th}$ day after administration, performed using Two-way ANOVA Fisher's LSD test.

The invention claimed is:
1. A peptide urea derivative, or the pharmaceutically acceptable salt thereof, wherein the peptide urea derivative is a compound formed by chelation of compound A with $^{68}Ga^{3+}$, and the structure of the compound A is:
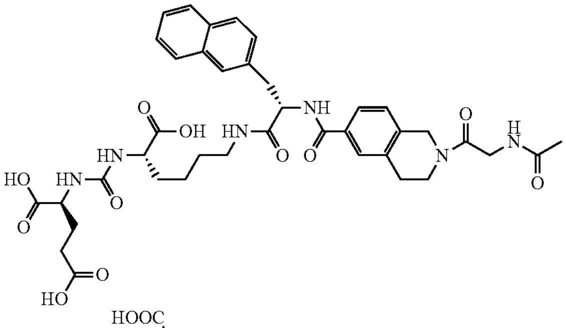
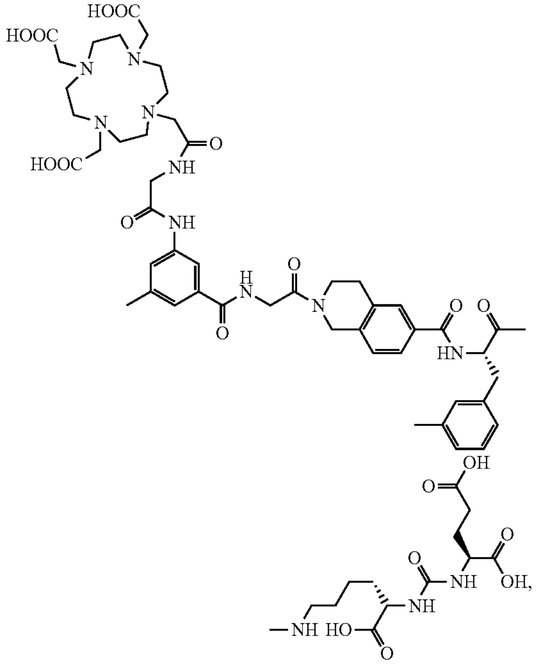
, or
-continued
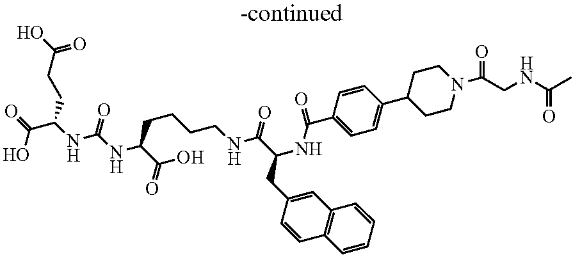
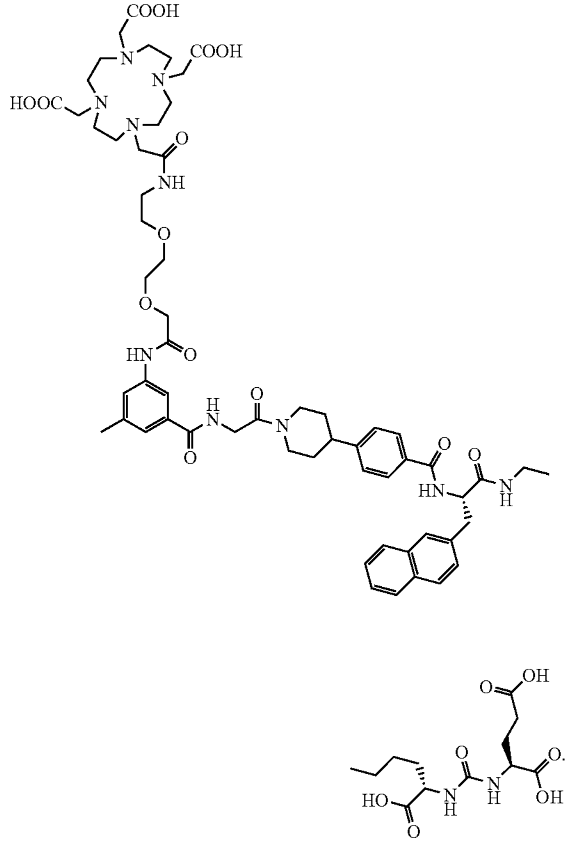
2. A compound, wherein the compound is

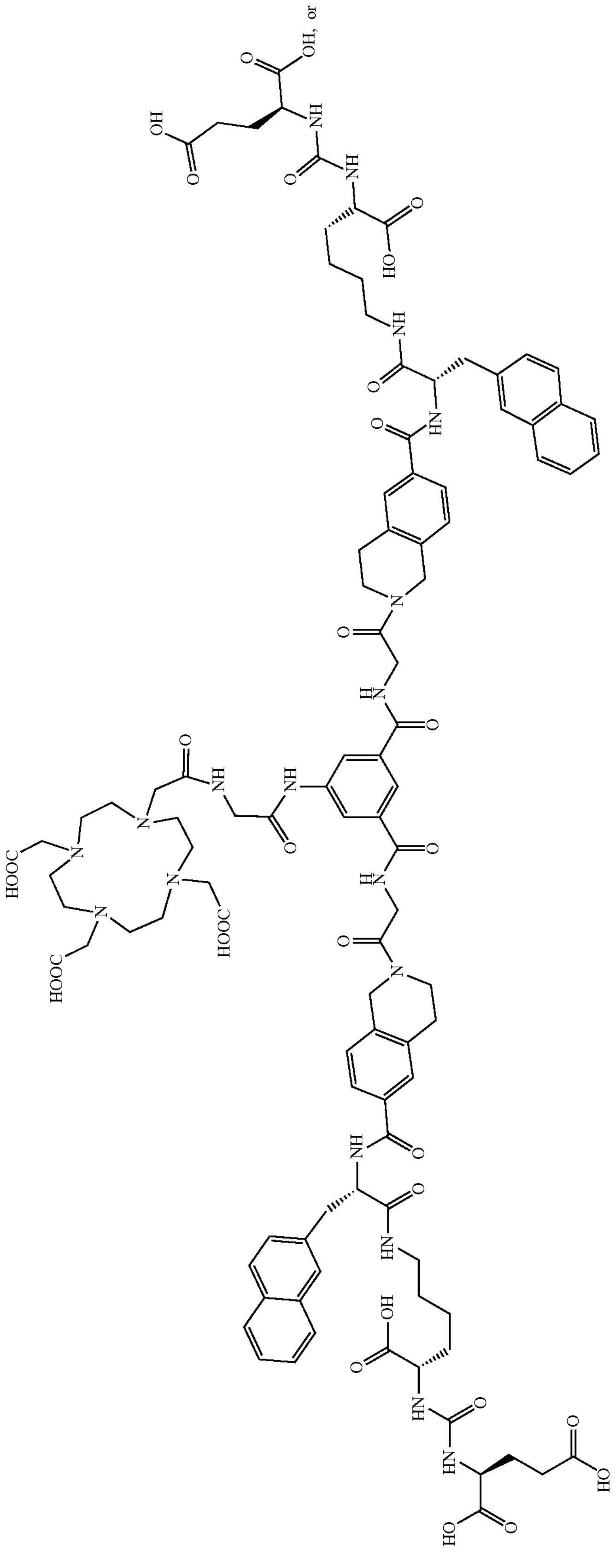
or

-continued
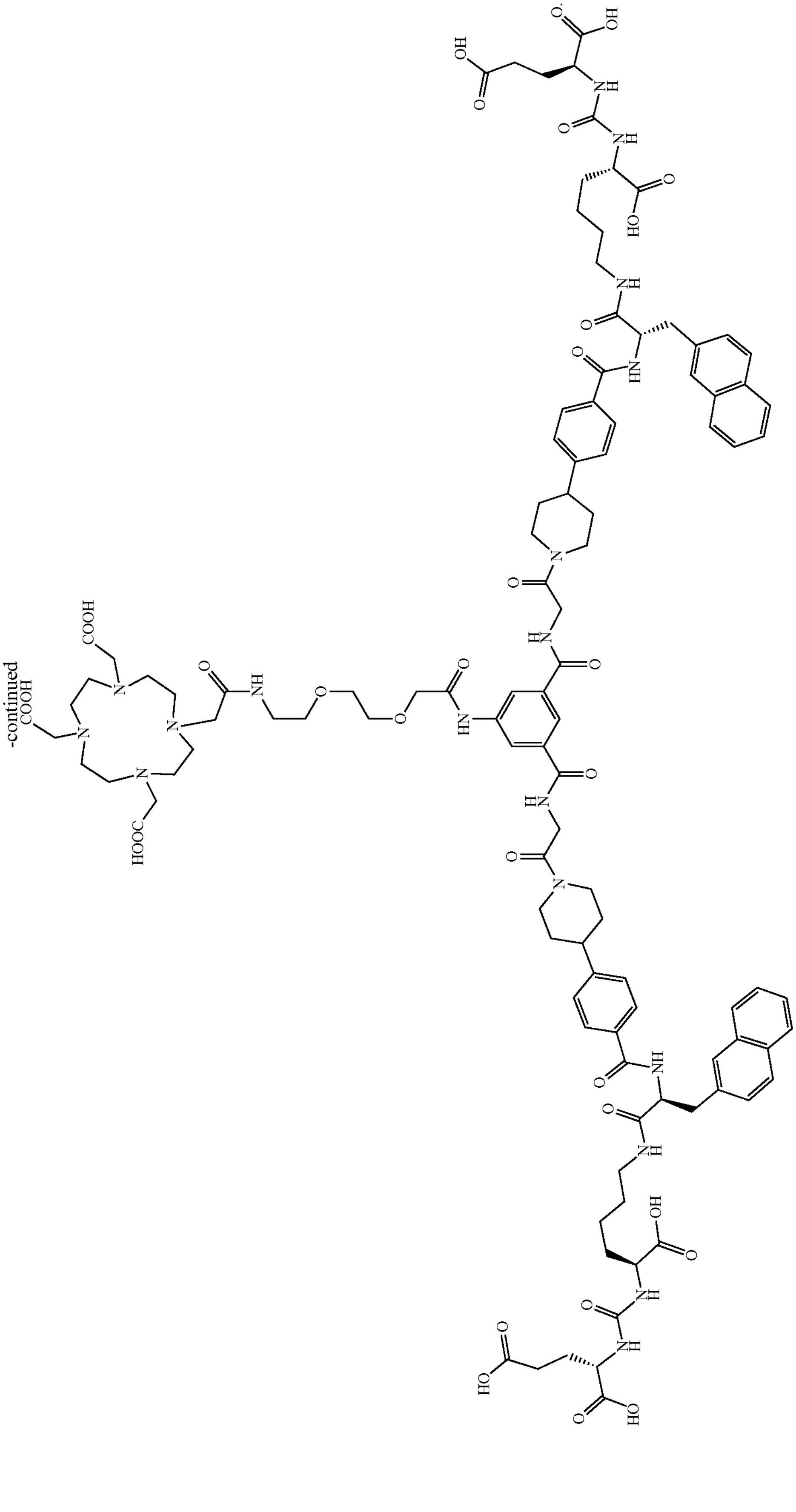

3. A peptide urea derivative, or the pharmaceutically acceptable salt thereof, wherein the peptide urea derivative is a compound formed by chelation of compound A with $^{177}Lu^{3+}$, and the structure of the compound A:

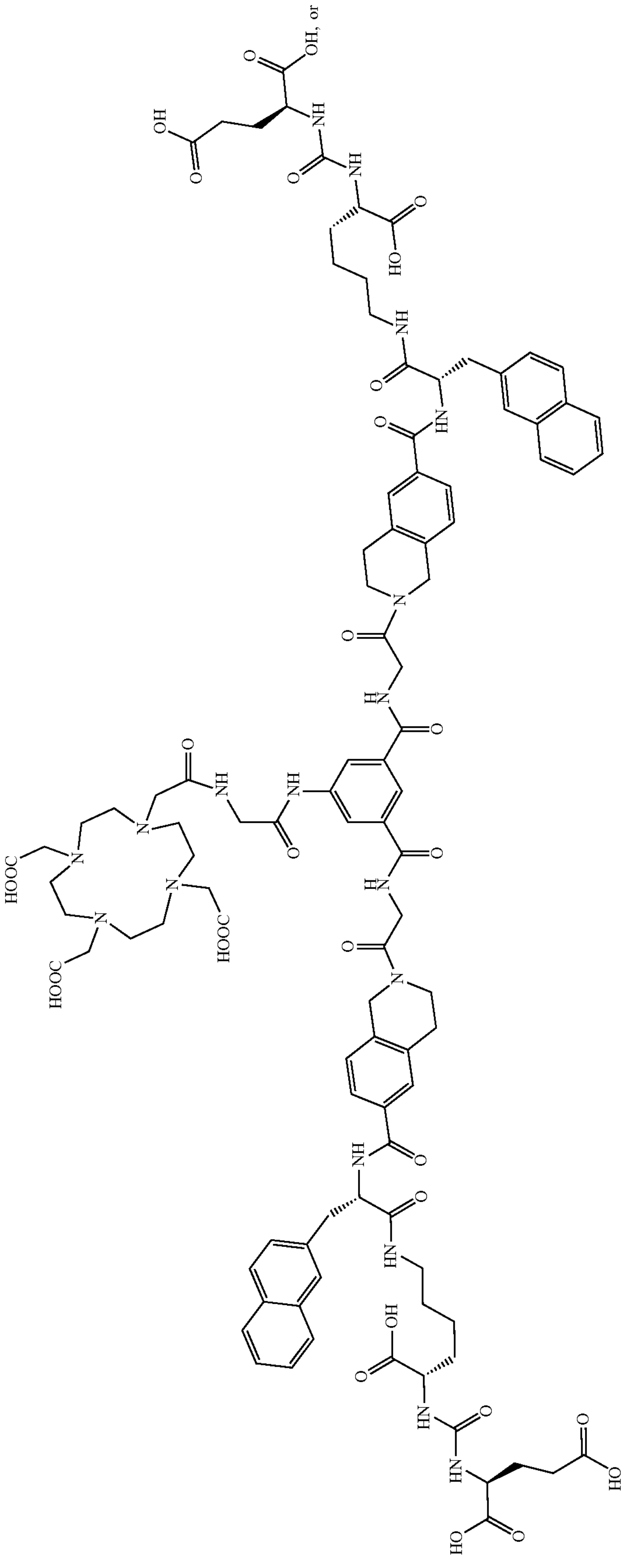
or

-continued
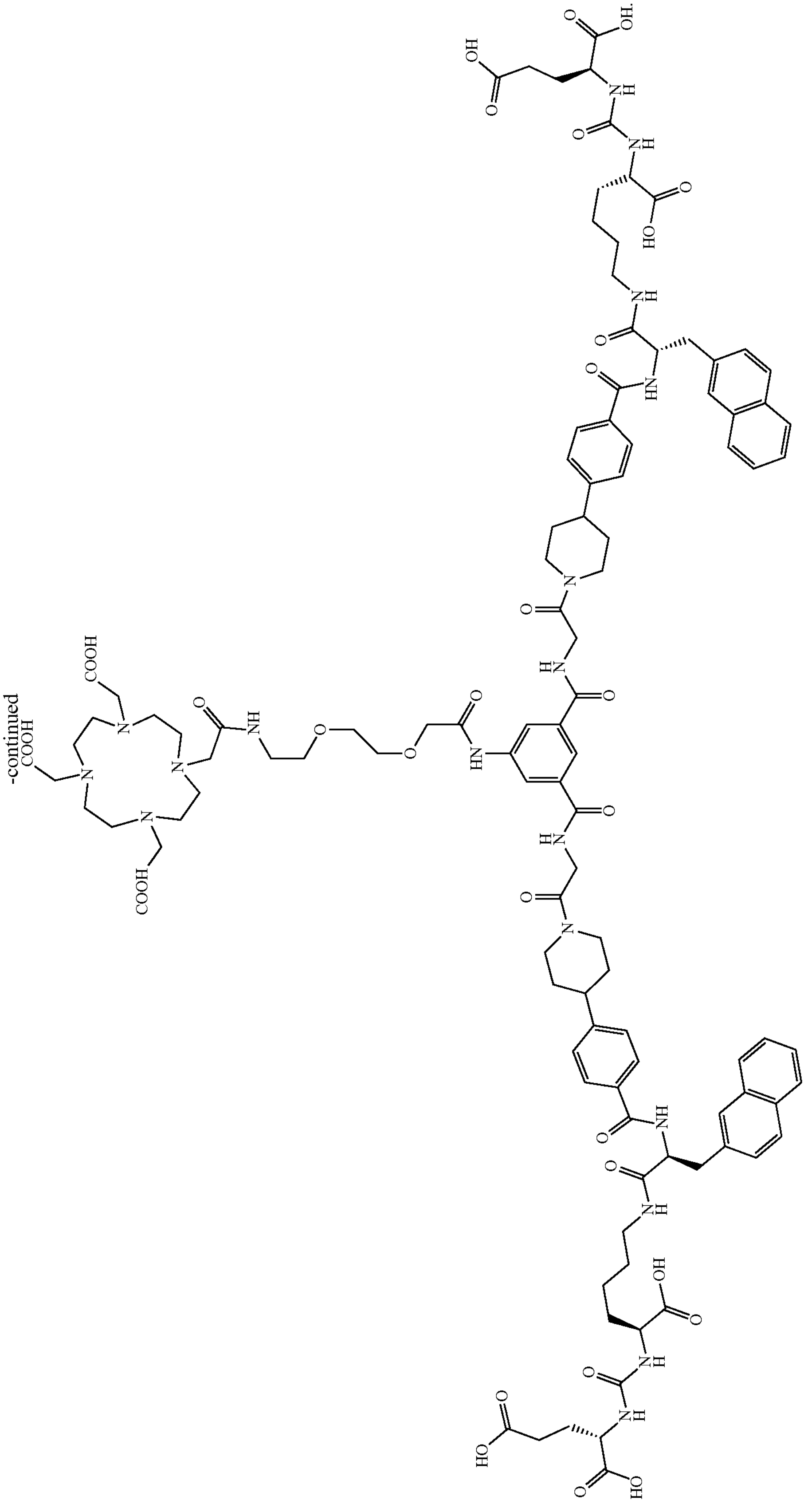
* * * * *